US009834571B2

(12) United States Patent
Zhu et al.

(10) Patent No.: US 9,834,571 B2
(45) Date of Patent: Dec. 5, 2017

(54) COMPOUNDS FOR INHIBITING CELL PROLIFERATION IN EGFR-DRIVEN CANCERS

(71) Applicant: ARIAD Pharmaceuticals, Inc., Cambrbidge, MA (US)

(72) Inventors: Xiaotian Zhu, Newton, MA (US); Yihan Wang, Newton, MA (US); William C. Shakespeare, Southborough, MA (US); Wei-Sheng Huang, Acton, MA (US); David C. Dalgarno, Brookline, MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/044,382

(22) Filed: Feb. 16, 2016

(65) Prior Publication Data
US 2016/0244469 A1 Aug. 25, 2016

Related U.S. Application Data

(63) Continuation of application No. 14/398,893, filed as application No. PCT/US2013/032713 on Mar. 15, 2013, now abandoned.

(60) Provisional application No. 61/643,228, filed on May 5, 2012, provisional application No. 61/723,779, filed on Nov. 7, 2012, provisional application No. 61/724,283, filed on Nov. 8, 2012, provisional application No. 61/801,953, filed on Mar. 15, 2013.

(51) Int. Cl.
| | |
|---|---|
| C07D 239/46 | (2006.01) |
| C07D 239/50 | (2006.01) |
| C07D 401/12 | (2006.01) |
| C07D 403/12 | (2006.01) |
| C07D 413/12 | (2006.01) |
| C07D 265/36 | (2006.01) |
| A61K 31/506 | (2006.01) |
| A61K 31/4025 | (2006.01) |
| A61K 31/444 | (2006.01) |
| A61K 31/4523 | (2006.01) |
| A61K 31/538 | (2006.01) |
| A61K 31/553 | (2006.01) |
| C07F 9/6512 | (2006.01) |
| C07D 239/48 | (2006.01) |
| C07F 9/6521 | (2006.01) |
| C07F 9/6558 | (2006.01) |
| C07F 9/6561 | (2006.01) |
| C07F 9/6584 | (2006.01) |
| A61K 31/505 | (2006.01) |
| A61K 31/675 | (2006.01) |
| A61K 45/06 | (2006.01) |
| C07F 9/28 | (2006.01) |
| C07D 239/42 | (2006.01) |
| A61K 35/00 | (2006.01) |

(52) U.S. Cl.
CPC ........ *C07F 9/65127* (2013.01); *A61K 31/505* (2013.01); *A61K 31/506* (2013.01); *A61K 31/675* (2013.01); *A61K 45/06* (2013.01); *C07D 239/42* (2013.01); *C07D 239/48* (2013.01); *C07D 403/12* (2013.01); *C07F 9/28* (2013.01); *C07F 9/6561* (2013.01); *C07F 9/6584* (2013.01); *C07F 9/65217* (2013.01); *C07F 9/65583* (2013.01); *C07F 9/65586* (2013.01); *C07F 9/65846* (2013.01)

(58) Field of Classification Search
CPC .. C07D 239/46; C07D 239/50; C07D 401/12; C07D 403/12; C07D 413/12; C07D 265/36; A61K 31/506; A61K 31/4025; A61K 31/444; A61K 31/4523; A61K 31/538; A61K 31/553
USPC ......... 544/243, 105; 514/272, 230.5, 211.05; 540/524
See application file for complete search history.

(56) References Cited

U.S. PATENT DOCUMENTS

| 4,966,622 A | 10/1990 | Rempfler et al. |
| 5,521,184 A | 5/1996 | Zimmermann |

(Continued)

FOREIGN PATENT DOCUMENTS

| CA | 2598893 A1 | 4/2008 |
| EP | 0242081 A1 | 10/1987 |

(Continued)

OTHER PUBLICATIONS

Abbott, "On the Offensive", Nature, 2002, pp. 470-474, vol. 416.

(Continued)

*Primary Examiner* — Venkataraman Balasubramanian
(74) *Attorney, Agent, or Firm* — Fangli Chen; Proskauer Rose LLP

(57) ABSTRACT

The invention features compounds, pharmaceutical compositions and methods for treating patients who have an EGFR-driven cancer of Formula I:

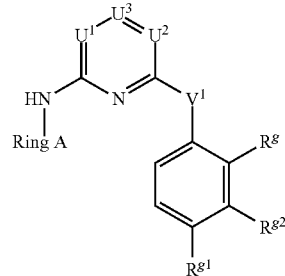

wherein the variables are as defined herein.

16 Claims, No Drawings

(56) References Cited

U.S. PATENT DOCUMENTS

| | | |
|---|---|---|
| 5,612,340 A | 3/1997 | Zimmermann |
| 6,008,234 A | 12/1999 | Kochanny et al. |
| 6,015,455 A | 1/2000 | Yano et al. |
| 6,030,977 A | 2/2000 | Stock et al. |
| 6,048,390 A | 4/2000 | Yano et al. |
| 6,107,301 A | 8/2000 | Aldrich et al. |
| 6,432,963 B1 | 8/2002 | Hisamichi et al. |
| 6,573,044 B1 | 6/2003 | Gray et al. |
| 6,770,652 B2 | 8/2004 | Gangjee |
| 6,878,697 B2 | 4/2005 | Metcalf et al. |
| 6,949,644 B2 | 9/2005 | Ding et al. |
| 7,151,096 B2 | 12/2006 | Ren et al. |
| 7,169,817 B2 | 1/2007 | Pan et al. |
| 7,176,312 B2 | 2/2007 | Ding et al. |
| 7,189,729 B2 | 3/2007 | Chopiuk et al. |
| 7,253,166 B2 | 8/2007 | Ding et al. |
| 7,256,206 B2 | 8/2007 | Pan et al. |
| 7,338,957 B2 | 3/2008 | Ding et al. |
| 7,371,750 B2 | 5/2008 | Sim et al. |
| 7,423,031 B2 | 9/2008 | Wan et al. |
| 7,423,038 B2 | 9/2008 | Ren et al. |
| 7,449,582 B2 | 11/2008 | Ding et al. |
| 7,514,446 B2 | 4/2009 | Davis-Ward et al. |
| 7,521,457 B2 | 4/2009 | Stadtmueller et al. |
| 7,569,561 B2 | 8/2009 | Stadtmueller et al. |
| 7,569,593 B2 | 8/2009 | Gray et al. |
| 7,589,101 B2 | 9/2009 | Okram et al. |
| 7,605,131 B2 | 10/2009 | Mano et al. |
| 7,642,255 B2 | 1/2010 | Sim et al. |
| 7,671,063 B2 | 3/2010 | Baenteli et al. |
| 7,713,958 B2 | 5/2010 | Wan et al. |
| 7,728,120 B2 | 6/2010 | Mano et al. |
| 7,745,437 B2 | 6/2010 | Ren et al. |
| 7,868,018 B2 | 1/2011 | Xie et al. |
| 7,893,074 B2 | 2/2011 | Garcia-Echeverria et al. |
| 7,939,519 B2 | 5/2011 | Pan et al. |
| 7,943,629 B2 | 5/2011 | Luecking et al. |
| 7,964,592 B2 | 6/2011 | Garcia-Echeverria et al. |
| 7,964,710 B2 | 6/2011 | Mano et al. |
| 7,968,557 B2 | 6/2011 | Choi et al. |
| 8,039,479 B2 | 10/2011 | Michellys et al. |
| 8,071,609 B2 | 12/2011 | Wang et al. |
| 8,101,608 B2 | 1/2012 | Wan et al. |
| 8,197,818 B2 | 6/2012 | Mano et al. |
| 8,383,793 B2 | 2/2013 | Morris et al. |
| 8,450,335 B2 | 5/2013 | Singh et al. |
| 9,012,462 B2 | 4/2015 | Wang et al. |
| 9,273,077 B2 | 3/2016 | Wang et al. |
| 2003/0130234 A1 | 7/2003 | Shakespeare et al. |
| 2003/0171583 A1 | 9/2003 | Ding et al. |
| 2003/0186324 A1 | 10/2003 | Liao et al. |
| 2003/0191312 A1 | 10/2003 | Ding et al. |
| 2004/0048857 A1 | 3/2004 | Pan et al. |
| 2004/0121316 A1 | 6/2004 | Birkus et al. |
| 2004/0235841 A1 | 11/2004 | Ren et al. |
| 2004/0248952 A1 | 12/2004 | Pan et al. |
| 2005/0014753 A1 | 1/2005 | Ding et al. |
| 2005/0038049 A1 | 2/2005 | Ding et al. |
| 2005/0113398 A1 | 5/2005 | Argade et al. |
| 2005/0124637 A1 | 6/2005 | Cheng et al. |
| 2005/0136396 A1 | 6/2005 | McDermott |
| 2005/0136397 A1 | 6/2005 | McDermott |
| 2005/0136398 A1 | 6/2005 | McDermott |
| 2005/0153955 A1 | 7/2005 | Wan et al. |
| 2005/0159391 A1 | 7/2005 | Ding et al. |
| 2005/0159446 A1 | 7/2005 | Chew et al. |
| 2005/0171105 A1 | 8/2005 | Chopiuk et al. |
| 2005/0187230 A1 | 8/2005 | Ding et al. |
| 2005/0192301 A1 | 9/2005 | Li |
| 2005/0197320 A1 | 9/2005 | Chen et al. |
| 2005/0203114 A1 | 9/2005 | Armistead et al. |
| 2005/0209197 A1 | 9/2005 | Arimilli et al. |
| 2005/0209224 A1 | 9/2005 | Singh et al. |
| 2005/0209285 A1 | 9/2005 | Gray et al. |
| 2005/0222177 A1 | 10/2005 | Sim et al. |
| 2005/0234049 A1 | 10/2005 | Singh et al. |
| 2005/0239054 A1 | 10/2005 | Arimilli et al. |
| 2005/0261295 A1 | 11/2005 | Stadtmueller |
| 2005/0267304 A1 | 12/2005 | Cox et al. |
| 2005/0288327 A1 | 12/2005 | Uesugi et al. |
| 2006/0009642 A1 | 1/2006 | Ding et al. |
| 2006/0035891 A1 | 2/2006 | Li et al. |
| 2006/0079543 A1 | 4/2006 | Sum et al. |
| 2006/0115815 A1 | 6/2006 | Birkus et al. |
| 2006/0128692 A1 | 6/2006 | Chen et al. |
| 2006/0148800 A1 | 7/2006 | Stadtmueller |
| 2006/0167249 A1 | 7/2006 | Argade et al. |
| 2006/0211709 A1 | 9/2006 | Buhr et al. |
| 2006/0229329 A1 | 10/2006 | Heaton et al. |
| 2006/0247241 A1 | 11/2006 | Garcia-Echeverria et al. |
| 2006/0247262 A1 | 11/2006 | Baenteli et al. |
| 2007/0010489 A1 | 1/2007 | Arimilli et al. |
| 2007/0010668 A1 | 1/2007 | Davis-Ward et al. |
| 2007/0032514 A1 | 2/2007 | Zahn et al. |
| 2007/0032637 A1 | 2/2007 | Yokoyama et al. |
| 2007/0066660 A1 | 3/2007 | Stahle et al. |
| 2007/0167439 A1 | 7/2007 | Singh et al. |
| 2007/0179140 A1 | 8/2007 | Argade et al. |
| 2007/0190523 A1 | 8/2007 | Birkus et al. |
| 2007/0191380 A1 | 8/2007 | Ding et al. |
| 2007/0203161 A1 | 8/2007 | Argade et al. |
| 2007/0207999 A1 | 9/2007 | Stadtmueller |
| 2007/0208164 A1 | 9/2007 | Olszewski et al. |
| 2007/0225286 A1 | 9/2007 | Ren et al. |
| 2007/0225495 A1 | 9/2007 | Singh et al. |
| 2007/0259904 A1 | 11/2007 | Noronha et al. |
| 2007/0299060 A1 | 12/2007 | Li et al. |
| 2008/0009484 A1 | 1/2008 | Argade et al. |
| 2008/0009494 A1 | 1/2008 | Li et al. |
| 2008/0021020 A1 | 1/2008 | Argade et al. |
| 2008/0027045 A1 | 1/2008 | Argade et al. |
| 2008/0051412 A1 | 2/2008 | Argade et al. |
| 2008/0058358 A1 | 3/2008 | Luecking et al. |
| 2008/0090776 A1 | 4/2008 | Mano et al. |
| 2008/0108616 A1 | 5/2008 | Ding et al. |
| 2008/0113986 A1 | 5/2008 | Ren et al. |
| 2008/0132504 A1 | 6/2008 | Garcia-Echeverria et al. |
| 2008/0167330 A1 | 7/2008 | Luecking et al. |
| 2008/0176866 A1 | 7/2008 | Jautelat et al. |
| 2008/0188483 A1 | 8/2008 | Ren et al. |
| 2008/0194605 A1 | 8/2008 | Heinrich et al. |
| 2008/0221098 A1 | 9/2008 | Sim et al. |
| 2008/0221192 A1 | 9/2008 | Wan et al. |
| 2008/0227783 A1 | 9/2008 | Wan et al. |
| 2008/0227786 A1 | 9/2008 | Ferlita et al. |
| 2008/0255112 A1 | 10/2008 | Zhang et al. |
| 2008/0269170 A1 | 10/2008 | Bosch et al. |
| 2008/0280946 A1 | 11/2008 | Nazare et al. |
| 2008/0287432 A1 | 11/2008 | Okram et al. |
| 2008/0300246 A1 | 12/2008 | Xie et al. |
| 2008/0300267 A1 | 12/2008 | Okram et al. |
| 2008/0312438 A1 | 12/2008 | Singh et al. |
| 2009/0036423 A1 | 2/2009 | Pan et al. |
| 2009/0069327 A1 | 3/2009 | Ding et al. |
| 2009/0099193 A1 | 4/2009 | Mano et al. |
| 2009/0105250 A1 | 4/2009 | Sim et al. |
| 2009/0118273 A1 | 5/2009 | Nagle et al. |
| 2009/0137555 A1 | 5/2009 | Wan et al. |
| 2009/0137804 A1 | 5/2009 | Ding et al. |
| 2009/0156596 A1 | 6/2009 | Wang et al. |
| 2009/0181991 A1 | 7/2009 | Zhang et al. |
| 2009/0221555 A1 | 9/2009 | Ahmed et al. |
| 2009/0258910 A1 | 10/2009 | Gray et al. |
| 2009/0286789 A1 | 11/2009 | Hood et al. |
| 2009/0306101 A1 | 12/2009 | Solca et al. |
| 2009/0312321 A1 | 12/2009 | Ren et al. |
| 2009/0318687 A1 | 12/2009 | Singh et al. |
| 2010/0016296 A1 | 1/2010 | Singh et al. |
| 2010/0029610 A1 | 2/2010 | Singh et al. |
| 2010/0081679 A1 | 4/2010 | Greul et al. |
| 2010/0093668 A1 | 4/2010 | Babin et al. |
| 2010/0240673 A1 | 9/2010 | Mano et al. |
| 2010/0249092 A1 | 9/2010 | Singh et al. |
| 2010/0249126 A1 | 9/2010 | Burger et al. |

(56) References Cited

U.S. PATENT DOCUMENTS

| | | |
|---|---|---|
| 2010/0298156 A1 | 11/2010 | Lee-Hoeflich et al. |
| 2010/0298295 A1 | 11/2010 | Marsilje et al. |
| 2010/0324062 A1 | 12/2010 | Nagle et al. |
| 2011/0021524 A1 | 1/2011 | Adrian et al. |
| 2011/0046108 A1 | 2/2011 | Kettle et al. |
| 2011/0053932 A1 | 3/2011 | Sim et al. |
| 2011/0092491 A1 | 4/2011 | Cheng et al. |
| 2011/0098280 A1 | 4/2011 | Garcia-Echeverria et al. |
| 2011/0105472 A1 | 5/2011 | Greul et al. |
| 2011/0144107 A1 | 6/2011 | Chatterjee et al. |
| 2011/0207736 A1 | 8/2011 | Gray et al. |
| 2011/0212077 A1 | 9/2011 | Noronha et al. |
| 2011/0230478 A1 | 9/2011 | Greul et al. |
| 2011/0230494 A1 | 9/2011 | Singh et al. |
| 2011/0230545 A1 | 9/2011 | Mano et al. |
| 2011/0256546 A1 | 10/2011 | Morris et al. |
| 2011/0263541 A1 | 10/2011 | Luo et al. |
| 2011/0288091 A1 | 11/2011 | Gray et al. |
| 2011/0312908 A1 | 12/2011 | Gray et al. |
| 2012/0024620 A1 | 2/2012 | Parodi |
| 2012/0040961 A1 | 2/2012 | Gray et al. |
| 2012/0094999 A1 | 4/2012 | Gray et al. |
| 2012/0108572 A1 | 5/2012 | Wagner et al. |
| 2012/0122902 A1 | 5/2012 | Chen et al. |
| 2012/0252818 A1 | 10/2012 | Chiosis et al. |
| 2012/0316135 A1* | 12/2012 | Dalgarno ............. C07D 405/12 514/81 |
| 2013/0053409 A1 | 2/2013 | Butterworth et al. |
| 2013/0158095 A1 | 6/2013 | Mano et al. |
| 2013/0225527 A1 | 8/2013 | Wang et al. |
| 2013/0225528 A1 | 8/2013 | Wang et al. |
| 2014/0024620 A1 | 1/2014 | Dalgarno et al. |
| 2014/0066406 A1 | 3/2014 | Wang et al. |
| 2015/0166591 A1 | 6/2015 | Zhu et al. |
| 2015/0225436 A1 | 8/2015 | Wang et al. |
| 2016/0376297 A1 | 12/2016 | Wang et al. |

FOREIGN PATENT DOCUMENTS

| | | |
|---|---|---|
| EP | 0382375 A2 | 8/1990 |
| EP | 0468684 A2 | 1/1992 |
| EP | 0472053 A2 | 2/1992 |
| EP | 0542420 A1 | 5/1993 |
| EP | 0564409 B1 | 10/1993 |
| EP | 0372729 B1 | 1/1995 |
| EP | 0763576 A2 | 3/1997 |
| EP | 1054004 A1 | 11/2000 |
| EP | 1132387 A1 | 9/2001 |
| EP | 2123654 A1 | 11/2009 |
| EP | 2172461 A1 | 4/2010 |
| FR | 2911138 A1 | 7/2008 |
| GB | 1129797 | 10/1968 |
| JP | 11-60573 | 3/1999 |
| WO | WO 95/09847 | 4/1995 |
| WO | WO 96/28427 | 9/1996 |
| WO | WO 97/10887 | 3/1997 |
| WO | WO 97/19065 | 5/1997 |
| WO | WO 97/20822 | 6/1997 |
| WO | WO 98/11094 | 3/1998 |
| WO | WO 98/15547 | 4/1998 |
| WO | WO 99/03854 | 1/1999 |
| WO | WO 99/63821 | 12/1999 |
| WO | WO 00/15645 | 3/2000 |
| WO | WO 00/27825 | 5/2000 |
| WO | WO 00/31068 | 6/2000 |
| WO | WO 00/33844 | 6/2000 |
| WO | WO 00/46203 | 8/2000 |
| WO | WO 00/67900 | 11/2000 |
| WO | WO 00/78731 | 12/2000 |
| WO | WO 01/09134 | 2/2001 |
| WO | WO 01/47507 | 7/2001 |
| WO | WO 01/64200 | 9/2001 |
| WO | WO 01/64654 | 9/2001 |
| WO | WO 01/64656 | 9/2001 |
| WO | WO 01/72744 | 10/2001 |
| WO | WO 01/85699 | 11/2001 |
| WO | WO 01/85700 | 11/2001 |
| WO | WO 02/00024 | 1/2002 |
| WO | WO 02/04429 | 1/2002 |
| WO | WO 02/22597 | 3/2002 |
| WO | WO 02/46318 | 6/2002 |
| WO | WO 02/059110 | 8/2002 |
| WO | WO 02/083653 | 10/2002 |
| WO | WO 02/102800 | 12/2002 |
| WO | WO 03/000186 | 1/2003 |
| WO | WO 03/030909 | 4/2003 |
| WO | WO 03/037891 | 5/2003 |
| WO | WO 03/057165 | 7/2003 |
| WO | WO 03/066601 | 8/2003 |
| WO | WO 03/078404 | 9/2003 |
| WO | WO 03/094920 | 11/2003 |
| WO | WO 2004/011443 | 2/2004 |
| WO | WO 2004/014382 | 2/2004 |
| WO | WO 2004/018435 | 3/2004 |
| WO | WO 2004/041789 | 5/2004 |
| WO | WO 2004/046118 | 6/2004 |
| WO | WO 2004/074244 | 9/2004 |
| WO | WO 2004/074261 | 9/2004 |
| WO | WO 2004/074262 | 9/2004 |
| WO | WO 2004/080980 | 9/2004 |
| WO | WO 2004/085385 | 10/2004 |
| WO | WO 2004/085409 | 10/2004 |
| WO | WO 2004/096818 | 11/2004 |
| WO | WO 2005/013996 | 2/2005 |
| WO | WO 2005/016528 | 2/2005 |
| WO | WO 2005/016893 | 2/2005 |
| WO | WO 2005/016894 | 2/2005 |
| WO | WO 2005/026130 | 3/2005 |
| WO | WO 2005/026158 | 3/2005 |
| WO | WO 2005/061458 | 7/2005 |
| WO | WO 2005/070890 | 8/2005 |
| WO | WO 2006/021454 | 3/2006 |
| WO | WO 2006/038594 | 4/2006 |
| WO | WO 2006/068826 | 6/2006 |
| WO | WO 2006/074057 | 7/2006 |
| WO | WO 2006/078846 | 7/2006 |
| WO | WO 2006/084015 | 8/2006 |
| WO | WO 2006/101977 | 9/2006 |
| WO | WO 2006/123165 | 11/2006 |
| WO | WO 2006/124874 | 11/2006 |
| WO | WO 2006/128129 | 11/2006 |
| WO | WO 2006/128172 | 11/2006 |
| WO | WO 2006/129100 | 12/2006 |
| WO | WO 2006/133426 | 12/2006 |
| WO | WO 2007/015923 | 2/2007 |
| WO | WO 2007/021937 | 2/2007 |
| WO | WO 2007/042299 | 4/2007 |
| WO | WO 2007/043835 | 4/2007 |
| WO | WO 2007/048064 | 4/2007 |
| WO | WO 2007/053452 | 5/2007 |
| WO | WO 2007/056151 | 5/2007 |
| WO | WO 2007/067506 | 6/2007 |
| WO | WO 2007/071455 | 6/2007 |
| WO | WO 2007/085833 | 8/2007 |
| WO | WO 2007/089768 | 8/2007 |
| WO | WO 2007/113254 | 10/2007 |
| WO | WO 2007/113256 | 10/2007 |
| WO | WO 2007/120339 | 10/2007 |
| WO | WO 2007/125351 | 11/2007 |
| WO | WO 2007/130468 | 11/2007 |
| WO | WO 2008/005538 | 1/2008 |
| WO | WO 2008/009458 | 1/2008 |
| WO | WO 2008/009963 | 1/2008 |
| WO | WO 2008/039359 | 4/2008 |
| WO | WO 2008/045978 | 4/2008 |
| WO | WO 2008/049123 | 4/2008 |
| WO | WO 2008/051493 | 5/2008 |
| WO | WO 2008/057280 | 5/2008 |
| WO | WO 2008/073687 | 6/2008 |
| WO | WO 2008/079719 | 7/2008 |
| WO | WO 2008/079907 | 7/2008 |
| WO | WO 2008/080964 | 7/2008 |
| WO | WO 2008/080965 | 7/2008 |

(56) References Cited

FOREIGN PATENT DOCUMENTS

| | | |
|---|---|---|
| WO | WO 2008/092049 | 7/2008 |
| WO | WO 2008/092199 | 8/2008 |
| WO | WO 2008/094737 A2 | 8/2008 |
| WO | WO 2008/099073 | 8/2008 |
| WO | WO 2008/115738 | 9/2008 |
| WO | WO 2008/115742 | 9/2008 |
| WO | WO 2008/118822 | 10/2008 |
| WO | WO 2008/121670 | 10/2008 |
| WO | WO 2008/151183 | 12/2008 |
| WO | WO 2009/012421 | 1/2009 |
| WO | WO 2009/020990 | 2/2009 |
| WO | WO 2009/032668 | 3/2009 |
| WO | WO 2009/032694 | 3/2009 |
| WO | WO 2009/032703 | 3/2009 |
| WO | WO 2009/051822 | 4/2009 |
| WO | WO 2009/071535 | 6/2009 |
| WO | WO 2009/080638 | 7/2009 |
| WO | WO 2009/082697 | 7/2009 |
| WO | WO 2009/082701 | 7/2009 |
| WO | WO 2009/087225 | 7/2009 |
| WO | WO 2009/102446 | 8/2009 |
| WO | WO 2009/109605 | 9/2009 |
| WO | WO 2009/112490 | 9/2009 |
| WO | WO 2009/126514 | 10/2009 |
| WO | WO 2009/126515 | 10/2009 |
| WO | WO 2009/127642 | 10/2009 |
| WO | WO 2009/127822 | 10/2009 |
| WO | WO 2009/131687 | 10/2009 |
| WO | WO 2009/143018 | 11/2009 |
| WO | WO 2009/143389 | 11/2009 |
| WO | WO 2009/158571 | 12/2009 |
| WO | WO 2010/008739 | 1/2010 |
| WO | WO 2010/028236 | 3/2010 |
| WO | WO 2010/048149 | 4/2010 |
| WO | WO 2010/051781 | 5/2010 |
| WO | WO 2010/056311 | 5/2010 |
| WO | WO 2010/062571 | 6/2010 |
| WO | WO 2010/068292 | 6/2010 |
| WO | WO 2010/093928 | 8/2010 |
| WO | WO 2010/098866 | 9/2010 |
| WO | WO 2010/106097 | 9/2010 |
| WO | WO 2010/111406 | 9/2010 |
| WO | WO 2010/112210 | 10/2010 |
| WO | WO 2010/123870 | 10/2010 |
| WO | WO 2010/129053 | 11/2010 |
| WO | WO 2010/136559 | 12/2010 |
| WO | WO 2010/142766 | 12/2010 |
| WO | WO 2010/146132 | 12/2010 |
| WO | WO 2011/002807 | 1/2011 |
| WO | WO 2011/002808 | 1/2011 |
| WO | WO 2011/022440 | 2/2011 |
| WO | WO 2011/031896 | 3/2011 |
| WO | WO 2011/034907 | 3/2011 |
| WO | WO 2011/036566 | 3/2011 |
| WO | WO 2011/053518 | 5/2011 |
| WO | WO 2011/079231 | 6/2011 |
| WO | WO 2011/082285 | 7/2011 |
| WO | WO 2011/090760 | 7/2011 |
| WO | WO 2011/103196 | 8/2011 |
| WO | WO 2011/140338 | 11/2011 |
| WO | WO 2011/143495 | 11/2011 |
| WO | WO 2011/162515 | 12/2011 |
| WO | WO 2012/021444 | 2/2012 |
| WO | WO 2012/022045 | 2/2012 |
| WO | WO 2012/051587 | 4/2012 |
| WO | WO 2012/061299 | 5/2012 |
| WO | WO 2012/061303 | 5/2012 |
| WO | WO 2012/064706 | 5/2012 |
| WO | WO 2012/151561 | 11/2012 |
| WO | WO 2013/014448 | 1/2013 |
| WO | WO 2013/042006 | 3/2013 |
| WO | WO 2013/169401 | 11/2013 |
| WO | WO 2015/175632 | 11/2015 |
| WO | WO 2015/195228 | 12/2015 |
| WO | WO 2016/065028 A1 | 4/2016 |
| WO | WO 2016/183278 A1 | 11/2016 |

OTHER PUBLICATIONS

Bennet & Plum (edited by), Cecil Textbook of Medicine, 1996, W.B. Saunders Co., pp. 1004-1010, 20th edition, vol. 1.

Bruning et al., "Role of Brain Insulin Receptor in Control of Body Weight and Reproduction", Science, 2000, pp. 2122-2125, vol. 289.

Caira, "Crystalline Polymorphism of Organic Compounds", Topics in Current Chemistry, Springer, Berlin, DE, 1998, vol. 198; pp. 163-208.

Carmi et al., "Novel Irreversible Epidermal Growth Factor Receptor Inhibitors by Chemical Modulation of the Cysteine-Trap Portion", J. Med. Chem., 2010, pp. 2038-2050, vol. 53.

Chiarle et al, "The Anaplastic Lymphoma Kinase in the Pathogenesis of Cancer", Nature Reviews, 2008, pp. 11-23, vol. 8.

Cohen, "The Development and Therapeutic Potential of Protein Kinase Inhibitors", Current Opinion in Chemical Biology, 1999, pp. 459-465, vol. 3.

Dalgarno et al., "Structural Basis of Src Tyrosine Kinase Inhibition with a New Class of Potent and Selective Trisubstituted Purine-based Compounds", Chem. Biol. Drug Des., 2006, pp. 46-57, vol. 67.

Database Caplus on STN. Accession No. 1969:28936. Pesticidal Pyrimidinyl Phosphates. Abstract #28936d, Chem Imperial Industries, 1969, p. 324.

Definition of "moiety", 2013, http://goldbook.iupac.org/M03968.html, accessed Sep. 16, 2013.

Dermer, "Another Anniversary for the War on Cancer", Bio/Technology, 1994, p. 12, vol. 320.

Doebele et al, "New Strategies to Overcome Limitations of Reversible EGFR Tyrosine Kinase Inhibitor Therapy in Non-Small Cell Lung Cancer", Lung Cancer, 2010, pp. 1-12, vol. 69.

Dubinina et al, "Novel 5,7-disubstituted 6-amino-5H-pyrrolo [3,2-b]pyrazine-2,3-dicarbonitriles, the promising protein kinase inhibitors with antiproliferative activity", European Journal of Medicinal Chemistry, 2006, pp. 727-737, vol. 41.

Eck et al., "Structural and Mechanistic Underpinnings of the . . . of EGFR Mutations in Non-small Cell Lung Cancer", Biochimica et Biophysica Acta, 2010, pp. 559-566.

Fabbro et al., "Protein Kinases as Targets for Anticancer Agents; from Inhibitors to Useful Drugs", Pharmacology & Therapeutics, 2002, pp. 79-98, vol. 93.

Ferrara, "VEGF as a Therapeutic Target in Cancer", Oncology, 2005, pp. 11-16, vol. 69(suppl).

Fletcher, "Approval Heralds New Generation of Kinase Inhibitors?", Nature Biotechnology, 2001, pp. 599-600, vol. 19.

Fresheny, Culture of Animal Cells, A Manual of Basic Techniques, 1983, Alan R. Liss, Inc., New York, p. 4.

Galkin et al., "Indentification of NVP-TAE684, a Potent, Selective, and Efficacious Inhibitor of NPM-ALK", PNAS, 2007, pp. 270-275 & 2024-2025, vol. 104.

Gautschi et al., "Aurora Kinases as Anticancer Drug Targets", Clin. Cancer Res., 2008, pp. 1639-1648, vol. 14(6).

Giurginca et al., "Subsituted Triazines With Phosphonyl Group as Antioxidants for Elastomers and Their Compounds", Polymer Degradation and Stability, 2001, pp. 477-480, vol.

Golub et al., "Molecular Classification of Cancer: Class Discovery and Class Prediction by Gene Expression Monitoring", Science, 1999, pp. 531-537, vol. 286.

Grande et al., "Targeting Oncogenic ALK: A Promising Strategy for Cancer Treatment", Molecular Cancer Therapeutics, 2011, pp. 569-579 + 1529, vol. 10.

Gundla et al., "Discovery of Novel Small-Molecule Inhibitors of Human Epidermal Growth Factor Receptor-2: Combined Ligand and Target-Based Approach", J. Med. Chem., 2008, pp. 3367-3377, vol. 51.

Haluska et al, "In vitro and in vivo Antitumor Effects of the Dual Insulin-Like Growth Factor-I/Insulin Receptor Inhibitor, BMS-554417", Cancer Res, 2006, pp. 362-371, vol. 66.

(56) References Cited

OTHER PUBLICATIONS

Jain et al., "Lessons from Phase III Clinical Trials on Anti-VEGF Therapy for Cancer", Nature Clinical Practice Oncology, 2006, pp. 24-40, vol. 3(I).
Katayama et al., "Therapeutic Strategies to Overcome Crizotinib Resistance in Non-Small Cell Lung Cancers Harboring the Fusion Oncogene EML4-ALK", PNAS, 2011, pp. 7535-7540, vol. 108 (18).
Kitamura et al., "Insulin Receptor Knockout Mice", Annu. Rev. Physiol., 2003, pp. 313-332, vol. 65.
Klutchko et al., "Tyrosine Kinase Ihibitors. 19. 6-Alkynamides of 4-Anilinoquinazolines and 4-Anilinopyrido[3,4-d]pyrimidines as Irreversible Inhibitors of the erbB Family of Tyrosine Kinase Receptors ", J. Med. Chem., 2006, pp. 1475-1485, vol. 49.
Kulkarni et al., "Tissue-Specific Knockout of the Insulin Receptor in Pancreatic B Cells Creates an Insulin Secretory Defect Similar to that in Type 2 Diabetes", Cell, 1999, pp. 329-339, vol. 96.
Kwak et al., "Irreversible Inhibitors of the EGF Receptor May Circumvent Acquired Resistance to Gefitinib", PNAS, 2005, pp. 7665-7670, vol. 102, No. 21.
Li et al, "Development of Anaplastic Lymphoma Kinase (ALK) Small-Molecule Inhibitors for Cancer Therapy", Med Res Rev, 2008, pp. 372-412, vol. 28(3).
Liao, "Molecular Recognition of Protein Kinase Binding Pockets for Design of Potent and Selective Kinase Inhibitors", Jrnl of Medicinal Chemistry, 2007, pp. 409-424, vol. 50.
Mass, "The HER Receptor Family: A Rich Target for Therapeutic Development", Int. J. Radiation Oncology Biol. Phys., 2004, pp. 932-940, vol. 58(3).
McCormick, "New-age Drug Meets Resistance", Nature, 2001, pp. 281-282, vol. 412.
McDermott et al., "Identification of Genotype-Correlated Sensitivity to Selective Kinase Inhibitors by Using High-throughput Tumor Cell Line Profiling", PNAS, 2007, pp. 19936-19941, vol. 104(50).
McDermott et al., "Genomic Alterations of Anaplastic Lymphoma Kinase May Sensitize Tumors to Anaplastic Lymphoma Kinase Inhibitors", Cancer Research, 2008, pp. 3389-3395, vol. 68(9).
McDermott et al., "Acquired Resistance of Non-small Cell Lung Cancer Cells to MET Kinase Inhibition is Mediated by a Switch to Epidermal Growth Factor Receptor Dependency", Cancer Research, 2010, pp. 1625-1634, vol. 70(4).
Michael et al., "Loss of Insulin Signaling in Hepatocytes Leads to Severe Insulin Resistance and Progressive Hepatic Dysfunction", Molecular Cell, 2000, pp. 87-97, vol. 6.
Michalczyk et al., "Structural Insights Into How Irreversible Inhibitors Can Overcome Drug Resistance in EGFR", Bioorganic & Medicinal Chem, 2008, pp. 3482-3488, vol. 16.
Mishani et al., "High-Affinity Epidermal Growth Factor Receptor (EGFR) Irreversible Inhibitors with Diminished Chemical Reactivities as Positron Emission Tomography (PET)-Imaging Agent Candidates of EGFR Overexpressing Tumors", J. Med. Chem., 2005, pp. 5337-5348, vol. 48.
Mountzios et al., "Aurora Kinases as Targets for Cancer Therapy", Cancer Treatment Reviews, 2008, pp. 175-182, vol. 34.
NCI-NIH, "Targeted Cancer Therapies", (2010), http://www.cancer.gov/cancertopics/factsheet/therapy/targeted, accessed Jan. 12, 2011.
NCI-NIH, "Cancer Prevention Overview", (2012), http://www.cancer.gov/cancertopics/pdq/prevention/overview/patient, accessed Nov. 14, 2012.
Ogiso et al., "Crystal Structure of the Complex of Human Epidermal Growth Factor and Receptor Extracellular Domains", Cell., 2002, pp. 775-787, vol. 110.
Okamoto et al., "Transgenic Rescue of Insulin Receptor-deficient Mice", The Journal of Clinical Investigation, 2004, pp. 214-223, vol. 114.
Palmer et al, "Anaplastic Lymphoma Kinase: Signaling in Development and Disease", Biochem J., 2009, pp. 345-361, vol. 420.
Pao et al., "Rational, Biologically Based Treatment of EGFR-mutant Non-small-cell Lung Cancer", Nature, 2010, pp. 760-774, vol. 10.
Porter et al, "Discovery of 4-azaindoles as novel inhibitors of c-Met kinase", Bioorganic & Medicinal Chemistry Letters, 2009, pp. 2780-2784, vol. 19.
Pyne et al., "Sphingosine Kinase Inhibitors and Cancer: Seeking the Golden Sword of Hercules", Cancer Res, 2011, pp. 6576-6582, vol. 71.
Qiu et al., "Signaling Network of the BTK Family Kinases", Oncogene, 2000, pp. 5651-5661, vol. 19.
Remon et al., "Beyond EGFR TKI in EGFR-mutant Non-Small Cell Lung Cancer Patients: Main Challenges Still to be Overcome", Cancer Treatment Reviews, 2014, pp. 723-729, vol. 40.
Schindler et al, "Structual Mechanism for STI=571 Inhibition of Abelson Tyrosine Kinase", Science, 2000, pp. 1938-1942, vol. 289.
Simone, "Oncology; Introduction", Cecil Textbook of Medicine, 20th Edition, 1996, pp. 1004-1010, vol. 1.
Smaill et al., "Tyrosine Kinase Inhbitors. 18. 6-Substituted 4-Anilinoquinazolines and 4-Anilinopyrido[3,4-d]pyrimidines as Soluble, Irreversible Inhibitors of the Epidermal Growth Factor Receptor", J. Med. Chem., 2001, pp. 429-440, vol. 44.
Solomon et al., "Current Status of Targeted Therapy for Anaplastic Lymphoma Kinase-Rearranged Non-Small Cell Lung Cancer", Clinical Pharmacology & Therapeutics, 2013, pp. 15-23, vol. 95(1).
Sos et al., "Chemogenomic Profiling Provides Insights into the Limited Activity of Irreversible EGFR Inhibitors in Tumor Cells Expressing the T790M EGFR Resistance Mutation", Cancer Research, 2010, pp. 868-874, vol. 70.
Tartari et al, "Characterization of Some Molecular Mechanisms Governing Autoactivation of the Catalytic Domain of the Anaplastic Lymphoma Kinase", Journal of Biological Chemistry, 2008, pp. 3743-3750, vol. 283(7).
Traxler, "Review: Oncolgic, Endocrine, Metabolic Protein Tyrosine Kinase Inhibitors in Cancer Treatment, Exp.Opin. Ther. Patents", 1997, pp. 571-588, vol. 7(6).
Voskoglou-Nomikos et al, "Clinical Predictive Value of the In Vitro Cell Line, Human Xenograft, and Mouse Allograft Preclinical Cancer Models", Clinical Cancer Research, 2003, pp. 4227-4239, vol. 9.
Wakeling et al., "ZD1839 (Iressa): An Orally Active Inhibitor of Epidermal Growth Factor Signaling with Potential for Cancer Therapy", Cancer Research, 2002, pp. 5749-5754.
Wang et al., "Bone-Targeted 2,6,9-Trisubstituted Purines: Novel Inhibitors of Src Tyrosine Kinase for the Treatment of Bone Diseases", Bioorganic & Medicinal Chemistry Letters, 2003, pp. 3067-3070, vol. 13.
Wissner et al., Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)J. Med. Chem., 2003, pp. 49-63, vol. 46.
Wu et al., "Design and Synthesis of Tetrahydropyridothieno[2,3-d]pyrimidine Scaffold Based Epidermal Growth Factor Receptor (EGFR) Kinase Inhibitors: The Role of Side Chain Chirality and Michael Acceptor Group for Maximal Potency", J. Med. Chem., 2010, pp. 7316-7326, vol. 53.
Yun et al., "The T790M Mutation in EGFR Kinase Causes Drug Resistance by Increasing the Affinity for ATP", PNAS, 2008, pp. 2070-2075, vol. 105, No. 6.
Zhou et al., "Novel Mutant-Selective EGFR Kinase Inhibitors Against EGFR T790M", Nature, 2009, pp. 1070-1074, vol. 462.
Zhou et al., "Cell Culture and Reagents", Nature, Supplemental Information, 2009, pp. 1-39, vol. 462.
Zimmerman et al, "Potent and selective inhibitors of the ABL-kinase: phenylamino-pyrimidine (PAP) derivatives", Biorg. Med. Chem. Letters, 1997, pp. 187-192, vol. 7(2).
Office Action from the European Patent Office for EP Patent Appl. No. 09751617.3, dated Apr. 14, 2014, 7 pages.
Response to Office Action filed in the European Patent Office for EP Patent Appl. No. 09751617.3 dated Aug. 13, 2014, 126 pages.
CN Search Report dated Oct. 14, 2014 for CN Appl. 2012800217027, 2 pages.
EA Search Report dated Jul. 1, 2011 for EA Appl. 201071339, 3 pages.

(56) References Cited

OTHER PUBLICATIONS

EA Search Report dated Sep. 4, 2013 for EA Appl. 201390550, 4 pages.
Extended EP Search Report dated May 31, 2005 for EP Appl. 02742236.9, 5 pages.
Extended EP Search Report dated Jul. 10, 2012 for EP Appl. 09832253.0, 6 pages.
Extended EP Search Report dated Aug. 13, 2012 for EP Appl. 09751617.3, 7 pages.
Extended EP Search Report dated Oct. 5, 2012 for EP Appl. 09826414.6, 7 pages.
Extended EP Search Report dated Feb. 27, 2014 for EP Appl. 11833524.9, 9 pages.
Extended EP Search Report dated Oct. 9, 2014 for EP Appl. 12779411.3, 4 pages.
Extended EP Search Report dated Oct. 21, 2015 for EP Appl. 13788352.6, 5 pages.
Int'l Search Report dated Jan. 7, 2003 for PCT/US2002/19631 filed Jun. 21, 2002, 3 pages.
Int'l Search Report & Written Opinion dated Aug. 24, 2009 for PCT/US2009/44918 filed May 21, 2009, 8 pages.
Int'l Search Report & Written Opinion dated Feb. 24, 2010 for PCT/US2009/06520 filed Dec. 11, 2009, 9 pages.
Int'l Search Report & Written Opinion dated Mar. 11, 2010 for PCT/US2009/06057 filed Nov. 12, 2009, 9 pages.
Int'l Search Report & Written Opinion dated Mar. 1, 2012 for PCT/US2011/56457 filed Oct. 14, 2011, 9 pages.
Int'l Search Report & Written Opinion dated Aug. 7, 2012 for PCT/US2012/36683 filed May 4, 2012, 8 pages.
Int'l Search Report & Witten Opinion dated Jun. 12, 2013 for PCT/US2013/032713 filed Mar. 15, 2013, 9 pages.
Int'l Search Report & Written Opinion dated Aug. 7, 2015 for PCT/US2015/30576 filed May 13, 2015, 31 pages.
Int'l Search Report & Written Opinion dated Aug. 14, 2015 for PCT/US2015/30522 filed May 13, 2015, 22 pages.
Int'l Search Report & Written Opinion dated Feb. 11, 2016 for PCT/US2015/056701 filed Oct. 21, 2015, 15 pages.
Berasain et al., Epidermal Growth Factor Receptor (EGFR) Crosstalks in Liver Cancer, Cancers, 2011, pp. 2444-2461, vol. 3.
Bethune et al., "Epidermal Growth Factor Receptor (EGFR) in Lung Cancer: An Overview and Update", Journal of Thoracic Disease, 2010, pp. 48-51, vol. 2.
Ciardiello et al., "EGFR Antagonists in Cancer Treatment", The New England Journal of Medicine, (2008), pp. 1160-1174, vol. 358.
Godin-Heymann et al., "The T790M "gatekeeper" Mutation in EGFR Mediates Resistance to Low Concentrations of an Irreversible EGFR Inhibitor", Mol Cancer Ther, 2008, pp. 874-879, vol. 7.
Huang et al., "Discovery of Brigatinib (AP26113), a Phosphine Oxide-Containing, Potent, Orally Active Inhibitor of Anaplastic Lymphoma Kinase", J. Med. Chem., (2016), pp. 4948-4964, vol. 59.
Nair, "Epidermal Growth Factor Receptor Family and Its Role in Cancer Progression", Current Science, (2005), pp. 890-898, vol. 88 (6).
NCI-NIH, "Targeted Cancer Therapies", (2015), http://www.cancer.gov/about-cancer/treatment/types/targeted-therapies/targeted-therapies-fact-sheet, pp. 1-6, retrieved Dec. 8, 2015.
Zhang et al., "Crizotinib-Resistant Mutants of EML4-ALK Identified Through an Accelerated Mutagenesis Screen", Chem. Biol. Drug Des., 2011, pp. 999-1005, vol. 78.
Zhang et al., "The Potent ALK Inhibitor Brigatinib (AP261113) Overcomes Mechanisms of Resistance to First- and Second-Generation ALK Inhibitors in Preclinical Models", Clinical Cancer Research, (2016), pp. OF1-OF12 and Supplemental pp. 1-18.
Zhou et al., "Discovery of Selective Irreversible Inhibitors for EGFR-T790M", Bioorganic & Medicinal Chemistry Letters, 2011, pp. 638-643, vol. 21.
Int'l Search Report & Written Opinion dated Aug. 16, 2016 for PCT/US2016/031996 filed May 12, 2016, 9 pages.

\* cited by examiner

COMPOUNDS FOR INHIBITING CELL PROLIFERATION IN EGFR-DRIVEN CANCERS

CROSS-REFERENCE TO RELATED APPLICATIONS

This application is a continuation of U.S. Serial No. 14/398,893, filed Nov. 4, 2014, which claims priority under 35 U.S.C. §371 to International Application No. PCT/US2013/032713, filed Mar. 15, 2013, which claims the benefit of priority under 35 U.S.C. §119(e) to U.S. Provisional Patent Application No. 61/643,228, filed May 5, 2012, U.S. Provisional Patent Application No. 61/723,779, filed Nov. 7, 2012, U.S. Provisional Patent Application No. 61/724,283 filed Nov. 8, 2012 and U.S. Provisional Patent Application No. 61/801,953, filed Mar. 15, 2013. The entire contents of each of the above-referenced applications are hereby incorporated by reference in their entirety.

BACKGROUND OF THE INVENTION

This invention relates to pharmaceutical compositions and methods for inhibiting the proliferation of cells.

In human clinical studies with non-small cell lung cancer (NSCLC) patients, the kinase inhibitors, erlotinib and gefitinib have been found to be effective, but in only a subset of patients. It was later determined that the responsive patients had certain mutations in the gene for epidermal growth factor receptor (EGFR). The mutant forms of EGFR are enzymatically active without the need for ligand stimulation. They are also particularly sensitive to kinase inhibitors like erlotinib and gefitinib, which competitively bind to the ATP binding site of the EGFR kinase domain. Those mutations have been cataloged and described at length in the scientific literature. They include small deletions or point mutations in the kinase domain as has previously been written about extensively. See e.g., Sharma, Nat. Rev. Cancer 7:169 (2007) (exon 19 mutations characterized by in-frame deletions of amino-acids 747 account for 45% of mutations, exon 21 mutations resulting in L858R substitutions account for 40-45% of mutations, and the remaining 10% of mutations involve exon 18 and 20); Sordella et al., Science 305:1163 (2004); and Mulloy et al., Cancer Res. 67:2325 (2007).

Unfortunately, additional mutations in the EGFR gene, e.g., the T790M mutation, render drugs like erlotinib and gefitinib less effective. Those mutations are associated with resistance to the drugs and to relapse in patients with cancer cells having the T790M mutation.

New therapies are needed for the treatment of EGFR-driven cancers in which mutations confer resistance to front line tyrosine kinase inhibitor ("TKI") therapies. In particular, new therapies for inhibiting cells expressing such gefitinib-resistant or erlotinib-resistant EGFR genes could be of profound benefit.

SUMMARY OF THE INVENTION

This invention relates to the discovery of a class of compounds that inhibit EGFR and medically significant mutant forms thereof. Those mutants include mutant EGFR proteins that are enzymatically active in the absence of protein ligand and mutants such as the T790M EGFR mutant that are resistant to the EGFR inhibitors erlotinib and gefitinib. Compounds of this invention possessing desirable selectivity for the intended biological targets and advantageous pharmaceutical properties make them of interest for treating cancers characterized by the expression of EGFR or an EGFR mutant, especially in cases that are resistant or refractory to erlotinib or gefitinib.

This invention provides a compound of Formula (I):

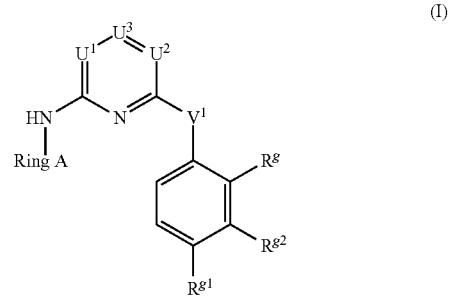

or a pharmaceutically acceptable salt thereof, wherein $U^1$ and $U^2$ are both N and $U^3$ is C—$R^e$; or $U^3$ is N, one of $U^1$ and $U^2$ is N, and the other is C—$R^d$; or $U^3$ is C—$R^e$, one of $U^1$ and $U^2$ is N, and the other is C—$R^d$;

$V^1$ is O, S, $NR^V$, CO, $CH_2$, or $CF_2$;

$R^V$ is H, alkyl, alkenyl, alkynyl, cycloalkyl, cycloalkenyl, cycloalkynyl, or aryl;

$R^d$ is H, halo, CN, alkyl, cycloalkyl, alkoxy, haloalkyl, alkenyl, haloalkenyl or halocycloalkyl;

$R^e$ is H or $NH_2$; or, $R^d$ and $R^e$, together with the ring atom to which each is attached, form a 5- or 6-membered ring containing one, two or three heteroatoms, independently selected from N, S and O, wherein the 5- or 6-membered ring so formed is substituted with $R^h$ which is $C_{1-4}$ alkyl or halo;

$R^g$ is H, F, —P(O)($R^{3A}$)($R^{3B}$), —S(O)N($R^{3C}$)($R^{3D}$), —S(O)$_2R^{3E}$, —C(O)N($R^{3F}$)($R^{3G}$), —OC(O)N($R^{3F}$)($R^{3G}$), —$NR^{3H}$C(O)$OR^{3I}$ or a 5- or 6-membered heterocyclic ring comprising 1, 2, 3 or 4 N atoms;

each $R^{3A}$, $R^{3B}$, $R^{3C}$, $R^{3D}$, $R^{3E}$, $R^{3F}$, $R^{3G}$, $R^{3H}$, and $R^{3I}$ is independently selected from H, alkyl, alkenyl, alkynyl, cycloalkyl, cycloalkenyl, cycloalkynyl, and heteroalkyl, or $R^{3A}$ and $R^{3B}$, or $R^{3C}$ and $R^{3D}$, or $R^{3F}$ and $R^{3G}$, together with the atom to which each is attached, form an unsubstituted or substituted 5- or 6-membered heterocyclic ring;

$R^{g2}$ is H, F, —P(O)($R^{3A}$)($R^{3B}$), —S(O)N($R^{3C}$)($R^{3D}$), —S(O)$_2R^{3E}$, —C(O)N($R^{3F}$)($R^{3G}$), —OC(O)N($R^{3F}$)($R^{3G}$), —$NR^{3H}$C(O)$OR^{3I}$, $C_{1-6}$ alkoxy or $C_{1-4}$ alkyl;

or, $R^{g2}$ and $R^g$ together with the atom to which each is attached form an unsubstituted or substituted 5- to 7-membered heterocyclic ring comprising 1-3 heteroatoms independently selected from P, N, O and S;

$R^{g1}$ is H, F, —$OR^2$, —P(O)($R^{3A}$)($R^{3B}$), —S(O)N($R^{3C}$)($R^{3D}$), —S(O)$_2R^{3E}$, —C(O)N($R^{3F}$)($R^{3G}$), —OC(O)N($R^{3F}$)($R^{3G}$), —$NR^{3H}$C(O)$OR^{3I}$, or substituted or unsubstituted 5- or 6-membered heterocyclic ring;

Ring A is:

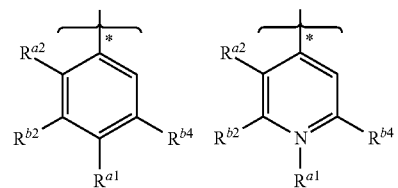

-continued

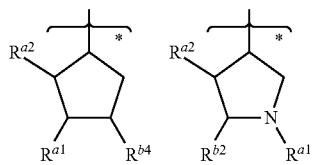

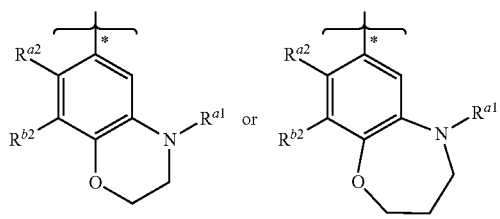

$R^{b2}$ is H, F, or an optionally substituted 5- or 6-membered heterocyclic ring containing 1, 2 or 3 N or O atoms;

$R^{b4}$ is H, F, $W^1$, $C_{1-6}$ alkoxy, $C_{3-6}$ alkenyloxy, $C_{3-6}$ cycloalkoxy, —OC(O)N($R^{5A}$)($R^{5B}$), —NR$^{5C}$C(O)OR$^{5D}$, or substituted or unsubstituted 5- or 6-membered heterocyclic ring comprising 1, 2 or 3 N or O atoms;

each $R^{5A}$, $R^{5B}$, $R^{5C}$ and $R^{5D}$ is independently H, alkyl, alkenyl, alkynyl or heteroalkyl, or $R^{5A}$ and $R^{5B}$, together with the atom to which each is attached, form a substituted or unsubstituted 5- or 6-membered heterocyclic ring;

$R^{a1}$ is H, halo, $W^1$, —CN, —NO$_2$, —$R^1$, —OR$^2$, —O—NR$^1$R$^2$, —NR$^1$R$^2$, —NR$^1$—NR$^1$R$^2$, —NR$^1$—OR$^2$, —C(O)YR$^2$, —OC(O)YR$^2$, —NR$^1$C(O)YR$^2$, —SC(O)YR$^2$, —NR$^1$C(=S)YR$^2$, —OC(=S)YR$^2$, —C(=S)YR$^2$, —YC(=NR$^1$)YR$^2$, —YC(=N—OR$^1$)YR$^2$, —YC(=N—NR$^1$R$^2$)YR$^2$, —YP(=O)(YR$^1$)(YR$^2$), —S(O)$_r$R$^2$, —SO$_2$NR$^1$R$^2$, —NR$^1$SO$_2$NR$^1$R$^2$ or

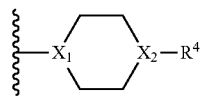

and $X_1$ and $X_2$ are each independently CH or N;

or $R^{a1}$ and $R^{b4}$, together with the atom to which each is attached, form an optionally substituted 5- or 6-membered heterocyclic ring comprising 1, 2 or 3 heteroatoms independently selected from N and O;

$R^{a2}$ is H, halo, $C_{1-6}$ alkyl, $C_{2-6}$ alkenyl, $C_{3-6}$ cycloalkyl, $C_{1-6}$ alkoxy, $C_{2-6}$ alkenyloxy, $C_{3-6}$ cycloalkyloxy or 4- to 7-membered heterocyclyl, wherein the alkyl, alkenyl, cycloalkyl, alkoxy, $C_{2-6}$ alkenyloxy, cycloalkyloxy and heterocyclyl are unsubstituted or substituted with one or more halo, amino, $C_{1-6}$ alkylamino, or di-$C_{1-6}$ alkylamino groups;

Y is independently a bond, —O—, —S— or —NR$^1$—;

$R^1$ and $R^2$ are independently H or $R^{15}$;

$R^4$ is alkyl, alkenyl, alkynyl, cycloalkyl, cycloalkenyl, cycloalkynyl, aryl, heteroalkyl, heterocyclic and heteroaryl;

$W^1$ is —NR$^7$C(O)C(R$^{11}$)=CR$^9$R$^{10}$, —C(O)C(R$^{11}$)=CR$^9$R$^{10}$, —CH$_2$P(O)C(R$^{11}$)=CR$^9$R$^{10}$, —OP(O)C(R$^8$)=CR$^9$R$^{10}$, —NR$^7$S(O)$_2$C(R$^9$)(R$^{10}$)(R$^X$), —NR$^7$S(O)$_2$C(R$^{11}$)=CR$^9$R$^{10}$, —NR$^7$C(O)C≡C—R$^{14}$, —NR$^7$C(O)C(R$^9$)(R$^{10}$)(R$^X$),

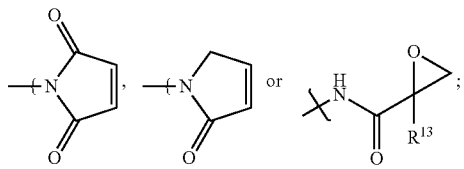

$R^X$ is halo;

$R^7$ is H, alkyl or heteroalkyl, wherein the alkyl and heteroalkyl groups are independently optionally substituted with an amino, alkylamino or dialkylamino group;

$R^8$ is $C_{1-6}$ alkyl;

$R^9$ and $R^{10}$ are independently H, halo, —C(O)R$^{16}$, alkyl, alkoxy, alkenyl, alkynyl, cycloalkyl, cycloalkenyl, cycloalkynyl, aryl, heteroalkyl, heterocyclyl or heteroaryl, wherein $R^9$ and $R^{10}$, if not H, are optionally substituted with one or more halo, amino, alkylamino, dialkylamino, alkoxy, cycloalkyl, heterocyclyl or heteroaryl groups, wherein said group, if not halo, is optionally substituted with one or more halo, $C_{1-4}$ alkyl, alkoxyl, halo($C_{1-4}$)alkyl or $C_{3-7}$ cycloalkyl groups;

$R^{11}$ is H, halo, —C(O)—OR$^{12}$, alkyl, alkenyl, alkynyl, cycloalkyl, cycloalkenyl, cycloalkynyl, aryl, heteroalkyl, heterocyclic, or heteroaryl, wherein $R^{11}$, if not H, is optionally substituted with one or more halo, amino, alkoxyl, cycloalkyl, heterocyclic or heteroaryl groups, wherein said group, if not halo, is optionally substituted with one or more halo or alkyl, alkoxyl, cycloalkyl or heterocyclyl groups, wherein the alkyl, alkoxyl, cycloalkyl and heterocyclyl group is optionally substituted with one or more alkyl, halo or hydroxyl substituents;

or $R^9$ and $R^{11}$, taken together with the atom to which each is attached, form a cycloalkenyl or heterocyclic ring;

$R^{12}$ is alkyl, alkenyl, alkynyl, cycloalkyl, cycloalkenyl, cycloalkynyl, aryl, heteroalkyl, heterocyclic, or heteroaryl;

$R^{13}$ is H or $C_{1-4}$ alkyl;

$R^{14}$ is $R^T$ or $R^W$;

$R^{15}$ is alkyl, alkenyl, alkynyl, cycloalkyl, cycloalkenyl, cycloalkynyl, aryl, heteroalkyl, 4- to 7-membered heterocyclyl, or heteroaryl, wherein each $R^{15}$ is optionally substituted with one or more halo, cycloalkyl, heterocyclic or heteroaryl groups, wherein said cycloalkyl, heterocyclic or heteroaryl groups(s) are independently optionally substituted with one or more halo, alkyl, haloalkyl, hydroxyalkyl, amino, dialkylamino or cycloalkyl groups;

$R^{16}$ is OH, —O-alkyl, cycloalkyl, heterocyclyl, —NH$_2$, —NH-alkyl, or —N-dialkyl wherein the alkyl, cycloalkyl or heterocyclyl moiety is optionally substituted with halo, amino, alkylamino, dialkylamino, alkyl or hydroxyl;

$R^T$ is H or —CH$_3$;

$R^W$ is halo; substituted methyl; or an optionally substituted group selected from ($C_{2-6}$)alkyl, ($C_{1-6}$)heteroalkyl, heterocyclyl, aryl and heteroaryl; wherein the substituents on the optionally substituted ($C_{2-6}$)alkyl, ($C_{1-6}$)heteroalkyl, heterocyclyl, aryl and heteroaryl groups are selected from halo, haloalkyl, alkoxy, heterocyclyl, substituted heterocyclyl, amino, alkylamino, and dialkylamino, and in the case of an optionally substituted heterocyclyl, the optional substituents may further be selected from hydroxyl, alkyl, haloalkyl, hyroxyalkyl, alkoxyalkyl, amino, alkylamino and dialkylamino;
wherein
(a) the compound is not one of the following two compounds:

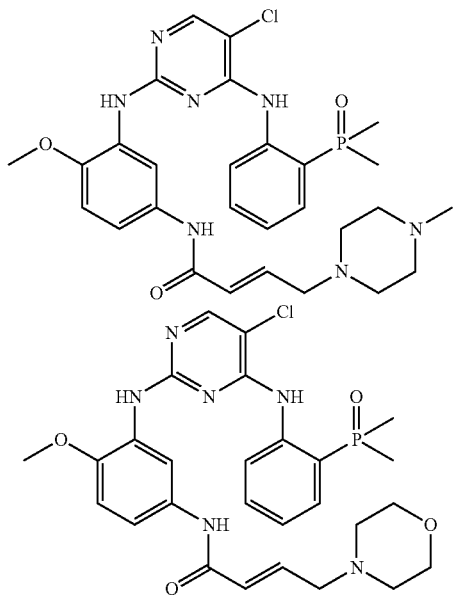

(b) at least one of $R^{a1}$, $R^{g2}$, and $R^{b4}$ is $W^1$;
(c) the compound comprises at least one —P(O)($R^{3A}$)($R^{3B}$); and
(d) the compound further has one or more of the following features:
$R^d$ is halo($C_{3-6}$)cycloalkyl;
$R^{a2}$ is halo; substituted alkyl, substituted alkoxy, or optionally substituted cycloalkyl, wherein substituents on the alkyl, alkoxy or cycloalkyl groups are selected from halo, amino and dialkylamino groups;
$R^{a1}$ is an optionally substituted 4-membered heterocycle;
$R^{a1}$ is alkyl, alkenyl, alkynyl, cycloalkyl, cycloalkenyl or heteroalkyl, and is substituted with one or more groups selected from halo, OH, heterocyclyl, substituted heterocyclyl, heteroaryl, and substituted heteroaryl;
$R^{a1}$ is heterocyclyl or heterocyclyl-O—, wherein $R^{a1}$ is substituted with one or more groups selected from —OH, halo, 4-membered heterocyclyl, substituted 4-membered heterocyclyl and $R^{18}$, wherein $R^{18}$ is alkyl, alkenyl, alkynyl, cycloalkyl, cycloalkenyl or heteroalkyl, and $R^{18}$ is optionally substituted;
$R^{a1}$ and $R^{b4}$, together with the atom to which each is attached, form an optionally substituted 5-membered heterocyclic ring;
$R^{a2}$ is an optionally substituted 4- to 7-membered membered heterocycle;
$R^{b4}$ is —$NR^7C(O)C(R^{11})$=$CR^9R^{10}$ or —$NR^7C(O)C$—C≡C—$R^W$;
$R^{g1}$ is —$OR^2$;
$R^9$ or $R^{10}$ is cycloalkyl, —$CO_2H$, —$CO_2$-alkyl, —C(O)-heterocyclyl, —$C(O)NH_2$, —C(O)NH-alkyl or —C(O)N-dialkyl wherein an alkyl, cycloalkyl or heterocyclyl substituent or portion of a substituent is optionally substituted with amino, alkylamino, dialkylamino, alkyl or hydroxyl;

one or more of $R^9$, $R^{10}$ and $R^{11}$ is halo, haloalkyl, alkyl, alkoxy, heteroalkyl, alkenyl, alkynyl, cycloalkyl, cycloalkenyl, cycloalkynyl, aryl, heterocyclyl, heterocyclylalkyl, heteroaryl, heteroarylalkyl or arylalkyl wherein alkyl, heterocylic, heteroaryl or aryl substituent, or an alkyl, heterocylic, heteroaryl or aryl portion of a substituent, is optionally substituted with one or more groups selected from halo, haloalkyl, hydroxyl, hydroxyalkyl, amino, alkylamino, dialkylamino, alkyl, alkenyl, $SO_2$alkyl, oxo, heterocyclyl and heterocycle substituted with one or more alkyl, amino alkylamino, dialkylamino, hydroxyl, hydroxyalkyl, $SO_2$alkyl substituents; and,
$R^9$ and $R^{11}$, taken together with the atom to which each is attached, form a cycloalkenyl or heterocyclic ring.

Unless otherwise specified, (a) each non-cyclic alkyl group contains 1-6 carbon atoms, each non-cyclic alkenyl or alkynyl group contains 2-8 carbon atoms, each cycloalkyl and cycloalkenyl group contains 3-13 carbon atoms, each cycloalkynyl group contains 8-13 carbon atoms, and each heteroalkyl group is a branched or unbranched alkyl, alkenyl or alkynyl group of up to 7 carbon atoms in addition to 1-4 heteroatoms independently selected from N, O, S and P; (b) each heterocycle is a non-aromatic ring or ring system having five to fourteen ring atoms of which one or more, preferably one to four, is each a heteroatom independently selected from N, O, S or P, and the remainder of ring atoms are carbon; (c) each aryl group is an aromatic carbocyclic ring or ring system containing 6-14 ring atoms; and (d) each heteroaryl moiety is an aromatic ring or ring system having five to fourteen ring atoms of which one or more, often one to four, is each a heteroatom independently selected from N, O, S or P, and the remainder of ring atoms are carbon. Optional substituents for the various embodiments of the invention are illustrated in the copious examples and detailed disclosure below. Briefly, optional substituents for alkyl, alkenyl, alkynyl, cycloalkyl, cycloalkenyl, cycloalkynyl, heteroalkyl and heterocyclyl moieties include among others, amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, haloalkoxy, =O, =S, =NH, =$NNR^2R^3$, =$NNHC(O)R^2$, =$NNHCO_2R^2$, =$NNHSO_2R^2$ and —P(O)($R^3$)$_2$. Optional substituents for the aryl and heteroaryl moieties include among other groups, amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy.

The foregoing definitions and non-limiting choices for substituents are further elaborated upon and exemplified below, and collectively apply to all subsequent occurrences except to the extent otherwise specified.

In one embodiment of the compounds of Formula I,
$R^d$ is H, halo, CN, alkyl, alkoxy, haloalkyl, alkenyl, haloalkenyl or halocycloalkyl;

$W^1$ is —$NR^7C(O)C(R^{11})$=$CR^9R^{10}$, —$C(O)C(R^{11})$=$CR^9R^{10}$, —$CH_2P(O)C(R^{11})$=$CR^9R^{10}$, —$OP(O)C(R^8)$=$CR^9R^{10}$, —$NR^7S(O)_2C(R^{11})$=$CR^9R^{10}$, —$NR^7C(O)C≡C—R^{14}$,

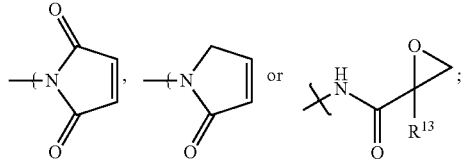

$R^g$ is H, —$P(O)(R^{3A})(R^{3B})$, —$S(O)N(R^{3C})(R^{3D})$, —$S(O)_2R^{3E}$, —$C(O)N(R^{3F})(R^{3G})$, —$OC(O)N(R^{3F})(R^{3G})$, —$NR^{3H}C(O)OR^{3I}$, a 5- or 6-membered heterocyclic ring comprising 1, 2, 3 or 4 N atoms, wherein each of $R^{3A}$, $R^{3B}$, $R^{3C}$, $R^{3D}$, $R^{3E}$, $R^{3F}$, $R^{3G}$, $R^{3H}$, and $R^{3I}$ is, independently, selected from H, alkyl, alkenyl, alkynyl, cycloalkyl, cycloalkenyl, cycloalkynyl, and heteroalkyl, or $R^{3A}$ and $R^{3B}$, or $R^{3C}$ and $R^{3D}$, or $R^{3F}$ and $R^{3G}$, together with the atoms to which each is attached, form an optionally substituted 5- or 6-membered heterocyclic ring; and, $R^{g1}$ is H, F, —$P(O)(R^{3A})(R^{3B})$, —$S(O)N(R^{3C})(R^{3D})$, —$S(O)_2R^{3E}$, —$C(O)N(R^{3F})(R^{3G})$, —$OC(O)N(R^{3F})(R^{3G})$, —$NR^{3H}C(O)OR^{3I}$, or an optionally substituted 5- or 6-membered heterocyclic ring; wherein the variable terms are as defined for Formula (I).

In one embodiment of the compounds of the invention and their pharmaceutically acceptable salts, $U^1$ is N, $U^2$ is $C—R^d$, and $U^3$ is $C—R^e$.

In another embodiment $U^1$ is $C—R^d$, $U^2$ is N, and $U^3$ is $C—R^e$.

In another embodiment $U^1$ is N, $U^2$ is N, and $U^3$ is $C—R^e$.

In another embodiment $U^1$ is N; $U^2$ is $C—R^d$; $U^3$ is $C—R^e$; $R^{a2}$ is $OCH_3$. $R^g$ or $R^{g1}$ is —$P(O)(R^{3A})(R^{3B})$; each of $R^{3A}$ and $R^{3B}$ is, independently, selected from alkyl, alkenyl, alkynyl, cycloalkyl, cycloalkenyl, cycloalkynyl, and heteroalkyl, or $R^{3A}$ and $R^{3B}$, together with the atom to which each is attached, form a 5- or 6-membered heterocyclic ring which is unsubstituted or substituted; $R^{b4}$ is $W^1$ as defined in Formula (I). In one class of these compounds $V^1$ is NH. In another $V^1$ is O. In certain embodiments of both classes $R^d$ is Cl. In certain embodiments of both classes $R^g$ or $R^{g1}$ is —$P(O)(CH_3)_2$ or —$P(O)(CH_2CH_3)_2$.

In another embodiment $U^3$ is N, one of $U^1$ and $U^2$ is N, and the other is $C—R^d$.

Certain compounds of the invention are described by any of Formulas (IIIa)-(IIIe), or a pharmaceutically acceptable salt thereof:

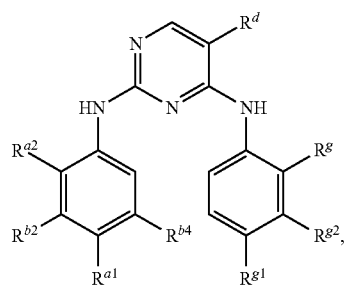
(IIIa)

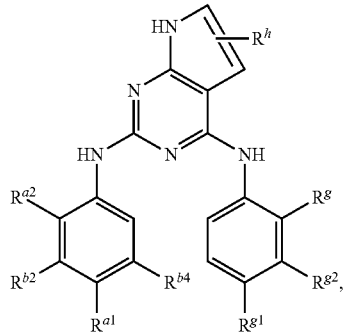
(IIIb)

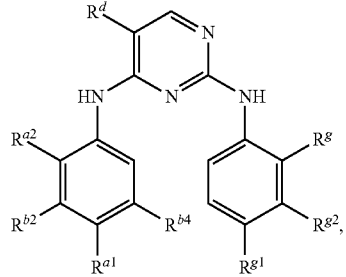
(IIIc)

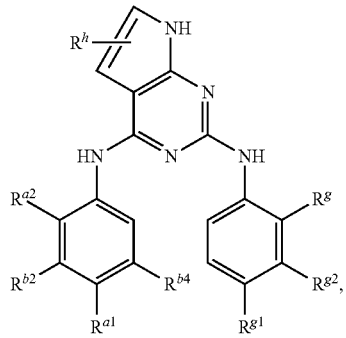
(IIId)

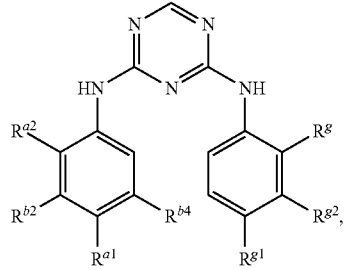
(IIIe)

wherein $R^{a1}$; $R^{a2}$; $R^{b2}$; $R^{b4}$; $R^g$; $R^{g1}$; $R^{g2}$; $R^d$; and $R^h$ are as defined in Formula (I).

Other embodiments are described by any of Formulas (IVa)-(IVe), or a pharmaceutically acceptable salt thereof:

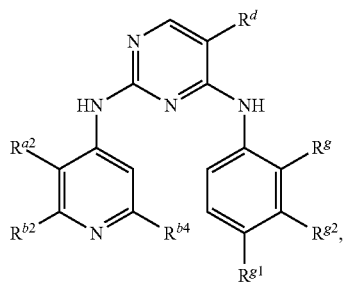 (IVa)

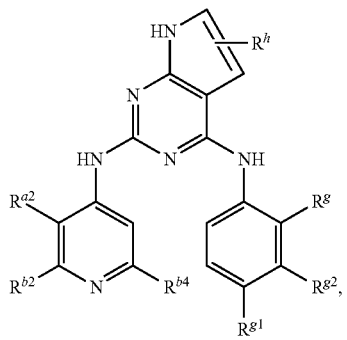 (IVb)

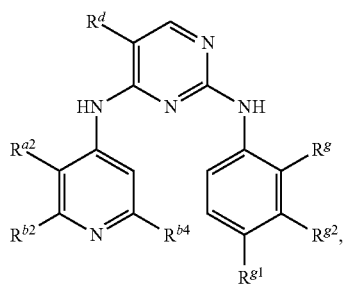 (IVc)

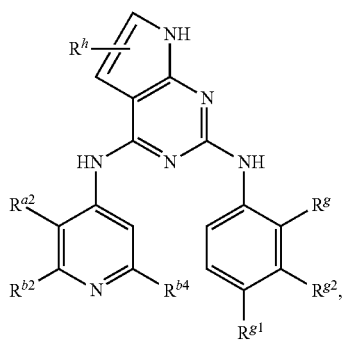 (IVd)

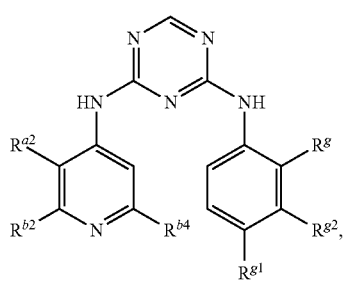 (IVe)

wherein $R^{a2}$; $R^{b2}$; $R^{b4}$; $R^{g}$; $R^{g1}$; $R^{g2}$; $R^{d}$; and $R^{h}$ are as defined in Formula (I).

Further embodiments are described by any of Formulas (Va)-(Ve), or a pharmaceutically acceptable salt thereof:

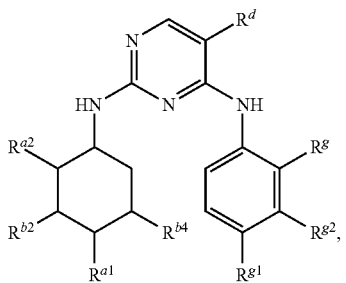 (Va)

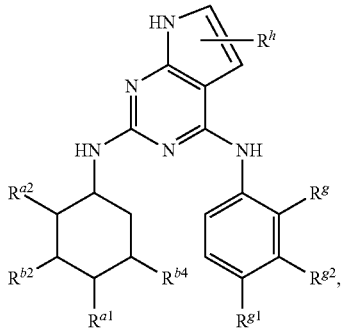 (Vb)

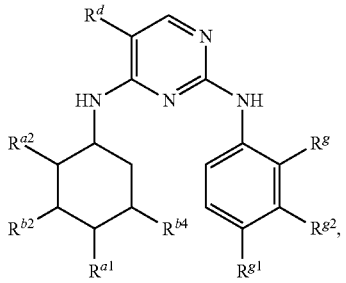 (Vc)

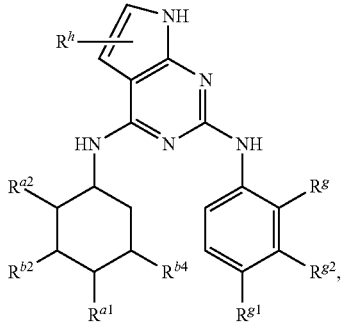 (Vd)

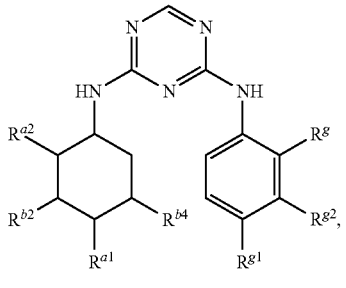 (Ve)

wherein $R^{a1}$; $R^{a2}$; $R^{b2}$; $R^{b4}$; $R^{g}$; $R^{g1}$; $R^{g2}$; $R^{d}$; and $R^{h}$ are as defined in Formula (I).

Other embodiments are described by any of Formulas (VIa)-(VIe), or a pharmaceutically acceptable salt thereof:

(VIa)
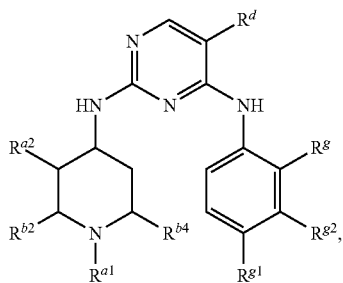

(VIb)
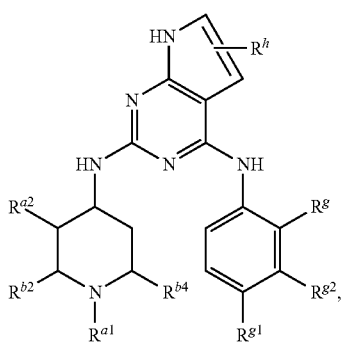

(VIc)
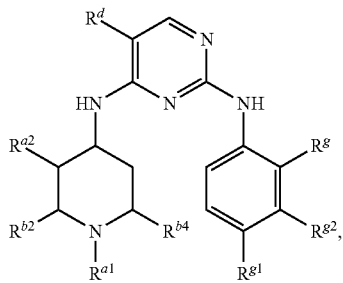

(VId)
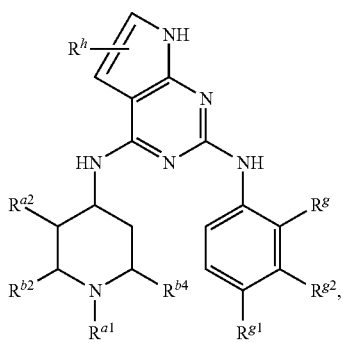

(VIe)
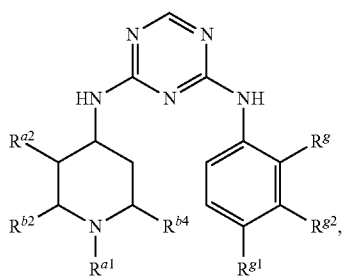

wherein $R^{a2}$; $R^{b2}$; $R^{b4}$; $R^g$; $R^{g1}$; $R^{g2}$; $R^d$; and $R^h$ are as defined in Formula (I), and $R^{a1}$ is selected from $W^1$, —$R^1$, —C(O)YR², —C(=S)YR², —C(=NR¹)YR², —C(=NOR¹)YR², —C(=N—NR¹R²)YR², —S(O)ᵣR², and

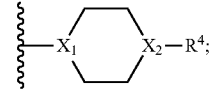

each Y is, independently, a bond, —O—, —S— or —NR¹—;

each occurrence of R¹ and R² is, independently, selected from H, alkyl, alkenyl, alkynyl, cycloalkyl, cycloalkenyl, cycloalkynyl, aryl, heteroalkyl, heterocyclic and heteroaryl;

each of X₁ and X₂ is, independently, selected from CH and N;

W¹ is as defined in Formula (I); and

R⁴ is selected from alkyl, alkenyl, alkynyl, cycloalkyl, cycloalkenyl, cycloalkynyl, aryl, heteroalkyl, heterocyclic and heteroaryl.

Certain embodiments in which Ring A is cyclopentyl are described by any of Formulas (VIIa)-(VIIe), or a pharmaceutically acceptable salt thereof:

(VIIa)
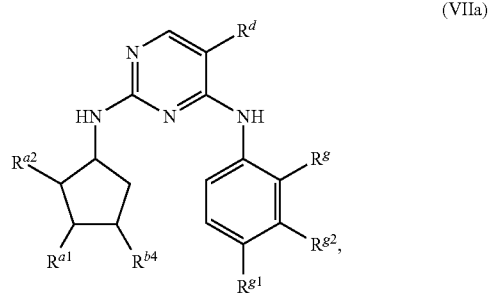

(VIIb)
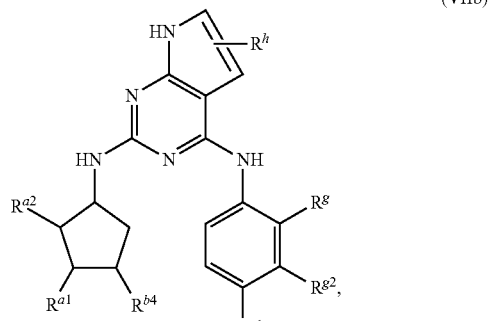

(VIIc)
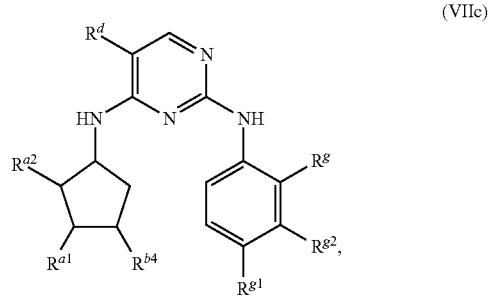

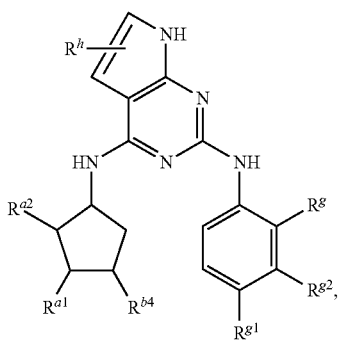

(VIId)

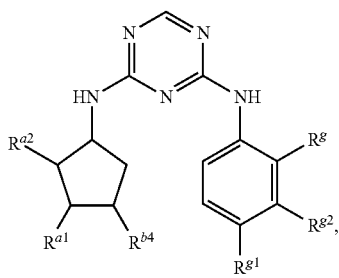

(VIIe)

wherein R$^{a1}$; R$^{a2}$; R$^{b4}$; R$^g$; R$^{g1}$; R$^{g2}$; R$^d$; and R$^h$ are as defined in Formula (I).

Other embodiments are described by any of Formulas (VIIIa)-(VIIIe), or a pharmaceutically acceptable salt thereof:

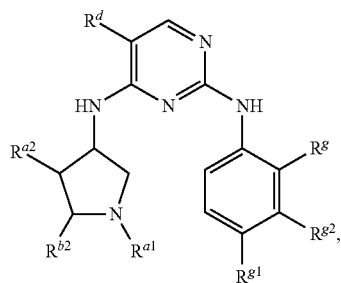

(VIIIa)

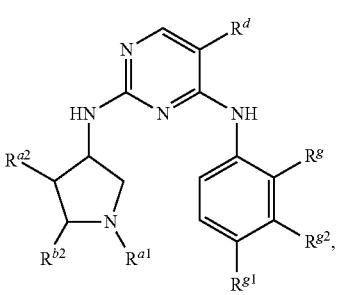

(VIIIb)

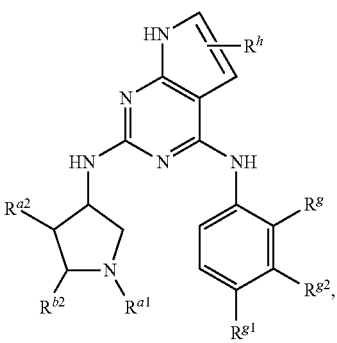

(VIIIc)

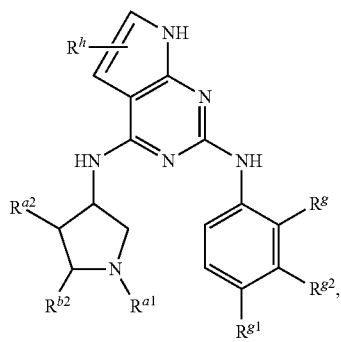

(VIIId)

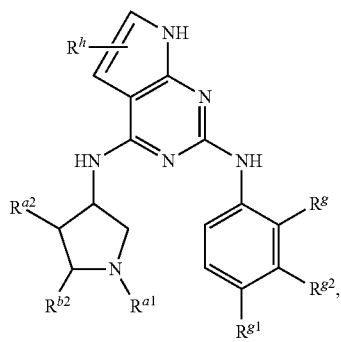

(VIIIe)

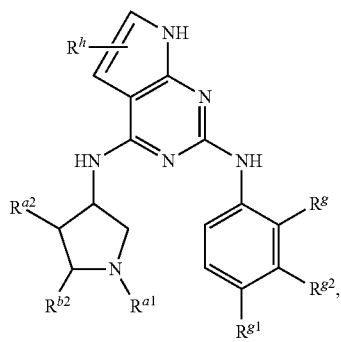

wherein R$^{a2}$; R$^{b2}$; R$^g$; R$^{g1}$; R$^{g2}$; R$^d$; and R$^h$ are as defined in Formula (I), R$^{a1}$ is selected from W$^1$, —R$^1$, —C(O)YR$^2$, —C(=S)YR$^2$, —C(=NR$^1$)YR$^2$, —C(=N—OR$^1$)YR$^2$, —C(=N—NR$^1$R$^2$)YR$^2$, —S(O)$_r$R$^2$, and

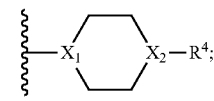

each Y is, independently, a bond, —O—, —S— or —NR$^1$—;

W$^1$ is as defined in Formula (I);

each occurrence of R$^1$ and R$^2$ is, independently, selected from H, alkyl, alkenyl, alkynyl, cycloalkyl, cycloalkenyl, cycloalkynyl, aryl, heteroalkyl, heterocyclic and heteroaryl;

each of X$_1$ and X$_2$ is, independently, selected from CH and N; and

R$^4$ is selected from alkyl, alkenyl, alkynyl, cycloalkyl, cycloalkenyl, cycloalkynyl, aryl, heteroalkyl, heterocyclic and heteroaryl.

Further embodiments are described by any of Formulas (IXa)-(IXe), or a pharmaceutically acceptable salt thereof:

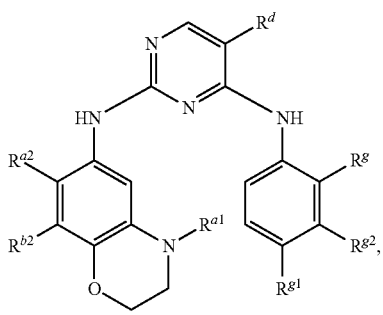

(IXa)

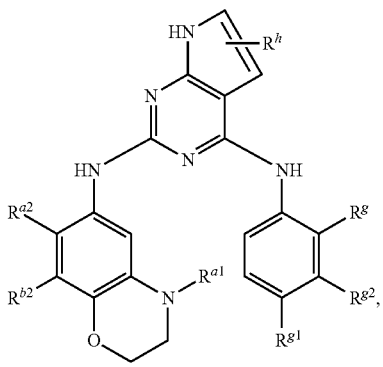

(IXb)

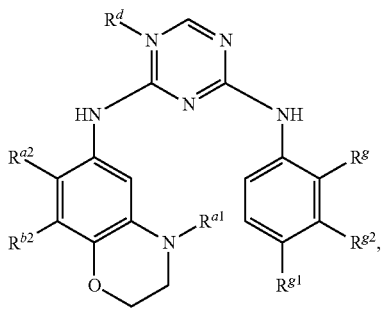

(IXc)

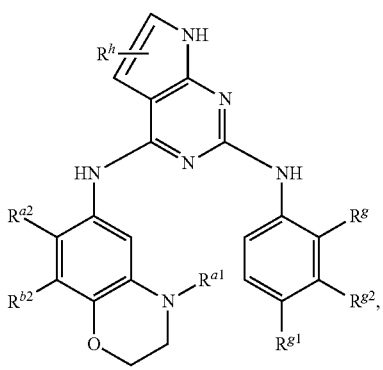

(IXd)

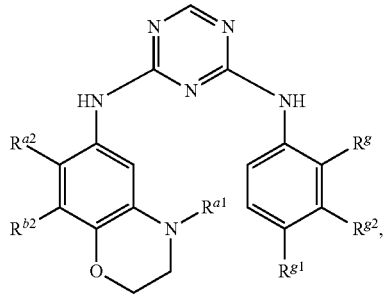

(IXe)

wherein $R^{a1}$ is $W^1$, —$R^1$, —C(O)$YR^2$, —C(=S)$YR^2$, —C(=$NR^1$)$YR^2$, —C(=N—$OR^1$)$YR^2$, —C(=N—$NR^1R^2$)$YR^2$, —S(O)$_r R^2$, or

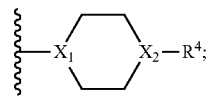

each Y is, independently, a bond, —O—, —S— or —$NR^1$—;

$R^{b2}$; $R^{b4}$; $R^g$; $R^{g1}$; $R^{g2}$; $R^d$; $R^h$ and $W^1$ are as defined in Formula (I);

each occurrence of $R^1$ and $R^2$ is, independently, selected from H, alkyl, alkenyl, alkynyl, cycloalkyl, cycloalkenyl, cycloalkynyl, aryl, heteroalkyl, heterocyclic and heteroaryl;

each of $X_1$ and $X_2$ is, independently, CH or N; and $R^4$ is alkyl, alkenyl, alkynyl, cycloalkyl, cycloalkenyl, cycloalkynyl, aryl, heteroalkyl, heterocyclic or heteroaryl.

Other embodiments are described by described by any of Formulas (Xa)-(Xe), or a pharmaceutically acceptable salt thereof:

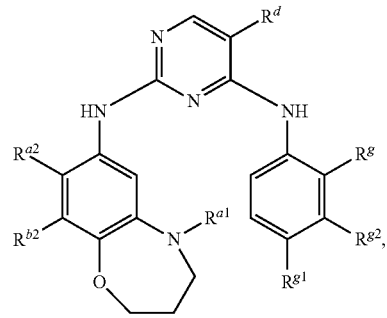

(Xa)

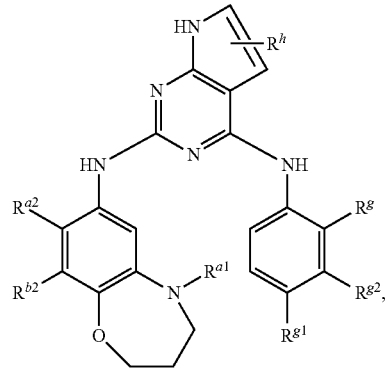

(Xb)

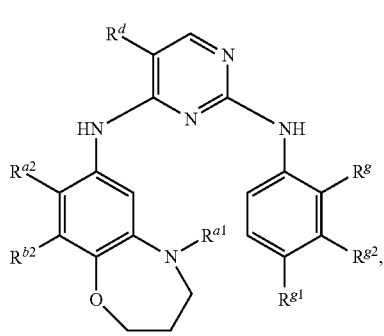

(Xc)

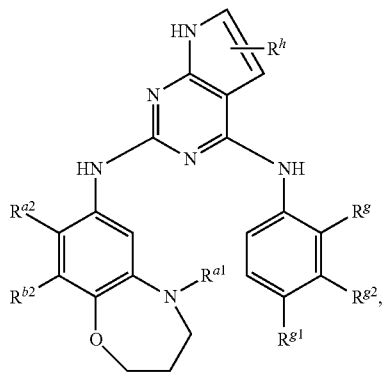

(Xd)

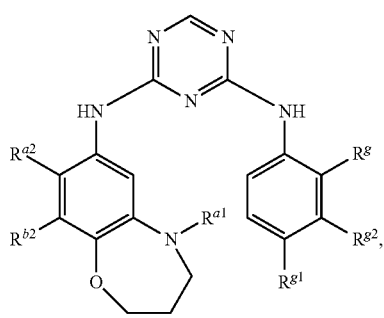

(Xe)

wherein $R^{b2}$; $R^{b4}$; $R^g$; $R^{g1}$; $R^{g2}$; $R^d$; and $R^h$ are as defined in Formula (I), $R^{a1}$ is selected from $W^1$, —$R^1$, —C(O)YR², —C(=S)YR², —C(=NR¹)YR², —C(=N—OR¹)YR², —C(=N—NR¹R²)YR², —S(O)ᵣR², and

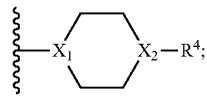

each Y is, independently, a bond, —O—, —S— or —NR¹—;

$W^1$ is as defined in Formula (I);

each occurrence of R¹ and R² is, independently, selected from H, alkyl, alkenyl, alkynyl, cycloalkyl, cycloalkenyl, cycloalkynyl, aryl, heteroalkyl, heterocyclic and heteroaryl;

each of X₁ and X₂ is, independently, selected from CH and N; and

R⁴ is selected from alkyl, alkenyl, alkynyl, cycloalkyl, cycloalkenyl, cycloalkynyl, aryl, heteroalkyl, heterocyclic and heteroaryl.

[1] In one embodiment of any of the Formulas above, i.e., any of Formula I, III(a)-(e), IV(a)-(e), V(a)-(e), VI(a)-(e), VII(a)-(e), VIII(a)-(e), IX(a)-(e), and X(a)-(e), $R^{a2}$ is H, F, Cl, —CH₃, —CF₃, —CH₂CH₃, —OCH₃, —OCF₃, —OCH₂CH₃ or -heterocyclyl-O—, e.g., a 4-membered heterocyclyl.

[2] In certain embodiments of any of Formulas I, III(a)-(e), IV(a)-(e), V(a)-(e), VI(a)-(e), VII(a)-(e), VIII(a)-(e), IX(a)-(e), and X(a)-(e), including among others the embodiment immediately above, $R^d$ is H, Cl, F, Br, I, CN, CH₃, CF₃, cyclopropyl or —CH₂CH₂=CH₂.

[3] In particular embodiments of any of Formulas I, III(a)-(e), IV(a)-(e), V(a)-(e), VI(a)-(e), VII(a)-(e), VIII(a)-(e), IX(a)-(e), and X(a)-(e), including among others each of the embodiments immediately above, $R^{b2}$ is H.

[4] In certain embodiments of any of Formulas I, III(a)-(e), IV(a)-(e), V(a)-(e), VI(a)-(e), VII(a)-(e), VIII(a)-(e), IX(a)-(e), and X(a)-(e), including among others each of the embodiments immediately above, $R^{g1}$ is H and $R^{h2}$ is H, F, $C_{1-6}$ alkyl, or $C_{1-6}$ alkoxy.

[5] In certain embodiments of any of Formulas I, III(a)-(e), IV(a)-(e), V(a)-(e), VI(a)-(e), VII(a)-(e), VIII(a)-(e), IX(a)-(e), and X(a)-(e), including among others each of the embodiments immediately above, $R^g$ is —P(O)(R³ᴬ)(R³ᴮ), wherein $R^{3A}$ and $R^{3B}$, are as defined in Formula (I). In some cases $R^g$ is —P(O)(CH₃)₂ or —P(O)(CH₂CH₃)₂.

[6] In certain embodiments of any of Formulas I, III(a)-(e), IV(a)-(e), V(a)-(e), VI(a)-(e), VII(a)-(e), VIII(a)-(e), IX(a)-(e), and X(a)-(e), including among others each of the first four embodiments immediately above, $R^g$ is —S(O)₂R³ᴱ), wherein $R^E$ is as defined in Formula (I). For example, in some cases $R^g$ is —S(O)₂CH(CH₃)₂.

[7] In certain embodiments of any of Formulas I, III(a)-(e), IV(a)-(e), V(a)-(e), VI(a)-(e), VII(a)-(e), VIII(a)-(e), IX(a)-(e), and X(a)-(e), including among others each of the embodiments immediately above, $R^{a1}$ is a 5- or 6-membered heteroaryl ring optionally substituted with an —OH, halo, alkyl, substituted alkyl substituent.

[8] In certain embodiments of any of Formulas I, III(a)-(e), IV(a)-(e), V(a)-(e), VI(a)-(e), VII(a)-(e), VIII(a)-(e), IX(a)-(e), and X(a)-(e), including among others each of the first six embodiments immediately above, $R^{a1}$ is a 4-, 5-, 6- or 7-membered heterocycle which is optionally substituted with one or more groups selected from halo and R¹⁷. R¹⁷ is an alkyl, cycloalkyl, heteroalkyl, 4- to 7-membered heterocyclyl or heteroaryl group, and R¹⁷ is optionally substituted with one or more halo, alkyl, cycloalkyl, heterocyclic or heteroaryl groups, of which, the cycloalkyl, heterocyclic or heteroaryl substituent is optionally substituted with one or more halo, alkyl, haloalkyl, hydroxyalkyl, amino, dialkylamino or cycloalkyl groups.

In one class of compounds of the foregoing embodiment, $R^{a1}$, is selected from the following:

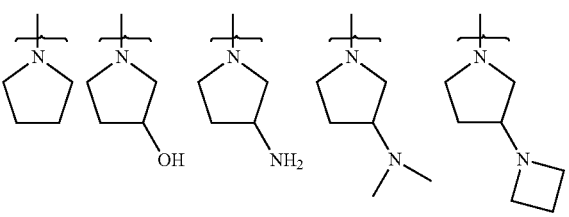

-continued
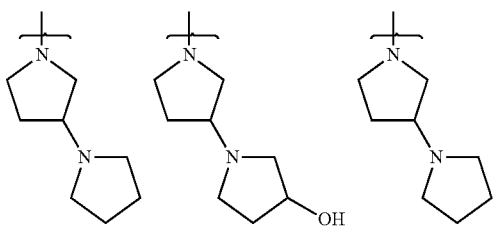
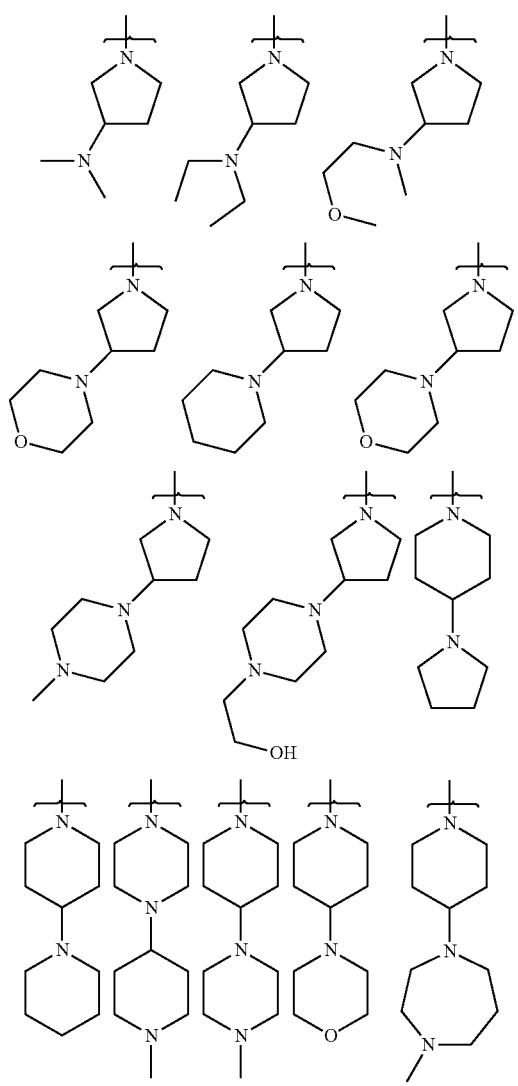
-continued
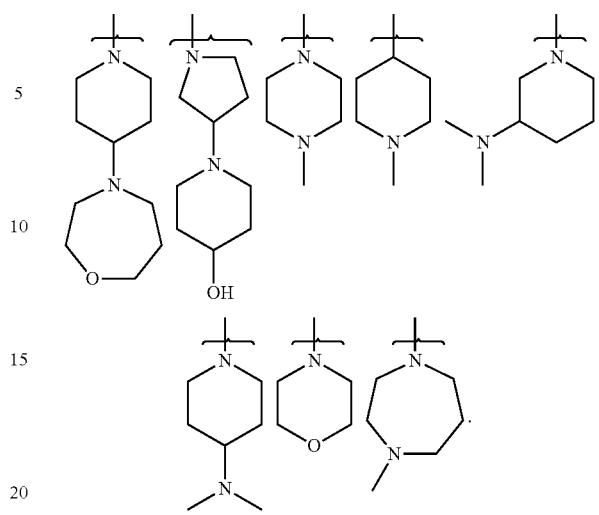
[9] In other embodiments of any of Formulas I, III(a)-(e), IV(a)-(e), V(a)-(e), VI(a)-(e), VII(a)-(e), VIII(a)-(e), IX(a)-(e), and X(a)-(e), including among others each of the first six embodiments immediately above, $R^{a1}$ is —$OR^2$, as defined in Formula (I). For example, $R^{a1}$ is selected from the following:
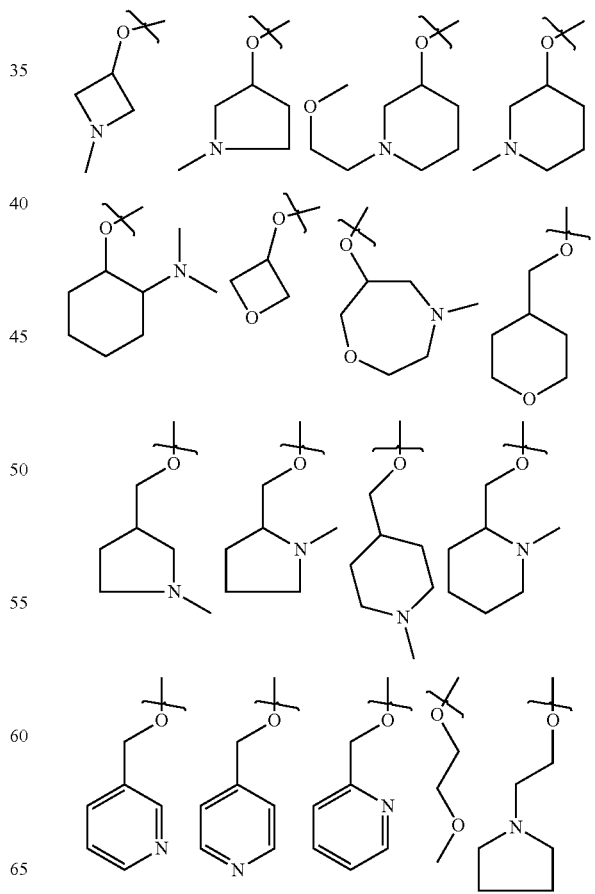

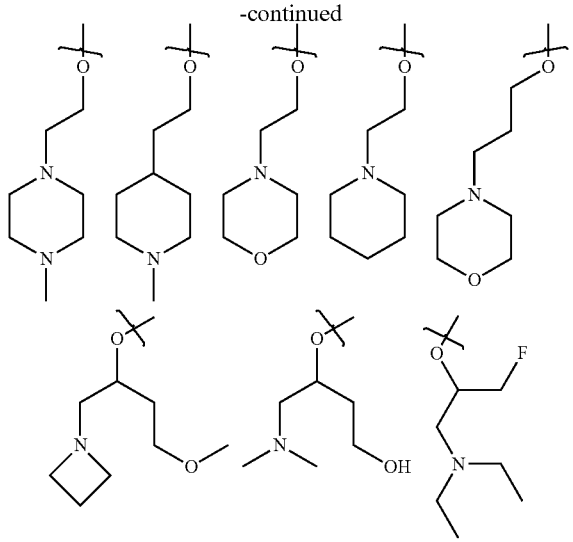

[10] In certain embodiments of any of Formulas I, III(a)-(e), IV(a)-(e), V(a)-(e), VI(a)-(e), VII(a)-(e), VIII(a)-(e), IX(a)-(e), and X(a)-(e), including among others each of the first six embodiments immediately above, $R^{a1}$ is an optionally substituted alkyl, alkenyl, alkynyl, cycloalkyl, cycloalkenyl, cycloalkynyl, or heteroalkyl group, wherein optional substituents are selected from halo, cycloalkyl, heterocyclic or heteroaryl groups, wherein said cycloalkyl, heterocyclic and heteroaryl substituent(s) are independently optionally substituted with one or more halo, alkyl, haloalkyl, hydroxyalkyl, amino, dialkylamino or cycloalkyl groups. For example,
$R^{a1}$ may be selected from the following:

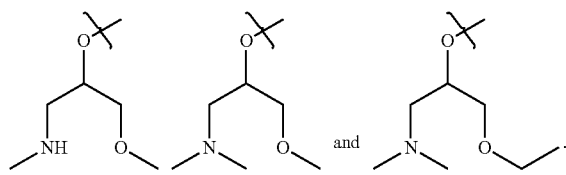

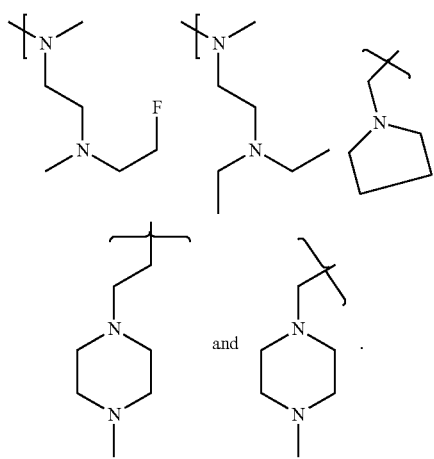

In other embodiments of any of Formulas I, III(a)-(e), IV(a)-(e), V(a)-(e), VI(a)-(e), VII(a)-(e), VIII(a)-(e), IX(a)-(e), and X(a)-(e), including among others each of the first six embodiments immediately above, IV is of the Formula:

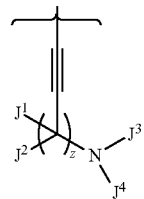

wherein:

$J^1$ and $J^2$ are independently H, halo or $R^J$; or $J^1$ and $J^2$ together with the atom to which each is attached form an optionally substituted ring which is $C_{3-8}$ cycloalkyl, 3- to 7-membered heterocyclic, or heteroaryl;

$J^3$ and $J^4$ are independently H or $R^J$; or $J^3$ and $J^4$ together with the atom to which each is attached form an optionally substituted ring which is 3- to 7-membered heterocyclic or heteroaryl ring;

$R^J$ is $C_{1-6}$ alkyl, $C_{3-8}$ cycloalkyl, $C_{1-8}$ heteroalkyl, or 3- to 7-membered heterocyclyl, wherein each $R^J$ is independently selected from halo, haloalkyl, hydroxyl, hydroxyalkyl, amino, alkylamino, dialkylamino, cycloalkyl, alkoxy, cycloalkoxy and heterocyclic groups, wherein the alkyl, cycloalkyl, and heterocyclic groups on $R^J$ are optionally substituted with one or more halo, alkyl, haloalkyl, hydroxyalkyl, alkoxyalkyl, amino, alkylamino, dialkylamino or cycloalkyl groups; and, z is 1-3.

By way of non-limiting example, $R^{a1}$ may be selected from the following:

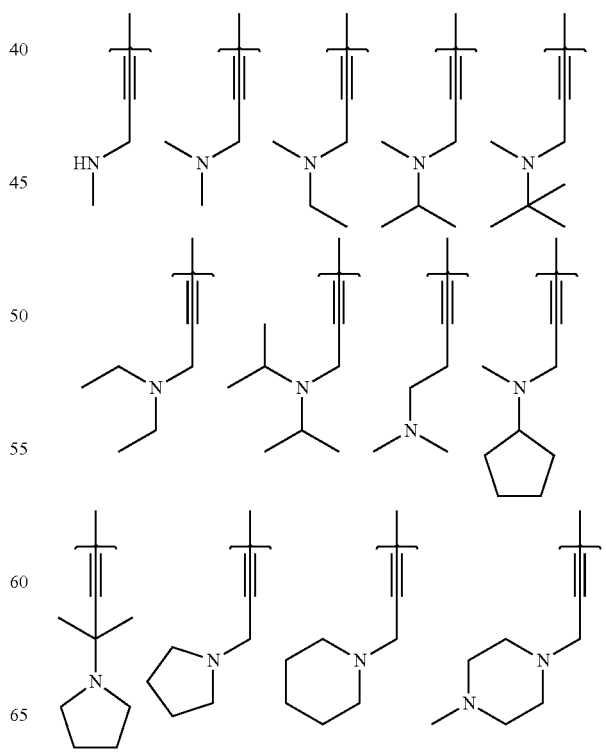

-continued

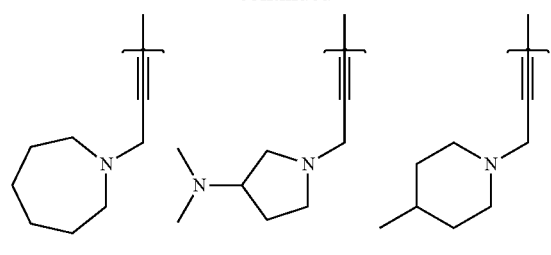

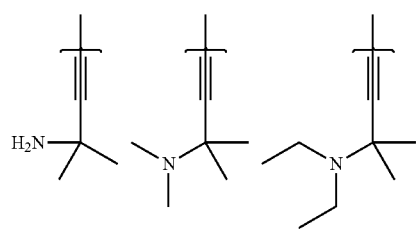

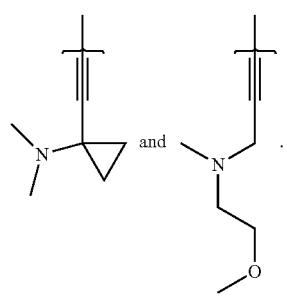

-continued

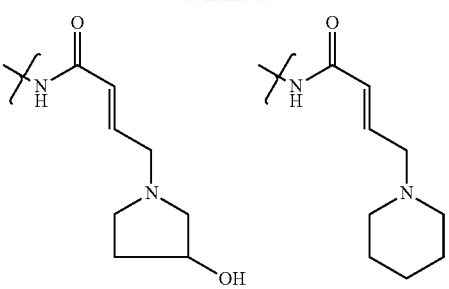

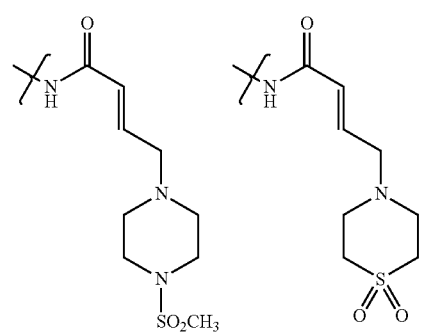

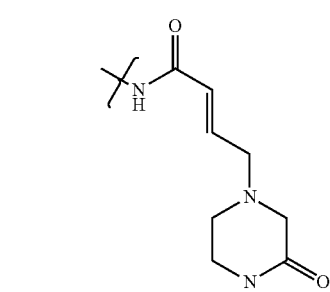

In particular embodiments of any of Formulas I, III(a)-(e), IV(a)-(e), V(a)-(e), VI(a)-(e), VII(a)-(e), VIII(a)-(e), IX(a)-(e), and X(a)-(e), including among others each of the embodiments immediately above, $R^{b4}$ is —NR$^7$C(O)C(R$^{11}$)=CR$^9$R$^{10}$, —NR$^7$S(O)$_2$C(R$^9$)(R$^{10}$)(R$^X$), —NR$^7$C(O)C≡C—R$^{14}$, or —NR$^7$C(O)C(R$^9$)(R$^{10}$)(R$^X$), wherein R$^7$, R$^9$, R$^{10}$, R$^{11}$, R$^{14}$, and R$^X$ are as defined in Formula (I).

For example, in cases in which $R^{b4}$ may be —NHC(O)CH=CH$_2$ or may be selected from the following:

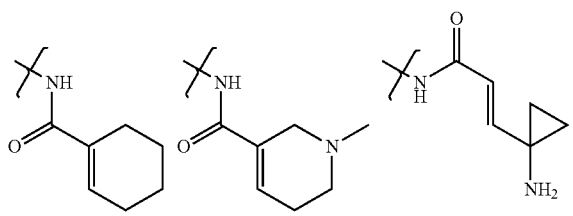

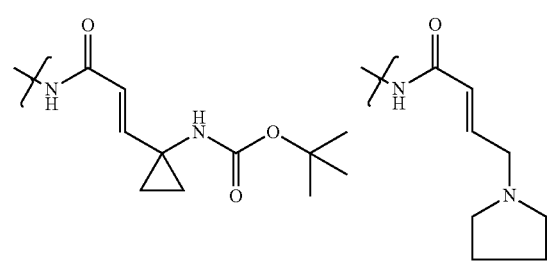

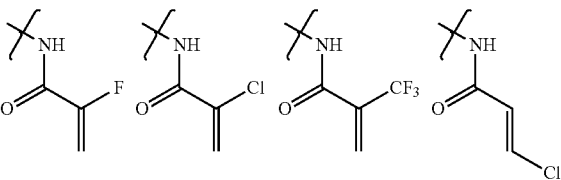

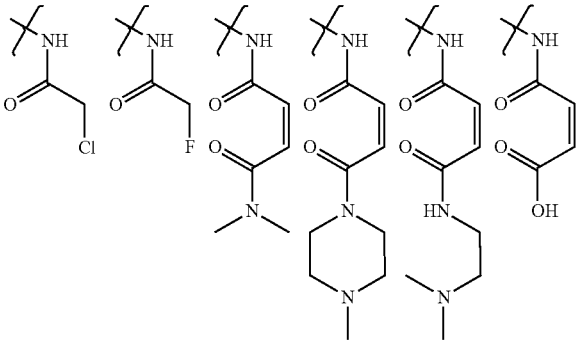

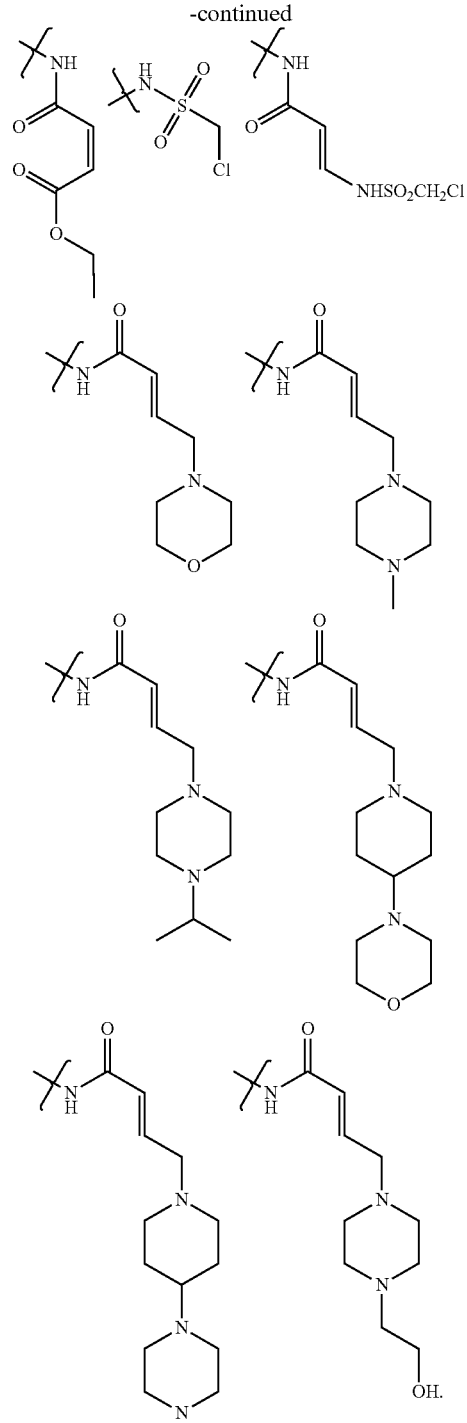
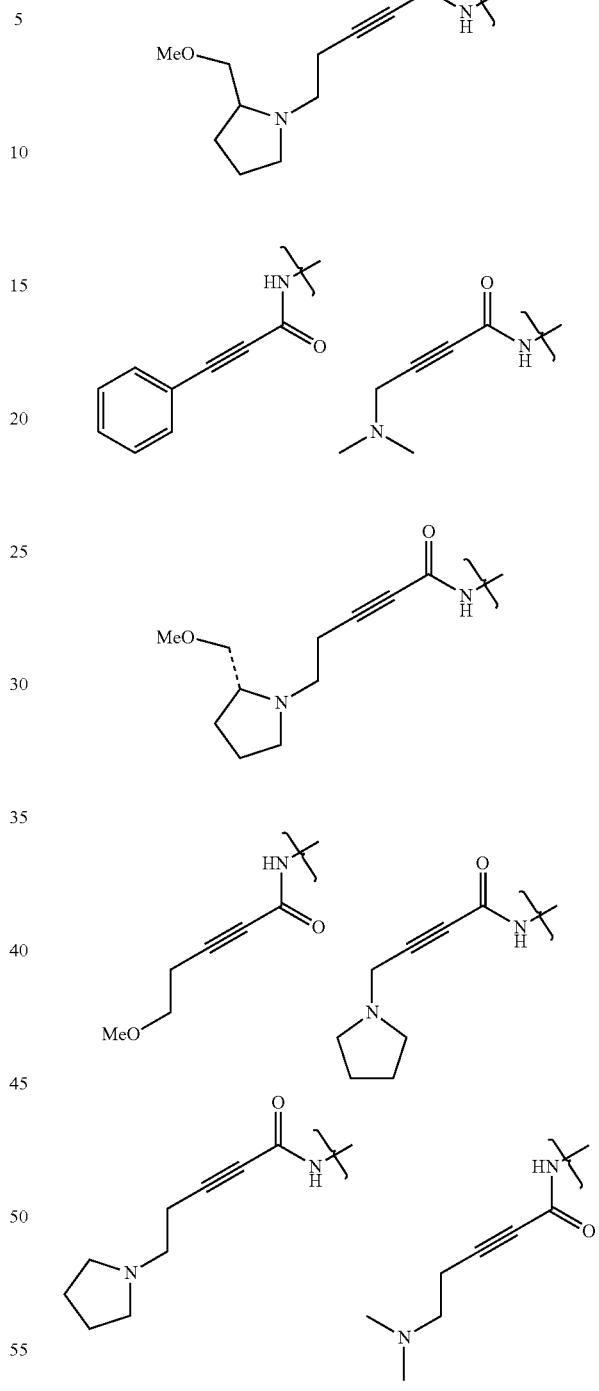
In other embodiments $R^{b4}$ is —NHC(O)C≡CH or may be selected from the following:
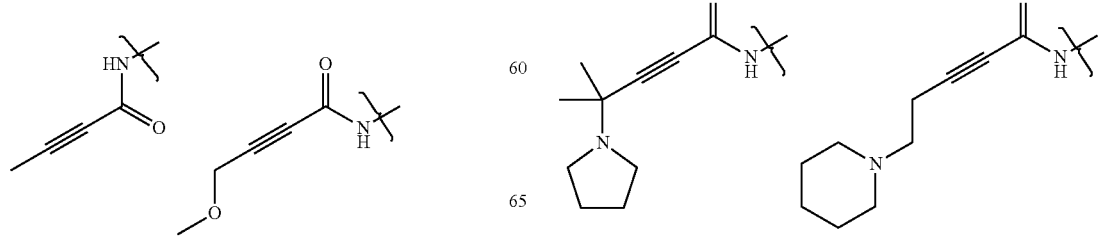

-continued

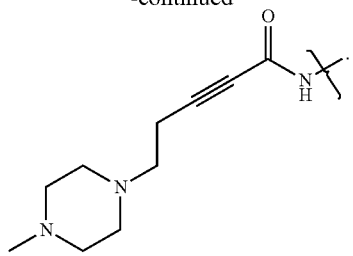

In one class of compounds of any of Formulas I, III(a)-(e), IV(a)-(e), V(a)-(e), VI(a)-(e), VII(a)-(e), VIII(a)-(e), IX(a)-(e), and X(a)-(e), and their pharmaceutically acceptable salts, including compounds with the various $R^{a1}$ groups disclosed above, $R^{b4}$ is $W^1$ as defined in Formula (I). In one subclass thereof, $R^{a2}$ is H, halo, —CH$_3$, —CF$_3$, —CH$_2$CH$_3$, —OCH$_3$, —OCF$_3$, —OCH$_2$CH$_3$, —OCH$_2$CH$_2$N(CH$_3$)$_2$ or —O-heterocyclyl. In a particular embodiment of that subclass, $R^g$ is —P(O)($R^{3A}$)($R^{3B}$), wherein $R^{3A}$ and $R^{3B}$, are as defined in Formula (I), e.g., $R^g$ is —P(O)(CH$_3$)$_2$ or —P(O)(CH$_2$CH$_3$)$_2$. In another embodiment of that subclass, $R^g$ is —S(O)$_2$$R^{3E}$), wherein $R^{3E}$ is as defined in Formula (I), e.g., $R^g$ is —S(O)$_2$CH(CH$_3$)$_2$. In either embodiment of the subclass, $R^d$ may be Cl, F, Br, I, or CH$_3$.

In certain embodiments of any of the above formulas, $R^{g1}$ is H and $R^{g2}$ is H, F, C$_{1-6}$ alkyl, or C$_{1-6}$ alkoxy.

In particular embodiments of any of the above formulas, $R^g$ is —P(O)($R^{3A}$)($R^{3B}$) or S(O)$_2$$R^{3E}$, wherein $R^{3A}$; $R^{3B}$; and $R^{3E}$ are as defined in formula (I). For example, $R^g$ can be selected from —P(O)(CH$_3$)$_2$ and —S(O)$_2$(CH(CH$_3$)$_2$).

In certain embodiments of any of the above formulas, $R^{a1}$ is a 5 or 6 member heterocyclic ring including 1 or 2 N or O atoms which is unsubstituted or substituted with an alkyl group. For example, $R^{a1}$ can be selected from any of the following groups:

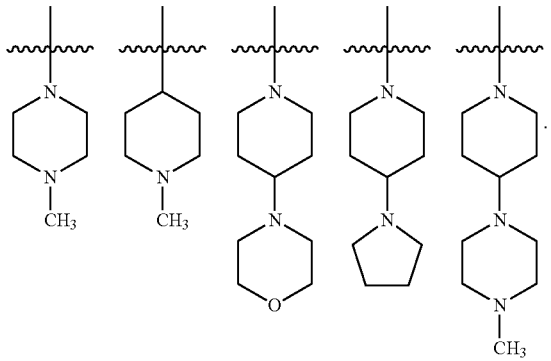

In particular embodiments of any of the above formulas, $R^{a2}$ is methoxy; $R^d$ is Cl, F, Br, I, or CH$_3$; and $R^g$ is —P(O)(CH$_3$)$_2$ or —S(O)$_2$(CH(CH$_3$)$_2$).

In certain embodiments of the compounds of formula (I), $U^1$ is N, $U^2$ is C—$R^d$, and $U^3$ is C—$R^e$; $U^1$ is C—$R^d$, $U^2$ is N, and $U^3$ is C—$R^e$; $U^1$ is N, $U^2$ is N, and $U^3$ is C—$R^e$; or $U^3$ is N, one of $U^1$ and $U^2$ is N, and the other is C—$R^d$.

In still other embodiments of the compounds of formula (I), $U^1$ is N; $U^2$ is C—$R^d$; $U^3$ is C—$R^e$; $R^{a2}$ is OCH$_3$; $R^g$ or $R^{g1}$ is —P(O)($R^{3A}$)($R^{3B}$); each of $R^{3A}$ and $R^{3B}$ is, independently, selected from alkyl, alkenyl, alkynyl, cycloalkyl, cycloalkenyl, cycloalkynyl, and heteroalkyl, or $R^{3A}$ and $R^{3B}$, together with the atoms to which they are attached, combine to form a 5- or 6-membered heterocyclic ring which is unsubstituted or substituted; $R^{b4}$ is —NHC(O)C(R ii)=CR$^9$R$^{10}$; each occurrence of R$^9$ and R$^{10}$ is, independently, selected from H, alkyl, alkenyl, alkynyl, cycloalkyl, cycloalkenyl, cycloalkynyl, aryl, heteroalkyl, heterocyclic and heteroaryl; R$^{11}$ is —C(O)—OR$^{12}$, —CH$_2$N(CH$_3$)$_2$, H, alkyl, alkenyl, alkynyl, cycloalkyl, cycloalkenyl, cycloalkynyl, aryl, heteroalkyl, heterocyclic, or heteroaryl; and R$^{12}$ is alkyl, alkenyl, alkynyl, cycloalkyl, cycloalkenyl, cycloalkynyl, aryl, heteroalkyl, heterocyclic, or heteroaryl. Exemplary compounds include those in which $V^1$ is NH, $V^1$ is O, $R^d$ is Cl, $R^g$ or $R^{g1}$ is —P(O)(CH$_3$)$_2$ or —P(O)(CH$_2$CH$_3$)$_2$, and/or $R^{b4}$ is —NHC(O)C(R$^{11}$)=CH$_2$. In particular embodiments, $R^{b4}$ is —NHC(O)C(R$^{11}$)=CH$_2$; R$^{11}$ is —C(O)—OR$^{12}$, —CH$_2$N(CH$_3$)$_2$, H, alkyl, alkenyl, alkynyl, cycloalkyl, cycloalkenyl, cycloalkynyl, aryl, heteroalkyl, heterocyclic, or heteroaryl; R$^{12}$ is alkyl, alkenyl, alkynyl, cycloalkyl, cycloalkenyl, cycloalkynyl, aryl, heteroalkyl, heterocyclic, or heteroaryl; $R^d$ is Cl; and $R^g$ or $R^{g1}$ is selected from —P(O)(CH$_3$)$_2$ and —P(O)(CH$_2$CH$_3$)$_2$.

In one embodiment of the compounds of any of Formulas (I), (Ia)-(Ic), (IIa)-(IIc), (IIIa)-(IIIe), (IVa)-(IVe), (Va)-(Ve), (VIa)-(VIe), (VIIIa)-(VIIIe), (IXa)-(IXe), and (Xa)-(Xe), $R^{b4}$ is —NHC(O)CH=CH$_2$.

DETAILED DESCRIPTION

The invention features a method for treating an EGFR-driven cancer in a subject by administering to the subject a therapeutically effective amount of a compound of the invention, or a pharmaceutically acceptable salt thereof.

In a related aspect, the invention features a method for treating an EGFR-driven cancer in a subject, the method including (a) providing a subject having an EGFR-driven cancer characterized by the presence of a mutation in epidermal growth factor receptor kinase (EGFR), and (b) administering to the subject a therapeutically effective amount of a compound of the invention, or a pharmaceutically acceptable salt thereof. In certain embodiments, EGFR-driven cancer is characterized by the presence of one or more mutations selected from: (i) L858R, (ii) T790M, (iii) both L858R and T790M, (iv) delE746_A750, and (v) both delE746_A750 and T790M.

In the above methods, the EGFR-driven cancer can be a non-small cell lung cancer (NSCLS); glioblastoma; pancreatic cancer; head and neck cancer (e.g., squamous cell carcinoma); breast cancer; colorectal cancer; epithelial cancer; ovarian cancer; prostate cancer; an adenocarcinoma, or any EGFR-driven cancer described herein.

In certain embodiments of the above methods, the method further includes administering to the subject a first kinase inhibitor selected from erlotinib, gefitinib, and pharmaceutically acceptable salts thereof, within 6 days (e.g., within 2 weeks, 1 week, 6 days, 5 days, 4 days, 3 days, 2 days, 1 day, or simultaneously) of administering the compound of the invention (e.g., a compound of any of Formulas (I), (Ia)-(Ic), (IIa)-(IIc), (IIIa)-(IIIe), (IVa)-(IVe), (Va)-(Ve), (VIa)-(VIe), (VIIIa)-(VIIIe), (IXa)-(IXe), and (Xa)-(Xe)), wherein each of the compound of the invention and the first kinase inhibitor are administered in an amount that together is sufficient to treat the EGFR-driven cancer.

In a related aspect, the invention features a method of inhibiting the proliferation of a cell expressing an EGFR mutant, the method including contacting the cell with a compound of the invention, or a pharmaceutically acceptable salt thereof, in an amount sufficient to inhibit the proliferation. For example, the EGFR mutant can be characterized by the presence of one or more mutations in epidermal growth factor receptor kinase (EGFR) selected from: (i) L858R, (ii) T790M, (iii) both L858R and T790M, (iv) delE746_A750, (v) both delE746_A750 and T790M, and any other EGFR mutations described herein. In certain embodiments, the cell is a cancer cell (e.g., a cell from a non-small cell lung cancer (NSCLS); glioblastoma; pancreatic cancer; head and neck cancer (e.g., squamous cell carcinoma); breast cancer; colorectal cancer; epithelial cancer; ovarian cancer; prostate cancer; an adenocarcinoma, or any other EGFR expressing cancer described herein).

The invention further features a method of treating an EGFR-driven cancer refractory to a first kinase inhibitor selected from erlotinib, gefitinib, and pharmaceutically acceptable salts thereof, in a subject by administering to the subject a compound of the invention, or a pharmaceutically acceptable salt thereof, in an amount sufficient to treat the cancer.

In any of Formulas I, III(a)-(e), IV(a)-(e), V(a)-(e), VI(a)-(e), VII(a)-(e), VIII(a)-(e), IX(a)-(e), and X(a)-(e), the compound can be either in its free base form, or a pharmaceutically acceptable salt.

The response criteria for the methods of the invention can be graded according to the response evaluation criteria in solid tumors (RECIST) guidelines (see Eur. J. Cancer 45:228 (2009)) that define when cancer patients improve ("respond"), stay the same ("stabilize"), or worsen ("progression") during treatments. A complete response is characterized by: (i) disappearance of all target lesions; and (ii) any pathological lymph nodes (whether target or non-target) must have reduction in short axis to <10 mm. A partial response is characterized by: (i) at least a 30% decrease in the sum of diameters of target lesions, taking as reference the baseline sum diameters. A progressive disease is characterized by (i) at least a 5%, 10%, or 20% increase in the sum of diameters of target lesions, taking as reference the smallest sum on study (this includes the baseline sum if that is the smallest on study); or (ii) the appearance of one or more new lesions.

The term "administration" or "administering" refers to a method of giving a dosage of a pharmaceutical composition to a mammal, where the method is, e.g., oral, intravenous, intraperitoneal, intraarterial, or intramuscular. The preferred method of administration can vary depending on various factors, e.g., the components of the pharmaceutical composition, site of the potential or actual disease and severity of disease.

By "EGFR-driven cancer" is meant a cancer characterized by inappropriately high expression of an EGFR gene or by a mutation in an EGFR gene that alters the biological activity of an EGFR nucleic acid molecule or polypeptide. EGFR-driven cancers can arise in any tissue, including brain, blood, connective tissue, liver, mouth, muscle, spleen, stomach, testis, and trachea. EGFR-driven cancers can include non-small cell lung cancer (NSCLS), including one or more of squamous cell carcinoma, adenocarcinoma, adenocarcinoma, bronchioloalveolar carcinoma (BAC), BAC with focal invasion, adenocarcinoma with BAC features, and large cell carcinoma; neural tumors, such as glioblastomas; pancreatic cancer; head and neck cancers (e.g., squamous cell carcinoma); breast cancer; colorectal cancer; epithelial cancer, including squamous cell carcinoma; ovarian cancer; prostate cancer; adenocarcinomas; and including cancers which are EGFR mediated.

An "EGFR mutant" or "mutant" includes one or more deletions, substitutions, or additions in the amino acid or nucleotide sequences of EGFR protein, or EGFR coding sequence. The EGFR mutant can also include one or more deletions, substitutions, or additions, or a fragment thereof, as long as the mutant retains or increases tyrosine kinase activity, compared to wild type EGFR. In particular EGFR mutations, kinase or phosphorylation activity can be increased (e.g., by at least 5%, 10%, 15%, 20%, 30%, 40%, 50%, 60%, 70%, 80%, 90%, or even 100%), as compared to wild type EGFR. Particular EGFR mutants are described herein, where mutations are provided relative to the position of an amino acid in human EGFR, as described in the sequence provided in NCBI GenBank Reference Sequence: NP_005219.2.

As used herein, the term "inhibiting the proliferation of a cell expressing an EGFR mutant" refers to measurably slowing, stopping, or reversing the growth rate of the EGFR-expressing cells in vitro or in vivo. Desirably, a slowing of the growth rate is by at least 10%, 20%, 30%, 50%, or even 70%, as determined using a suitable assay for determination of cell growth rates (e.g., a cell growth assay described herein). The EGFR mutant can be any EGFR mutant described herein.

As used herein, the term "refractory" refers to a cancer which is progressive in response to a given particular therapy. The cancer can be refractory either from the initial administration of the therapy; or become refractory over time in response to the therapy.

The term "sequence identity" is meant the shared identity between two or more nucleic acid sequence, or two or more amino acid sequences, expressed in the terms of the identity between the sequences. Sequence identity can be measured in terms of percentage identity; the higher the percentage, the more identical the sequences are. Homologs or orthologs of nucleic acid or amino acid sequences possess a relatively high degree of sequence identity when aligned using standard methods. Methods of alignment of sequences for comparison are well known in the art. Various programs and alignment algorithms are described in: Smith and Watermann, Adv. Appl. Math. 2:482 (1981); Needleman and Wunsch, J. Mol. Biol. 48:443 (1970); Pearson and Lipman, Proc. Natl. Acad. Sci. U.S.A. 85:2444 (1988); Corpet et al., Nuc. Acid Res. 16:10881 (1988); Huang et al., Computer Appls. in the Biosciences 8:155 (1992); and Pearson et al., Meth. Mol. Biol. 24:307 (1994). Altschul et al. (J. Mol. Biol. 215:403 (1990)) presents a detailed consideration of sequence alignment methods and homology calculations. The NCBI Basic Local Alignment Search Tool (BLAST) (Altschul et al., J. Mol. Biol. 215:403 (1990)) is available from several sources, including the National Center for Biological Information (NCBI) website, for use in connection with the sequence analysis programs blastp, blastn, blastx, tblastn, and tblastx. Additional information can be found at the NCBI website. BLASTN is used to compare nucleic acid sequences, while BLASTP is used to compare amino acid sequences. To compare two nucleic acid sequences, the option can be set as follows: —i is set to a file containing the first nucleic acid sequence to be compared; —j is set to a file containing the second nucleic acid sequence to be compared; —p is set to blastn; —o is set to any desired file name; —q is set to −1; —r is set to 2; and all other options are left at their default setting. Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 30, 35, 40, 45, 50, 60, 70, 80, 90, 100, 150, 200, 250, 300, 350, or 400 consecutive nucleotides or amino acid residues from a sequence set forth in an identified sequence), followed by multiplying the resulting value by 100. One indication that two nucleic acid molecules are closely related is that the two molecules hybridize to each other under stringent conditions. Stringent conditions are sequence-dependent and are different under different environmental parameters. Nucleic acid molecules that hybridize under stringent conditions to an EGFR gene sequence typically hybridize to a probe based on either an entire EGFR gene or selected portions of the gene (e.g., the kinase domain or a segment of the gene that contains the mutated codons described herein), under conditions described above.

As used herein, the term "treating" refers to administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

Where optional substitution of compounds of the invention is indicated, but one or more optional substituents is not specified, the substituent may be selected from those disclosed herein as generally appropriate in the given context, e.g. on an alkyl carbon, an aryl carbon, etc., and specifically include substitution exemplified in the examples. Other parameters of functional groups are also disclosed in detail below.

The term "alkyl" refers to linear, branched, cyclic, and polycyclic non aromatic hydrocarbon groups, which may be substituted or unsubstituted. Unless otherwise specified, "alkyl" groups contain one to eight, and typically one to six carbon atoms. Examples of alkyl include, without limitation, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, and n-heptyl, among others. Exemplary substituted alkyl groups include, without limitation, haloalkyl groups (e.g., fluoromethyl, difluoromethyl, trifluoromethyl, 2-fluoroethyl, 3-fluoropropyl), hydroxymethyl, 2-hydroxyethyl, 3-hydroxypropyl, benzyl, substituted benzyl, and phenethyl, among others. Note that as used herein, "alkyl" encompasses cyclic alkyl groups, which if not otherwise specified, contain 3-8 carbon atoms.

The term "alkoxy" refers to a subset of alkyl in which an alkyl group as defined above with the indicated number of carbons attached through an oxygen bridge, —O-alkyl, wherein the alkyl group contains 1 to 8 carbons atoms and is substituted or unsubstituted. Exemplary alkoxy groups include, without limitation, methoxy, ethoxy, n-propoxy, i-propoxy, t-butoxy, n-butoxy, s-pentoxy, —$OCF_3$, and —O-cyclopropyl.

The term "haloalkyl" refers to a subset of alkyl in which an alkyl group as defined above having one or more hydrogen atoms of the alkyl substituted with a halogen atom. Exemplary haloalkyl groups include, without limitation, fluoromethyl, trifluoromethyl, trichloromethyl, pentafluoroethyl and the like.

The term "alkenyl" refers to a branched or unbranched hydrocarbon group containing one or more double bonds and having from 2 to 8 carbon atoms. An alkenyl may optionally include monocyclic or polycyclic rings, in which each ring desirably has from three to six members. The alkenyl group may be substituted or unsubstituted. Alkenyl groups include, without limitation, vinyl, allyl, 2-cyclopropyl-1-ethenyl, 1-propenyl, 1-butenyl, 2-butenyl, 3-butenyl, 2-methyl-1-propenyl, and 2-methyl-2-propenyl.

The term "alkynyl" refers to a branched or unbranched hydrocarbon group containing one or more triple bonds and having from 2 to 8 carbon atoms. The alkynyl group may be substituted or unsubstituted. Alkynyls include, without limitation, ethynyl, 1-propynyl, 2-propynyl, 1-butynyl, 2-butynyl, and 3-butynyl.

The term "cycloalkyl" refers to cyclic or polycyclic hydrocarbon groups of from 3 to 13 carbon atoms, any of which is saturated. Cycloalkyl groups may be substituted or unsubstituted. Exemplary cycloalkyl groups include, without limitation, cyclopropyl, norbornyl, [2.2.2]bicyclooctane, and [4.4.0]bicyclodecane, and the like, which, as in the case of other alkyl moieties, may optionally be substituted.

The term "cycloalkenyl" refers to cyclic or polycyclic hydrocarbon groups of from 3 to 13 carbon atoms, preferably from 5 to 8 carbon atoms, containing one or more double bonds. Cycloalkenyl groups may be substituted or unsubstituted. Exemplary cycloalkenyl groups include, without limitation, cyclopentenyl, cyclohexenyl, and cyclooctenyl.

The term "cycloalkynyl" refers to cyclic or polycyclic hydrocarbon groups of from 5 to 13 carbon atoms containing one or more triple bonds. Cycloalkynyl groups may be substituted or unsubstituted.

The term "heteroalkyl" means a branched or unbranched alkyl, alkenyl, or alkynyl group having from 1 to 14 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Examples of heteroalkyls include, without limitation, polyethers, such as methoxymethyl and ethoxyethyl.

As used herein, "heterocyclic ring" and "heterocyclyl" refer to non-aromatic ring systems having five to fourteen ring atoms in which one or more ring carbons, preferably one to four, are each replaced by a heteroatom such as N, O, S, or P, which may be used alone or as part of a larger moiety as in "heterocyclyl-alkyl" (a heterocyclyl-substituted $C_{1-6}$ alkyl), "heterocyclyl-alkoxy" (a heterocyclyl-substituted $C_{1-6}$ alkoxy), or "heterocycloxy-alkyl" (a heterocycloxy-substituted $C_{1-6}$ alkyl), and includes aralkyl, aralkoxy, and aryloxyalkyl groups. Heterocyclic rings may be substituted or unsubstituted and may include one, two, or three fused or unfused ring systems. Desirably, the heterocyclic ring is a 5- to 7-membered monocyclic or 7- to 14-membered bicyclic heterocyclic ring consisting of 2 to 6 carbon atoms and 1, 2, 3, or 4 heteroatoms independently selected from N, O, and S and including any bicyclic group in which any of the above-defined heterocyclic rings is fused to a benzene ring. Exemplary heterocyclic rings include, without limitation, 3-1H-benzimidazol-2-one, (1-substituted)-2-oxo-benzimidazol-3-yl, 2-tetrahydrofuranyl, 3-tetrahydrofuranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. A heterocyclyl group can include two or more of the ring systems listed above. Heterocyclic rings include those in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring.

The term "aryl" used alone or as part of a larger moiety as in "aralkyl" (an aryl-substituted $C_{1-6}$ alkyl), "aralkoxy" (an aryl-substituted $C_{1-6}$ alkoxy), or "aryloxyalkyl" (an aryloxy-substituted $C_{1-6}$ alkyl), refers to aromatic monocyclic or polycyclic ring groups having six to fourteen ring atoms, such as phenyl, 1-naphthyl, 2-naphthyl, 1-anthracyl, and 2-anthracyl and includes aralkyl, aralkoxy, and aryloxyalkyl groups. An "aryl" ring may be substituted or unsubstituted. The term "aryl" includes fused polycyclic aromatic ring systems in which an aromatic ring is fused to one or more rings. Non-limiting examples of aryl groups include phenyl, hydroxyphenyl, halophenyl, alkoxyphenyl, dialkoxyphenyl, trialkoxyphenyl, alkylenedioxyphenyl, naphthyl, phenanthryl, anthryl, phenanthro, 1-naphthyl, 2-naphthyl, 1-anthracyl, and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "heteroaryl" as used herein refers to stable heterocyclic, and polyheterocyclic aromatic moieties having 5-14 ring atoms. Heteroaryl groups may be substituted or unsubstituted and include both monocyclic and polycyclic ring systems. Examples of typical heteroaryl rings include 5-membered monocyclic rings, such as thienyl, pyrrolyl, imidazolyl, pyrazolyl, furyl, isothiazolyl, furazanyl, isoxazolyl, and thiazolyl; 6-membered monocyclic rings, such as pyridyl, pyrazinyl, pyrimidinyl, pyridazinyl, and triazinyl; and polycyclic heterocyclic rings, such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl (see e.g. Katritzky, Handbook of Heterocyclic Chemistry). Exemplary heteroaryl rings include, without limitation, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolyl, indolyl, isoindolyl, acridinyl, and benzoisoxazolyl. Heteroaryl groups further include a group in which a heteroaromatic ring is fused to one or more aromatic or nonaromatic rings where the radical or point of attachment is on the heteroaromatic ring, such as tetrahydroquinoline, tetrahydroisoquinoline, and pyrido[3,4-d]pyrimidinyl, imidazo[1,2-a]pyrimidyl, imidazo[1,2-a]pyrazinyl, imidazo[1,2-a]pyiridinyl, imidazo[1,2-c]pyrimidyl, pyrazolo[1,5-a][1,3,5]triazinyl, pyrazolo[1,5-c]pyrimidyl, imidazo[1,2-b]pyridazinyl, imidazo[1,5-a]pyrimidyl, pyrazolo[1,5-b][1,2,4]triazine, quinolyl, isoquinolyl, quinoxalyl, imidazotriazinyl, pyrrolo[2,3-d]pyrimidyl, triazolopyrimidyl, and pyridopyrazinyl.

An aryl group or heteroaryl group may contain one or more substituents. Exemplary substituents for aryl or heteroaryl group include halogen (F, Cl, Br or I), alkyl, alkenyl, alkynyl, heteroalkyl, —$NO_2$, —CN, —$R^A$, —$OR^B$, —S(O)$_r R^B$, (wherein r is 0, 1 or 2), —$SO_2 NR^A R^B$, —$NR^A R^B$, —O—$NR^A R^B$, —$NR^A$—$NR^A R^B$, —(CO)$YR^B$, —O(CO)$YR^B$, —$NR^A$(CO)$YR^B$, —S(CO)$YR^B$, —$NR^A C(=S)YR^B$, —OC(=S)$YR^B$, —C(=S)$YR^B$, —YC(=$NR^A$)$YR^B$, —YC(=N—$OR^A$)$YR^B$, —YC(=N—$NR^A R^B$)$YR^B$, —$COCOR^B$, —$COMCOR^B$ (where M is a $C_{1-6}$ alkyl group), —YP(O)($YR^C$)($YR^C$), —P(O)($R^C$)$_2$, —Si($R^C$)$_3$, —$NR^A SO_2 R^B$, and —$NR^A SO_2 NR^A R^B$, wherein each occurrence of Y is, independently, —O—, —S—, —$NR^A$—, or a chemical bond (i.e., —(CO)$YR^B$ thus encompasses —C(=O)$R^B$, —C(=O)$OR^B$, and —C(=O)$NR^A R^B$).

$R^C$ is selected from alkyl, alkenyl, alkynyl, cycloalkyl, cycloalkenyl, cycloalkynyl, aryl, heteroaryl, and heterocyclyl. At each occurrence, each of $R^A$ and $R^B$ is, independently, selected from hydrogen, alkyl, alkenyl, alkynyl, cycloalkyl, cycloalkenyl, cycloalkynyl, aryl, heteroaryl, and heterocyclyl.

Each of $R^A$, $R^B$ and $R^C$ optionally bears one or more substituents selected from amino, alkylamino, dialkylamino, aminocarbonyl, halogen, alkyl, aryl, heteroalkyl, heteroaryl, carbocycle, heterocycle, alkylaminocarbonyl, dialkylaminocarbonyl, alkylaminocarbonyloxy, dialkylaminocarbonyloxy, nitro, cyano, carboxy, alkoxycarbonyl, alkylcarbonyl, alkoxy, haloalkoxy groups, hydroxy, protected hydroxyl groups (e.g., —O—X, where X is acyl, phenyl, substituted phenyl, benzyl, substituted benzyl, phenethyl, or substituted phenethyl), -M-heteroaryl, -M-heterocycle, -M-aryl, -M-$OR^B$, -M-$SR^B$, -M-$NR^A R^B$, -M-OC(O)$NR^A R^B$, -M-C(=$NR^B$)$NR^A R^B$, -M-C(=$NR^A$)$OR^B$, -M-P(=O)($R^C$)$_2$, Si($R^C$)$_3$, -M-$NR^A C(O)R^B$, -M-$NR^A C(O)OR^B$, -M-C(O)$R^B$, -M-C(=S)$R^B$, -M-C(=S)$NR^A R^B$, -M-C(O)$NR^A R^B$, -M-C(O)$NR^B$-M-$NR^A R^B$, -M-$NR^B C(NR^A)NR^A R^B$, -M-$NR^A C(S)NR^A R^B$, -M-S(O)$_2 R^A$, -M-C(O) $R^A$, -M-OC(O) $R^A$, -MC(O)$SR^B$, -M-S(O)$_2 NR^A R^B$, —C(O)-M-C(O)$R^B$, -$MCO_2 R^B$, -MC(=O)$NR^A R^B$, -M-C(=NH)$NR^A R^B$, and -M-OC(=NH)$NR^A R^B$, wherein M is a $C_{1-6}$ alkyl group. Non-limiting illustrations of a substituted $R^A$, $R^B$ or $R^C$ group include haloalkyl and trihaloalkyl, alkoxyalkyl, halophenyl, chloromethyl, trichloromethyl, trifluoromethyl, methoxyethyl, alkoxyphenyl, halophenyl, —$CH_2$-aryl, —$CH_2$-heterocycle, —$CH_2 C(O)NH_2$, —C(O)$CH_2 N(CH_3)_2$, —$CH_2 CH_2 OH$, —$CH_2 OC(O)NH_2$, —$CH_2 CH_2 NH_2$, —$CH_2 CH_2 CH_2 NEt_2$, —$CH_2 OCH_3$, —C(O)$NH_2$, —$CH_2 CH_2$-heterocycle, —C(=S)$CH_3$, —C(=S)$NH_2$, —C(=NH)$NH_2$, —C(=NH)OEt, —C(O)NH-cyclopropyl, —C(O)$NHCH_2 CH_2$-heterocycle, —C(O)$NHCH_2 CH_2 OCH_3$, —C(O)$CH_2 CH_2 NHCH_3$, —$CH_2 CH_2 F$, —C(O)$CH_2$-heterocycle, —$CH_2 C(O)NHCH_3$, —$CH_2 CH_2 P(=O)(CH_3)_2$, and —Si($CH_3$)$_3$.

An alkyl, alkenyl, alkynyl, alkoxy, haloalkyl, heteroalkyl, cycloalkyl, cycloalkenyl, cycloalkynyl, or heterocyclic group may contain one or more substituents selected from those listed above for aryl and heteroaryl groups, in addition to =O, =S, =NH, =$NNR^A R^B$, =$NNHC(O)R^B$, =$NNHCO_2 R^B$, or =$NNHSO_2 R^8$, wherein $R^A$ and $R^B$ are as defined above.

In drawings of chemical structures in this document, atoms not indicated by label or line are understood to be H.

Other features and advantages of the invention will be apparent from the following detailed description and the claims.

EGFR Mutants

The EGFR-driven cancers which can be treated using the compositions and method of the invention include, for example, EGFR mutants including one or more deletions, substitutions, or additions in the amino acid or nucleotide sequences of EGFR, or fragments thereof.

Mutations in EGFR can occur in any part of the EGFR sequence. Generally, EGFR mutants arise from mutations in the kinase domain (i.e., exons 18-24 in the EGFR sequence) or in the extracellular domain (i.e., exons 2-16 in the EGFR sequence). For example, mutations typically occur in the kinase domain, including one or more of a point mutation in exon 18 (e.g., L688P, V689M, P694L/S, N700D, L703V, E709K/Q/A/G/V, I715S, L718P, G719C/A/S/R, or S720P/F), a deletion in exon 19 that may or may not include an insertion (e.g., delG719, delE746_E749, delE746_A750, delE746_A750insRP, delE746_A750insQP, delE746_T751, delE746_T751insA/I/V, delE746_T751 insVA, delE746_S752, delE746_S752insA/V/D, delE746_P53insLS, delL747_E749, delL747_A750, delL747_A750insP, delL747_T751, delL747_T751insP/S/Q, delL747_T751insPI, delL747_S752, delL747_S752insQ, delL747_P753, delL747_P753insS/Q, delL747_L754insSR, delE749_A750, delE749_A750insRP, delE749_T751, delT751_I759, delT751_I759 insS/N, or delS752_I759), a duplication in exon 19 (e.g., K739_144 dupKIPVAI), a point mutation in exon 19 (e.g., L730F, W731 Stop, P733L, G735S, V742A, E746V/K, A750P, T751I, S752Y, P753S, A754P, or D761Y), an in-frame insertion in exon 20 (e.g., D761_E762insEAFQ, A767_S768insTLA, V769_D770insY, V769_D770insCV, V769_D770insASV, D770_N771insD/G, D770_N771insNPG, D770_N771insSVQ, P772_H773insN/V, P772_H773insYNP, or V774_C775insHV), a deletion in exon 20 that may or may not include an insertion (e.g., delM766_A767, delM766_A767insAI, delA767_V769, delD770, or delP772_H773insNP), a duplication in exon 20 (e.g., S768_D770 dupSVD, A767_V769dupASV, or H773dupH), a point mutation in exon 20 (e.g., D761N, A763V, V765A/M, S768I, V769L/M, S768I, P772R, N771T, H773R/Y/L, V774M, R776G/H/C, G779S/F, T783A, T784F, L792P, L798H/F, T790M, R803W, K806E, or L814P), or a point mutation in exon 21 (e.g., G810S, N826S, L833V, H835L, L838V, A839T, K846R, T847I, H850N, V851I/A, I853T, L858M/R, A859T, L861Q/R, G863D, A864T, E866K, or G873E). In lung cancer, activation mutants are typical, and 90% deletion of 746-750 (ELREA) and L858R result in sustained phosphorylation of EGFR without ligand stimulation. In particular, drug resistance in 50% of lung cancers arises from the T790M point mutation.

For example, in glioblastoma, mutations typically, but not exclusively, occur in the extracellular domain, including EGFR variant I (EGFRvI) lacking the extracellular domain and resembling the v-erbB oncoprotein; EGFRvII lacking 83 amino acids from domain IV; and EGFRvIII lacking amino acids 30-297 from domains I and II, which is the most common amplification and is reported in 30-50% of glioblastomas and 5% of squamous cell carcinoma. Other mutations for glioblastoma include one or more of point mutations in exon 2 (e.g., D46N or G63R), exon 3 (e.g., R108K in domain I), exon 7 (e.g., T263P or A289D/T/V in domain II), exon 8 (e.g., R324L or E330K), exon 15 (e.g., P596L or G598V in domain IV), or exon 21 (L861Q in the kinase domain).

EGFR mutants also include those with a combination of two or more mutations, as described herein. Exemplary combinations include S768I and G719A; S768I and V769L; H773R and W731Stop; R776G and L858R; R776H and L861Q; T790M and L858R; T790M and delE746_A750; R803W and delE746_T751insVA; delL747_E749 and A750P; delL747_S752 and E746V; delL747_S752 and P753S; P772_H773insYNP and H773Y; P772_H773insNP and H773Y; and D770_N771insG and N771T. Other exemplary combinations include any including T790M (e.g., T790M and L858R or T790M and delE746_A750, with or without concomitant inhibition of single mutants L858R and delE746_A750).

EGFR mutants can be either activation mutants or resistant mutants. Activation mutants include those with substitutions that increase drug sensitivity (e.g., G719C/S/A, delE746_A750, or L858R). Resistant mutants include those with substitutions that increase drug resistance (e.g., T790M or any combination including T790M).

EGFR-driven cancers include those having any mutant described herein. For example, EGFRvIII is commonly found in glioblastoma and has also been reported in breast, ovarian, prostate, and lung carcinomas. Exemplary EGFR-driven cancers: glioblastoma, lung cancer (e.g., squamous cell carcinoma, non-small cell lung cancer, adenocarcinoma, bronchioloalveolar carcinoma (BAC), BAC with focal invasion, adenocarcinoma with BAC features, and large cell carcinoma), pancreatic cancer, head and neck cancers (e.g., squamous cell carcinoma), breast cancer, colorectal cancer, epithelial cancer (e.g., squamous cell carcinoma), ovarian cancer, and prostate cancer.

In particular, the invention described herein would benefit patient populations having higher risk for TKI-resistant mutations. About 8,000 to 16,000 new cases per year can be estimated based on: incidence of non-small cell lung cancer (about 160,000 new cases in the U.S.), the response to erlonitinib in the general population (about 10%, resulting in a sensitive population of 16,000), the presence of activation mutations (10-20% in white and 30-40% in Asian population, resulting in a sensitive population of 16,000-32,000), acquisition of secondary resistance (most if not all patients, resulting in a sensitive population of 16,000-32,000), and percentage of patients carrying the T790M point mutations (about 50%, resulting in a sensitive population of 8,000-16,000). Patients having TKI-resistant mutations include those patients having cancers resistant to one or more of erlotinib, gefitinib, CL-387,785, BIBW 2992 (CAS Reg. No, 439081-18-2), CI-1033, neratinib (HKI-272), MP-412 (AV-412), PF-299804, AEE78, and XL64.

In particular, the inventions relates to treatment of EGFR-driven cancers having the T790M point mutation. Generally, reversible inhibitors (e.g., CI-1033, neratinib (HKI-272), and PF-299804) are less potent in cell lines having the T790M mutation and do not inhibit T790M at clinically achievable concentrations. Since the ATP Km of T790M and WT are similar, concentrations that inhibit the mutant will inhibit the WT and result in gastrointestinal and cutaneous events.

An EGFR mutant also includes other amino acid and nucleotide sequences of EGFR with one or more deletions, substitutions, or additions, such as point mutations, that retain or increase tyrosine kinase or phosphorylation activity. Where the mutant is a protein or polypeptide, preferable substitutions are conservative substitutions, which are substitutions between amino acids similar in properties such as structural, electric, polar, or hydrophobic properties. For example, the substitution can be conducted between basic amino acids (e.g., Lys, Arg, and His), or between acidic amino acids (e.g., Asp and Glu), or between amino acids having non-charged polar side chains (e.g., Gly, Asn, Gln, Ser, Thr, Tyr, and Cys), or between amino acids having hydrophobic side chains (e.g., Ala, Val, Leu, Ile, Pro, Phe, and Met), or between amino acids having branched side chains (e.g., Thr, Val, Leu, and Ile), or between amino acids having aromatic side chains (e.g., Tyr, Trp, Phe, and His).

Where the mutant is a nucleic acid, the DNA encoding an EGFR mutant protein may comprise a nucleotide sequence capable of hybridizing to a complement sequence of the nucleotide sequence encoding an EGFR mutant, as defined herein, under stringent conditions. As used herein, the stringent conditions include low, medium or high stringent conditions. An example of the stringent conditions includes hybridization at approximately 42-55° C. in approximately 2-6×SSC, followed by wash at approximately 50-65° C. in approximately 0.1-1×SSC containing approximately 0.1-0.2% SDS, where 1×SSC is a solution containing 0.15 M NaCl and 0.015 M Na citrate, pH 7.0. Wash can be performed once or more. In general, stringent conditions may be set at a temperature approximately 5° C. lower than a melting temperature (Tm) of a specific nucleotide sequence at defined ionic strength and pH.

The amino acid and nucleotide sequences of EGFR and DNAs encoding them are available from known databases such as NCBI GenBank (USA), EMBL (Europe), etc. For example, GenBank accession numbers for EGFR [*Homo sapiens*] include MIM131550, AAI28420, NM_005228, NP_005219.2, and GeneID: 1956.

Characterization of EGFR-Driven Cancers

The compositions and methods of the invention can be used to treat subjects having an EGFR-driven cancer (i.e., cancers characterized by EGFR mutant expression or overexpression). EGFR mutant expression or overexpression can be determined in a diagnostic or prognostic assay by evaluating levels of EGFR mutants in biological sample, or secreted by the cell (e.g., via an immunohistochemistry assay using anti-EGFR antibodies or anti-p-EGFR antibodies; FACS analysis, etc.). Alternatively, or additionally, one can measure levels of EGFR mutant-encoding nucleic acid or mRNA in the cell, e.g., via fluorescent in situ hybridization using a nucleic acid based probe corresponding to an EGFR mutant-encoding nucleic acid or the complement thereof; (FISH; see WO98/45479, published October, 1998), Southern blotting, Northern blotting, or polymerase chain reaction (PCR) techniques, such as real time quantitative PCR (RT-PCR). One can also study EGFR mutant expression by measuring shed antigen in a biological sample, such as serum, e.g., using antibody-based assays (see also, e.g., U.S. Pat. No. 4,933,294, issued Jun. 12, 1990; WO91/05264, published Apr. 18, 1991; U.S. Pat. No. 5,401,638, issued Mar. 28, 1995; and Sias et al., J. Immunol. Methods 132:73 (1990)). Aside from the above assays, various in vivo assays are available to the skilled practitioner. For example, one can expose cells within the body of the mammal to an antibody which is optionally labeled with a detectable label, e.g., a radioactive isotope, and binding of the antibody to cells in the mammal can be evaluated, e.g., by external scanning for radioactivity or by analyzing a biopsy taken from a mammal previously exposed to the antibody.

Examples of biological properties that can be measured in isolated cells include mRNA expression, protein expression, and DNA quantification. Additionally, the DNA of cells isolated by the methods of the invention can be sequenced, or certain sequence characteristics (e.g., polymorphisms and chromosomal abnormalities) can be identified using standard techniques, e.g., FISH or FOR. The chemical components of cells, and other analytes, may also be assayed after isolation. Cells may also be assayed without lysis, e.g., using extracellular or intracellular stains or by other observation, e.g., morphology or growth characteristics in various media.

While any hybridization technique can be used to detect the gene rearrangements, one preferred technique is fluorescent in situ hybridization (FISH). FISH is a cytogenetic technique which can be used to detect and localize the presence or absence of specific DNA or RNA sequences on chromosomes. FISH incorporates the use of fluorescently labeled nucleic acid probes which bind only to those parts of the chromosome with which they show a high degree of sequence similarity. Fluorescence microscopy can be used to find out where the fluorescent probe bound to the chromosome. The basic steps of FISH are outlined below. Exemplary FISH probes include Vysis EGFR SpectrumOrange/ CEP SpectrumGreen Probe (Abbott, Downers Grove, Ill.), which hybridizes to band 7p12; and ZytoLight SPEC EGFR/ CEN 7 Dual Color Probe (ZytoVision), which hybridizes to the alpha-satellite sequences of the centromere of chromosome 7.

For FISH, a probe is constructed that is long enough to hybridize specifically to its target (and not to similar sequences in the genome), but not too large to impede the hybridization process. Probes are generally labeled with fluorophores, with targets for antibodies, with biotin, or any combination thereof. This can be done in various ways, for example using random priming, nick translation, and PCR using tagged nucleotides.

Generally, a sample or aliquot of a population of cells is used for FISH analysis. For example, in one method of preparation, cells are trypsinized to disperse into single cells, cytospun onto glass slides, and then fixed with paraformaldehyde before storing in 70% ethanol. For preparation of the chromosomes for FISH, the chromosomes are firmly attached to a substrate, usually glass. After preparation, the probe is applied to the chromosome RNA and starts to hybridize. In several wash steps, all unhybridized or partially hybridized probes are washed away. If signal amplification is necessary to exceed the detection threshold of the microscope (which depends on many factors such as probe labeling efficiency, the kind of probe, and the fluorescent dye), fluorescent tagged antibodies or strepavidin are bound to the tag molecules, thus amplifying the fluorescence.

An epifluorescence microscope can be used for observation of the hybridized sequences. The white light of the source lamp is filtered so that only the relevant wavelengths for excitation of the fluorescent molecules arrive onto the sample. Emission of the fluorochromes happens, in general, at larger wavelengths, which allows one to distinguish between excitation and emission light by mean of another optical filter. With a more sophisticated filter set, it is possible to distinguish between several excitation and emission bands, and thus between several fluorochromes, which allows observation of many different probes on the same strand.

Depending on the probes used, FISH can have resolution ranging from huge chromosomes or tiny (~100 kilobase) sequences. The probes can be quantified simply by counting dots or comparing color.

Allele-specific quantitative real time-PCR may also be used to identify a nucleic acid encoding a mutant EGFR protein (see, for e.g., Diagnostic Innovations DxS BCR-ABL T3151 Mutation Test Kit, and Singer et al., Methods in Molec. Biol. 181:145 (2001)). This technique utilizes Taq DNA polymerase, which is extremely effective at distinguishing between a match and a mismatch at the 3'-end of the primer (when the 3'-base is mismatched, no efficient amplification occurs). Using this technique, the 3'-end of the primer may be designed to specifically hybridize to a nucleic acid sequence that corresponds to a codon that encodes a mutant amino acid in an EGFR mutant, as described herein. In this way, the specific mutated sequences can be selectively amplified in a patient sample. This technique further utilizes a Scorpion probe molecule, which is a bifunctional molecule containing a PCR primer, a fluorophore, and a quencher. The fluorophore in the probe interacts with a quencher, which reduces fluorescence. During a PCR reaction, when the Scorpion probe binds to the amplicon, the fluorophore and quencher in the Scorpion probe become separated, which leads to an increase in fluorescence from the reaction tube. Any of the primers described herein may be used in allele-specific quantitative real time PCR.

A biological sample can be analyzed to detect a mutation in an EGFR gene, or expression levels of an EGFR gene, by methods that are known in the art. For example, methods such as direct nucleic acid sequencing, altered hybridization, aberrant electrophoretic gel migration, binding or cleavage mediated by mismatch binding proteins, single-strand conformational polymorphism (SSCP) analysis, or restriction fragment length polymorphism (RFLP) analysis of PCR products derived from a patient sample can be used to detect a mutation in an EGFR gene; ELISA can be used to measure levels of EGFR polypeptide; and PCR can be used to measure the level of an EGFR nucleic acid molecule.

Any of these techniques may be used to facilitate detection of a mutation in a candidate gene, and each is well known in the art; examples of particular techniques are described, without limitation, in Orita et al. (Proc. Natl. Acad. Sci. USA 86:2766 (1989)) and Sheffield et al, (Proc. Natl. Acad. Sci. USA 86:232 (1989)). Furthermore, expression of the candidate gene in a biological sample (e.g., a biopsy) may be monitored by standard Northern blot analysis or may be aided by PCR (see, e.g., Ausubel et al., Current Protocols in Molecular Biology, John Wiley & Sons, New York, N.Y. (1995); PCR Technology: Principles and Applications for DNA Amplification, H. A. Ehrlich, Ed., Stockton Press, NY; Yap et al., Nucl. Acids, Res. 19:4294 (1991)).

One skilled in the art may identify in a nucleic acid or protein sequence a residue (e.g., amino acid or nucleotide) or codon that corresponds to a residue or codon in wild-type EGFR or EGFR mutants using a number of sequence alignment software programs (e.g., NCBI BLAST website). Such software programs may allow for gaps in the alignment of the compared sequences. Using such software, one skilled in the art may identify a nucleotide, amino acid, or amino acid that corresponding to a specific nucleotide, amino acid, or codon in wild-type EGFR or EGFR mutants.

Levels of EGFR expression (e.g., DNA, mRNA, or protein) in a biological sample can be determined by using any of a number of standard techniques that are well known in the art or described herein. Exemplary biological samples include plasma, blood, sputum, pleural effusion, bronchoalveolar lavage, or biopsy, such as a lung biopsy and lymph node biopsy. For example, EGFR expression in a biological sample (e.g., a blood or tissue sample) from a patient can be monitored by standard northern blot analysis or by quantitative PCR (see, e.g., Ausubel et al., supra; PCR Technology: Principles and Applications for DNA Amplification, H. A. Ehrlich, Ed., Stockton Press, NY; Yap et al., Nucl. Acids. Res. 19:4294 (1991)).

Synthesis

Compounds of Formula (I) can be prepared using methods and materials analogous to those described in the art, e.g., as disclosed in detail in International patent applications WO 2004/080980, WO 2005/016894, WO 2006/021454, WO 2006/021457, WO 2009/143389, and WO 2009/126515. For instance, compounds of Formula (I) in which Re is H and $R^d$ is H, Cl, $CF_3$, or $CH_3$, can be synthesized from 2,4-dichloropyrimidine, 2,4,5-trichloropyrimidine, 2,4-dichloro-5-(trifluoromethyl)pyrimidine, or 2,4-dichloro-5-methylpyrimidine, respectively, as described in PCT Publication No. WO/2009/143389.

Compounds of Formula (I) in which $R^d$ and $R^e$, together with the pyrimidine ring atoms to which they are attached, form a 5- or 6-membered ring containing one or two heteroatoms can be synthesized as described in PCT Publication No. WO2009/126515.

Compounds of Formula (I) in which $U^1$ and $U^2$ are N can be synthesized, for example, using methods analogous to those described in Scheme A1.

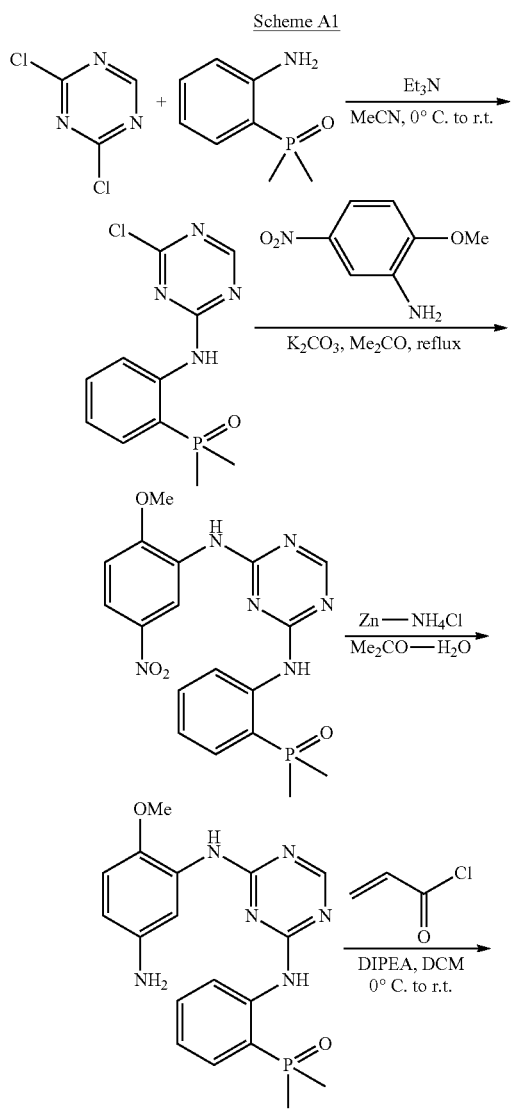

Scheme A1

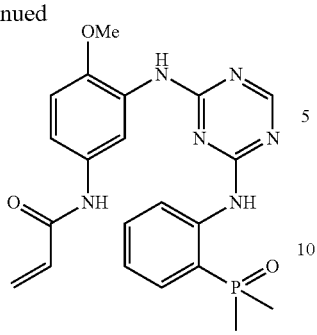

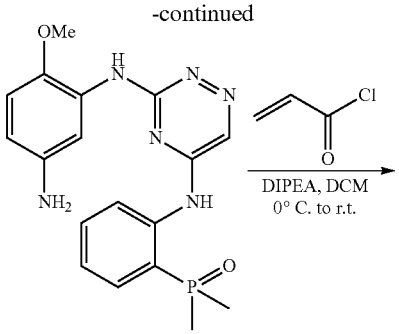

Compounds of Formula (I) in which $U^3$ is N, one of $U^1$ and $U^2$ is N, and the other is C—$R^d$ can be synthesized, for example, using methods analogous to those described in Scheme A2.

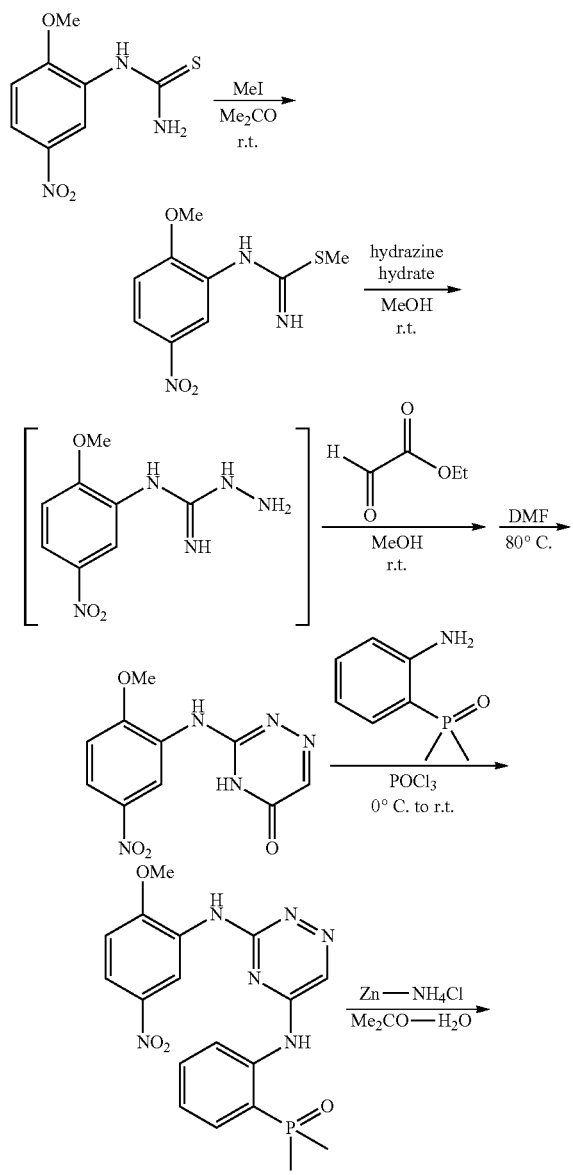

Further details are provided in the Examples.

Formulation

Compounds of Formula I can be Formulated into a pharmaceutical composition that comprises a compound of Formula I (as an active pharmaceutical ingredient) or a pharmaceutically acceptable salt thereof and a pharmaceutically acceptable excipient. As such, the present disclosure provides a pharmaceutical composition comprising a compound of Formula I or a pharmaceutically acceptable salt thereof and a pharmaceutically acceptable excipient.

Pharmaceutically acceptable compositions containing a compound of Formula I suitable for administration may be Formulated using conventional materials and methods, a wide variety of which are well known. Suitable dosage forms include those in solution, suspension or emulsion form, and solid oral dosage forms such as capsules, tablets, gel caps, caplets, etc. Methods well known in the art for making Formulations, including the foregoing unit dosage forms, are found, for example, in "Remington: The Science and Practice of Pharmacy" (20th ed., ed. A. R. Gennaro, 2000, Lippincott Williams & Wilkins).

Compounds of Formula (I) can be Formulated for any route of administration (e.g., orally, rectally, parenterally, intracisternally, intravaginally, intraperitoneally, topically (as by transdermal patch, powders, ointments, or drops), sublingually, bucally, as an oral or nasal spray) effective for use in the methods of the invention. For use in the methods of the invention, compounds of Formula (I) are preferably Formulated in dosage unit form for ease of administration and uniformity of dosage. For example, a compound of Formula (I) can be Formulated for as a capsule for oral administration containing nominally 10 mg, 50 mg, 100 mg, 150 mg, 250 mg, 500 mg, or any dosage amounts described herein as the free base or acid addition salt of the compound (e.g., the hydrochloride salt). The unit dosage forms of the invention can include a compound of the invention, or a salt thereof, Formulated with excipients, fillers, flow enhancers, lubricants, and/or disintegrants as needed. For example, a unit dosage form can include colloidal silicon dioxide (a flow enhancer), lactose anhydrous (a filler), magnesium stearate (a lubricant), microcrystalline cellulose (a filler), and/or sodium starch glycolate (a disintegrant). The compound of the invention and the inactive ingredients can be Formulated utilizing, for example, conventional blending, and encapsulation processes. Alternatively, compounds of Formula (I) are Formulated as described in PCT Publication Nos. WO2009/143389 and WO2009/126515.

Therapy

Compounds of Formula (I) can be useful for treating EGFR-driven cancers. In particular, the compounds can be useful for treating EGFR-driven cancers that express EGFR mutants and for treating EGFR-driven cancers that are refractory to TKI therapies (e.g., erlotinib or gefitinib).

Such cancers can include, among others, non-small cell lung cancer (NSCLS), including one or more of squamous cell carcinoma, adenocarcinoma, adenocarcinoma, bronchioloalveolar carcinoma (BAC), BAC with focal invasion, adenocarcinoma with BAC features, and large cell carcinoma; neural tumors, such as glioblastomas; pancreatic cancer; head and neck cancers (e.g., squamous cell carcinoma); breast cancer; colorectal cancer; epithelial cancer, including squamous cell carcinoma; ovarian cancer; prostate cancer; adenocarcinomas; and including cancers which are EGFR mediated.

The present invention is based upon the discovery that compounds of Formula (I) can be used to treat EGFR-driven cancers, EGFR-driven cancers that express EGFR mutants, and for treating EGFR-driven cancers that are refractory to TKI therapy, such as erlotinib or gefitinib. Compounds of Formula (I) can also be used in a maintenance role to prevent recurrence of cancer in patients in need of such a treatment.

The effective systemic dose of a compound of Formula (I) will typically be in the range of an average daily dose of from 10 mg to 2,000 mg of the compound per kg of patient body weight, administered in single or multiple doses. Generally, a compound of the invention may be administered to patients in need of such treatment in a daily dose range of about 50 to about 2,000 mg per patient. Administration may be once or multiple times daily, weekly (or at some other multiple-day interval) or on an intermittent schedule. For example, the compound may be administered one or more times per day on a weekly basis (e.g. every Monday) indefinitely or for a period of weeks, e.g. 4-10 weeks. Alternatively, it may be administered daily for a period of days (e.g. 2-10 days) followed by a period of days (e.g. 1-30 days) without administration of the compound, with that cycle repeated indefinitely or for a given number of repetitions, e.g. 4-10 cycles. As an example, a compound of the invention may be administered daily for 5 days, then discontinued for 9 days, then administered daily for another 5 day period, then discontinued for 9 days, and so on, repeating the cycle indefinitely, or for a total of 4-10 times.

When a TKI (e.g., erlotinib or gefitinib) is used in combination with a compound of Formula (I), each component of the combination therapy may be administered at their monotherapy dosing levels and schedules. For example, erlotinib has been administered orally for the treatment of NSCLC at 150 mg daily and of pancreatic cancer at 100 mg daily. In another example, gefitinib has been administered orally for the treatment of NSCLC at 250 mg daily.

The effective systemic dose of a compound of the invention will typically be in the range of an average daily dose of from 10 mg to 2,000 mg of the compound per kg of patient body weight, administered in single or multiple doses. Generally, a compound of the invention may be administered to patients in need of such treatment in a daily dose range of about 50 to about 2,000 mg per patient. Administration may be once or multiple times daily, weekly (or at some other multiple-day interval) or on an intermittent schedule. For example, the compound may be administered one or more times per day on a weekly basis (e.g. every Monday) indefinitely or for a period of weeks, e.g. 4-10 weeks. Alternatively, it may be administered daily for a period of days (e.g. 2-10 days) followed by a period of days (e.g. 1-30 days) without administration of the compound, with that cycle repeated indefinitely or for a given number of repetitions, e.g. 4-10 cycles. As an example, a compound of the invention may be administered daily for 5 days, then discontinued for 9 days, then administered daily for another 5 day period, then discontinued for 9 days, and so on, repeating the cycle indefinitely, or for a total of 4-10 times.

Alternatively, a TKI (e.g., erlotinib or gefitinib) is used in combination with a compound of Formula (I) with a reduced dosing level in one or both components.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

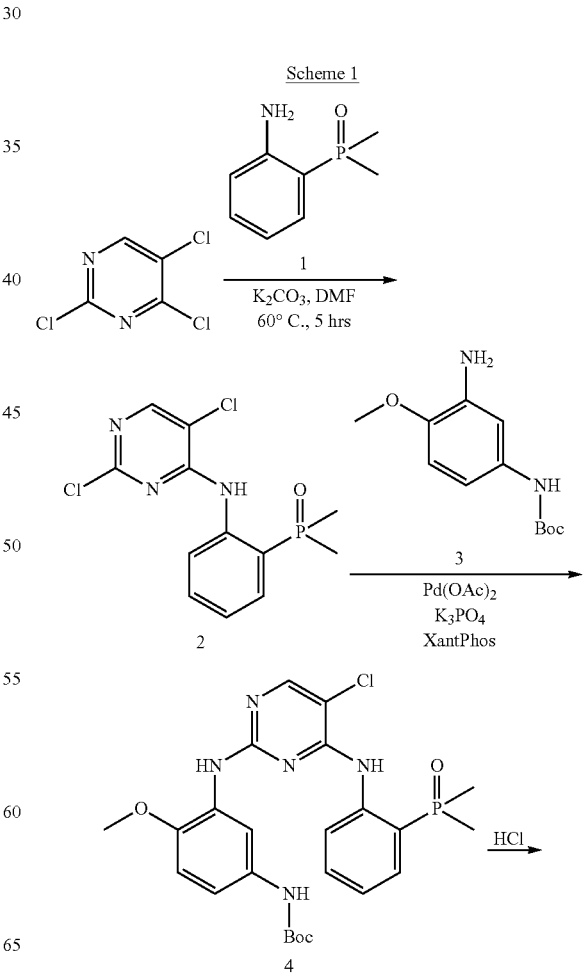

Scheme 1

-continued

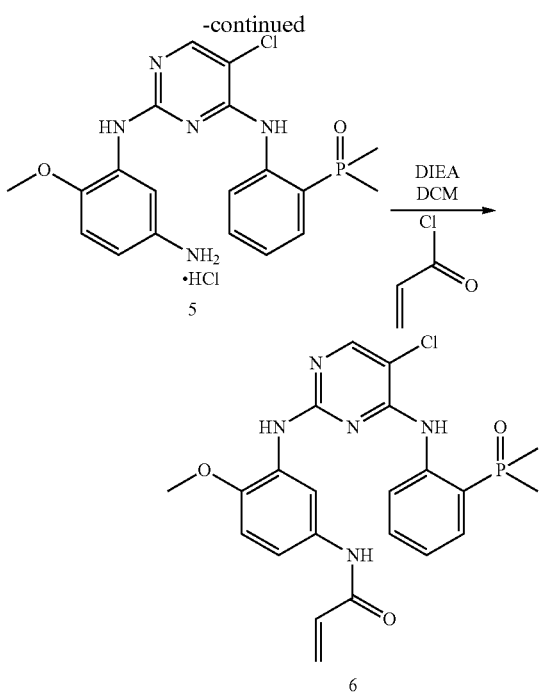

Step 1: Synthesis of Compound 1

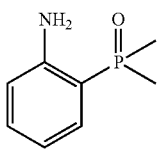

To a solution of 2-iodoaniline (1.0 eq) and dimethylphosphine oxide (1.1 eq) in DMF were added potassium phosphate (1.1 eq) and palladium acetate/Xantphos (catalytic). The reaction was stirred at 150° C. for 3 hours and cooled to room temperature. The solvent was evaporated and the residue was worked up with DCM/water. The crude product was purified with a column (EtOAc/MeOH 10:1) to give 1 as a brown solid (80% yield).

Step 2: Synthesis of 2

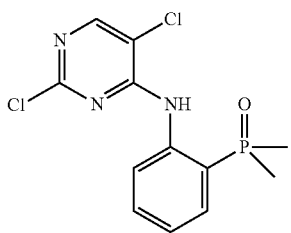 [SMILES: CP(C)(=O)c1ccccc1Nc1nc(Cl)ncc1Cl]

2,4,5-Trichloropyrimidine (1.57 eq), 1 (1.0 eq), and potassium carbonate (3.14 eq) in DMF were stirred at 60° C. for 5 hours and then cooled to room temperature. The mixture was filtered and the filtrate was concentrated. The residue was purified by column chromatography (ISCO machine) (DCM/MeOH 20:1) to give 2 as a yellow solid (61% yield).

Step 2a: Synthesis of 8 and 3

Scheme 1a

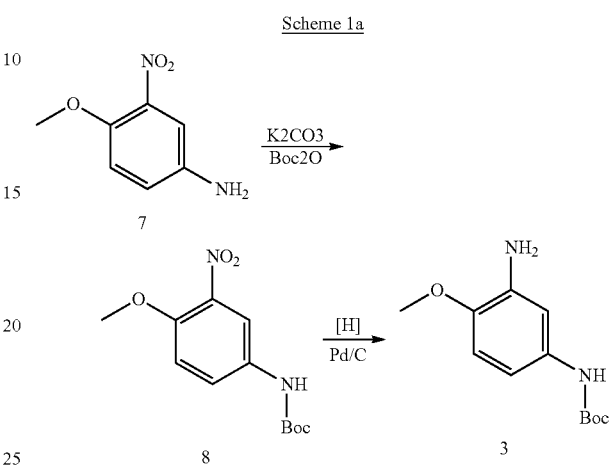

A suspension of 10 g (59.5 mmol, 1.0 eq) of 4-methoxy-3-nitroaniline in 65 mL of dioxane and 65 mL of water was adjusted to pH 12 with 40% NaOH, and then $Boc_2O$ (26 g, 119.1 mmol, 2.0 eq) was added in 3 portions under ice bath. The reaction was stirred at room temperature overnight. After standing, the mixture was filtered to give a yellow solid, 15 g, in 95% yield.

Compound 8 (6 g, 22.4 mmol) was dissolved in 55 mL of ethyl acetate and Pd/C (10%, wet, 0.5 g) was added. The reduction was shaken at room temperature under H2 (30 psi) for 1 hr and filtered. The filtrate was evaporated to a tan solid, 5.4 g, in a quantitative yield.

Step 3: Synthesis of 4

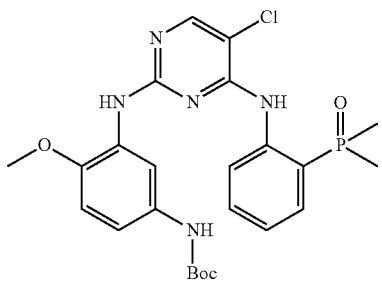

A suspension of 2 (1.27 g, 4.0 mmol), 3-Boc-amino-5-methoxyaniline(965 mg, 4.0 mmol), palladium acetate (133 mg, 0.59 mmol), XantPhos (352 mg, 0.61 mmol) and potassium phosphate (1.4 g, 6.6 mmol) in anhydrous DMF (35 mL) was heated at 120° C. overnight. After the reaction was cooling to room temperature, ethyl acetate was added to dilute the reaction and the content was filtered through celite. Solvent was removed under vacuum. The residue was purified by flash column chromatography on silica gel to give pure product 1.3 g (yield 62%) as a tan solid.

Step 4: Synthesis of 5

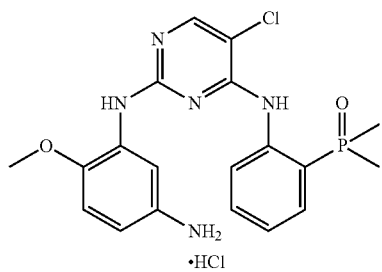
·HCl

HCl/dioxane (4N, 4 mL) was added to a solution of compound 4 (440 mg, 0.85 mmol) in MeOH (4 mL). The reaction mixture was stirred at room temp overnight. White precipitate was filtered and dried to give the title product as a white solid (339 mg, Yield 81%).

Step 5: Synthesis of 6

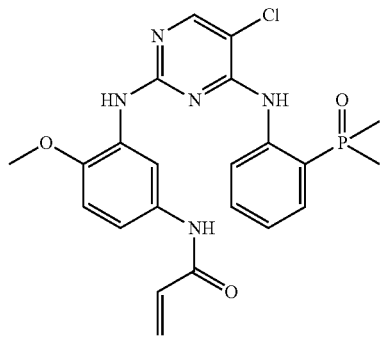

Compound 5 (100 mg, 0.15 mmol) was dissolved in CH₂Cl₂ (1.6 mL) and DIEA(174 μL, 1 mmol). The solution was cooled in an ice bath. Aryloyl chloride (13 ul, 0.165 mmol) was added dropwise. The content was stirred at room temp for an hour. Solvent was removed in vacuo and the residue was purified by a prep-TLC plate(7.5% MeOH/DCM) to give final product as a tan solid (24 mg, yield 34%).

Scheme 2

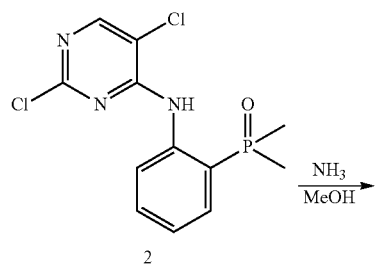

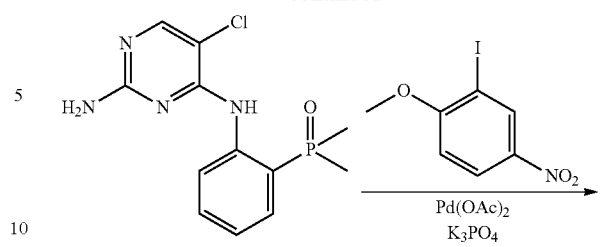

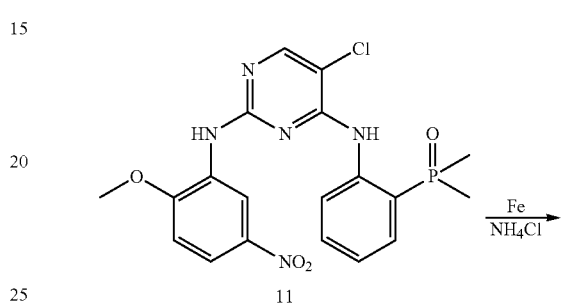

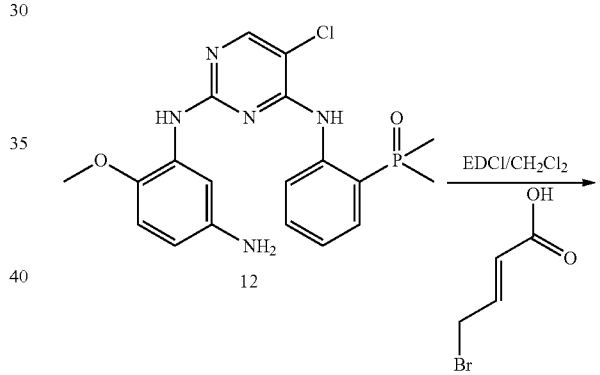

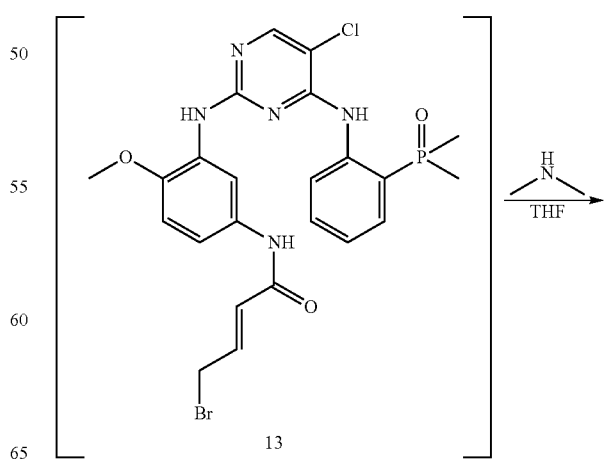

Step 1: Synthesis of 10

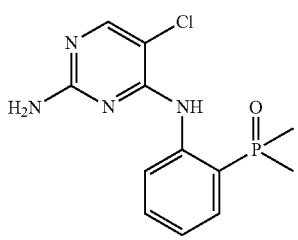 [SMILES: CP(C)(=O)c1ccccc1Nc1nc(N)ncc1Cl]

Compound 2 (2 g, 6.3 mmol) was dissolved in NH$_3$/MeOH(7N, 20 mL) in a sealed tube and the content was heated at 100° C. for 3 days. The volatile was evaporated and the residue partitioned between EtOAc/H2O, the organic layer was separated and aqueous was extracted with EtOAc(2x). Combined organic dried(Na$_2$SO$_4$). After concentration, the residue was column purified on Silica gel (10% MeOH/DCM) to give the product as a white solid(1.1 g, yield 57%).

Step 2: Synthesis of 11

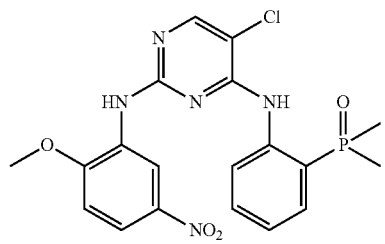

Compound 10 (908 mg, 3.0 mmol) and 2-iodo-4-nitroanisole (963 mg, 4.15 mmol) were dissolved in 25 mL anhydrous DMF in a sealed tube and was added Pd(OAc)$_2$ (86 mg, 0.38 mmol), XantPhos (227 mg, 0.30 mmol), K$_3$PO$_4$ (921 mg, 4.3 mmol). The content was heated at 120° C. overnight. After cooling to the room temp, EtOAc was added and the mixture was filtered through celite, washed with more EtOAc. Combined filtrate was conc in vacuo, and the residue was purified by CombiFlash(MeOH/DCM), The product (476 mg, 35.5%) was obtained as a tan solid.

Step 3: Synthesis of 12

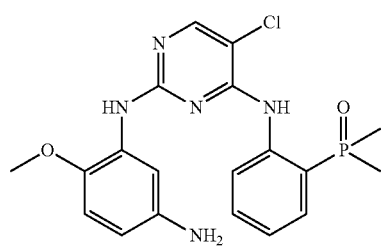

Compound 11 (476 mg, 1.1 mmol) was dissolved in THF(18 mL)/H$_2$O (13 mL) and was added Fe(300 mg) and NH$_4$Cl(300 mL). The mixture was heated at 65° C. overnight. The liquid was decanted and the solid residue was washed with more THF, Combined solution was conc to give a residue. The residue was dissolved in DCM and filtered through cotton. The solution again is conc to give crude product 480 mg.

Step 4: Synthesis of 14

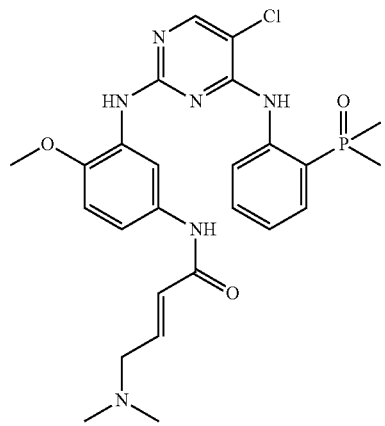

Compound 12 (125.4 mg, 0.3 mmol), 4-bromocrotonoic acid (49 mg, 0.3 mmol) was dissolved in 3 mL dry DCM. EDCl(63 mg, 0.33 mmol) was then added. The mixture was stirred at room temperature for 2 hrs. Volatiles were removed in vacuo and THF (3 mL) was added, followed by dimethylamine/H$_2$O solution (40%, 0.5 mL, 4.0 mmol). The mixture was stirred at room temperature for another 2 hrs. Solvent was removed in vacuo and the residue was purified by prep-TLC (10% MeOH/DCM) to give the final product as a tan solid (48 mg, yield 30.2%).

-continued

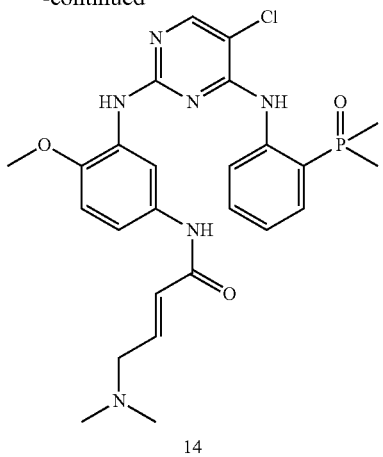

14

Scheme 5

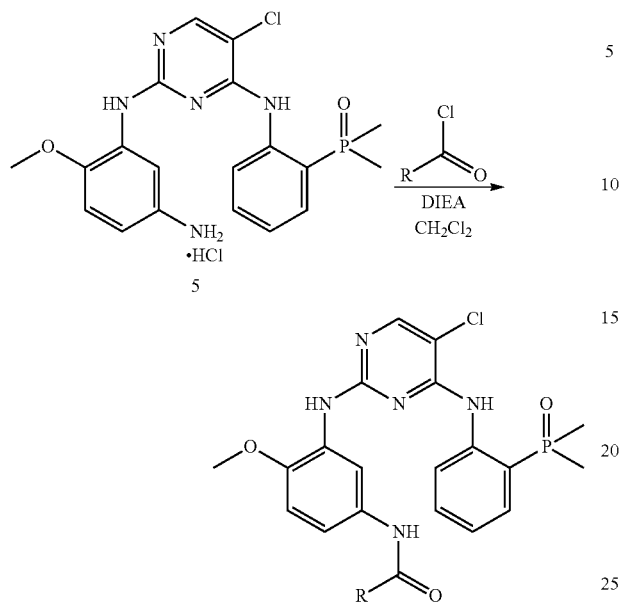

General procedures: compound 5 (100 mg, 0.15 mmol) was dissolved in CH$_2$Cl$_2$ (1.6 mL) at 0° C. and DIEA (174 μL, 1 mmol) was added. Acid chloride (13 μl, 0.165 mmol, 1.1 eq) was added dropwise. The content was stirred at room temp for an hour. Solvent was removed in vacuo and the residue was purified by a prep-TLC plate(10% MeOH/DCM), the corresponding bands were collected to give final products.

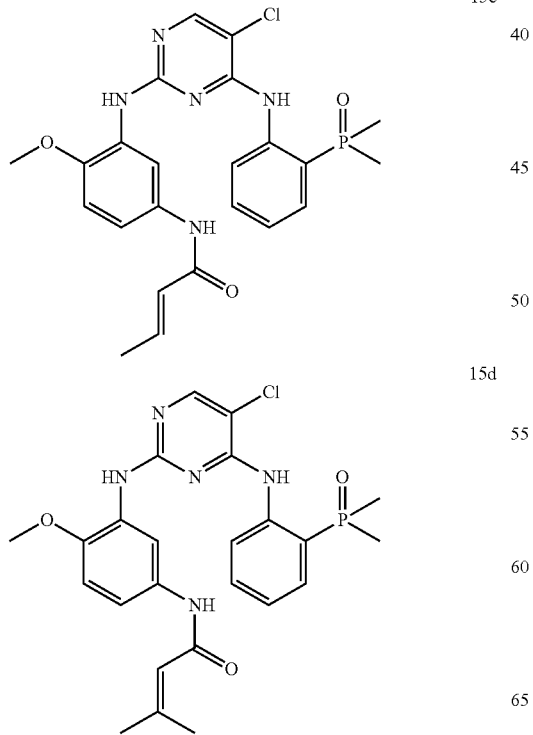

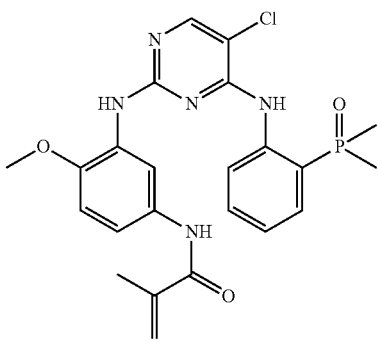

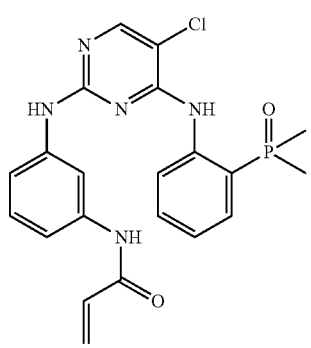

Scheme 6

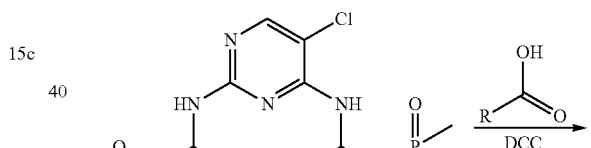

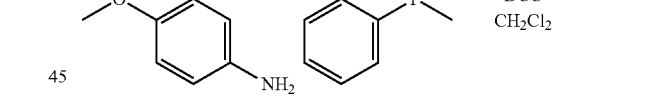

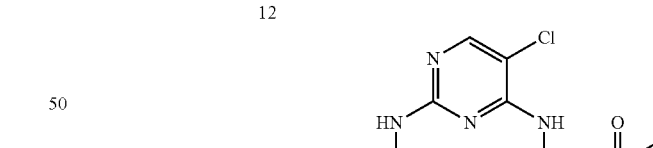

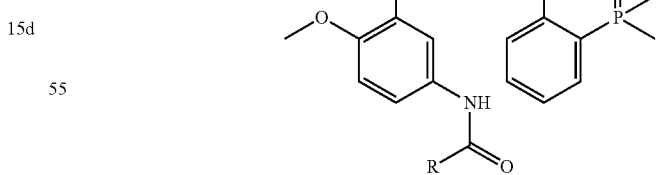

General procedures: compound 12 (84 mg, 0.20 mmol), respective acid (0.27 mmol, 1.35 eq.) were dissolved in dry DMF (2.0 mL). DCC (56 mg, 0.27 mmol, 1.35 eq) was added. The content was stirred at room temp overnight. Solvent was removed in vacuo and the residue was purified by a prep-TLC plate (6.5% MeOH/DCM), the corresponding bands were collected to give final products.

15g

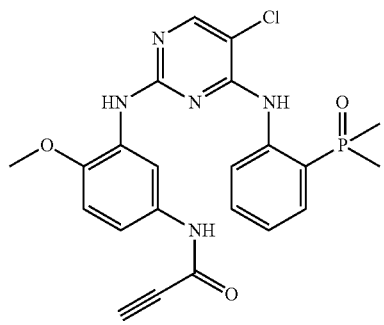

15h

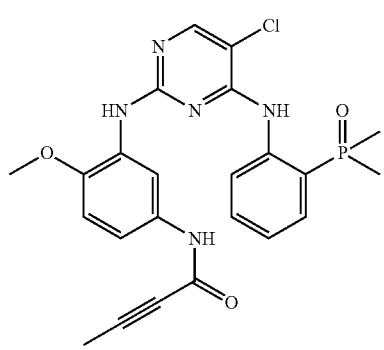

Scheme 7

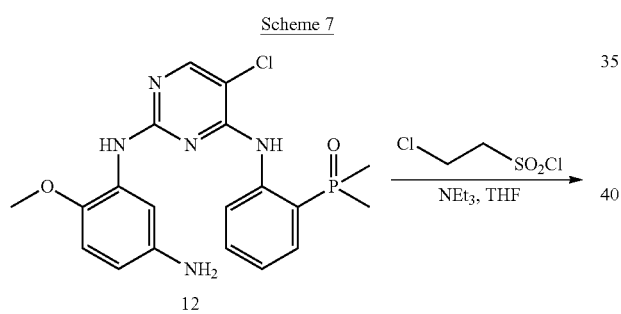

16

Scheme 8

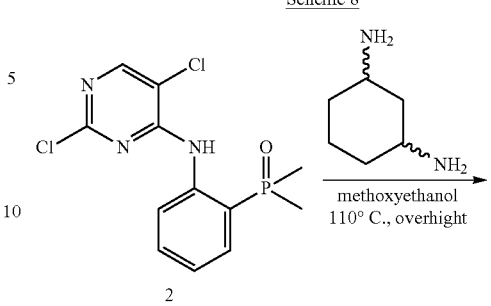

2

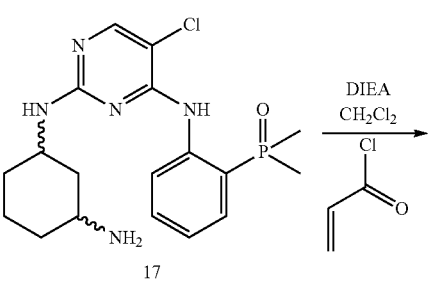

17

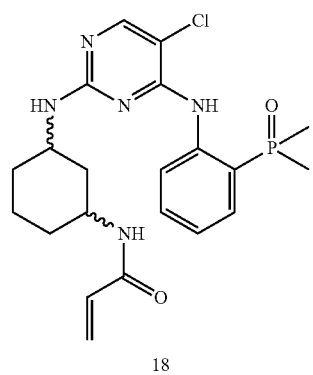

18

Step 1: Synthesis of 17

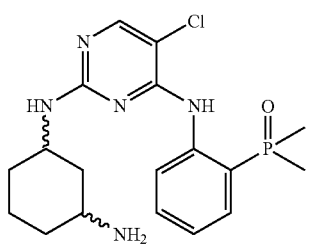 [SMILES: CP(C)(=O)c1ccccc1Nc1nc(NC2CCCC(N)C2)ncc1Cl]

Compound 12 (200 mg, 0.48 mmol), and NEt₃ (344 µL) was dissolved in 5 mL THF at room temperature, 2-chloroethylenesulfonyl chloride (115 µL, 1.1 mmol) was added and the content was stirred at room temperature for 1 hr. The volatile was removed in vacuo and the residue was purified on prep-TLC (2×) (7.5% MeOH/DCM). The product was a tan solid (56 mg, yield 23%).

Compound 2 (158 mg, 0.50 mmol), 1,3-diaminocyclohexane (57.1 mg, 0.5 mmol) was dissolved in methoxyethanol (1.6 mL) in a sealed tube and HCl/EtOH (200 µl) was added. The content was heated at 110° C. overnight. Solvent was removed in vacuo and the residue was purified by 2 prep-TLC plate (360 mL DCM/24 mL MeOH/12 mL 7N NH₃.MeOH) to give final product as a light colored solid (134 mg, yield 68%).

55
Step 2: Synthesis of 18

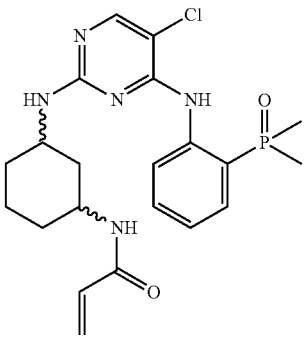 [SMILES: C=CC(=O)NC1CCCC(Nc2ncc(Cl)c(Nc3ccccc3P(C)(C)=O)n2)C1]

Compound 17 (70 mg, 0.177 mmol) was dissolved in CH$_2$Cl$_2$ (1.6 mL) at 0° C. and DIEA (174 µL, 1 mmol) was added. Aryloyl chloride (15 µl, 0.185 mmol) was added dropwise. The content was stirred at room temp for an hour. Solvent was removed in vacuo and the residue was purified by a prep-TLC plate (10% MeOH/DCM) to give two final product as tan solids (trans 29.4 mg, yield 43.8%; cis 14.1 mg, 21.4%).

Scheme 9

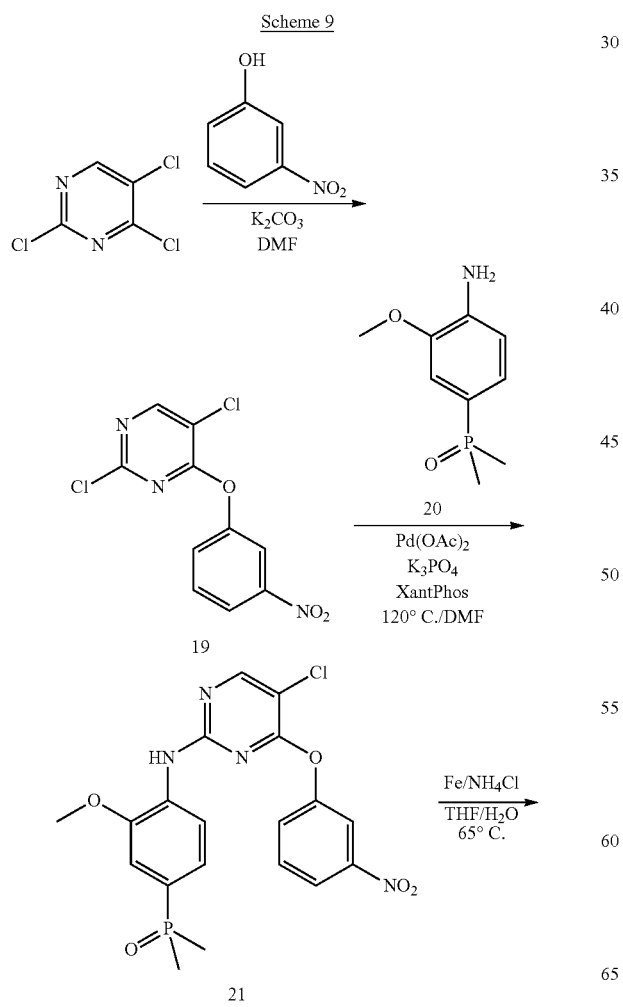

56

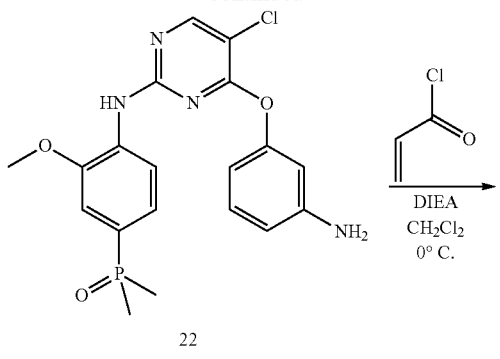

Step 1: Synthesis of 21

Compound 19 (154 mg, 0.54 mmol) and compound 20 (107 mg, 0.54 mmol) were dissolved in 4 mL anhydrous DMF in a sealed tube and was added Pd(OAc)$_2$ (14 mg, 0.062 mmol), XantPhos (37 mg, 0.064 mmol), and K$_3$PO$_4$ (150 mg, 0.71 mmol). The content was heated at 120° C. overnight. After cooling to the room temp, EtOAc was added and the mixture was filtered through celite, washed with more EtOAc. Combined filtrate was conc in vacuo, and the residue was purified by CombiFlash (MeOH/DCM). The product 21 (140 mg, yield 58%) was obtained as an orange solid.

Step 2: Synthesis of 22

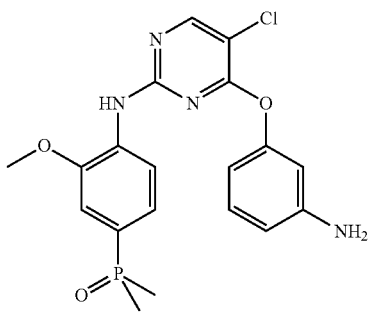 [SMILES: COc1cc(P(C)(C)=O)ccc1Nc1ncc(Cl)c(Oc2cccc(N)c2)n1]

Compound 21 (140 mg, 0.31 mmol) was dissolved in THF/water (3 mL/3 mL) mixture and Fe (75 mg), NH$_4$Cl (75 mg,) was added. The content was heated at 65° C. overnight. After cooling to room temp., the mixture was filtered through cotton. The filtrate was concentrated and the residue was dissolved in 7.5% MeOH/DCM and was filtered through cotton again. After solvent was removed in vacuo, the crude product was obtained as a tan solid (126 mg, yield 96%).

Step 3: Synthesis of 23

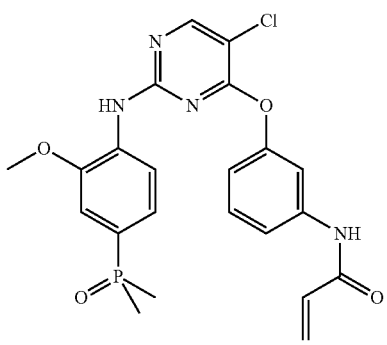 [SMILES: C=CC(=O)Nc1cccc(Oc2nc(Nc3ccc(P(C)(C)=O)cc3OC)ncc2Cl)c1]

Compound 22 (163 mg, 0.15 mmol) was dissolved in CH$_2$Cl$_2$ (1.6 mL) at 0° C. and DIEA (174 μL, 1 mmol) was added. Aryloyl chloride (13 μl, 0.165 mmol) was added dropwise. The content was stirred at room temp for an hour. Solvent was removed in vacuo and the residue was purified by a prep-TLC plate (7.5% MeOH/DCM) to give final product as a tan solid (40 mg, yield 56%).

Scheme 10

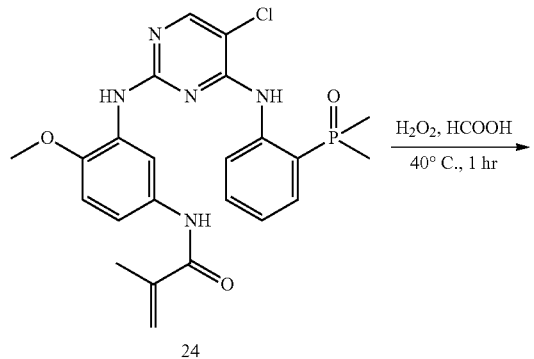

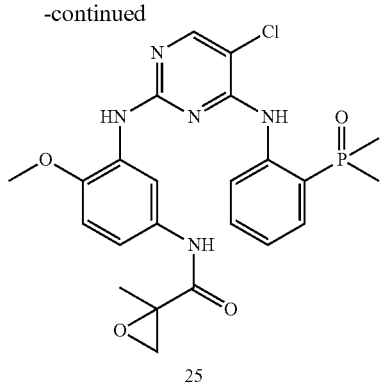

Procedure: compound 24 (49 mg, 0.1 mmol) was dissolved in 0.75 mL HCOOH and H$_2$O$_2$ (37%, 0.4 mL) was added. The content was heated at 40° C. for 1 hr. The volatiles were removed by N$_2$ blow and the residue was purified by prep-TLC (7.5% MeOH/DCM) to give the product as a tan solid (13.7 mg, yield 27%).

Scheme 12

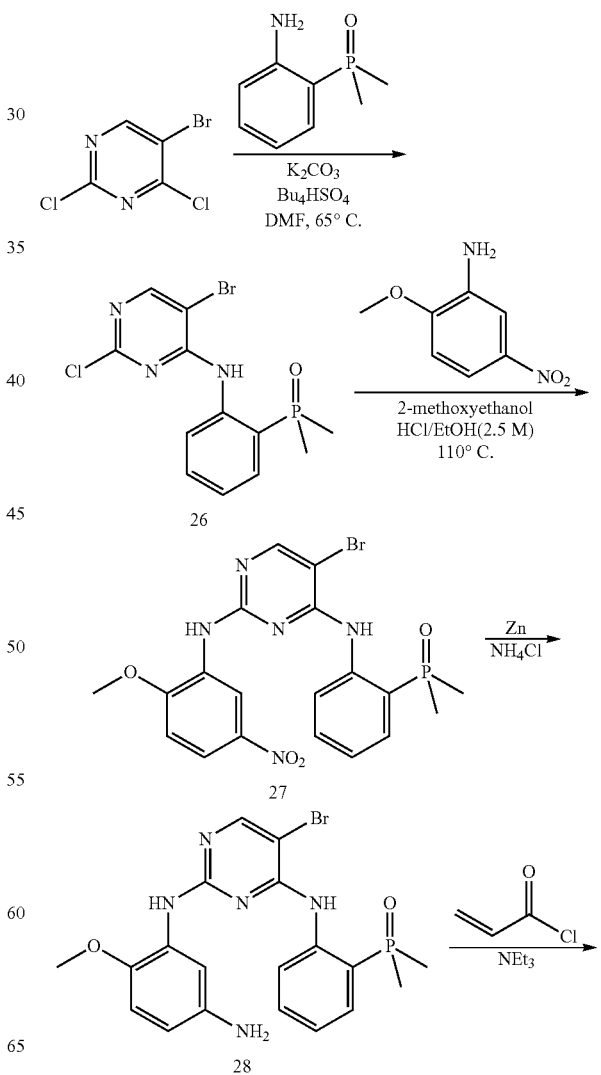

59
-continued

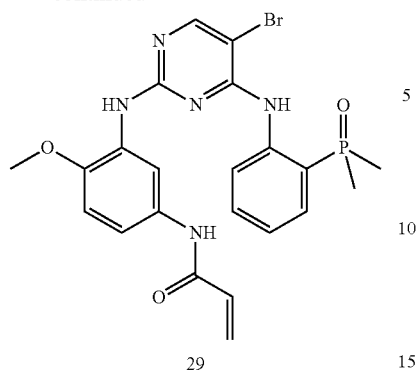

29

Step 1: Synthesis of 26

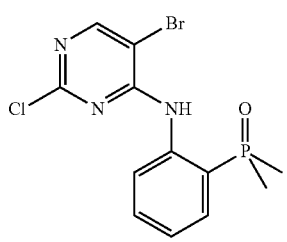 [SMILES: CP(C)(=O)c1ccccc1Nc1nc(Cl)ncc1Br]

A suspension of 5-bromo-2,4-dichloropyrimidine (2.8 g, 12.3 mmol, 1.0 eq), 2-dimethylphosphonylbenzeneamine (2.08 g, 12.3 mmol, 1.0 eq), K₂CO₃ (2.04 g, 14.8 mmol, 1.2 eq), and nBu₄HSO₄ (417 mg, 1.23 mmol, 0.1 eq) in 50 mL of DMF was stirred at 65° C. for 7 hours and cooled to room temperature. After a filtration, the filtrate was evaporated to an oil, which was chromatographed (DCM/MeOH 20:1) to give a yellow solid, 2.9 g, in 66% yield.

Step 2: Synthesis of 27

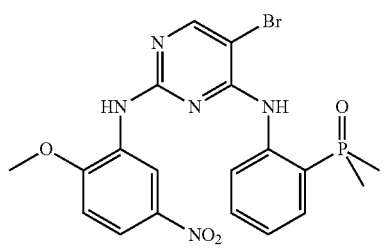

A mixture of 7 (1.42 g, 3.938 mmol, 1.0 eq), 2-methoxy-5-nitroaniline (927 mg, 5.513 mmol, 1.4 eq), and 2.5 M HCl/EtOH (6 mL) in 35 mL of 2-methoxyethanol was sealed and stirred at 110° C. for 5 hrs and cooled to room temperature. The mixture was worked up with sat. Na₂CO₃/DCM and purified with isco (MeOH/DCM 1:20) to give a yellow foam on oil pump, 520 mg, in 27% yield.

60

Step 3: Synthesis of 28

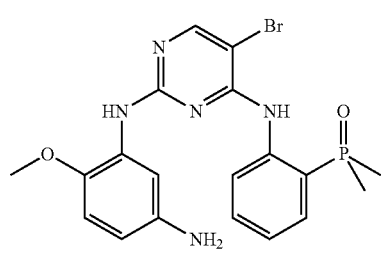

A mixture of the 27 (250 mg, 0.5 mmol), Zn (150 mg) and NH₄Cl (150 mg) in 2 mL of THF/H2O (5:1) was stirred at room temperature for 1.5 hours and filtered. The filtrate was worked up with saturated Na₂CO₃ and DCM. The crude product was purified with preparation plates to afford a yellow solid, 143 mg, in 61% yield.

Step 4: Synthesis of 29

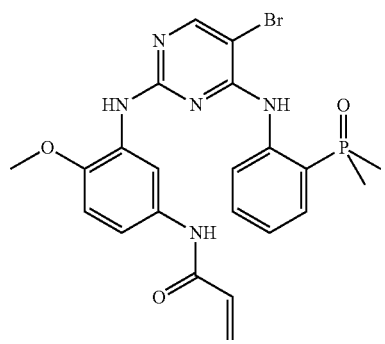

The aniline (280 mg, 0.606 mmol) was dissolved in 8 mL of DCM and 0.3 mL of triethylamine was added. The mixture was cooled to −35° C. and acryloyl chloride (54.8 mg, 49 μl, 0.606 mmol, 1.0 eq) was added in portions. The reaction was stirred around −30° C. for 15 min and quenched with saturated Na₂CO₃. The mixture was worked up with sat. Na₂CO₃/DCM and purified with preparation plates to give a light brown solid, 205 mg, in 66% yield.

Scheme 13

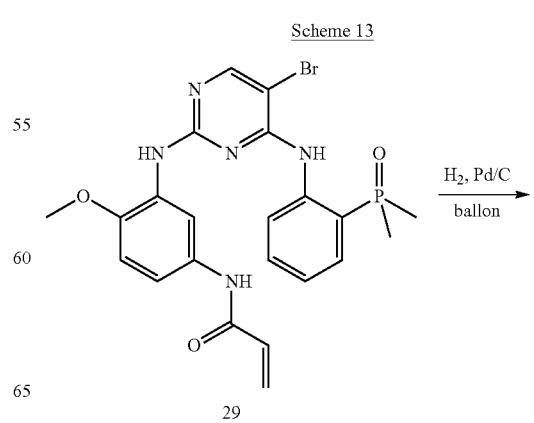

29

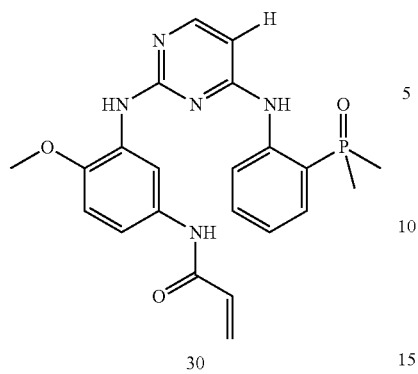

30

Procedure: 35 mg (0.0678 mmol) of 29 was dissolved in 1.5 mL of EtOH and Pd/C (10%, wet, 5 mg) was added. The mixture was stirred under H2 balloon at room temperature overnight. The mixture was filtered and purified with a preparation plate to afford a white solid 30, 8.9 mg, in 30% yield.

Scheme 14

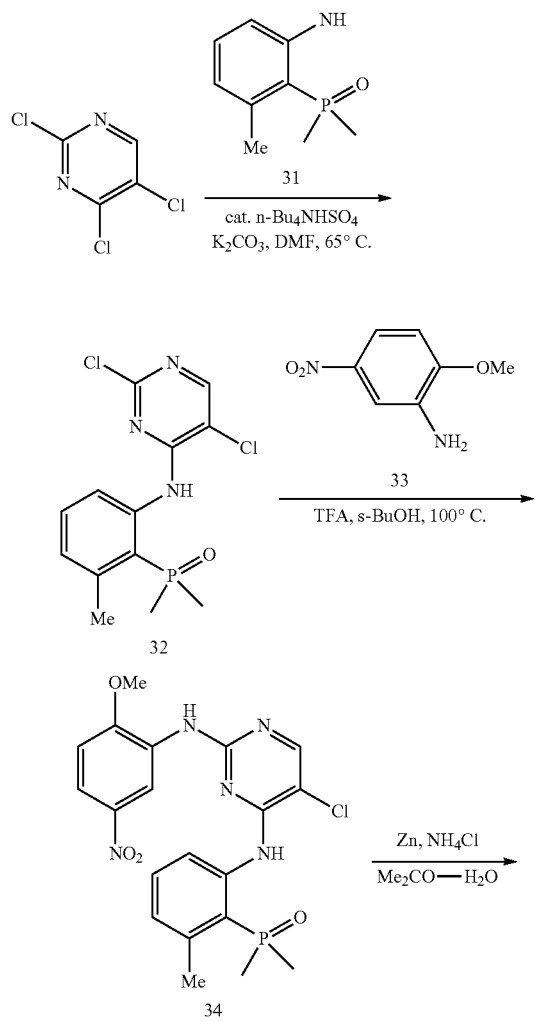

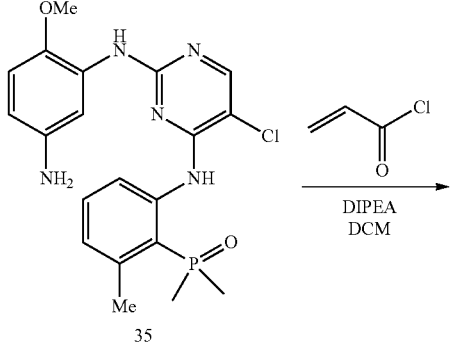

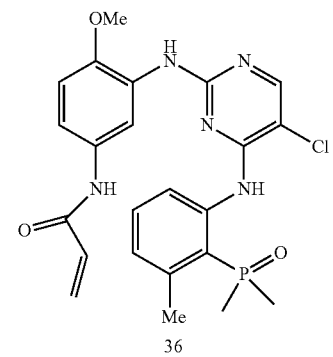

36

Step 1: Compound 31 was prepared according to the procedure described for the synthesis of compound 1 in Example 1, using 2-iodo-3-methylaniline instead of 2-iodoaniline as the starting material. A suspension of 31 (0.53 mmol), 2,4,5-trichloropyrimidine (1.0 eq), potassium carbonate (1.2 eq), and tetrabutylammonium hydrogensulfate (0.1 eq) in DMF was stirred at 65° C. for 18 hrs. Upon cooling the reaction mixture was filtered and the filtrate was concentrated. The residue was taken up into a mixture of EtOAc and water. After extraction with EtOAc (3×), the combined organic phases were concentrated to give essentially pure material which was used directly in next step reaction.

Step 2: A solution of 32 (0.82 mmol), 2-methoxy-5-nitroaniline 33 (1 eq) and TFA (3 eq) in 2-BuOH (3 mL) was heated at 100° C. for 18 hrs. Upon cooling EtOAc and aq. NaHCO$_3$ were added to the reaction mixture. Extraction (3×) and concentration of combined extracts gave a solid which was purified on silica gel column (ISCO machine) with 10% MeOH in CH$_2$Cl$_2$ as the eluents, furnishing 34 as a brownish solid (55%).

Step 3: To a suspension of 34 (0.46 mmol) and zinc powder (6 eq) in acetone (9 mL) and water (1 mL) was added ammonium chloride (10 eq) at 0° C. After the mixture was stirred at room temperature for 30 min, HPLC indicated a complete conversion. Acetone was removed on rotavap and the residue was suspended in DCM and water. Filtration was carried out and the filtrate was extracted with DCM. Concentration of combined organic layers gave crude aniline 35, which was used in the next step without purification.

Step 4: To a solution of aniline 35 (0.43 mmol) and N,N-diisopropylethylamine (1.1 eq) in DCM (2 mL) was added acryloyl chloride (1.05 eq) at 0° C. After the mixture was stirred at room temperature overnight, the volatile components were removed on rotavap. The residue was purified on silica gel column with 3% MeOH in DCM as eluents, furnishing amide 36 as beige solid (48 mg, 21%).

Scheme 16

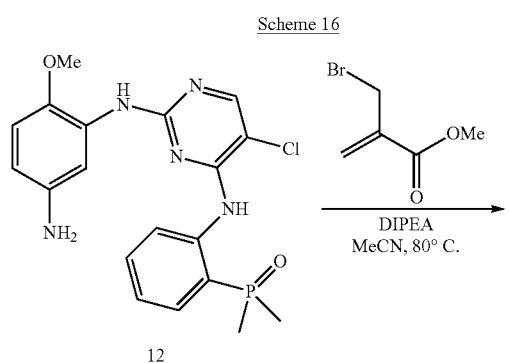

12

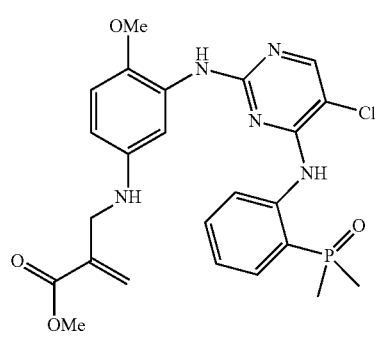

38

A solution of 12 (125 mg, 0.3 mmol), methyl 2-(bromomethyl)acrylate (1.3 eq) and N, N-diisopropylethylamine (1.3 eq) in MeCN (5 mL) was heated at 80° C. for 2 hrs. LC-MS indicated both mono- and bis-alkylation products were formed in almost equal amount, with small percentage of tris-alkylation products. The mixture was subjected to a prep-HPLC (reverse phase) purification and then a pre-TLC purification (normal phase silica gel, 10% MeOH in DCM as eluents), furnishing the title compound as a tan solid (15 mg, 10%).

Scheme 17

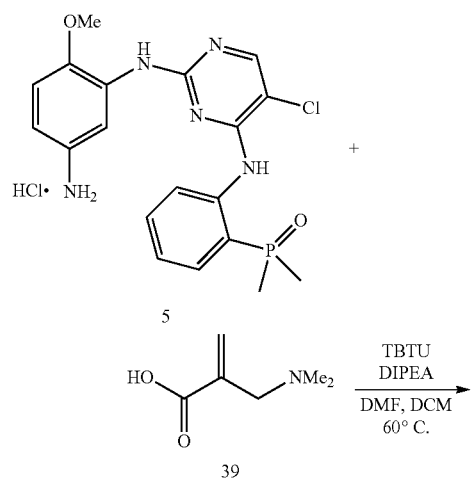

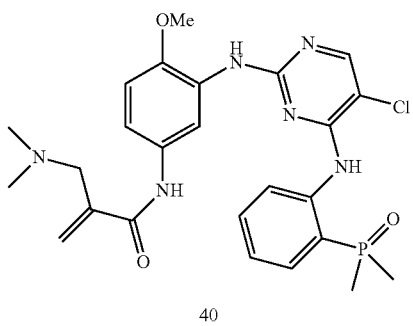

40

2-(Dimethylaminomethyl)acrylic acid 39 was prepared according to a literature procedure (*Synth. Comm.* 1995, 25, 641). To a solution of 39 (65 mg, 0.5 mmol), coupling reagent TBTU (1.2 eq) and N, N-diisopropylethylamine (3.0 eq) in DMF (5 mL) and DCM (20 mL) was added 5 (1 eq). After the mixture was stirred at room temperature overnight, the volatile components were removed on rotavap and the residue was purified by reverse phase prep-HPLC, furnishing the title compound as a tan solid (23 mg, 9%).

Scheme 18

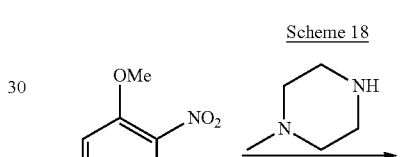

41

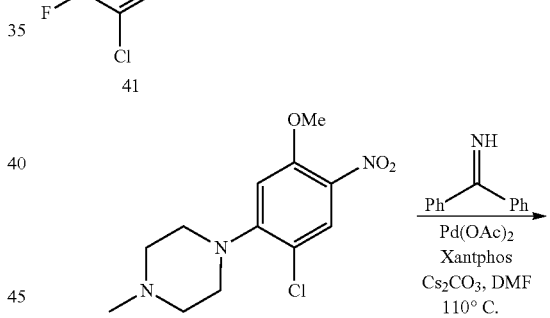

42

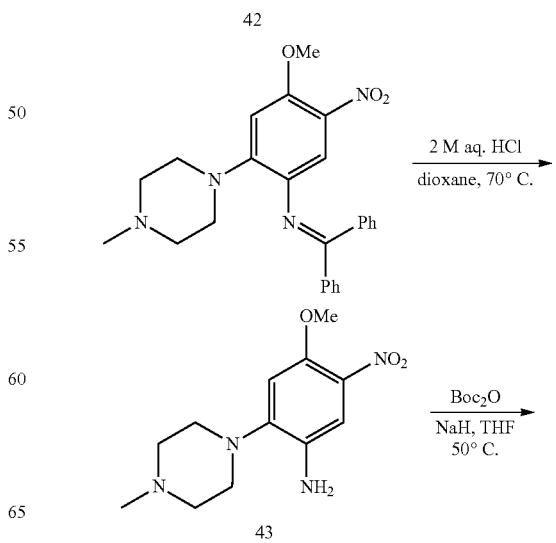

43

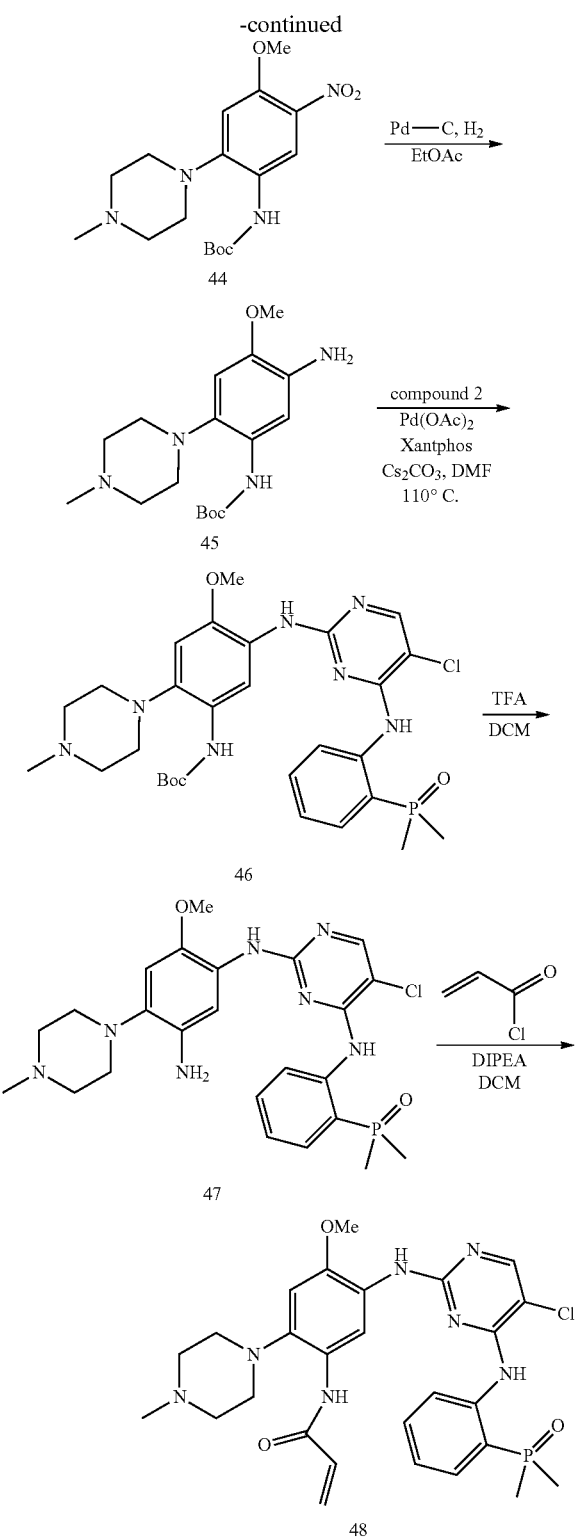

and water. Extraction and concentration followed by silica gel column chromatograph (10% MeOH in DCM as eluents) furnished 42 (1.26 g, 91%).

Steps 2 and 3: A degassed suspension of 42 (0.96 g, 3.4 mmol), benzophenone imine (1.5 eq), palladium acetate (0.1 eq), xantphos (0.2 eq) and cesium carbonate (1.6 eq) in DMF (20 mL) was heated at 110° C. overnight. Upon cooling the reaction mixture was filtered and the filtrate was concentrated. The solid residue was dissolved in dioxane and 2M aq. HCl (1:1, 40 mL) and then heated at 70° C. for 2 hrs. Upon removing dioxane on rotavap, the water layer was washed with DCM and then basified with aq. $NaHCO_3$. Extraction and concentration followed by silica gel column chromatograph (10% MeOH in DCM as eluents) furnished 43 (0.41 g, 45%).

Step 4: To a solution of 43 (0.38 g, 1.42 mmol) in THF (15 mL) was added NaH (2 eq.) under $N_2$ at 0° C. in multiple portions. After bubbles of $H_2$ were no longer observed, $Boc_2O$ (4 eq.) was added. The resulting reaction mixture was heated at 50° C. and then refluxed for 2 hrs. The reaction was quenched with MeOH. Usual workup followed by silica gel column chromatograph (5% MeOH in DCM as eluents) furnished 44 (0.46 g, 88%).

Step 5: With EtOAc as the solvent 44 (0.46 g) was hydrogenated under 50 psi to afford 45 (0.42 g, 99%). Upon removing the solvent, the crude material was used directly in the next step.

Step 6: A degassed suspension of 45 (0.42 g, 3.4 mmol), 2 (1.5 eq), palladium acetate (0.1 eq), xantphos (0.2 eq) and cesium carbonate (1.3 eq) in DMF (10 mL) was heated at 110° C. for 48 hrs. Usual workup followed by silica gel column chromatograph (5% MeOH in DCM as eluents) furnished 46 (0.49 g, 64%).

Step 7: To a solution of 46 in DCM was added excessive TFA. After the mixture was stirred at room temperature for 2 hrs, the volatile components were removed on rotavap. The residue was dissolved in EtOAC and the solution was basified with aq. $NaHCO_3$. Extraction and concentration gave 47 as tan solid.

Step 8: Crude 47 (100 mg) was converted to 48 by using the procedure described in Example 14, step 4. The final product was purified by reverse phase prep-HPLC (10.4 mg, 9%).

Scheme 19

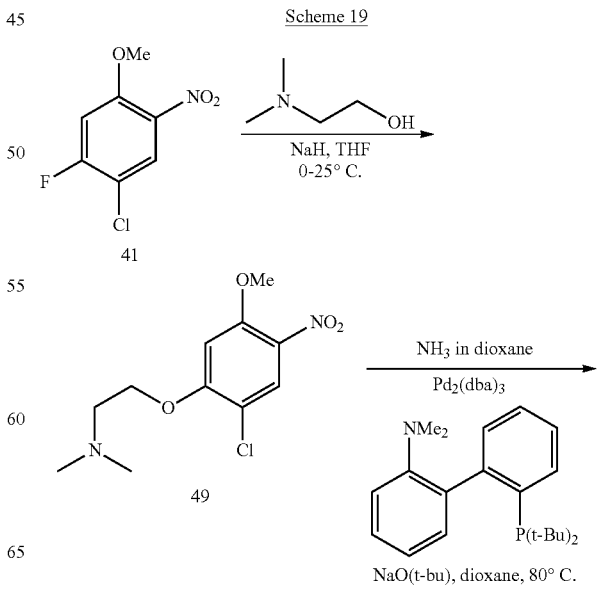

Step 1: the starting material 41 was prepared from 3-fluoro-4-chlorophenol via nitration and subsequent O-methylation, according to a published procedure (US Patent Publication No, 20080300242), The suspension of 41 (1.0 g, 4.86 mmol), 1-methylpiperzine (1 eq) and $K_2CO_3$ (1 eq) in DMF (20 mL) was heated at 80° C. for 4 hrs. DMF was removed and the residue was partitioned between DCM

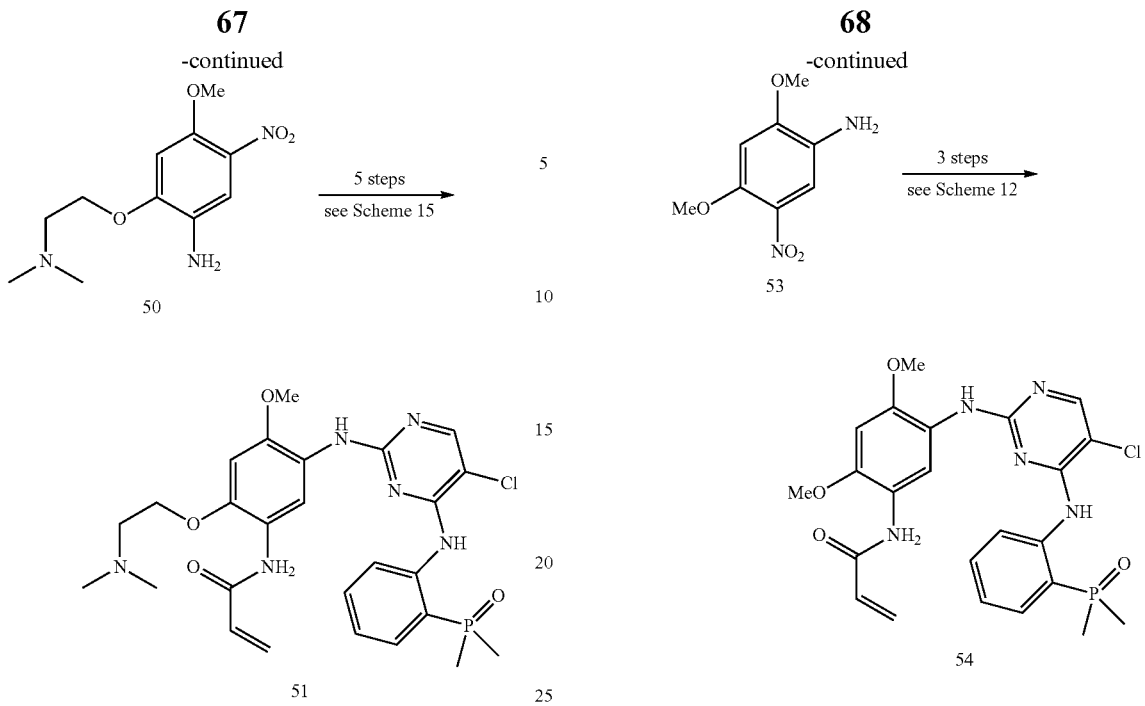

50

51

Step 1: Under N$_2$, to a suspension of 41 (0.5 g, 2.43 mmol) and NaH (1.5 eq) in THF (10 mL) was added dropwise a solution of 2-(dimethylamino)ethanol (1.1 eq) in THF (2 mL) at 0° C. The resulting mixture was stirred at room temperature for 3 hrs. Usual workup followed by silica gel column chromatograph (10% MeOH in DCM as eluents) furnished 49 (0.53 g, 79%).

Step 2: To a degassed suspension of 49 (0.275 g, 1.0 mmol), Pd$_2$(dba)$_3$ (0.1 eq), 2-(di-t-butylphosphino)-N, N-dimethylbiphenylamine (0.1 eq) and sodium t-butoxide (1.4 eq) in dioxane (10 mL) was added a solution of NH$_3$ in dioxane (0.5 M in a N$_2$-sealed bottle, 10 mL). The resulting mixture was heated at 80° C. for 3 hrs. Usual workup followed by silica gel column chromatograph (15% MeOH in DCM as eluents) furnished 50 (0.15 g, 55%).

Steps 3 to 7: The poly-substituted aniline 50 was converted to the title compound 51 according to the procedure described in Example 18 by substituting 50 for 43.

Scheme 20

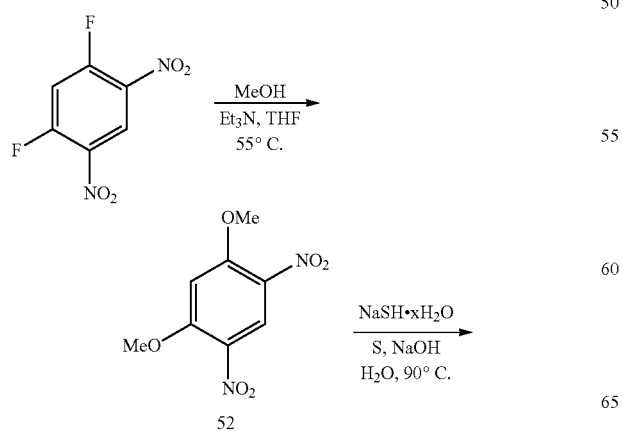

52

2,4-Dimethoxy-5-nitroaniline 53 was prepared from 1,5-difluoro-2,4-dinitrobenzene via double S$_N$Ar substitution to generate 52 and subsequent mono-reduction of nitro groups, according to a published procedure (*J. Org. Chem.* 2005, 70, 10660). This was converted to the title compound 54 as for Example 14 by substituting 53 for 33 and 2 for 32.

Scheme 21

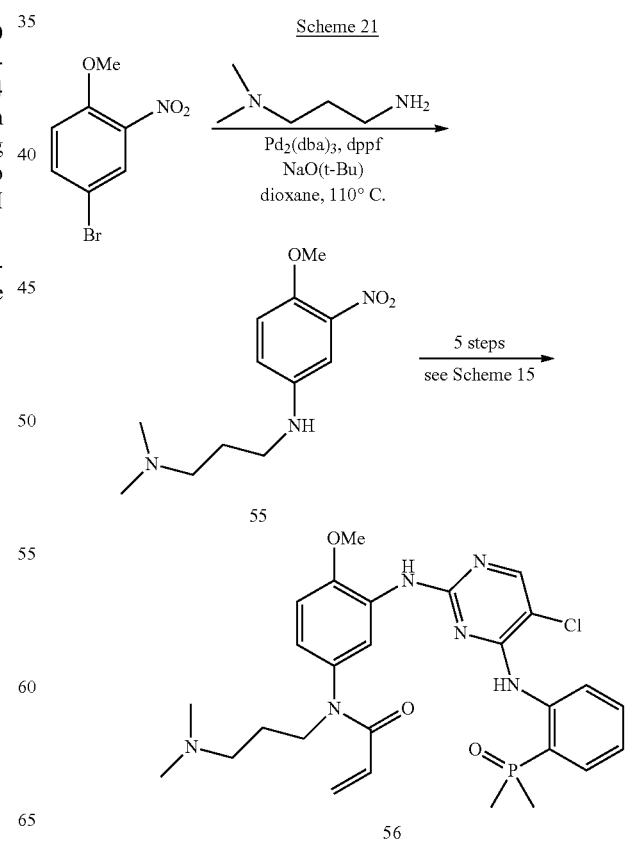

55

56

Step 1: A degassed suspension of 2-nitro-4-bromoanisole (2.32 g, 10 mmol), N,N-dimethyl-1,3-propanediamine (1.1 eq), Pd$_2$(dba)$_3$ (0.02 eq), dppf (0.04 eq) and sodium t-butoxide (1.5 eq) in dioxane (20 mL) was heated at 110° C. overnight. Upon cooling the reaction was quenched with water. The volatile components were removed on rotavap and the residue was partitioned between EtOAc and water. Extraction and concentration followed by silica gel column chromatograph (15% MeOH in DCM as eluents) furnished 55 (0.66 g, 26%).

Steps 2 to 6: The secondary amine 55 was converted to the title compound 56 as for Example 18 by substituting 55 for 43.

Scheme 22

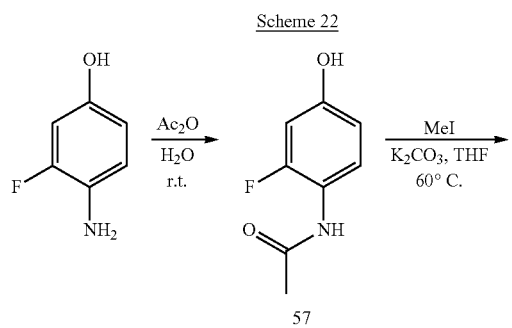

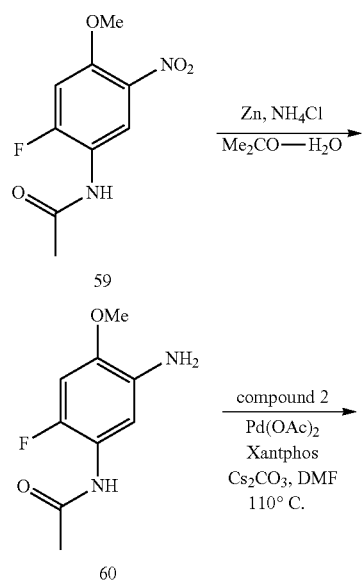

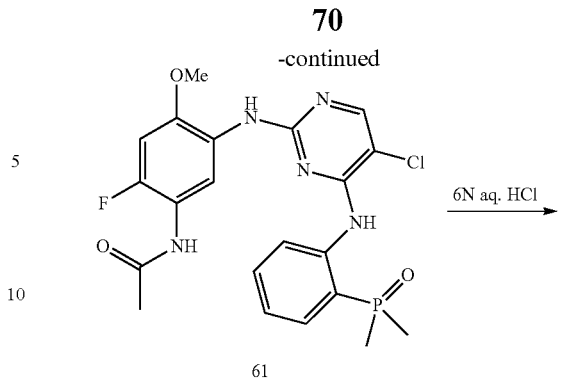

61

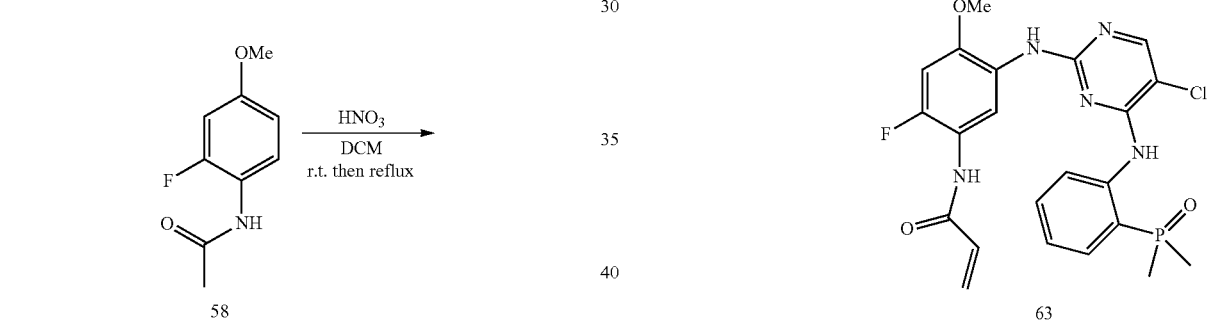

62

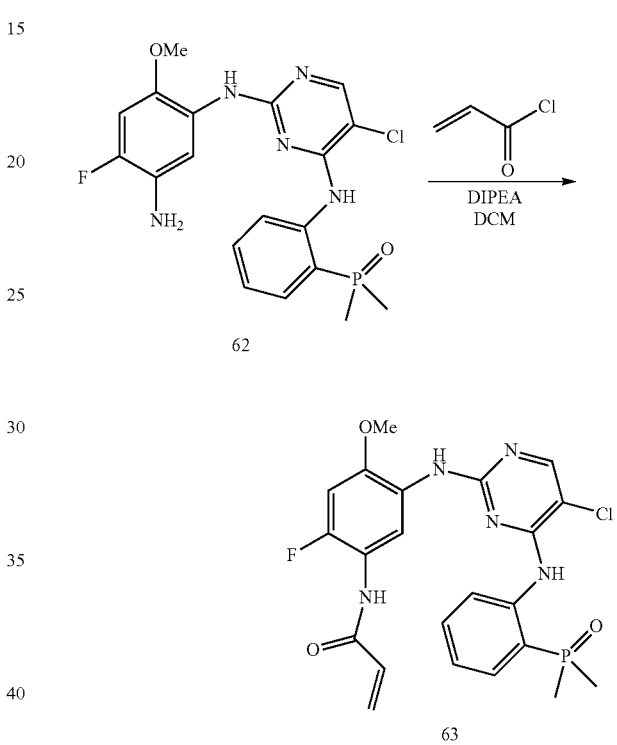

63

Step 1: Acetic anhydride (7.8 mL, 82.6 mmol) was added dropwise with vigorously stirring to a suspension of 3-fluoro-4-aminophenol (10 g, 78.6 mmol) in water (20 mL). Insoluble amide started to precipitate as a white solid in a few minutes. After the reaction mixture was stirred for 10 more minutes, the white solid was collected via filtration and washed with cold water. Silica gel column chromatograph (5% MeOH in DCM as eluent) gave pure 57 (8.75 g, 66%).

Step 2: To a suspension of 57 (8.75 g, 51.73 mmol) and K$_2$CO$_3$ (1.1 eq) in THF (30 mL) was added methyl iodide (1.2 eq). The mixture was heated in a sealed tube at 60° C. overnight. Filtration and concentration followed by silica gel column chromatograph (5% MeOH in DCM as eluent) furnished pure 58 (7.17 g, 89%).

Step 3: Nitric acid (70%, 3.83 mL) was added dropwise to a solution of 58 (7 g) in DCM (70 mL) with vigorously stirring. After stirred at room temperature for 1 hr, the reaction mixture was refluxed for 3 hrs. DCM was removed on rotavap and the residue was washed with cold water and then subjected to a silica gel column chromatograph purification (5% MeOH in DCM as eluent) to afford 59 (3.26 g, 37%).

Step 4: Poly-substituted nitrobenzene 59 was reduced to corresponding aniline 60 according to the procedure described in Example 14, step 3.

Step 5: Poly-substituted aniline 60 (200 mg, 1 mmol) was coupled with precursor 2 (1.5 eq) to afford 61 (320 mg, 67%) via the procedure described in Example 18, step 6.

Step 6: N-arylacetamide 61 (320 mg) was heated at reflux in 6N HCl for 30 min. After basification, extraction and concentration aryl amine 62 was obtained (290 mg, 98%).

Step 7: Crude 62 (150 mg) was converted to 63 by using the procedure described in Example 14, step 4. The final product was purified by reverse phase prep-HPLC (41 mg, 24%).

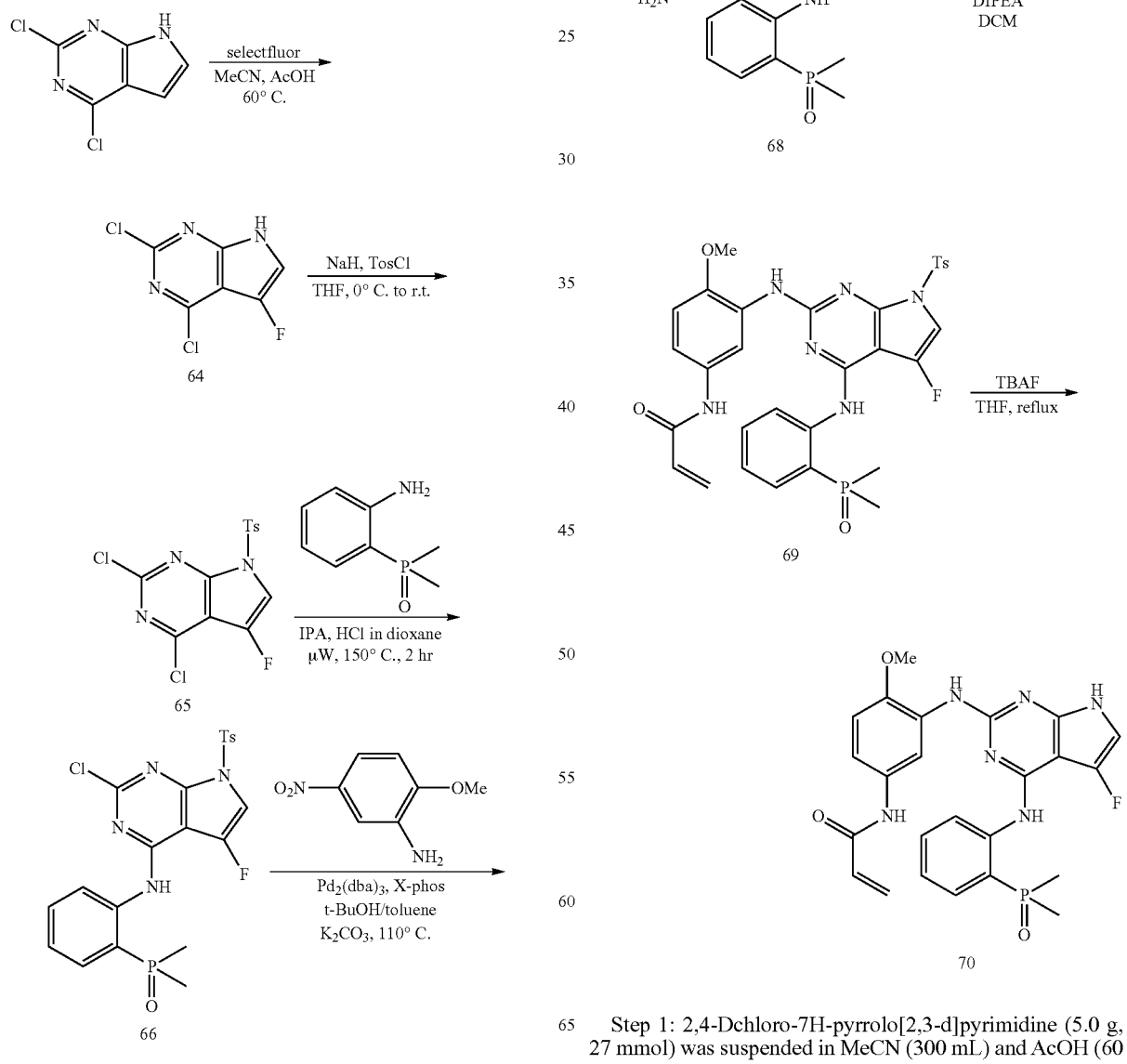

Step 1: 2,4-Dchloro-7H-pyrrolo[2,3-d]pyrimidine (5.0 g, 27 mmol) was suspended in MeCN (300 mL) and AcOH (60 mL); to this was added selectfluor (1-chloromethyl-4-fluoro- 1,4-diazoniabicyclo[2.2.2]octane bis(tetrafluoroborate), 1.4 eq, 13.2 g) in one portion. The reaction mixture was stirred at 60° C. overnight. HPLC monitoring indicated complete conversion. After the solvents were evaporated to the volume of ~100 mL, toluene (20 mL) was added and the suspension was filtered. The filtrate was evaporated to dryness and re-evaporated with toluene (2×20 mL). The residue was then purified via a short silica pad (washing with 1/1 DCM/EtOAc) and column chromatography (ISCO machine, EtOAc/DCM, EtOAc on a 0-100% gradient) to give the crude product. Upon standing the pure product was seen to precipitate from the column fractions. These were filtered and the mother liquors were combined to precipitate a 2$^{nd}$ crop. Total 1.23 g of the product 64 was obtained (22% yield, ~90% pure, Cl-isomer was the main impurity).

Step 2: A solution of 64 (1.22 g, 6 mmol) in THF (10 mL) was slowly added to a suspension of NaH (1 eq) in THF (10 mL) at 0° C. After the mixture was stirred for 10 min, a solution of tosyl chloride (1 eq) in THF (5 mL) was slowly added. Stirring was continued for 30 min at 0° C. and then at room temperature overnight. The reaction was shown to be complete via HPLC monitoring and was quenched via the addition of aq. NH$_4$Cl (1-2 mL). The reaction mixture was then filtered through celite and the filtrate was evaporated. The crude product was purified via column chromatography (ISCO machine, EtOAc/Heptane, EtOAc on a 0-100% gradient) to give 65 (1.22 g, 56%).

Step 3: In a microwave vessel (20 mL) were placed 65 (600 mg, 1.7 mmol), 1 (282 mg, 1.7 mmol) and isopropanol (10 mL). After HCl (1.3 mL, 4 M in dioxane) was added, the resulting mixture was stirred in the microwave reactor at 150° C. for 2 hrs. The solvents were evaporated and the residue was purified via silica column chromatography (ISCO machine, EtOAc/Heptane, 0-100% EtOAc to elute impurities and then MeOH/DCM, 0-20% MeOH) to give pure 66 (900 mg, 54%).

Step 4: Intermediate 66 (493 mg, 1 mmol), 2-methoxy-5-nitroaniline 33 (168 mg, 1 mmol), K$_2$CO$_3$ (1.4 mmol), Pd$_2$dba$_3$ (5 mol %) and X-Phos (10 mol %) were weighed into a 100 mL round bottom flask and placed under N$_2$. The solvents toluene (10 mL) and tert-butanol (2 mL) were added as a mixture and the stirring solution was evacuated and backfilled with N$_2$ three times. The resulting mixture was then stirred overnight at 110° C. HPLC showed the reaction to be complete and the solvents were evaporated. The residue was purified by silica column chromatography on ISCO machine (5% MeOH in DCM as eluents) to give coupling product 67 (570 mg, 91%).

Step 5: Poly-substituted nitrobenzene 67 was reduced to corresponding aniline 68 according to the procedure described in Example 14, step 3.

Step 6: Crude aniline 68 (123 mg) was converted to 69 by using the procedure described in Example 14, step 4. The product was purified by silica column chromatography on ISCO machine (5% MeOH in DCM as eluents). Yield: 69 mg, 51%.

Step 7: A solution of 69 (60 mg) and TBAF (1 M in THF, 0.3 mL) in THF (10 mL) was refluxed for 5 hrs. HPLC indicated a complete reaction. After the solvent was evaporated, the residue was purified by silica column chromatography on ISCO machine (5% MeOH in DCM as eluents). The product was co-eluted with TBAF; water wash furnished pure product (10 mg, 21%).

Scheme 24:

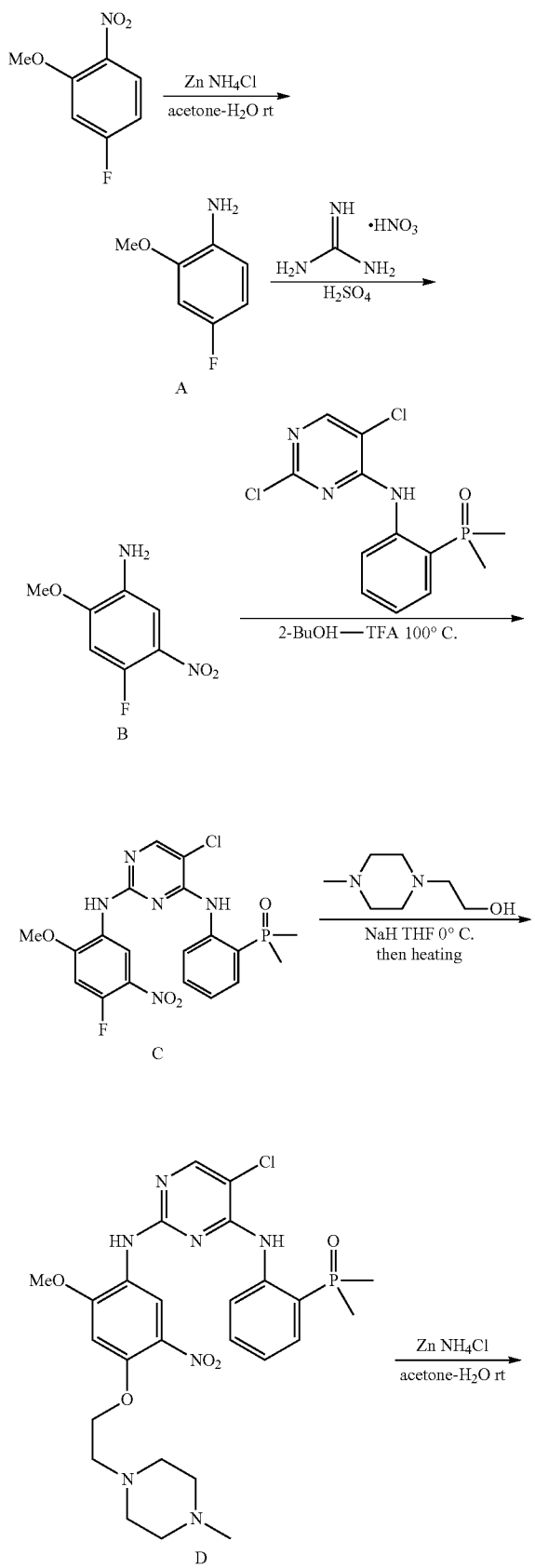

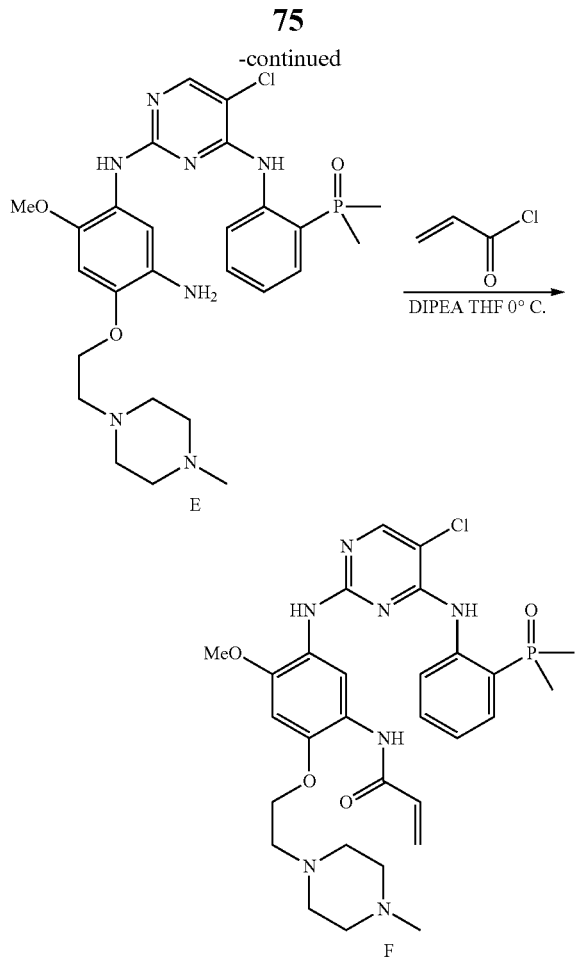

traces of water. The product was dried to afford C (0.19 g) which was directly used in the next step.

Step 4: NaH (0.039 g, 0.96 mmol, 60% dispersion in oil) was taken up in a dry capped microwave vial. To this, 1-(2-hydroxyethyl)-4-methylpiperazine (0.023 g, 0.16 mmol) dissolved in dry tetrahydrofuran 1.6 mL) was added dropwise. The mixture was stirred at rt for 20 min. Intermediate C (0.075 g, 0.16 mmol) was then added in one portion to this suspension and the mixture was heated to 67° C. in the closed seal tube for 25 min. The mixture was allowed to reach at rt and quenched with a few drops of methanol. Solvent was removed under vacuum and the resultant crude was subjected to FCC eluting with DCM-MeOH (95/5) to furnish the desired product D (0.081 g).

Step 5: Compound D (0.078 g, 0.13 mmol) was dissolved in a mixture of acetone (1.3 mL) and water (0.3 mL). To this, zinc nano powder (0.07 g, 1.3 mmol) was added immediately followed by addition of $NH_4Cl$ (0.16 g, 2.6 mmol) in small portions. The mixture was vigorously stirred at r.t for 30 min. Anhydrous $Na_2SO_4$ was then added to this stirring mixture and the resultant crude was filtered, solvents were evaporated and the residue were taken up in DCM and directly loaded on the silica gel cartridge and eluted with DCM-MeOH—$NH_3$ (90/10) to furnish the desired product E (0.044 g).

Step 6: To a solution of E (0.044 g, 0.078 mmol) in dry tetrahydrofuran (0.52 mL) was added DIPEA (0.027 mL, 0.156 mmol) at 0° C. under stirring. This was followed by the addition of acryloyl chloride (0.007 g, 0.078 mmol). The reaction was stirred at that temperature for additional 1 h, Solvent was stripped off under vacuum and the crude was purified by FCC using DCM-MeOH—$NH_3$ (90/10) to furnish a gum which was further triturated with $Et_2O$ to furnish a solid material F (0.02 g).

Step 1: To a suspension of 5-fluoro-2-nitroanisole (50 mmol, 8.5 g) and zinc powder (3.5 eq, 11.4 g) in acetone (45 mL) and water (5 mL) was added ammonium chloride (11 eq, 29.3 g) at 0° C. in multiple portions. After the mixture was stirred at r.t. overnight, HPLC indicated a complete conversion. Acetone was removed on rotavap and the residue was suspended in DCM and water. Filtration was carried out and the filtrate was extracted with DCM. Concentration of combined organic layers gave crude aniline (~7.0 g), which was used in the next step without purification.

Step 2: To a suspension of 4-fluoro-2-methoxyaniline (5.1 g, 36.1 mmol) in concentrated sulfuric acid (55 mL) was added guanidine nitrate (4.38 g, 36.1 mmol) in portion wise under ice cooling over 15 min. The mixture was stirred at the same temperature for additional 15 min. The reaction was then poured into a saturated cold $NaHCO_3$ solution and the precipitated solid were collected by filtration. The residue was taken up in EtOAc and dried over anhydrous $Na_2SO_4$. The solvent was stripped off to afford the B (4.72 g).

Step 3: The above compound B (0.1 g, 0.53 mmol) and 4-(ortho dimethyl phosphinyl anilino)-5-chloro-2-chloro pyrimidine (0.17 g, 0.53 mmol) were dissolved in a mixture of 2-butanol (1.2 mL) & trifluoroacetic acid (0.25 mL) and were heated to 100° C. in a seal tube for overnight. The reaction mixture was then cooled to rt and poured into a saturated $NaHCO_3$ solution while stirring to afford an orange solid which was filtered, washed with $Et_2O$ to remove final Scheme 25:

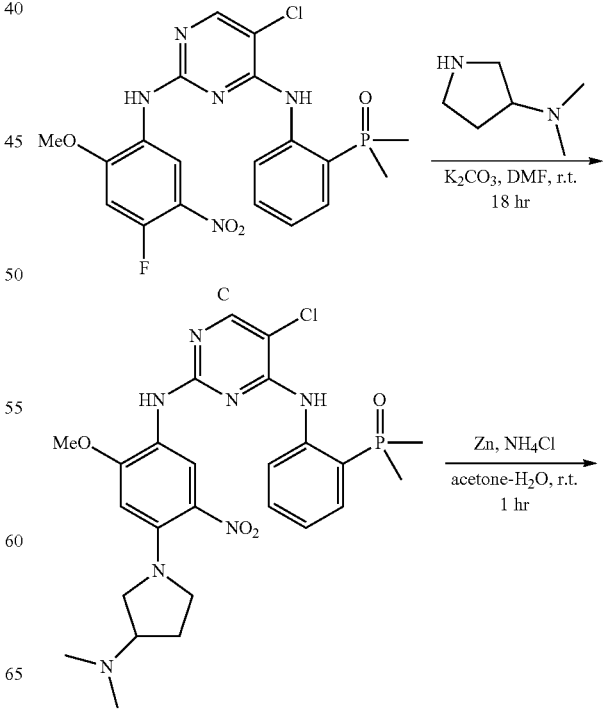

-continued

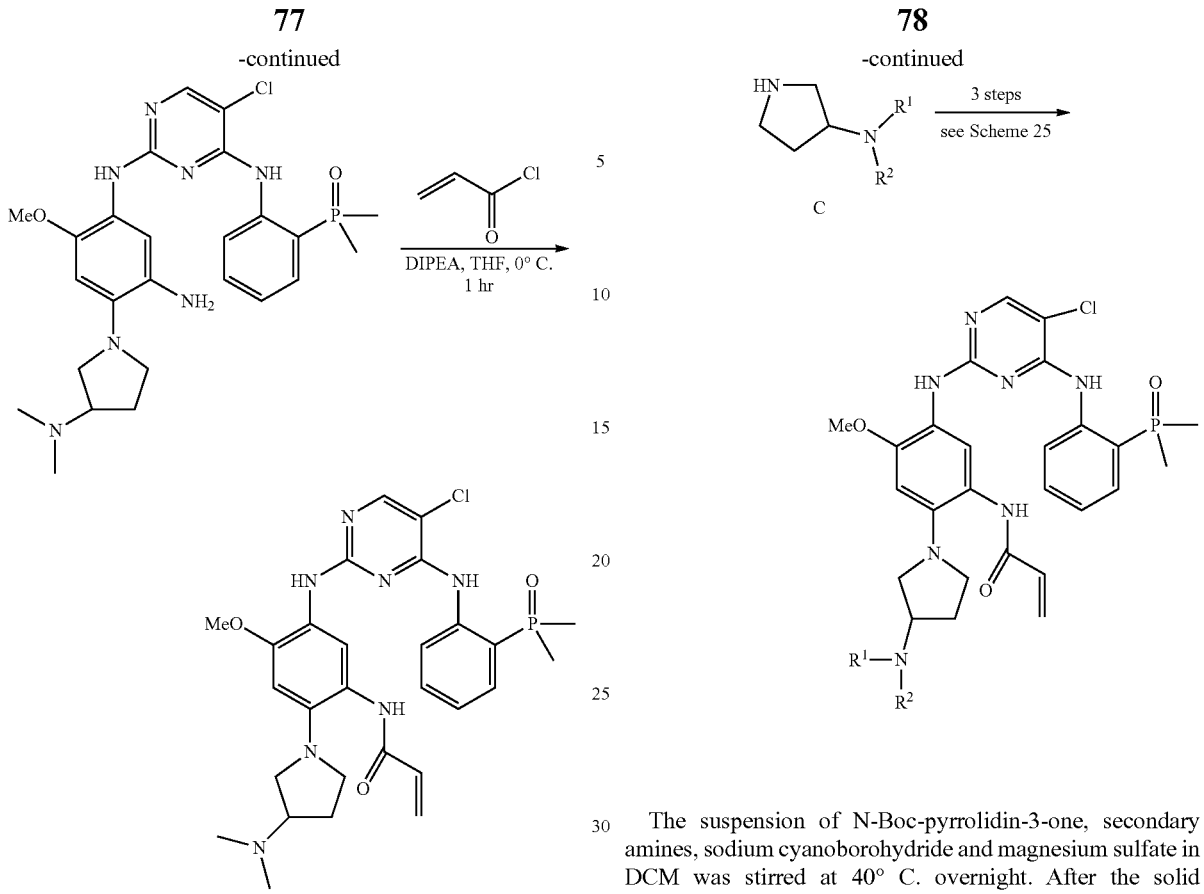

Step 1: The suspension of advanced intermediate C, (3-dimethylamino)pyrrolidine (1 eq) and K2CO3 (2 eq) in DMF was stirred at r.t. overnight. The solid components were filtered off and the filtrate was concentrated on rotavap and then on vacuum pump. The residue was essentially pure by HPLC analysis and was used directly in the next step.

Steps 2 and 3: these were carried out according to the procedure outlined in Scheme 24, steps 5 and 6.

Scheme 26:

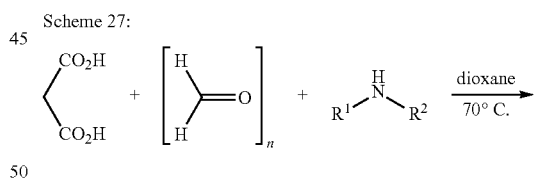

The suspension of N-Boc-pyrrolidin-3-one, secondary amines, sodium cyanoborohydride and magnesium sulfate in DCM was stirred at 40° C. overnight. After the solid components were removed by filtration, 2.5N HCl in MeOH was added to the filtrate and the resulting solution was stirred at r.t. for 30 min. Volatile components were removed on rotavap; the residue was partitioned between DCM and aq. NaHCO3. Combined organic phases were concentrated and the residue was purified by silica gel column chromatography to furnish (3-dialkylamino)pyrrolidine C, which was converted into final compounds by substituting C for (3-dimethylamino)pyrrolidine.

Scheme 27:

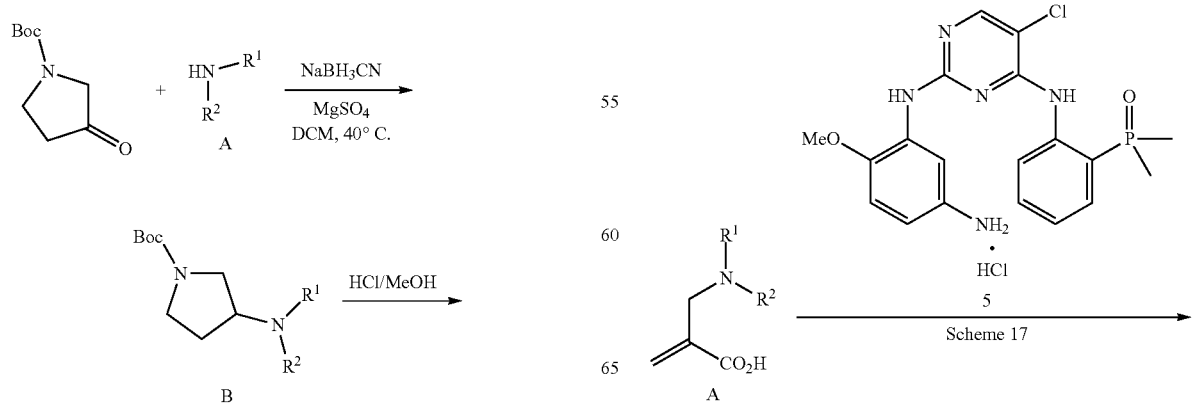

-continued

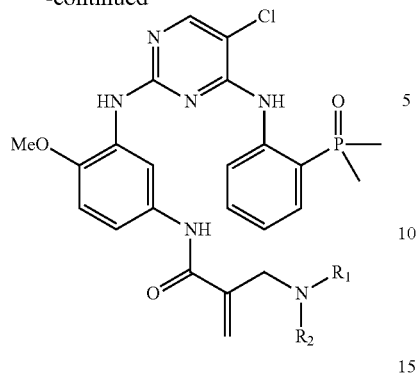

Secondary amines were converted into 2-(dialkylaminomethyl)acrylic acid A according to a literature method (*Synth. Comm.* 1995, 25, 641). These were converted into final compounds according to the procedure outlined in Scheme 17 by substituting A with 39.

Scheme 28:

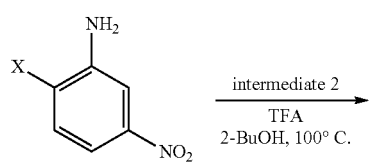

-continued

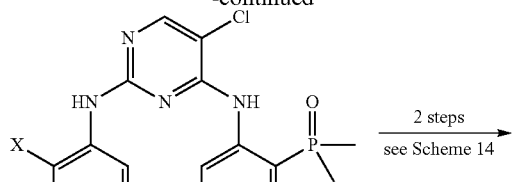

X = F, Me

2-Fluoro-5-nitroaniline or 2-methyl-5-nitroaniline was converted into desired compound according to the procedure outlined in Scheme 28.

Scheme 29

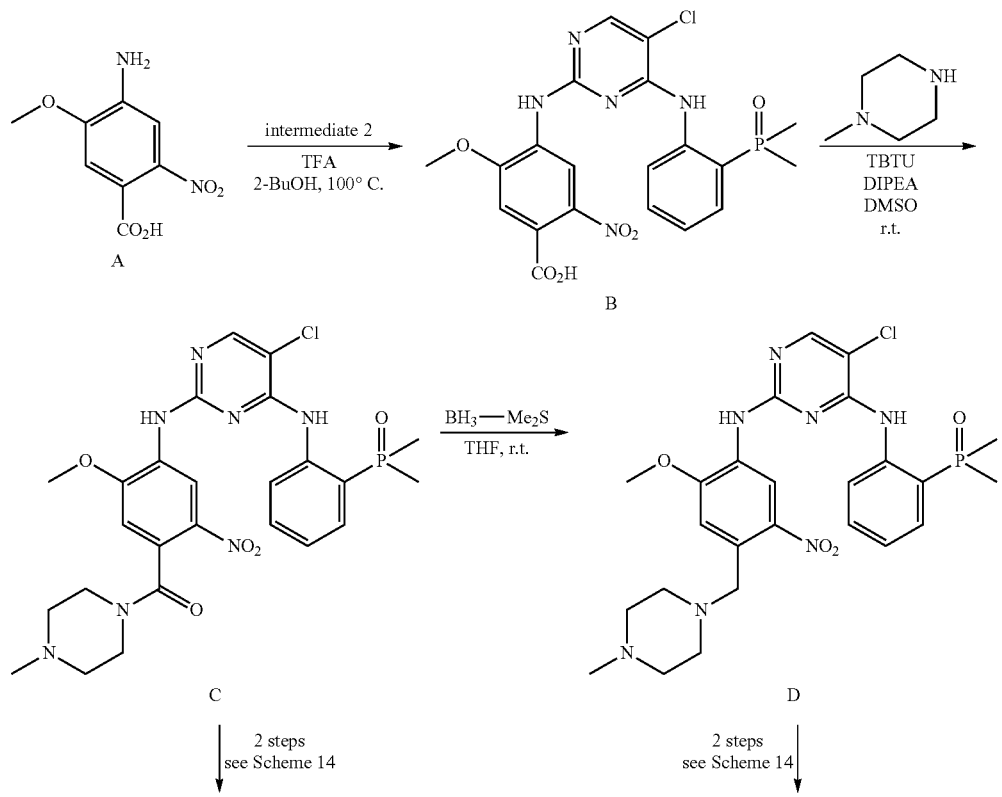

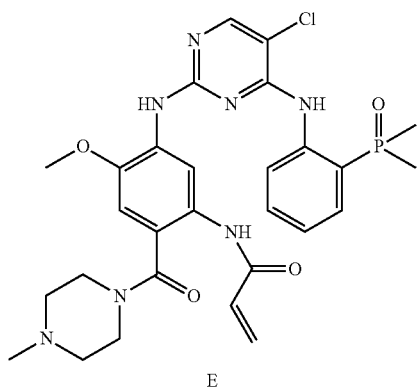

E

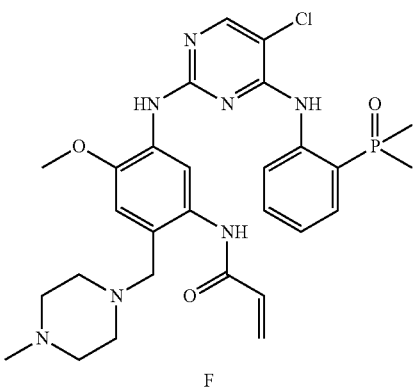

F

Step 1: the starting material A underwent a S_NAr reaction with intermediate 2 according to the procedure described in step 1 of Example 14.

Step 2: To a solution of compound B (246 mg, 0.5 mmol), coupling reagent TBTU (1.2 eq) and N, N-diisopropylethylamine (3.0 eq) in DMSO (10 mL) was added piperazine (1 eq). After the mixture was stirred at room temperature overnight, water and DCM was added to facilitate extraction. Combined extracts were washed with water to remove DMSO. After drying over Na2SO4 and concentration on rotavap the residue was purified by silica gel column chromatography with 5% MEOH in DCM as the eluents, furnishing compound C as a tan solid (154 mg, 54%).

Step 3: A solution of compound C (570 mg) and BH3-Me2S (2.0 M in THF, 5 eq, 0.6 mL) in THF (5 mL) was stirred at r.t. overnight. 6N aq. HCl (15 mL) was added and the resulting solution was stirred at r.t. for 5 hr. Solid K2CO3 was carefully added to basify the reaction mixture. After extractions with DCM the combined organic phases were dried, concentrated and purified by silica gel column chromatography with 5% MeOH in DCM as the eluents, furnishing compound D as a tan solid (300 mg, 54%).

Steps 4 and 5: Compounds C and D were converted into final compounds E and F respectively according to the procedure described in Example 14.

Scheme 30

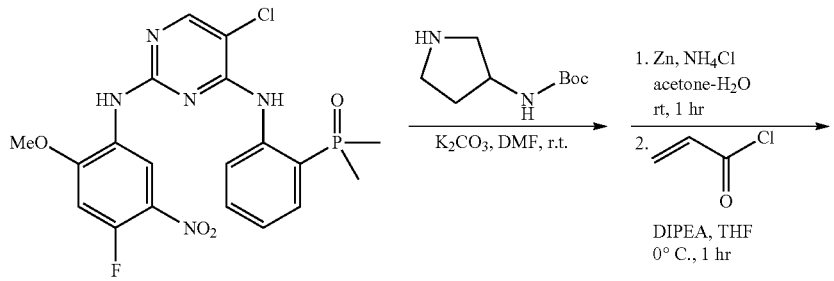

C in Scheme 24 and 25

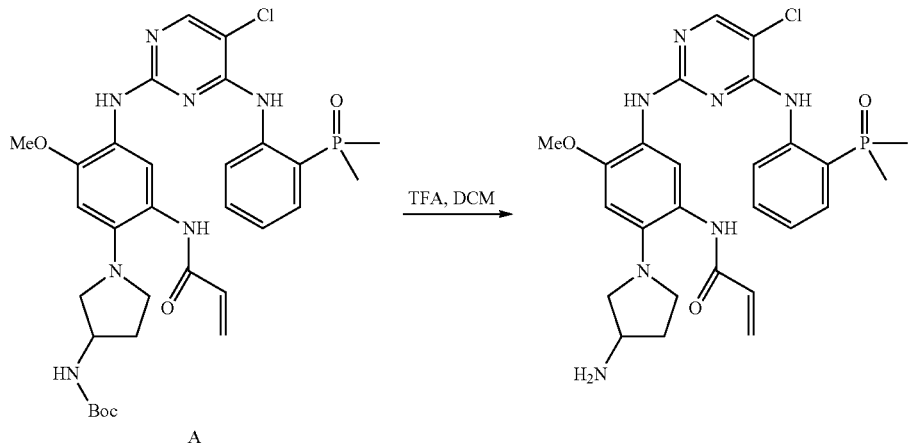

Compound A was synthesized according to the procedure outlined in Scheme 25 by substituting 3-(tert-butoxycarbonylamino)pyrrolidine for 3-(dimethylamino)pyrrolidine. Standard de-protection of Boc with TFA-DCM followed by basification and silica gel column chromatography (5% MeOH in DCM as the eluents) furnished title compound.

Scheme 31

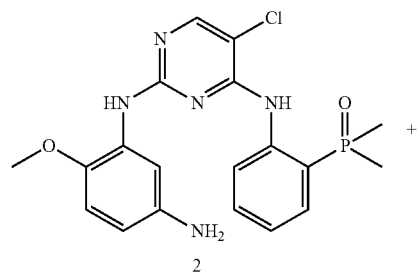

2

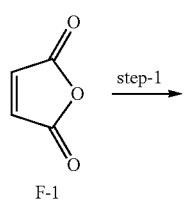

F-1 step-1

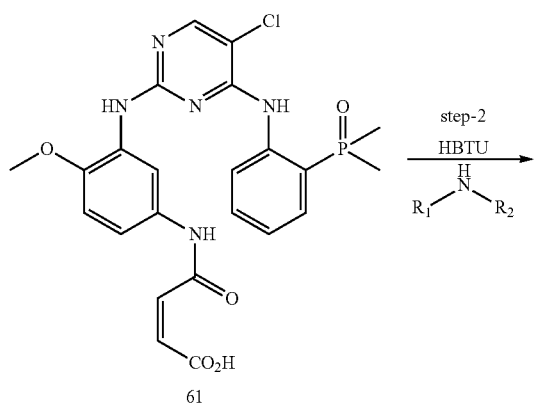

61 step-2
HBTU
$R_1\text{-NH-}R_2$

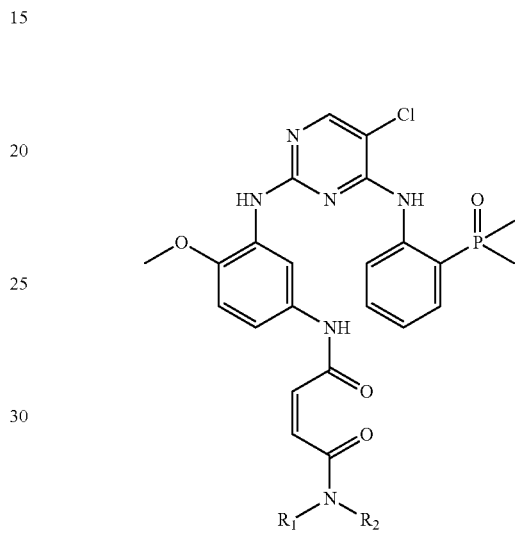

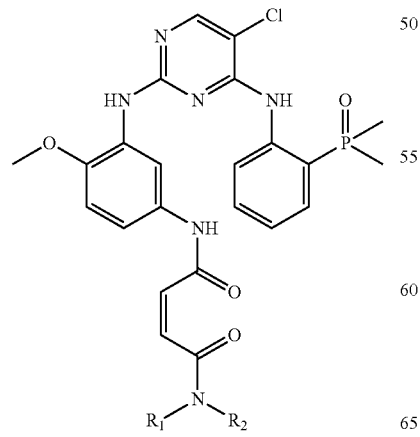

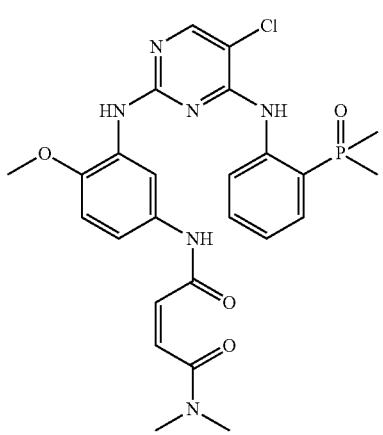

Step-1: Synthesis of 61

To a mixture of compound 2 (420 mg) in THF (2.0 mL) was added maleic anhydride (1.0 eq) at room temperature. The reaction was stirred at room temperature for 1 hour. The product was obtained by filtration and then washed with DCM (2.0 mL) to yield the product, 61, as a yellow solid (435 mg, yield 84%).

Step-2: Synthesis of Examples 62, 63 and 64

General procedures: The compound of Example 61 (77 mg, 0.15 mmol), prepared as in Step-1 (immediately above), was dissolved with the respective amine (0.15 mmol, 1.0 eq.) in dry DMF (2.0 mL). HBTU (80 mg) was added and followed by Et$_3$N (30 uL). The contents were stirred at room temp for 1 h. Solvent was removed in vacuo and the residue was purified by a prep-TLC plate (6.5% MeOH/DCM). The corresponding bands were collected to give the final products:

85
-continued
63
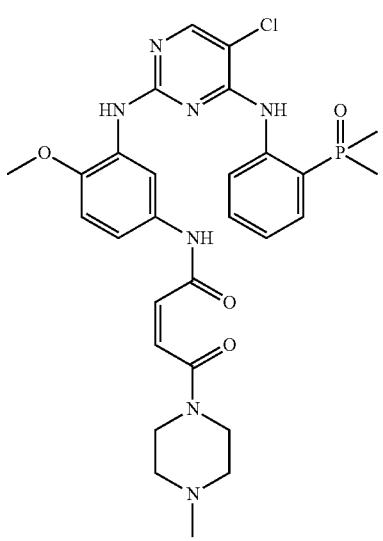
64
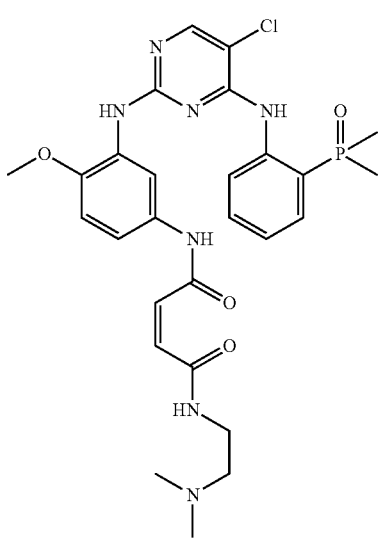
Synthesis of Example 75
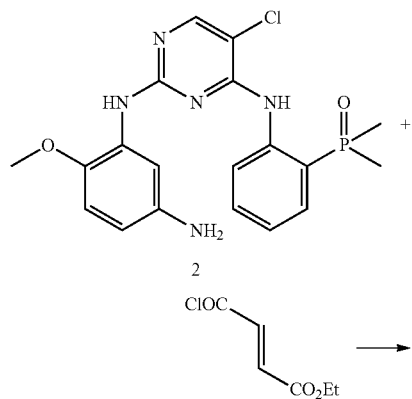
86
-continued
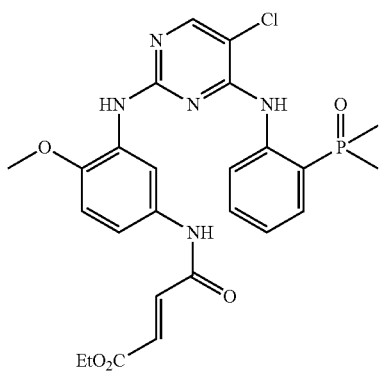
75
A solution of compound 2 (84 mg) in DCM (3.0 mL) and Et₃N (0.1 mL) was treated with Ethyl fumaroyl chloride (1.05 eq). The contents were stirred at room temp for an hour. Solvent was removed in vacuo and the residue was purified by a prep-TLC plate (7.5% MeOH/DCM) to give the product as a yellow solid (34 mg, yield 31%).
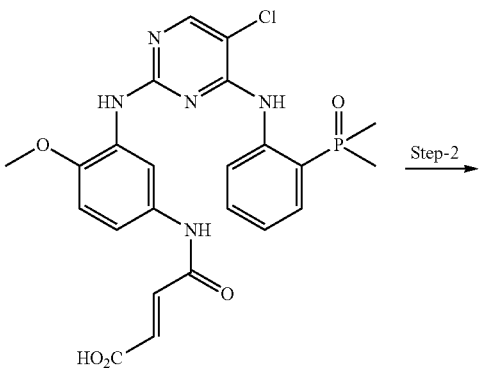

87

-continued

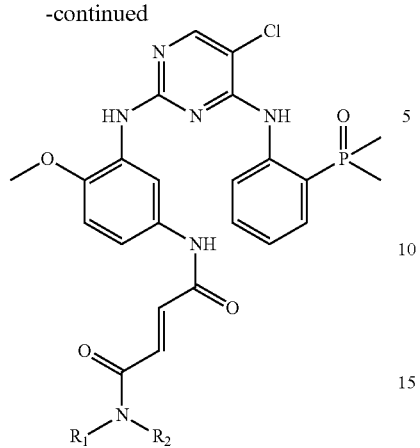

Step-1

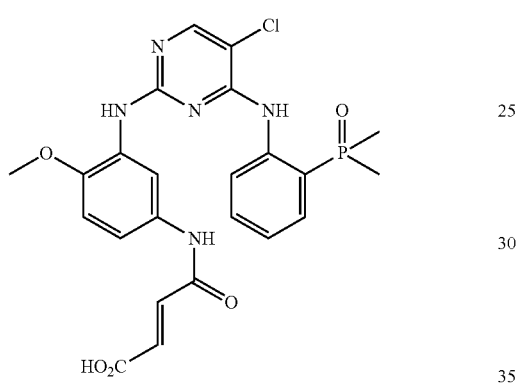

Example 75 (360 mg) in MeOH (1.5 mL) and water (0.5 mL) was treated with K$_2$CO$_3$ (1.0 g) at 50° C. for 2 h. The reaction mixture was cooled down to room temperature. The organic solution was transferred to a new vial and diluted with DCM (3.0 mL). The pH was adjusted to 6-7 by adding hydrochloric acid. The resulting organic layer was evaporated and the residue was washed with MeOH to give product as a yellow solid (304 mg, yield 89%)

Step-2

Compounds for Examples 60, 59 and 58 were made according to the general procedure for Example 62, using the appropriate amine:

60

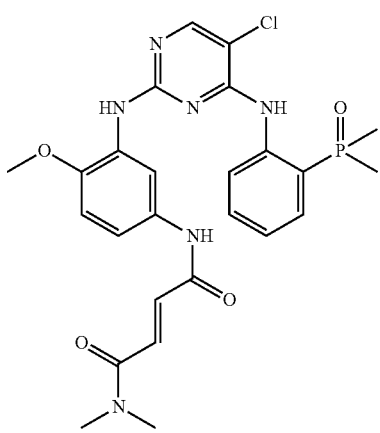

88

-continued

59

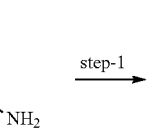

58

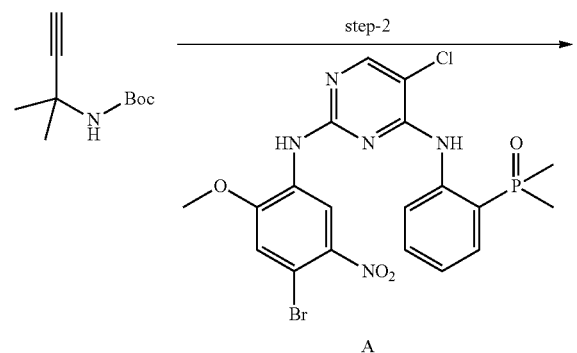

Scheme 32: Example 65

A

89

-continued

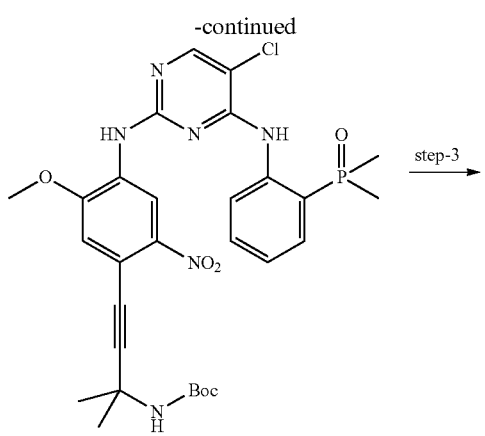

step-3 →

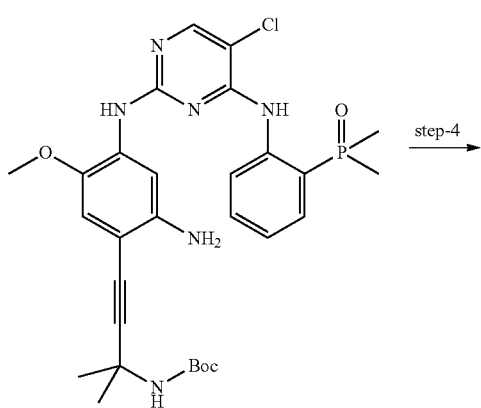

step-4 →

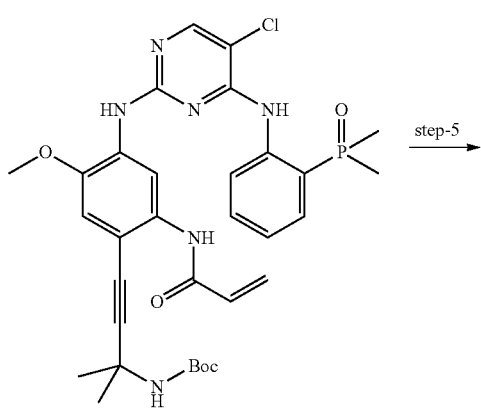

step-5 →

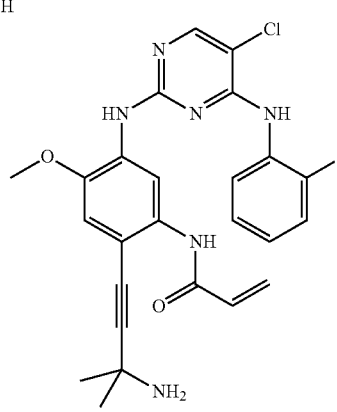

90

Step-1

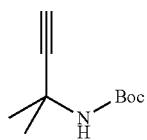

Molecular Weight: 183.25

A mixture of 1,1-dimethylpropargylamine (4.2 g) and Boc$_2$O (11 g) without solvent was warmed up to 50° C. for 30 min. The resulting solid was treated with n-hexane (10 mL) and the product was collected by filtration to give white solid (7.6 g, yield 82%)

Step-2

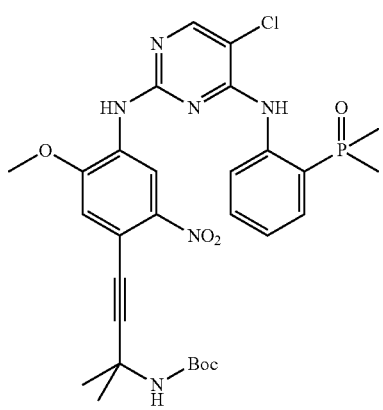

To a mixture of compound A (527 mg) and step-1 product (250 mg) in DMF (5.0 mL), was added (Ph$_3$P)$_2$PdCl$_2$ (0.1 g), CuI (0.05 g) and Et$_3$N (0.2 mL). The mixture was stirred at 80° C. for 4 h. The reaction mixture was concentrated and the residue was purified by a prep-TLC plate (8% MeOH/DCM) to give final product as a yellow solid (430 mg, yield 68%).

Step-3

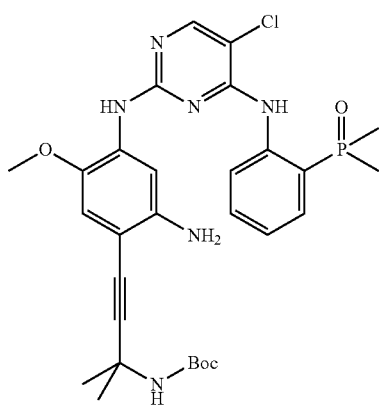

Molecular Weight: 599.06

Water was added dropwise to a mixture containing the product of step-2 (240 mg) in acetone (1.0 mL), Zn dust (0.3 g) and NH₄Cl (0.15 g). The mixture was stirring at room temperature for 15 min and then diluted with DCM (5 mL). After filtration, the organic solution was evaporated and the residue was used for next step.

0° C. The mixture warmed up to room temperature for 1 h. Solvent was evaporated, the residue was neutralized with aq. NaHCO₃, and the neutralized material was subjected to prep-TLC plate (20% MeOH/DCM) to give the desired product, 65, as a light yellow solid (42 mg, yield 62%).

Step-4

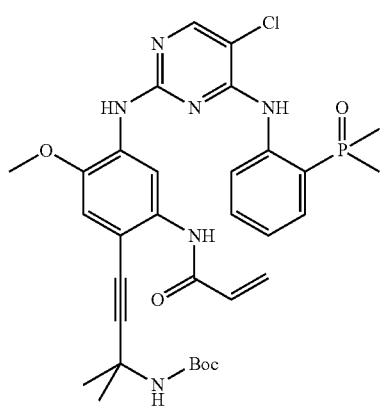

The residue from Step-3 was dissolved in THF (3.0 mL) and Et₃N (0.05 mL), and the resulting solution was treated with acroyl chloride. The reaction was monitored by HPLC until disappearance of starting material. The reaction was then quenched with aq. NaHCO₃ and extracted with DCM (2×5.0 mL). The organic solution was concentrated and the residue was purified by a prep-TLC plate (10% MeOH/DCM) to give product as a yellow solid (112 mg, yield 45% for two steps).

Step-5

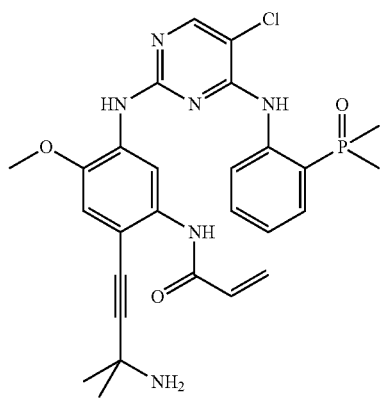

A solution of the product of Step-4 (80 mg) in MeOH (1.0 mL) and DCM (0.5 mL) was treated with TFA (0.5 mL) at Scheme 33

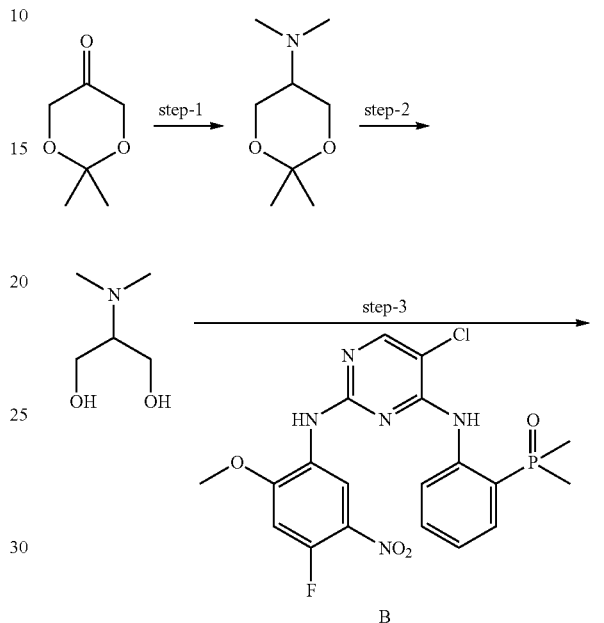

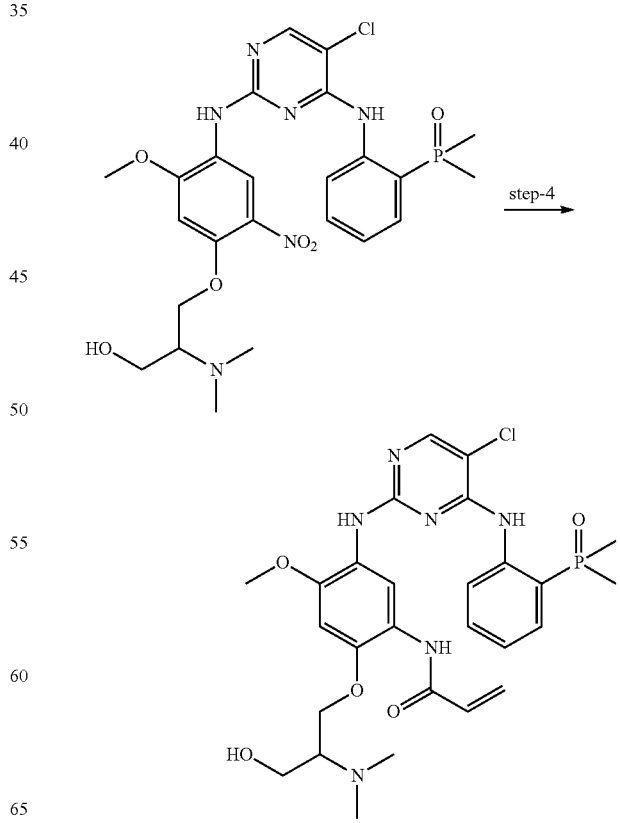

Step-1

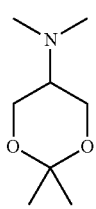

Molecular Weight: 159.23

To a mixture of 2,2-dimethyl-1,3-dioxan-5-one (2.6 g), dimethyl amine HCl salt (1.8 g) in DCM (50 mL) was added NaHB(OAc)₃ (6.0 g) and Et₃N (3.0 mL). The reaction mixture was stirred at room temperature overnight and then diluted with aq.NaHCO3. The organic layer was dried and evaporated to give colorless oil (2.5 g, yield 79%).

Step-2

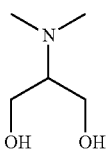

Molecular Weight: 119.16

A solution of step-1 product (2.4 g) in MeOH (5.0 mL) was treated with HCl (10 mL, 2N). The mixture was heated to reflux for 15 min. Solvent was evaporated and the residue was dissolved in DCM (6.0 mL). The organic solution was dried, filtered and evaporated to give colorless oil (1.5 g, yield 77%).

Step-3

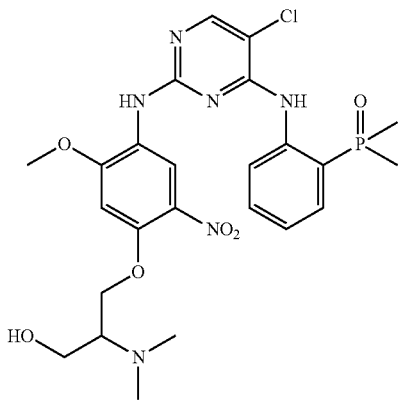

Molecular Weight: 564.96

The nitro compound was synthesized by reacting compound B and the product of step-2 according the general procedure.

Step-4

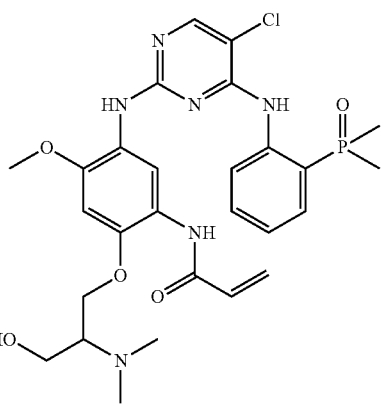

Reduction of the nitro group and formation of the corresponding acrylamide was carried out according to the procedure in Scheme 32, step-3 and step-4.

Scheme 34:

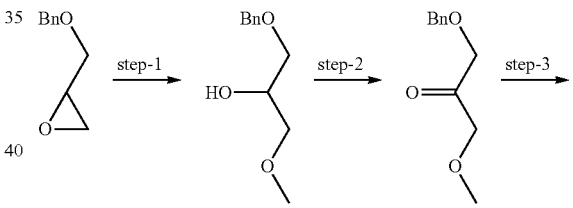

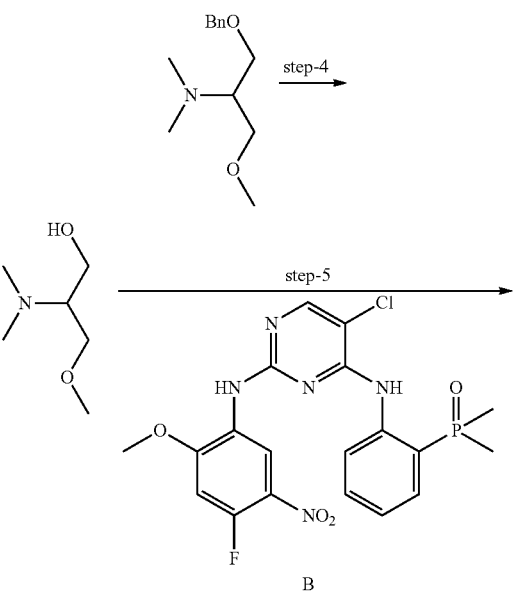

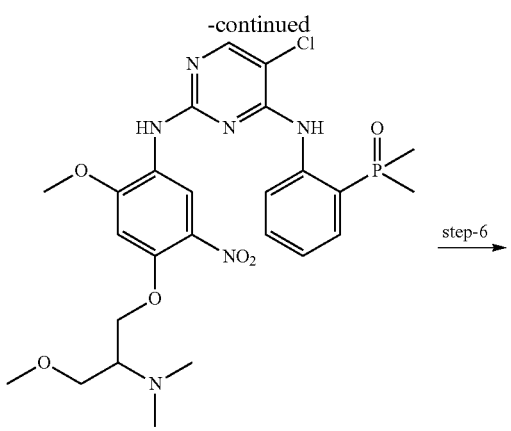

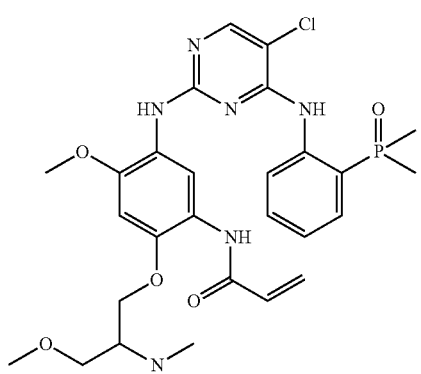

Step 1: To a solution of benzyl glycidyl ether (5.0 g) in MeOH (5.0 mL) was added NaOMe (5.0 mL, 25% in methanol). The mixture was warmed up to 50° C. for 1 h and then heated to reflux for 5 min. The mixture was treated with wet NaHCO$_3$ and filtered. Solvent was evaporated and the residue was dissolved in DCM (20 mL). The solution was dried and evaporated to give yellowish oil (4.8 g, yield 80%).

Step 2: A solution of step 1 product (3.0 g) in DCM (100 mL) was treated with PDC (6.0 g) and molecular sieves (4.0 g). The mixture was stirred at room temperature for 4 h and diluted with Et$_2$O (100 mL). The mixture was filtered through a Celite pad and solvent evaporated to give yellow oil (1.7 g, yield 57%).

Step 3: The compound was synthesized according to the following procedure: To a mixture of 2,2-dimethyl-1,3-dioxan-5-one (2.6 g), dimethyl amine HCl salt (1.8 g) in DCM (50 mL) was added NaHB(OAc)$_3$ (6.0 g) and Et$_3$N (3.0 mL). The reaction mixture was stirred at room temperature overnight and then diluted with aq. NaHCO$_3$. The organic layer was dried and evaporated to give colorless oil (2.5 g, yield 79%).

Step 4: A solution of step-3 product (1.5 g) in MeOH (10 mL) was charged with Pd—C (0.5 g, 10% wet) and hydrogenated under a hydrogen balloon at room temperature overnight. The catalyst was filtered off and the solvent was evaporated to give the product (0.64 g, yield 71%) as colorless oil.

Step 5: The compound was synthesized according the general procedure from compound B and step-4 product as a yellow solid.

Step 6: Example 37 was synthesized according to a similar procedure to the following: To a mixture of tert-butyl (4-(4-((5-chloro-4-((2-(dimethylphosphoryl)phenyl) amino) pyrimidin-2-yl)amino)-5-methoxy-2-nitrophenyl)-2-methylbut-3-yn-2-yl)carbamate (240 mg) in acetone (1.0 mL) and Zn dust (0.3 g), NH$_4$Cl (0.15 g), was added drops of water. The mixture was stirring at room temperature for 15 min and then diluted with DCM (5 mL). After filtration, the organic solution was evaporated and the residue was used for next step. The residue was dissolved in THF (3.0 mL) and Et$_3$N (0.05 mL) and solution was treated with acroyl chloride. The reaction was monitored by HPLC until start material disappear. The reaction was quenched with aq. NaHCO$_3$ and extracted with DCM (2×5.0 mL). The organic solution was concentrated and the residue was purified by a prep-TLC plate (10% MeOH/DCM) to give the desired product.

Scheme 35:

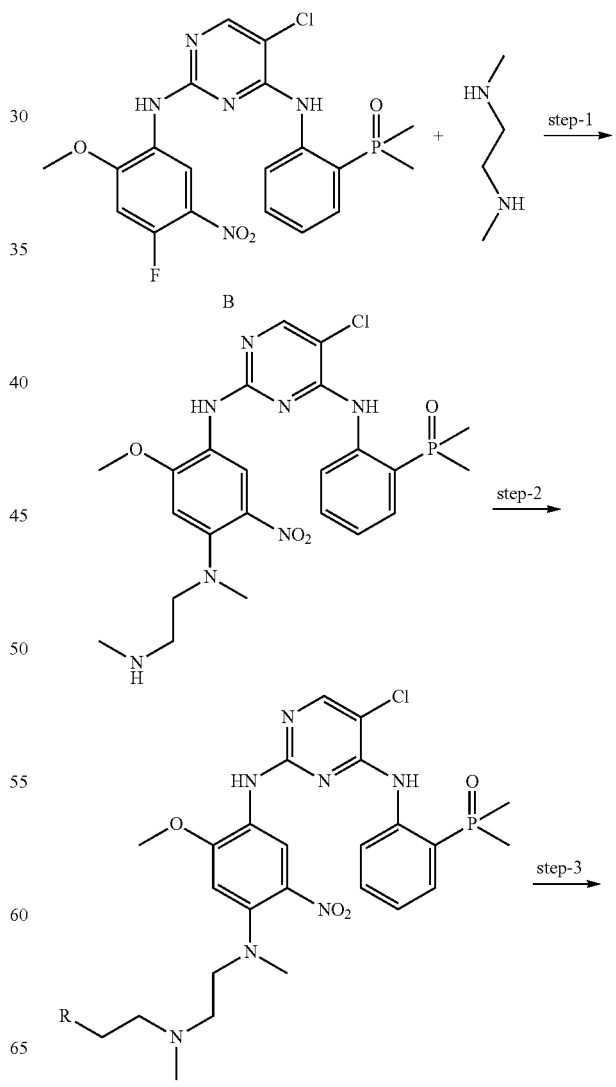

-continued

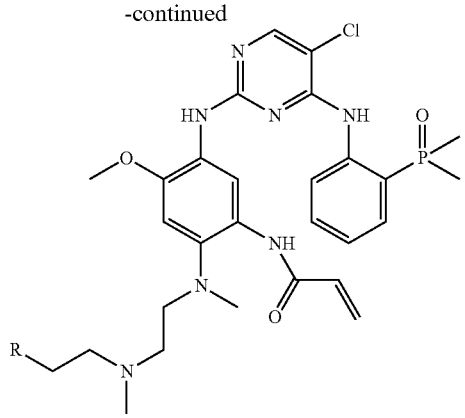

Step 1: To a solution of N,N'-dimethylethylenediamine (300 mg) in DMF (2.0 mL) was added K₂CO₃ (1.0 g) and compound B (466 mg). The mixture was heated at 80° C. for 3 h. Solvent was evaporated and the residue was extracted with DCM and then purified by a prep-TLC plate (10% MeOH/DCM with 1% NH₃ in methanol) to give product as a yellow solid (400 mg, yield 75%).

Step 2: A solution of step 1 product (1 eq) in DMF (3.0 mL) was treated with NaHCO₃ (0.5 g) and the respective bromide (2.5 eq) at 50° C. for 5 h. Solvent was evaporated and the products were purified by a prep-TLC plate (8% MeOH/DCM) to give product as yellow solids.

Step 3: Reduction of the nitro group and formation of the corresponding acrylamide was carried out according to the procedure in Scheme 32, step-3 and step-4.

The methoxy- and fluoro-compounds below were synthesized by this method:

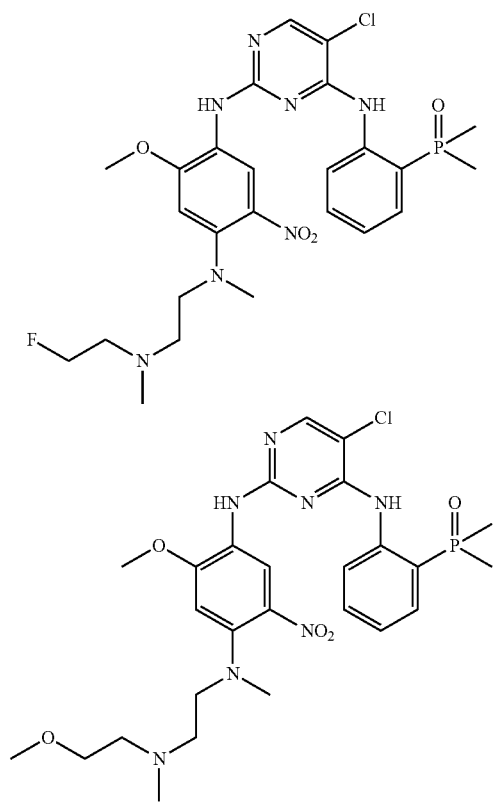

and were converted to the corresponding acrylamides. See Example 67.

Scheme 36:

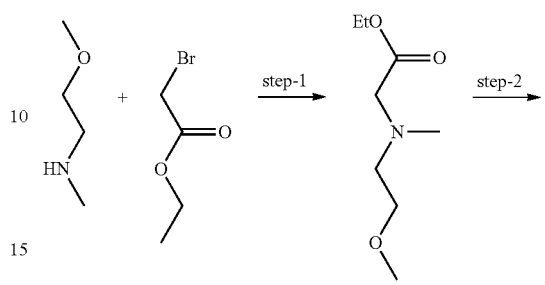

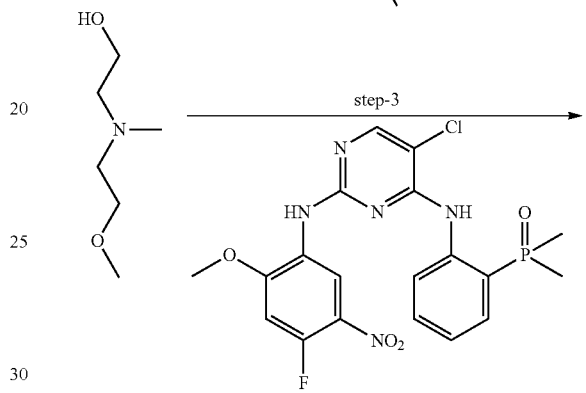

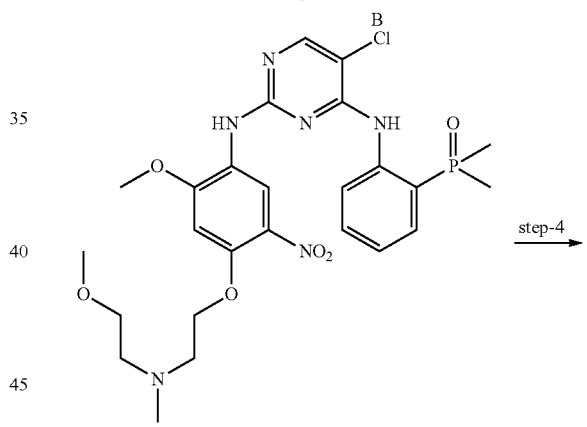

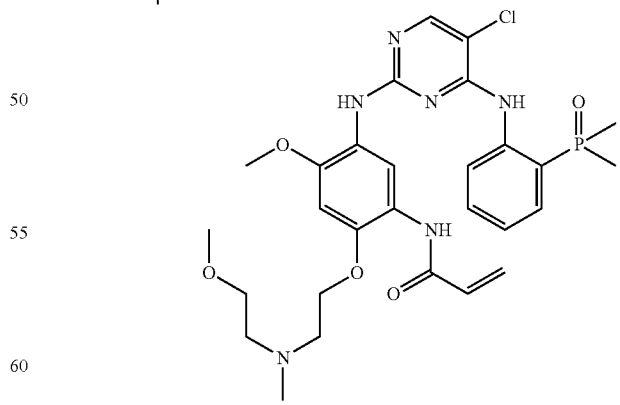

Step 1: A mixture of N-(2-methoxyethyl)methylamine (1.8 g) and ethyl bromoacetate (3.4 g) in acetonitrile (20 mL) was treated with K₂CO₃ (4.0 g) and NaI (20 mmol). The mixture was refluxed overnight. Solvent was evaporated and the residue was extracted with DCM and then purified on Silica gel column (0-8% MeOH/DCM) to give the product as colorless oil (3.2 g, yield 93%).

Step 2: To a solution of step-1 product (3.5 g) in THF (20 mL) was added LAH (800 mg) portion wise. The resulting mixture was stirred at room temperature overnight and then quenched with EtOAc and water. After filtration, the organic solution was evaporated to give colorless oil (2.0 g, yield 75%).

Step 3: The step 3 product compound was synthesized according the general procedure from compound B (400 mg) and step-4 product to give the title compound as a yellow solid (200 mg, yield 40%).

Step 4: Example 39 was synthesized according to a similar procedure to that used in Step 6 of Example 37.

Scheme 37

A.

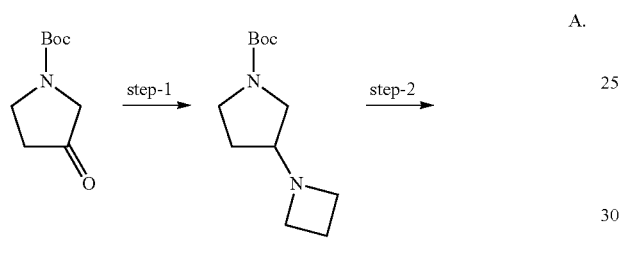

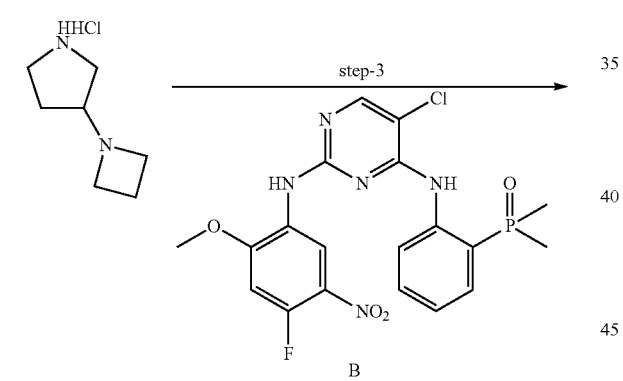

B

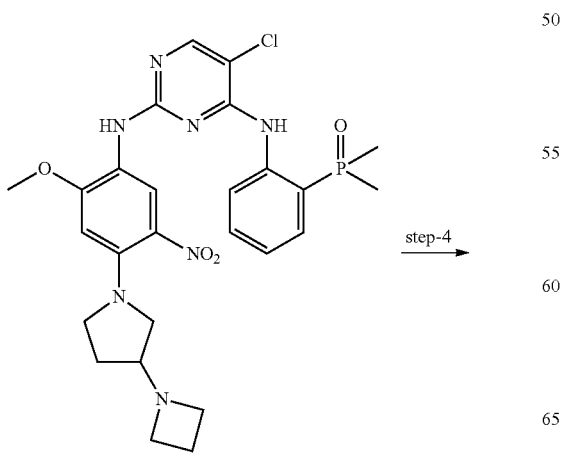

-continued

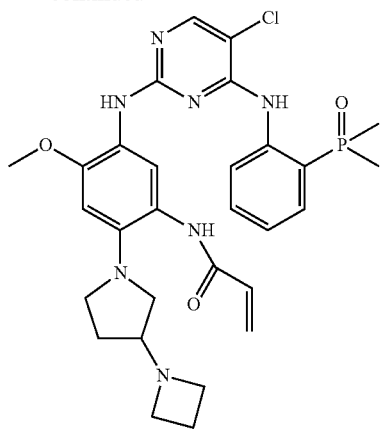

Step-1

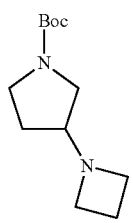

Molecular Weight: 226.32

To a mixture of 1-Boc-3-pyrrolidine (1.85 g), azetidine (0.65 g) in DCM (10 mL) was added NaHB(OAc)$_3$ (3.5 g) and molecular sieves (3.0 g). The reaction mixture was stirred at room temperature for 3 h and diluted with aq. NaHCO$_3$. The organic layer was dried and evaporated. The residue was column purified on Silica gel (5% MeOH/DCM) to give the product as a white solid (1.6 g, yield 71%).

Step-2

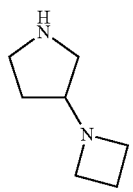

Molecular Weight: 126.20

To a solution of step-1 product (230 mg) in MeOH (1.0 mL) was added HCl in dioane (3.0 mL, 4.0M solution) at room temperature. The mixture was stirred for 1 h and solvent evaporated to give white solid for next step.

101

Step-3

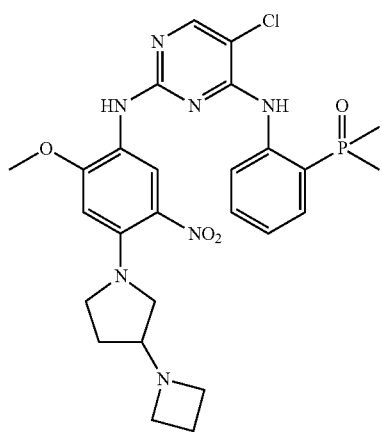

Molecular Weight: 572.00

To a mixture of compound B (450 mg), product of step-2 in DMF (3.0 mL) was added molecular sieves (1.0 g) and K₂CO₃ (1.0 g). The reaction mixture was heated at 60° C. for 30 min. Solvent was evaporated and the residue was purified by a prep-TLC plate (10% MeOH/DCM) to give product as a yellow solid (380 mg, yield 69%).

Step-4

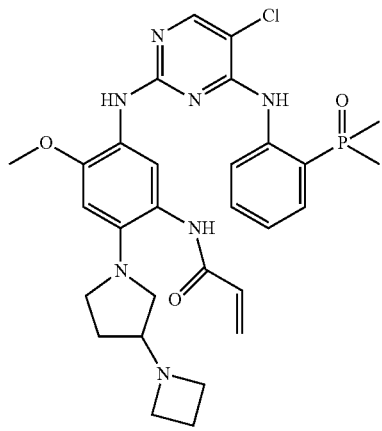

Step-4 was carried out using the procedures of Scheme 32 step-3 and step-4 to yield the desired product (Example 68) as a yellow solid (44 mg)

B.

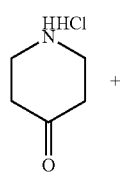

+

102

-continued

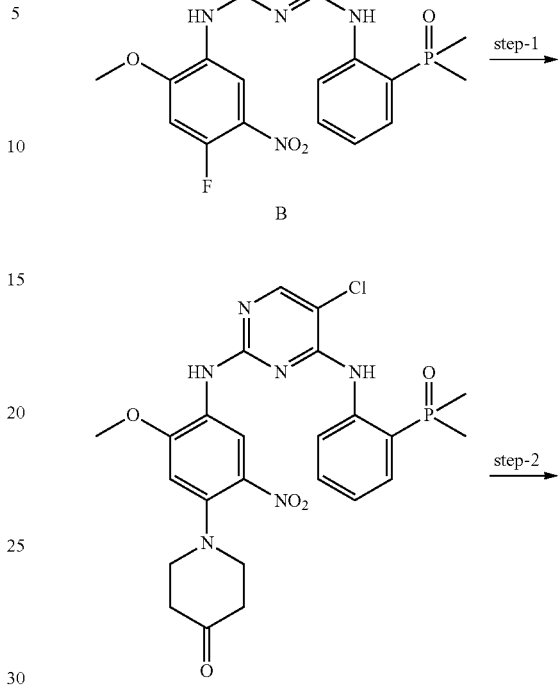

B step-1 step-2 step-3

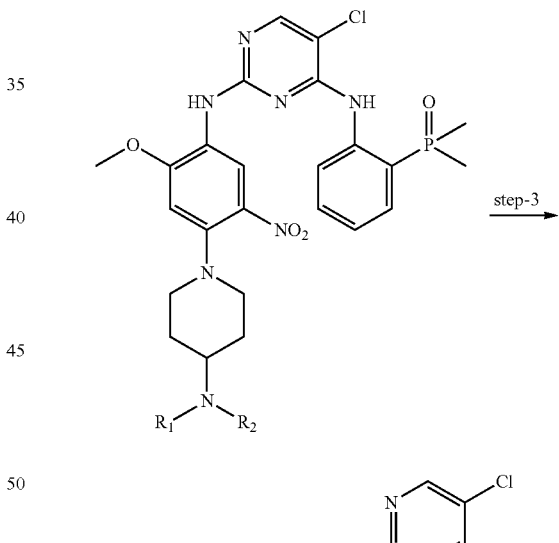

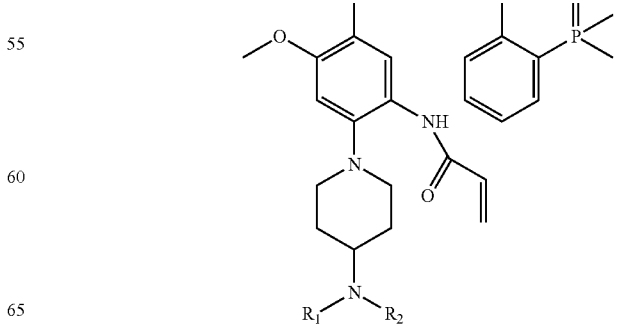

Step-1

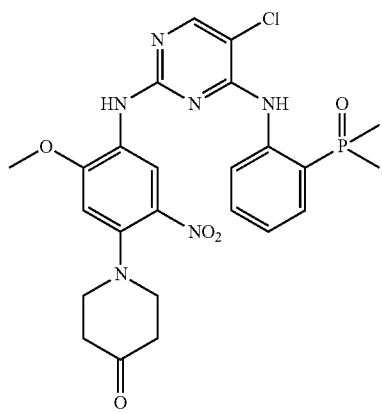

Molecular Weight: 544.93

To a mixture of compound B (3.0 g) and 4-piperidinone HCl salt in DMF (5.0 mL) was added K$_2$CO$_3$ (2.5 g). The mixture was heated at 70° C. for 3 h and solvent was evaporated.

The residue was extracted with DCM and purified by CombiFlash (MeOH/DCM). The product (1.6 g, yield 46%) was obtained as a red solid.

Step-2

General procedure of reductive amination: To a mixture of step-1 product (275 mg), respective amines (1.5 eq) in DCM was added NaHB(OAc)$_3$ (2 eq) and molecular sieves (0.3 g). The resulting mixture was shaked at room temperature for 4 h and treated with wet NaHCO$_3$. The organic solution was separated and purified by prep-TLC plates (7-15% MeOH/DCM) to give products.

Compounds synthesized by this method:

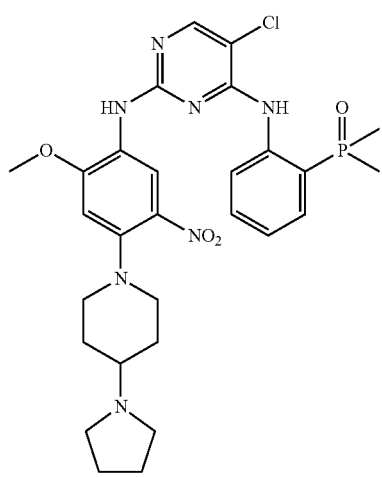

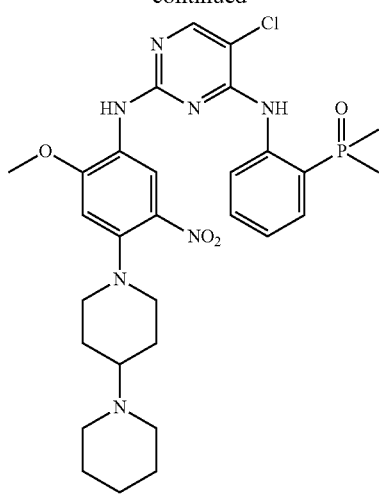

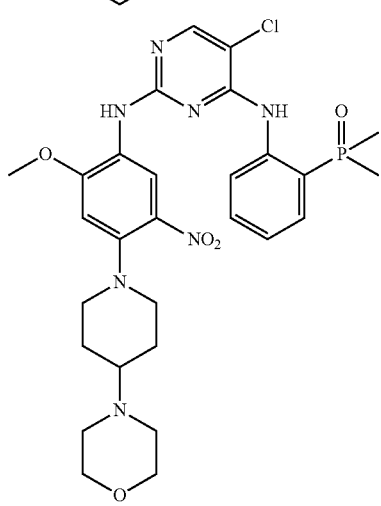

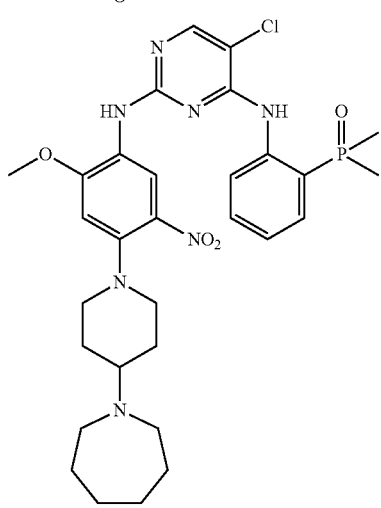

Step-3

Reduction of the nitro group and formation of the corresponding acrylamide was carried out according to the procedure in Scheme 32, step-3 and step-4.

105
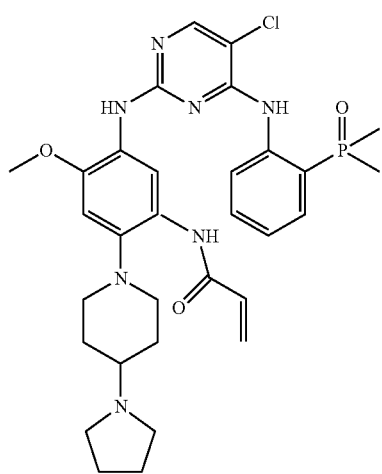
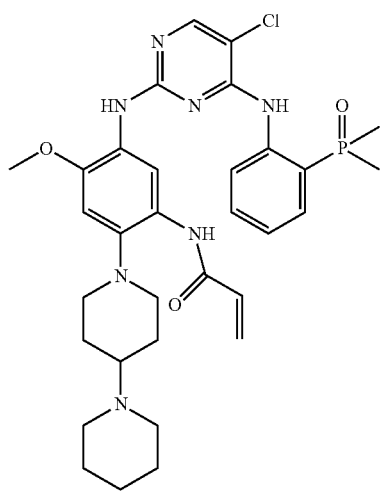
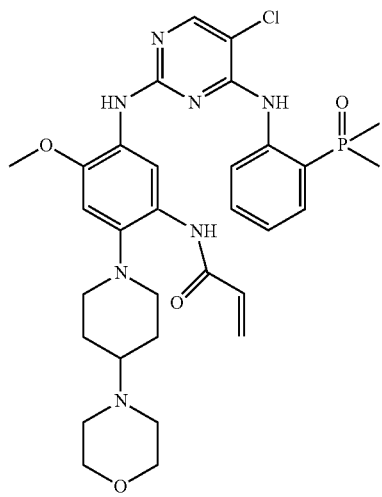
106
-continued
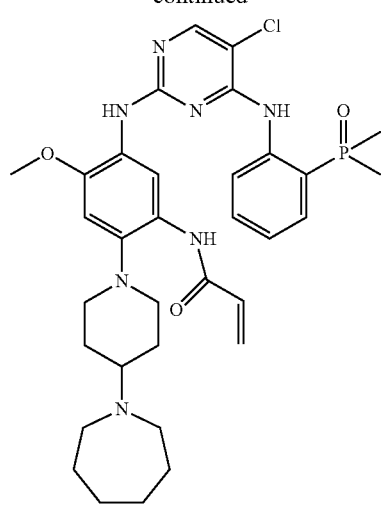
Scheme 38
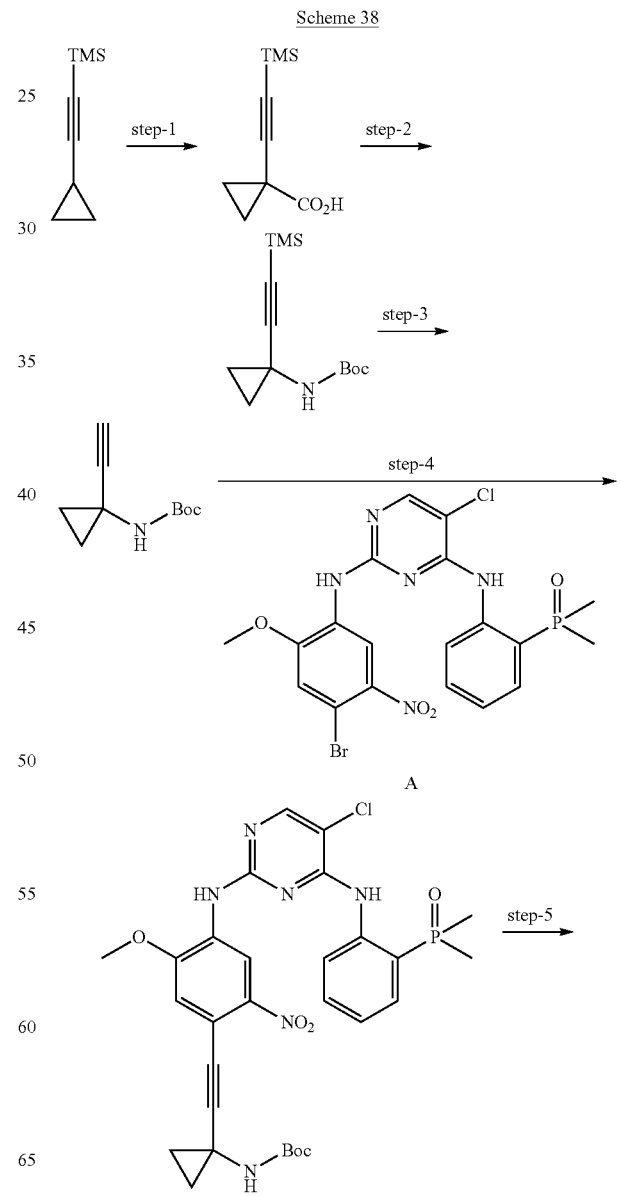

-continued

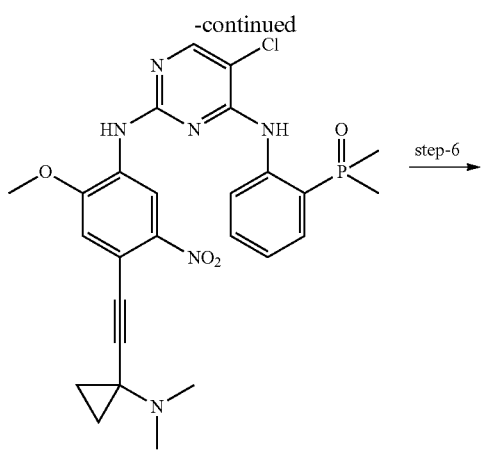

step-6 →

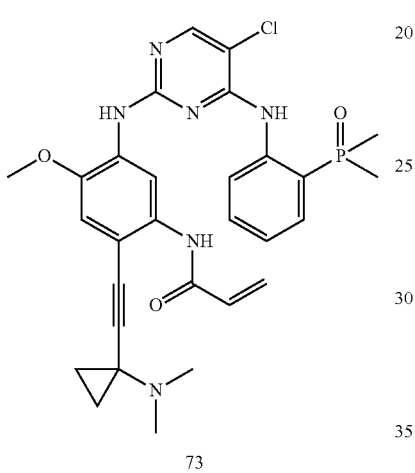

73

Step-1

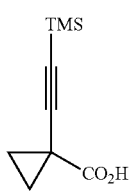

Molecular Weight: 182.29

To a solution of cyclopropyl(trimethylsilyl)acetylene (13.8 g) in ether (200 mL) was added n-BuLi (40 mL, 2.5M in hexane). The reaction mixture was stirred at room temperature overnight. The dark-yellow solution was cooled to −78° C. and a large excess of powdered dry ice was added in portions. The reaction mixture was allowed to warmed up to room temperature and poured into ice-cooled water. The layer was separated, and the aqueous layer was washed with Et$_2$O, acidified by adding 12N aq. HCl solution and extracted with Et$_2$O. The organic layer was dried and concentrated to give the title compound as a white solid (8.5 g, yield 47%).

Step-2

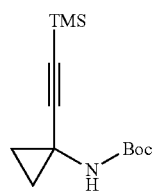

Molecular Weight: 253.41

To a solution of step-1 product (1.8 g) and DPPA (2.79 g) in t-BuOH (30 mL) was added Et$_3$N (2.02 g), The mixture was refluxed for 20 h. Solvent was evaporated and the residue was column purified on Silica gel (20% Et$_2$O)/heptane) to give the product as a white solid (1.3 g, yield 52%).

Step-3

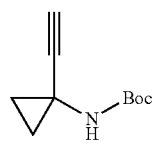

Molecular Weight: 181.23

A solution of step-2 product (1.2 g) in THF (10 mL) was treated with n-Bu$_4$NF (6.0 ml, 1.0M solution in THF). The mixture was stirred at room temperature for 1.5 h and solvent was evaporated. The residue was column purified on Silica gel (20% Et$_2$O)/heptane) to give the product as a white solid (0.75 g, yield 87%).

Step-4

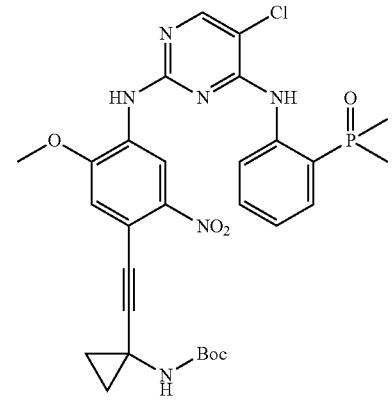

Molecular Weight 627.03

The product of Step-3 was then reacted with Compound A using the procedure of Scheme 32, step-2.

Step-5

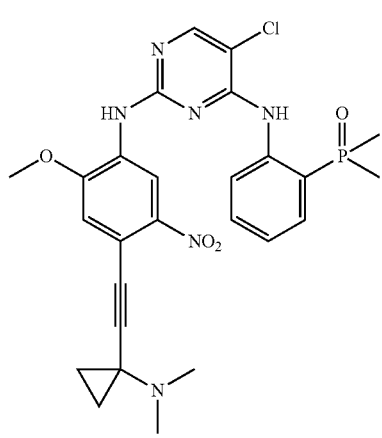

Molecular Weight 554.97

To a solution of step-4 product (250 mg) in DCM was added HCl in dioxane (1.5 mL, 4.0M solution) at −78° C. The mixture was warmed up slowly to room temperature. Solvent was evaporated and the residue was treated with aq. $K_2CO_3$ and then purified by a prep-TLC plate (10% MeOH/DCM) to give yellow solid (150 mg).

The yellow solid was dissolved in DCM (3.0 mL) and treated with formyl aldehyde (5 drops, 40% aq. solution) and MgSO4 (0.5 g, anhydrous) for 30 min. To the mixture was added $NaBH(OAc)_3$ (2 eq). The reaction mixture was stirred for 1 h and diluted with aq. $NaHCO_3$. The mixture was extracted with DCM and product was and purified by prep-TLC plates (10% MeOH/DCM) to give yellow solid (50 mg, yield 23%).

Step-6

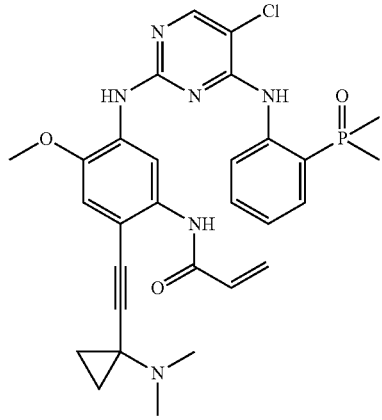

Reduction of the nitro group and formation of the corresponding acrylamide was carried out according to the procedure in Scheme 32, step-3 and step-4, to produce the final product pictured above (Example 73).

Scheme 39:

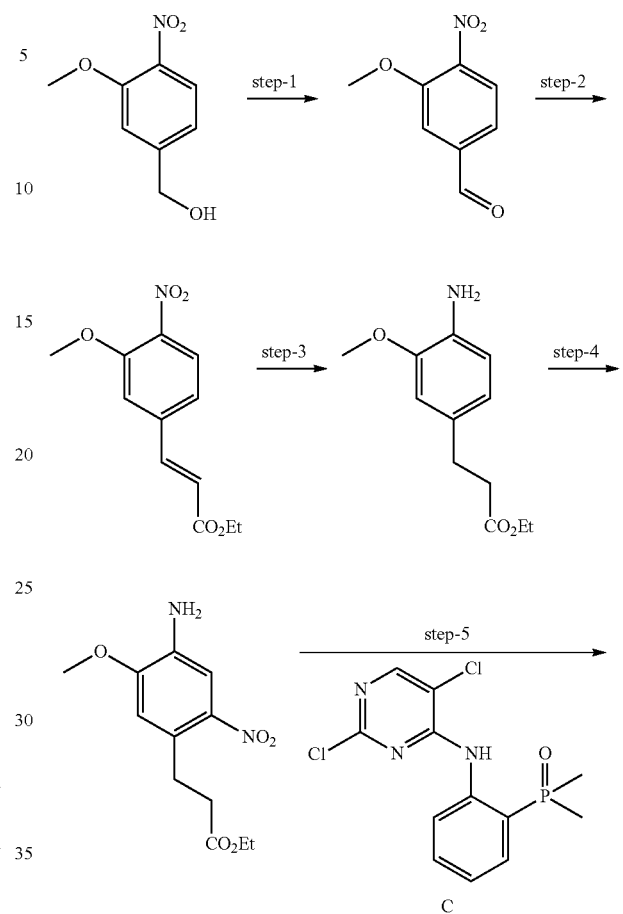

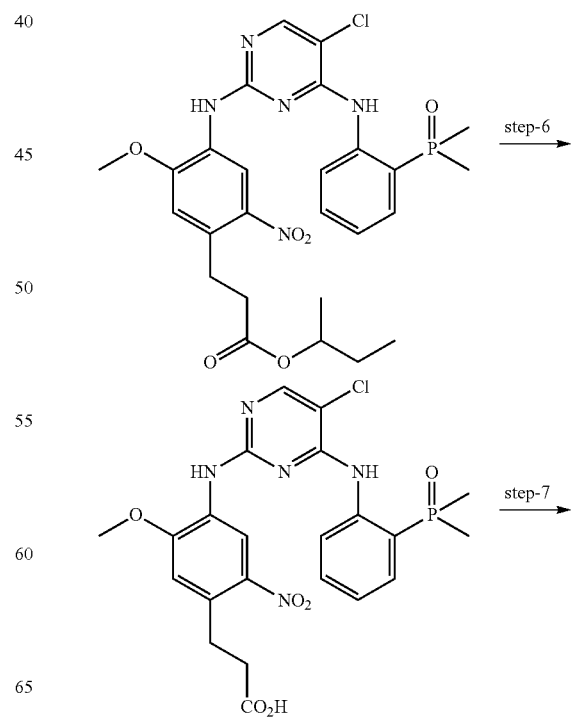

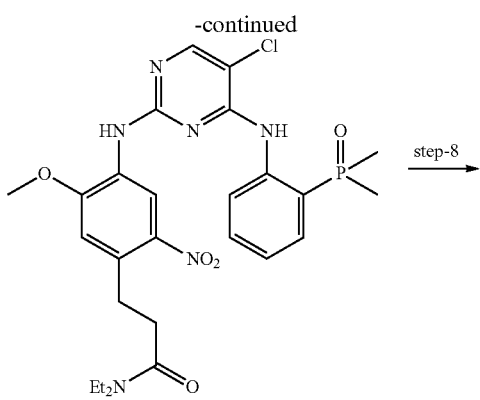

stirred at 0° C. for 2 h and at room temperature for 1 h. The mixture was treated with excess wet NaHCO3 and extracted with DCM (10 mL). The product was and purified by prep-TLC plates (8% MeOH/DCM) to give orange solid (0.34 g, yield 71%).

Step 5: A solution of compound C (320 mg), step-4 product (268 mg) and TFA (0.3 mL) in 2-BuOH (2 mL) was heated at 100° C. for 18 hrs. Upon cooling EtOAc and aq. NaHCO$_3$ were added to the reaction mixture. Extraction (3×) and concentration of combined extracts gave a solid which purified by prep-TLC plates (15% MeOH/DCM) to give orange solid (410 mg, yield 71%).

Step 6: To a suspension of step-5 product (400 mg) in MeOH (2.0 mL) was added K$_2$CO$_3$ (1.0 g) and water (0.5 mL). The reaction vial was capped and heated at 60° C. for 15 min. The mixture was cooled down to room temperature and the top layer was transferred to a new vial and diluted with water. The pH was adjusted to 5-6 by adding aq HCl (2N) and the product was collected by filtration as a yellow solid (310 mg, yield 86%).

Step 7: To a mixture of step-6 product (260 mg) and Et$_2$NH (1.1 mmol) in DMF (2.0 mL) was added HBTU (1.3 mmol) and Et$_3$N (0.14 mL). The mixture was stirred at room temperature for 2 h and diluted with DCM (5.0 mL). The mixture was washed with aq. K$_2$CO$_3$ and evaporated. The residue was purified by prep-TLC plates (15% MeOH/DCM) to give an orange solid (250 mg, yield 87%).

Step 8: To a solution of step-7 product (250 mg) in THF (1.0 mL) was added BH$_3$Me$_2$S (4.0 mL, 2.0M solution in THF). The mixture was stirred at 60° C. for 2 h and solvent was evaporated. The residue was dissolved in MeOH (2.0 ml) and treated with wet K$_2$CO$_3$ in a capped vial at 70° C. for 1 h. The organic solution was evaporated and the residue was purified by prep-TLC plates (25% MeOH/DCM) to give an orange solid (170 mg, yield 70%).

Step 9: Reduction of the nitro group and formation of the corresponding acrylamide was carried out according to the procedure in Scheme 32, step-3 and step-4, to produce the final product.

Scheme 40:

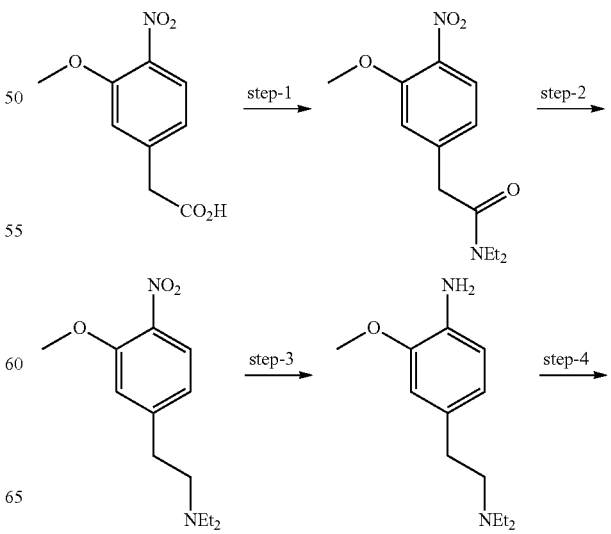

Step 1: To a solution of 3-methoxy-4-nitrobenzyl alcohol (5 g) in DCM (100 mL) was added PDC (1.5 eq) and molecular sieves (6.0 g). The mixture was stirred at room temperature for 2 h and diluted with Et$_2$O (100 mL). The mixture was filtered through a Celite pad and solvent was evaporated. The residue was washed with a small amount MeOH to give off white solid (3.7 g, yield 74%).

Step 2: To a solution of step-1 product (0.91 g) in DCM (10 mL) was added (Ethoxycarbonylmethlene)triphenylphosphorane (2.0 g). The mixture was stirred at room temperature for 30 min. Solvent was evaporated and the residue was column purified on Silica gel (20% Et$_2$O/heptane) to give a yellowish solid (1.1 g, yield 87%).

Step 3: A solution of step-2 product (0.52 g) in MeOH (10 mL) was charged with Pd—C (0.5 g, 10% wet) and hydrogenated under a hydrogen balloon at room temperature overnight. The catalyst was filtered off and solvent was evaporated to give yellow oil (0.45 g, yield 97%).

Step 4: A vial was charged with H$_2$SO$_4$ (2.0 mL) and cooled to 0° C. Step-3 product (0.4 g) was carefully introduced. Guanidine nitrate (1 eq) was added. The mixture was

113

-continued

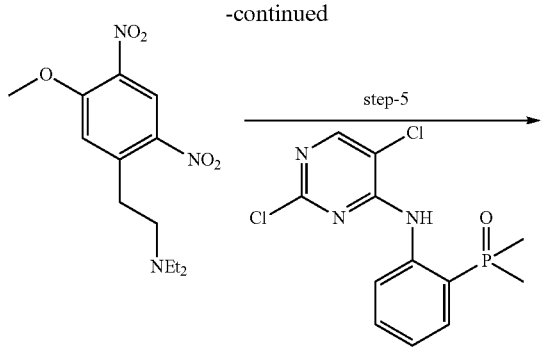

C

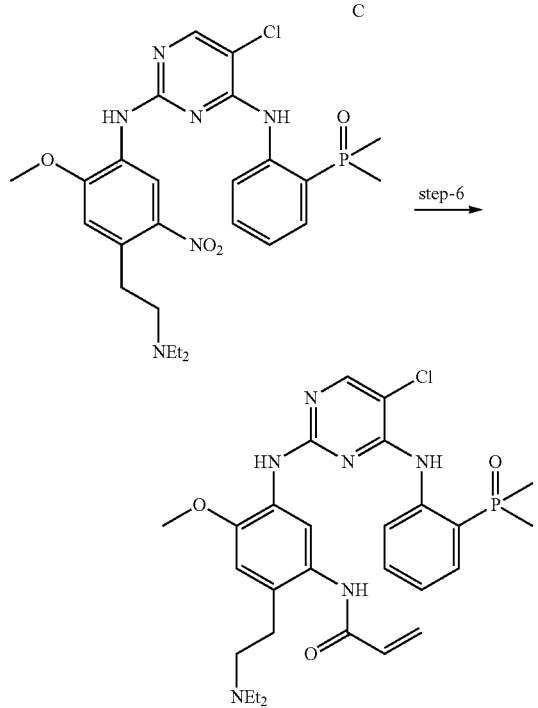

Step 1: N,N-diethyl-2-(3-methoxy-4-nitrophenyl)acetamide was made in accordance with the methods disclosed herein.

Step 2: To a solution of N,N-diethyl-2-(3-methoxy-4-nitrophenyl)acetamide (1.0 g) in THF (5.0 mL) was added BH$_3$Me$_2$S (20. mL, 2.0M solution in THF). The mixture was stirred at 60C. for 2 h and solvent was evaporated. The residue was dissolved in MeOH (10 ml) and treated with wet K$_2$CO$_3$ in a capped vial at 70° C. for 1 h. The organic solution was evaporated and the residue was purified on Silica gel column (5% MeOH/DCM) to give the product as an orange oil (0.62 g, yield 65%)

Step 3: A solution of step-2 product (600 mg) in MeOH (10 mL) was charged with Pd—C (0.5 g) and hydrogenated under a hydrogen balloon at room temperature for 3 h. The catalyst was filtered off and the solvent was evaporated to give a yellow oil (430 mg, yield 81%)

Step 4: The product of step 4 was synthesized according the procedure of step 4 of Scheme 39 as an orange oil.

Step 5: The product of step 4 was synthesized according the procedure of step 5 of Scheme 13 to afford an orange solid.

Step 6: Reduction of the nitro group and formation of the corresponding acrylamide was carried out according to the procedure in Scheme 32, step-3 and step-4, to produce the final product.

114

Scheme 41:

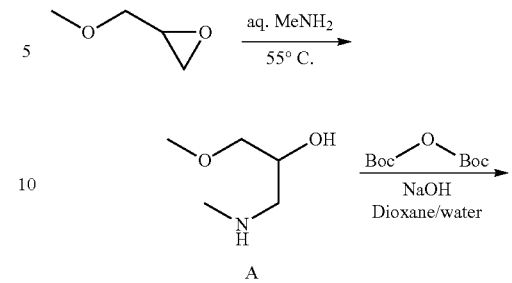

A

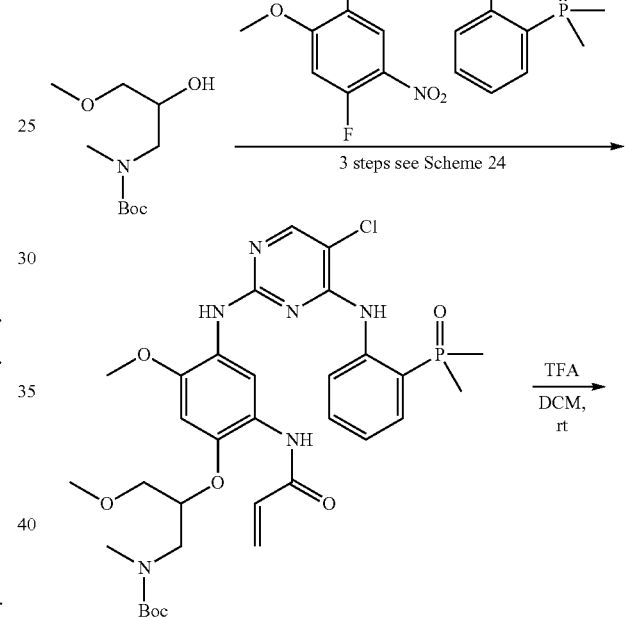

B

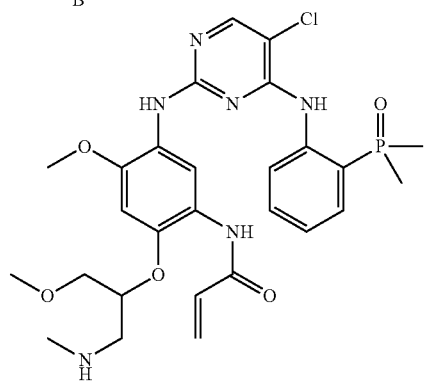

Step 1: A mixture of glycidyl methyl ether and aq. methylamine (1.5 eq) was heated at 55° C. for 2 hr. Removal of volatile components gave intermediate A which was used directly in next step.

Step 2: Intermediate A (400 mg, 3.34 mmol, 1.0 eq) in 4 ml of dioxane and 4 ml of water was adjusted to pH 12 with 4M NaOH, and cooled to 0° C. O(Boc)2 (806 mg, 3.69 mmol, 1.1 eq) was added in 2 portions and the mixture was stirred at R.T. overnight. The mixture was evaporated to reduce volume by one half and then treated with sat. NaHCO3 (3 ml). This was extracted with EtOAc (3×25 ml), dried, evaporated, and chromatographed (EtOAc/Heptane 1:2 to 1:1) to give an oil, 703 mg, in 96% yield.

Steps 3-5: the chemistry was carried out following the procedures described in Scheme 24.

Step 6: to a solution of intermediate B (304 mg) in DCM (5 mL) was added TFA (1.8 mL). The mixture was stirred at rt for 1 h then quenched with saturated sodium bicarbonate solution until pH=8.0. The organics were extracted with DCM (3×) and the combined organics were dried over anhydrous sodium sulfate, and the solvents were removed under reduced pressure to give the desired product as a pale brownish solid (262 mg, 95%).

EXAMPLE 128

Scheme 42:

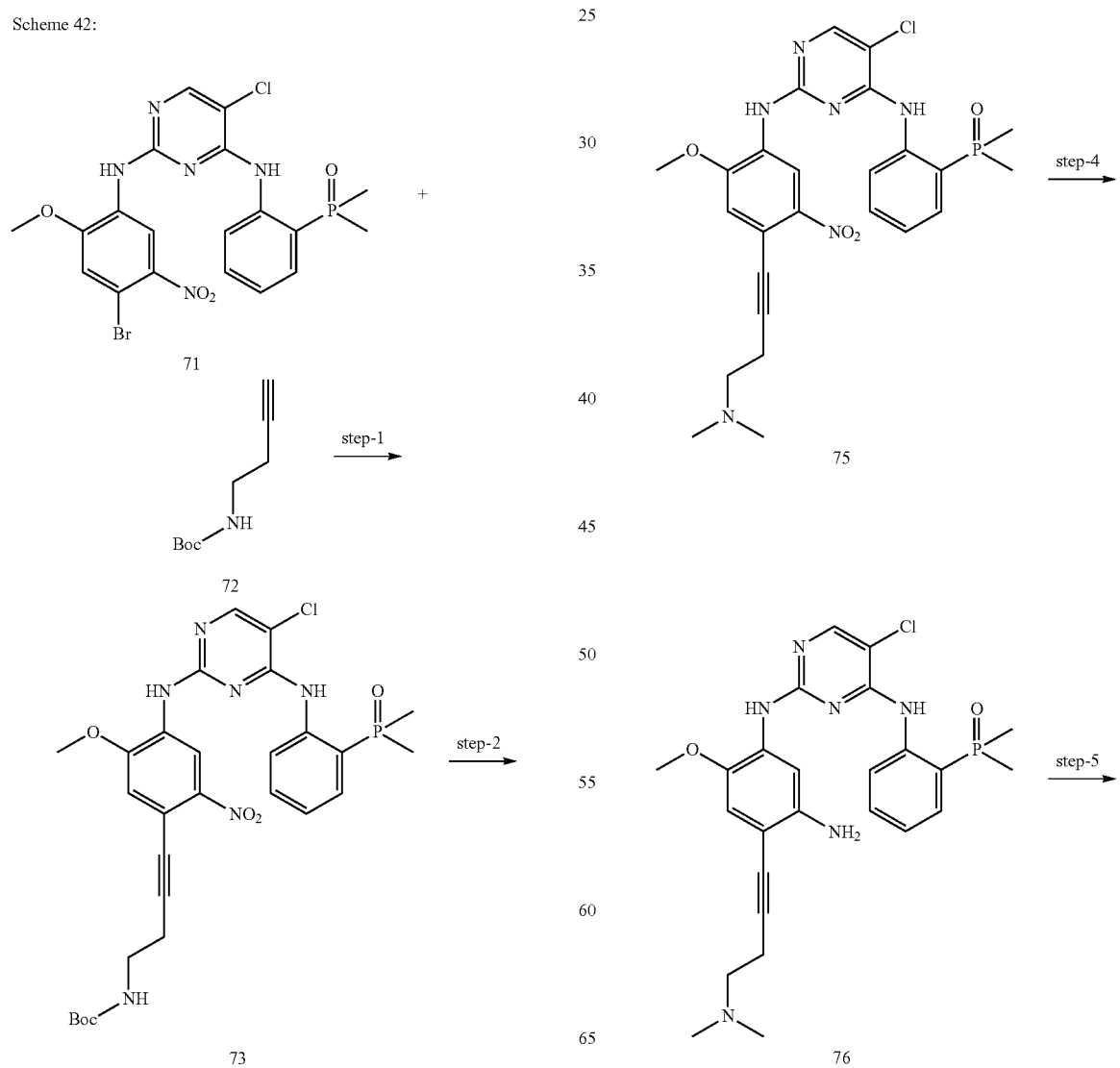

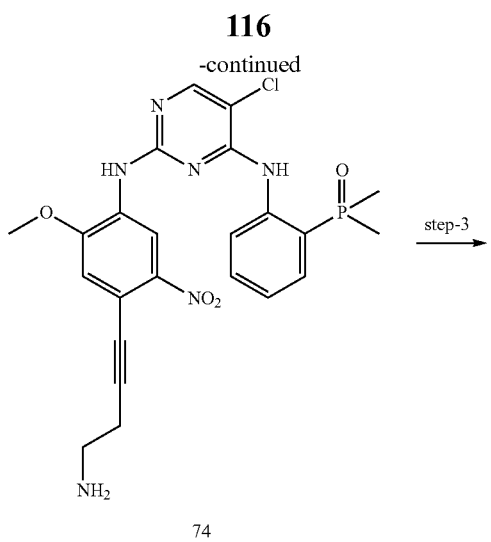

-continued

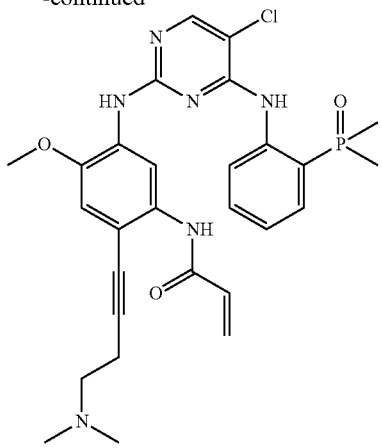

Step-1: to a solution of compound 71 (527 mg, 1.0 mmol) and tert-butyl (3-butynyl)carbamate (400 mg) in DMF (4.0 mL), was added (Ph₃P)₂PdCl₂ (0.1 g), CuI (0.05 g) and Et₃N (0.2 mL). This degased mixture was stirred at 80° C. for 3 h. The reaction mixture was concentrated and the residue was purified by a prep-TLC plate (8% MeOH/DCM) to give compound 73 as a yellow solid (280 mg, yield 46%).

Step-2: compound 73 (280 mg, 0.46 mmol) was dissolved in DCM (2.0 mL) and treated with HCl in dioxane (1.0 mL, 4.0 M) at room temperature for 20 min. Solvent was evaporated and the residue was treated with aq. sodium bicarbonate and extracted with DCM. Combined organic layers were dried and evaporated to give compound 74 (220 mg, 93%) as yellow solid.

Step-3: to a suspension of compound 74 (220 mg, 0.43 mmol) and MgSO₄ (0.5 g) in DCM (3.0 mL) was added 4 drops of formaldehyde solution (36.5%). After the resulting mixture was stirring for 20 min NaHB(OAc)₃ (250 mg) was added. The mixture was heated at 50° C. for 30 min and then quenched with aq. NaHCO₃. The product was purified by prep. TLC (DCM:MeOH=100:15) to give compound 75 (180 mg, 78%) as yellow solid.

Step-4: to a suspension of compound 75 (180 mg) and Zn dust (0.3 g) in acetone (1.0 mL) was added NH₄Cl (0.15 g) and drops of water. The mixture was stirring at room temperature for 15 min and then diluted with DCM (5 mL). After filtration, the organic solution was evaporated and the residue (140 mg) was used for next step.

Step-5: to a solution of compound 76 (~140 mg) in DCM (3.0 mL) was added acrylic acid (0.076 mL), EDC (200 mg), Et₃N (0.2 mL). The mixture was stirring at room temperature for 3 h. Solvent was evaporated and the residue was purified by prep TLC (DCM:MeOH=100:15) to give title compound (40 mg, 26%) as light yellow solid.

EXAMPLE 129

Scheme 43:

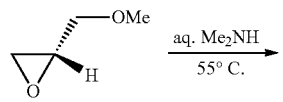 

-continued

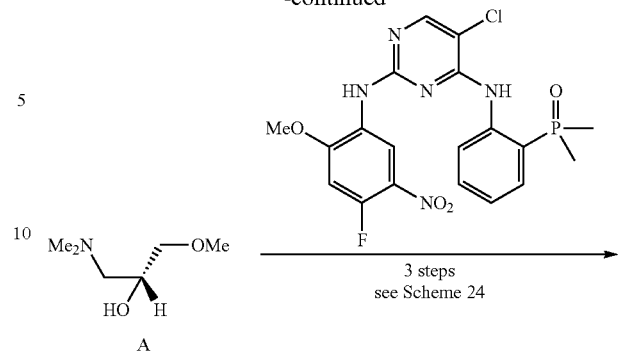

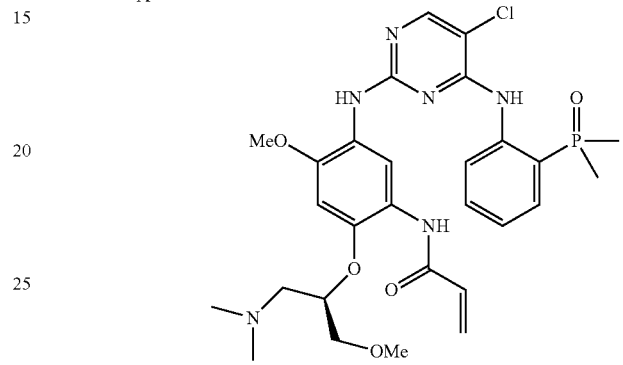

Using the procedure described in step 1 of Scheme 41 R-(−)-glycidyl methyl ether was converted into amino alcohol A. Title compound was obtained from transformation of A via a 3-step chemical sequence, as described in Scheme 24.

EXAMPLE 130

Title compound was prepared in a manner similar to Example 129 using S-(+)-glycidyl methyl ether as starting material.

EXAMPLE 131

Title compound was prepared in accordance with the method described in Scheme 12 by substituting 2,4-dichloro-5-methoxypyrimidine for 5-bromo-2,4-dichloropyrimidine.

EXAMPLE 132

Title compound was prepared in accordance with the method described in Scheme 5 by reacting intermediate 5 with 2-chloroacryloyl chloride.

EXAMPLE 133

Title compound was prepared in accordance with the method described in Scheme 12 by substituting 2,4,5-trichloropyrimidine for 5-bromo-2,4-dichloropyrimidine and 2-methoxy-4-methyl-5-nitroaniline for 2-methoxy-5-nitroaniline.

EXAMPLE 134

Title compound was prepared in accordance with the method described in Scheme 12 by substituting 2,4,5-trichloropyrimidine for 5-bromo-2,4-dichloropyrimidine and 2-(trifluoromethoxy)-5-nitroaniline for 2-methoxy-5-nitroaniline.

EXAMPLE 135

Title compound was prepared in accordance with the method described in Scheme 12 by substituting 2,4,5-trichloropyrimidine for 5-bromo-2,4-dichloropyrimidine and 2-ethyl-5-nitroaniline for 2-methoxy-5-nitroaniline.

Synthesis of Triazine Compound with $CF_3$ at $R^{a2}$

Title compound was prepared in accordance with the method described in Scheme 12 by substituting 2,4-dichloro-1,3,5-triazine for 5-bromo-2,4-dichloropyrimidine and 2-(trifluoromethoxy)-5-nitroaniline for 2-methoxy-5-nitroaniline.

EXAMPLE 136

Title compound was prepared in accordance with the method described in Scheme 12 by substituting 2,4,5-trichloropyrimidine for 5-bromo-2,4-dichloropyrimidine and 2-chloro-5-nitroaniline for 2-methoxy-5-nitroaniline.

EXAMPLE 137

Title compound was prepared in accordance with the method described in Scheme 5 by reacting intermediate 5 with 2-chloroacetyl chloride.

EXAMPLE 138

Scheme 45:

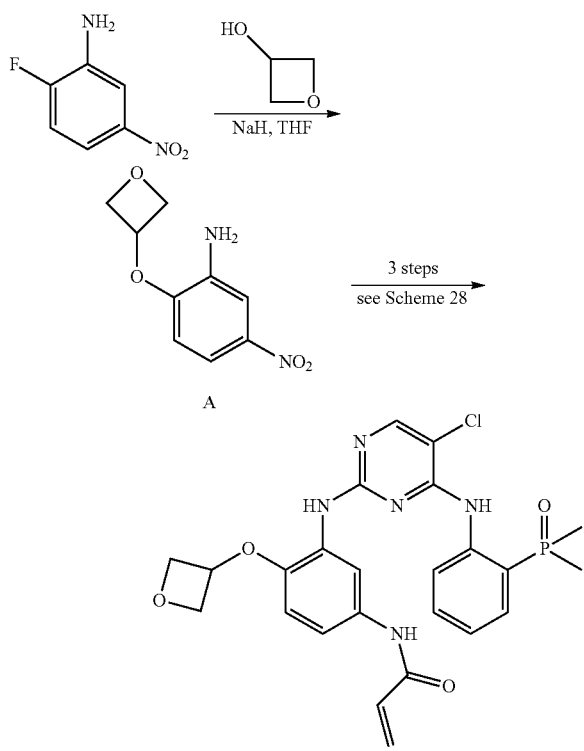

To a suspension of NaH (0.67 g, 5 eq) in THF (30 mL) was added dropwise a solution of oxetane-3-ol (0.24 g, 1 eq) in THF (5 mL) under N2 at r.t. After the mixture was stirred at r.t. for 1 hr, 2-fluoro-5-nitroaniline (0.51 g, 1 eq) was added. The resulting mixture was heated at 70° C. for 3 hr and then quenched with water. Concentration removed THF and the residue was taken up in DCM. Extraction, concentration and purification on silica gel column (0-100% EtOAc in heptane) furnished intermediate A as a yellow oil (52%).

Intermediate A was converted into desired final compound via a 3-step sequence outlined in Scheme 28.

EXAMPLE 139

Scheme 46:

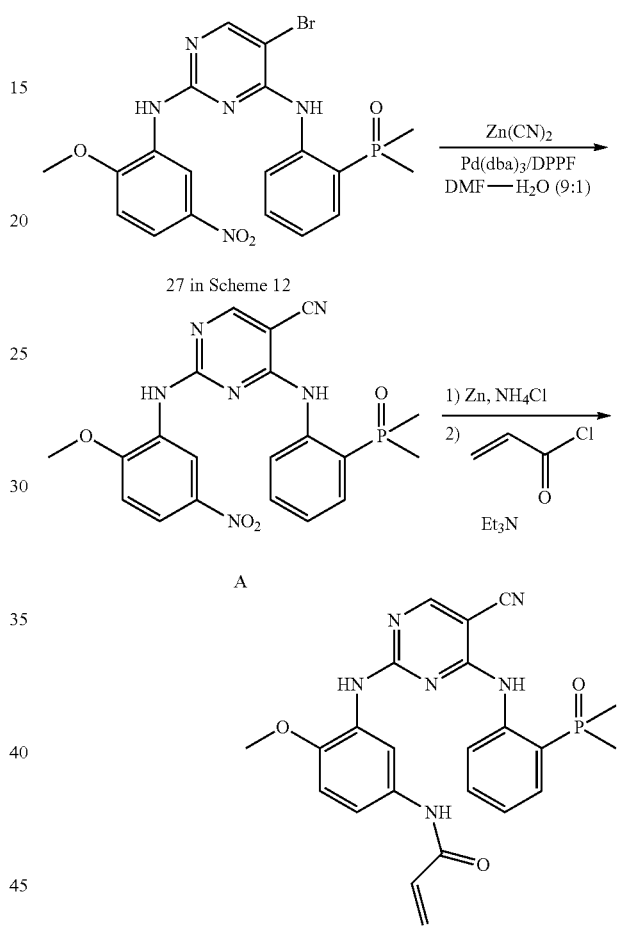

Zinc cyanide (70 mg, 0.65 eq), intermediate 27 (490 mg, 1 eq), $Pd_2(dba)^3$ (46 mg, 0.05 eq), DPPF (69 mg, 0.13 eq) was placed in a microwave tube containing DMF-H2O (3 mL). This mixture was flushed with Ar and then heated at 130° C. for 1.5 hr. The reaction mixture was evaporated and the residue was purified on silica gel column (0-5% MeOH in DCM) furnished intermediate A as a yellow solid (32%).

Intermediate A was converted into desired final compound via a 2-step sequence outlined in Scheme 12.

EXAMPLE 140

Title compound was prepared in a manner similar to Example 133 by substituting 2-chloroacetyl chloride for acryloyl chloride in last step.

EXAMPLE 141

Title compound was prepared in a manner similar to Example 137 by substituting 2,4-dichloro-5-methylpyrimidine for 2,4,5-trichloropyrimidine.

EXAMPLE 142

Title compound was prepared in accordance with the method described in Scheme 43 by substituting (±)-glycidyl ethyl ether for R-(−)-glycidyl methyl ether.

EXAMPLES 143-146

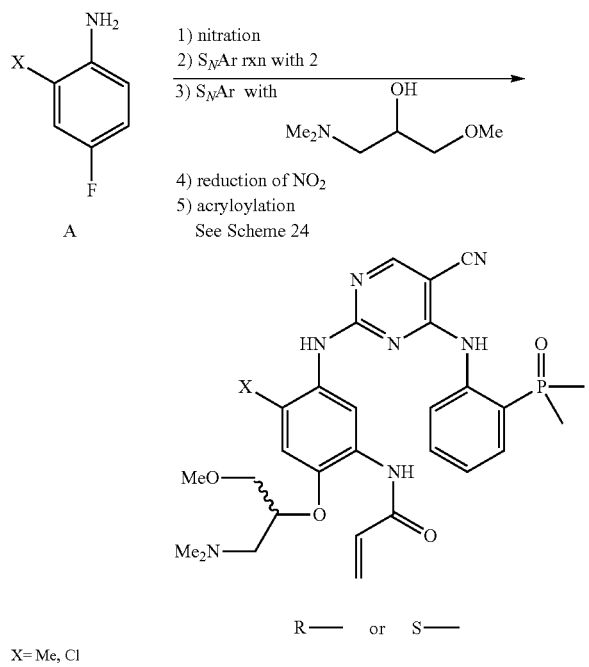

X= Me, Cl

The title compounds were prepared in accordance with the method described in Scheme 24 by substituting aniline A for 2-methoxy-4-fluoroaniline and optically pure 1-(dimethylamino)-3-methoxy-2-propanol for 1-(2-hydroxyethyl)-4-methylpiperazine. 1-(dimethylamino)-3-methoxy-2-propanol was synthesized via a procedure described in Scheme 43.

EXAMPLE 147

Title compound was prepared in accordance with the method described in Scheme 5 by reacting intermediate 5 with 2-fluoroacetyl chloride.

EXAMPLE 148

Title compound was prepared in accordance with the method described in Scheme 28 by substituting 2-chloroacetyl chloride for acryloyl chloride in last step.

EXAMPLE 149

Title compound was prepared in accordance with the method described in Scheme 22 by substituting 2-chloroacetyl chloride for acryloyl chloride in last step.

EXAMPLE 150

Title compound was prepared in accordance with the method described in Scheme 5 by reacting intermediate 5 with (chloromethyl)sulfonyl chloride.

EXAMPLES 151, 152, and 156

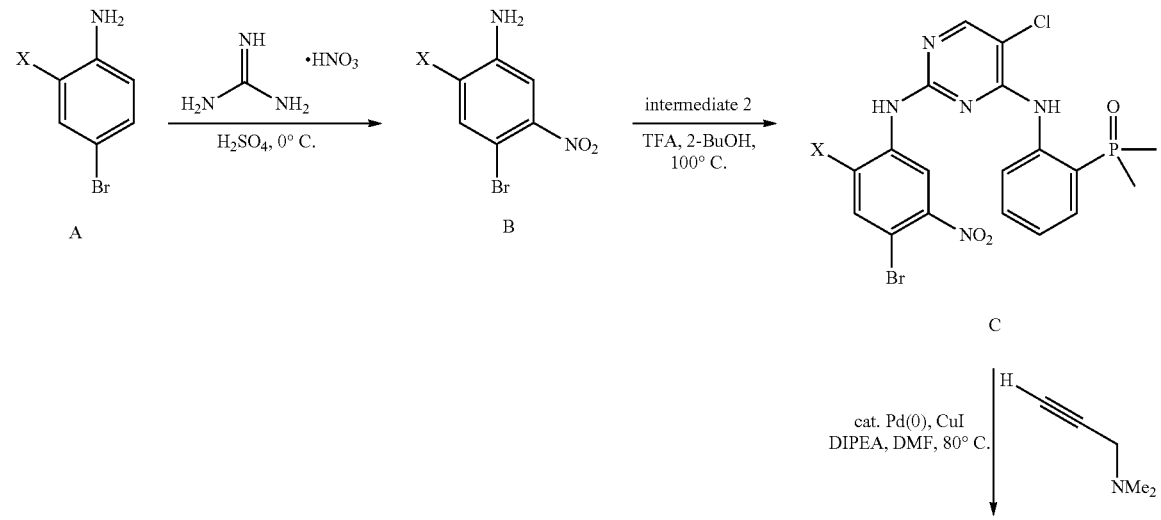

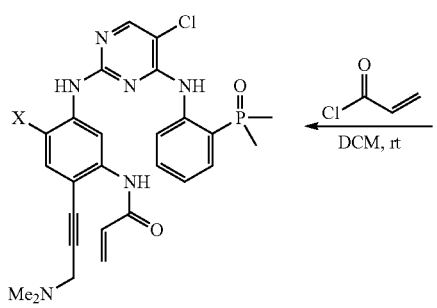

X= MeO, Me, Et, Cl

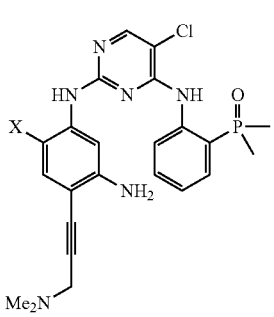

E

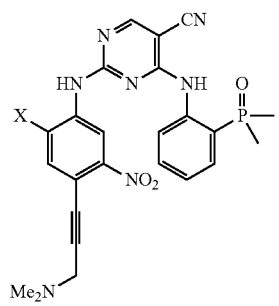

D

Steps 1-2: the chemistry was carried out according to the procedure described for steps 2 and 3 in Scheme 24.

Step 3: Into a Schlenk flask was loaded intermediate C (260 mg), PdCl2(PPh3)2 (5 mol %) and CuI (10 mol %). This flask was capped with a rubber septum and then degassed under vacuum for 1 min before N2 refill. Anhydrous DMF (4 mL) was added followed by the addition of DIPEA (0.1 mL) and 1-(dimethylamino)-3-butyne (0.1 mL, note this alkyne was purged with dry N2 gas immediately before use). The flask was sealed and the mixture was stirred at 80° C. for 16 h. Upon cooling, the reaction mixture was taken up in EtOAc and water. Extraction and concentration of combined organic layers afforded crude D which was used directly in the next step.

Steps 4-5: the chemistry was carried out according to the procedure described for steps 3 and 4 in Scheme 12.
m

EXAMPLE 153

Title compound was prepared in accordance with the method described in Scheme 48 by substituting 2-(isopropylsulfonyl)aniline for 2-(dimethylphosphoryl)aniline.

Examples 154 and 155

Scheme 49:

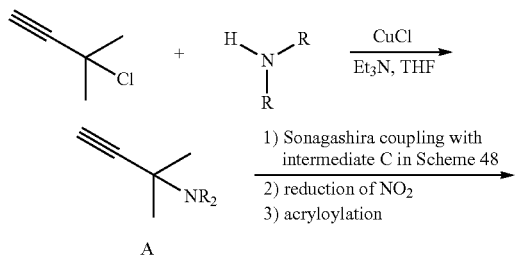

-continued

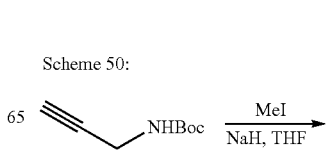

R = Me, Et

Step 1: To a stirred mixture of diethylamine (10.3 ml, 99.6 mmol), 3-chloro-3-methylbut-1-yne (10.2 g, 99.6 mmol), triethylamine (16.7 mL, 119 mmol), and THF (100 mL) at 0° C. was added copper (I) chloride (0.986 g, 9.96 mmol). The resulting suspension was allowed to warm to room temperature, and stirring continued for 4 hours. The reaction mixture was partitioned between diethyl ether (250 mL) and a saturated aqueous solution of NaHCO3 (100 mL). The phases were separated, and the aqueous phase was re-extracted with diethyl ether (100 mL). The combined organic phases were dried (Na2SO4), filtered, and concentrated. The brown oil was distilled (105-110° C.) at atmospheric pressure under N2. The product A was obtained as an oil (1.85 g, 9%).

Steps 2-4: intermediate A was converted into desired final compound in accordance with the method described in Scheme 48 by substituting A for N,N-dimethylpropargylamine.

EXAMPLE 160

Scheme 50:

125
-continued

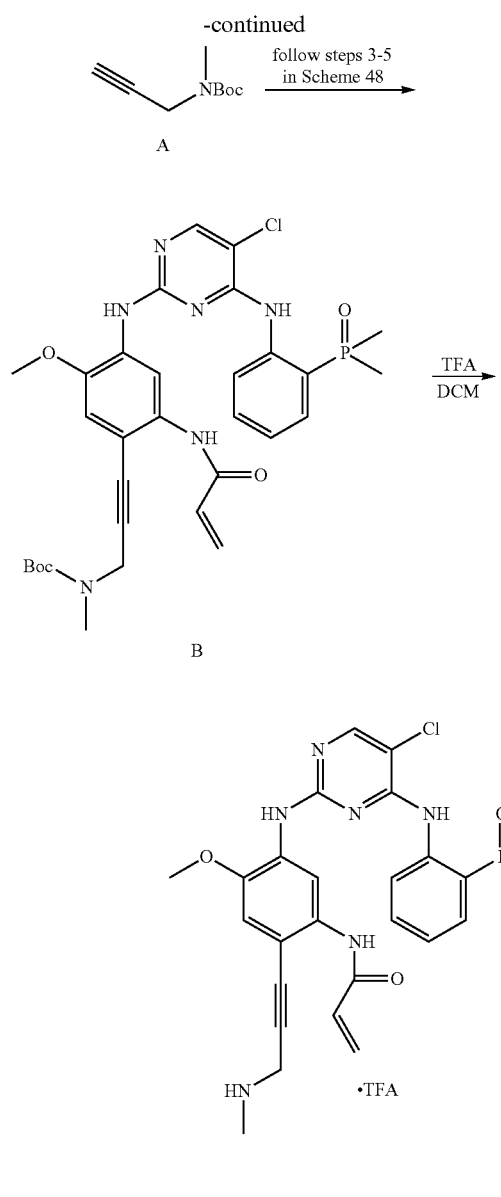

Step 1: to a solution of (N-Boc)propargylamine (3.1 g) in DMF (20 mL) was slowly added NaH (1.1 eq) at 0° C. under N2. After the mixture was stirred at r.t. for 1 hr, methyl iodide (1.1 eq) was added at 0° C. Ice bath was removed and the flask was warmed up naturally to r.t. Water was added to quench the reaction. After removal of solvents the residue was taken up in EtOAc and water. Extraction and concentration of combined organic phases gave essentially pure A (95%).

Steps 2-4: Intermediate A was converted into compound B in accordance with the method described in steps 3-5 of Scheme 48 by substituting A for N,N-dimethylpropargylamine.

Step 5: to a solution of compound B (189 mg) in DCM (3 mL) was added TFA (1 mL). The mixture was stirred at rt for 1 h. The volatile components were removed under reduced pressure to give a cloudy residue. Trituration with MTBE followed by filtration and wash with MTBE gave the desired product as a off-white powder (92 mg, 57%).

126
EXAMPLE 164

Title compound was prepared in accordance with the method described in Scheme 12 by substituting 2,4,5-trichloropyrimidine for 5-bromo-2,4-dichloropyrimidine and 3-amino-4-(dimethylphosphoryl)-pyridine A for 2-(dimethylphosphoryl)aniline 1. Compound A was prepared in accordance with the method described in step 1 of Scheme 1 for the synthesis of intermediate 1 using 3-amino-4-iodopyridine instead of 2-iodoaniline as starting material.

EXAMPLES 157, 158, 159, 161, 162, 165, 166, 167, 168, 177, 178, 179, 182, 183, 184

Scheme 51:

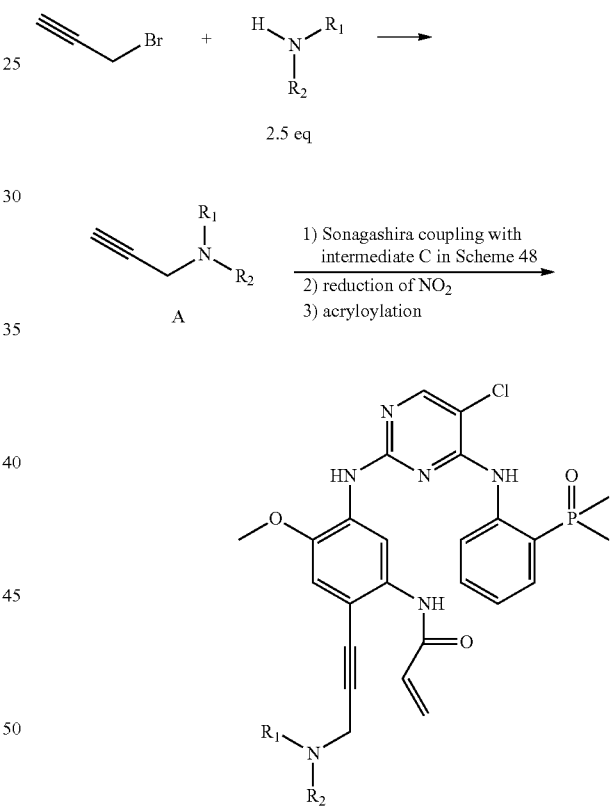

Step 1: a solution of appropriate secondary amine and propargyl bromide (supplied as a solution in toluene) in ether was stirred at 0° C. then r.t. for 3 hr. The precipitate was filtered off and the filtrate was carefully distilled to furnish product A. Contamination of A with small amount of toluene was unavoidable in some cases but this did not affect next step reaction. Certain compounds A with relatively high boiling points were purified by silica gel column chromatography (5% MeOH in DCM) to remove residual secondary amine which was found to directly displace the bromide in the next step.

Steps 2-4: Crude or pure A was converted into desired final compound in accordance with the method described in Scheme 48 by substituting A for N,N-dimethylpropargylamine.

EXAMPLE 180, 181

The corresponding propargyl nitro compound was prepared as described above, and the E and Z isomers of the reduced amino intermediate were separately recoverd. Acroylation using the general procedure yielded the title compounds:

Scheme 52:

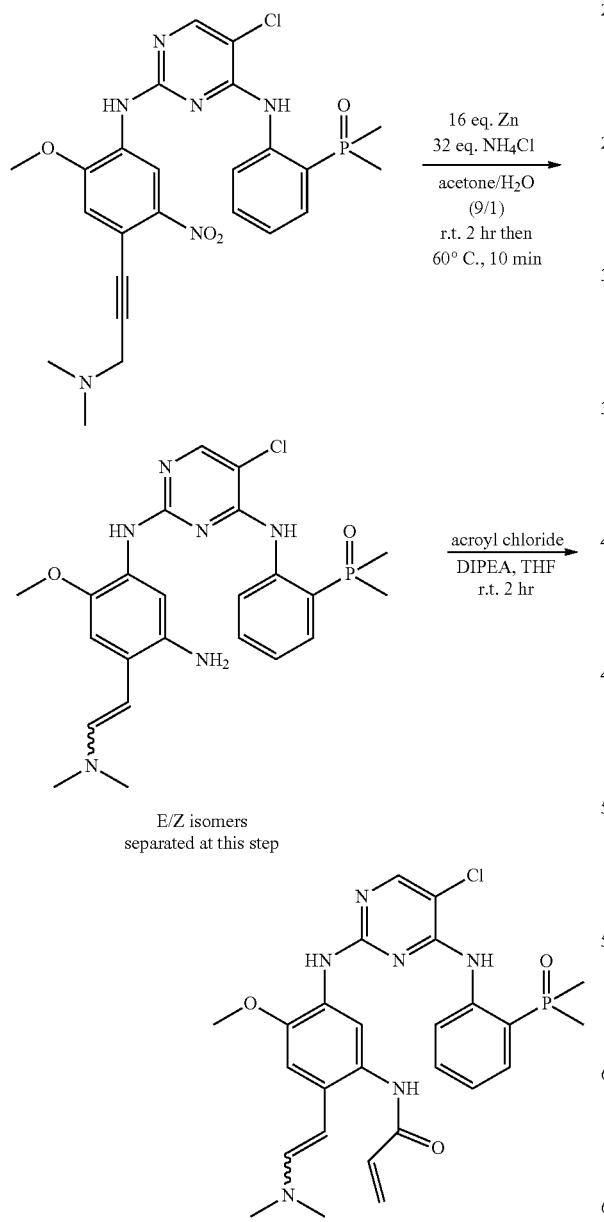

EXAMPLE 185

Scheme 53:

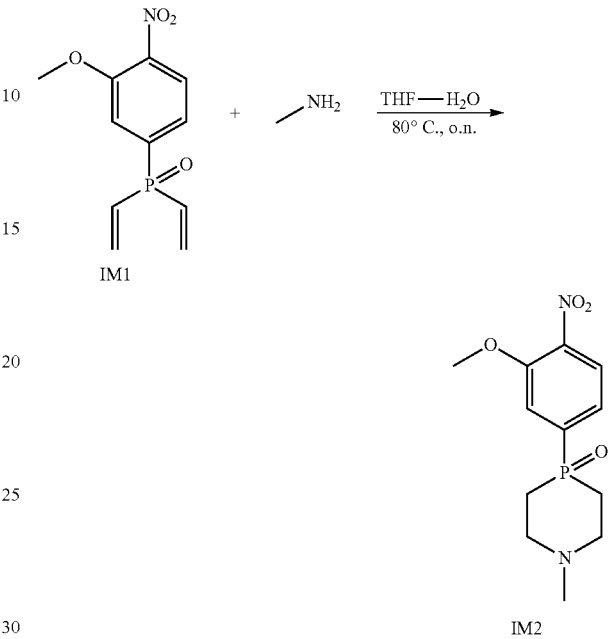

IM1 was prepared according to a literature procedure (WO 2009143389). A solution of IM1 (284 mg, 1.12 mmol) and dimethylamine (1.23 mmol, 1.1 mL, 40% in water) in THF-$H_2O$ (1:1, 4 mL) was stirred at 80° C. overnight. HPLC showed full conversion. The reaction mixture was concentrated under reduced pressure followed by partition between saturated sodium bicarbonate solution and DCM. Upon extraction the combined DCM extracts were dried over anhydrous sodium sulfate. The solvents were removed to give IM2 as yellow viscous oil (315 mg). No further purification was performed.

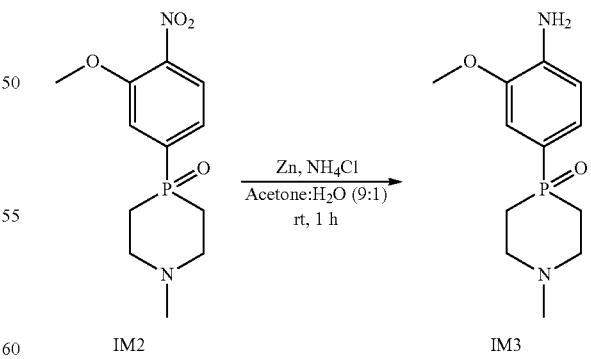

IM2 (315 mg) was reduced into IM3 using standard Zn/$NH_4Cl$ procedure described previously; a pale yellow oil was obtained (308 mg). This crude material was used directly in the next step.

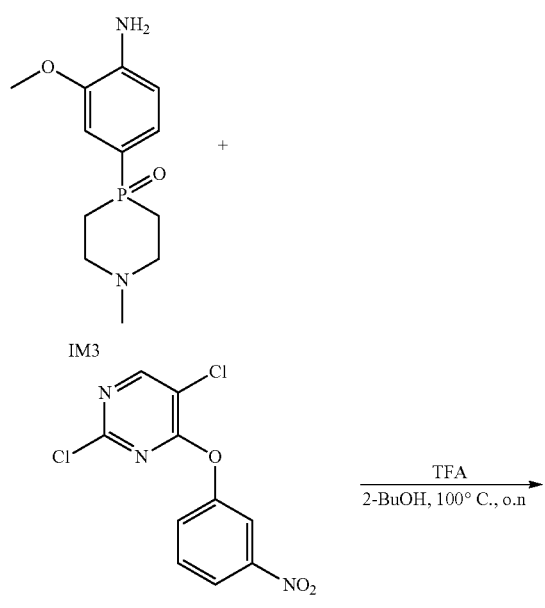

IM3

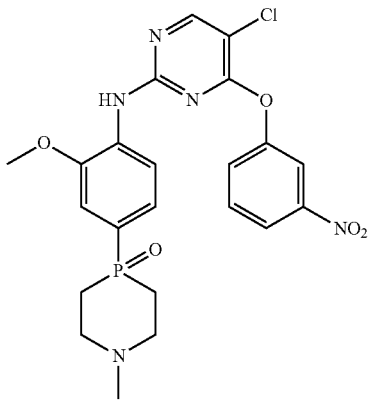

IM4

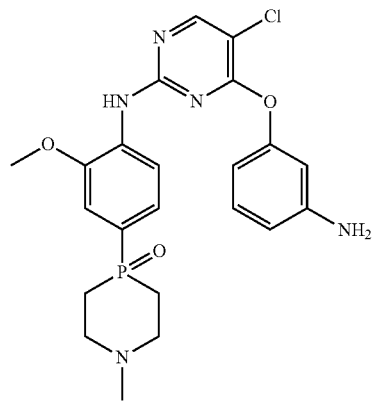

IM5

IM4 was prepared according to a literature procedure (Nature 2009, 462, 1070). This material (400 mg) underwent a S$_N$Ar reaction with IM3 (308 mg) under standard condition (TFA, 2-BuOH, 100° C., overnight). Conventional workup followed by flash chromatography on silica gel (eluent: 0-15% MeOH in DCM) afforded IM5 as a white foam (89 mg, 15%).

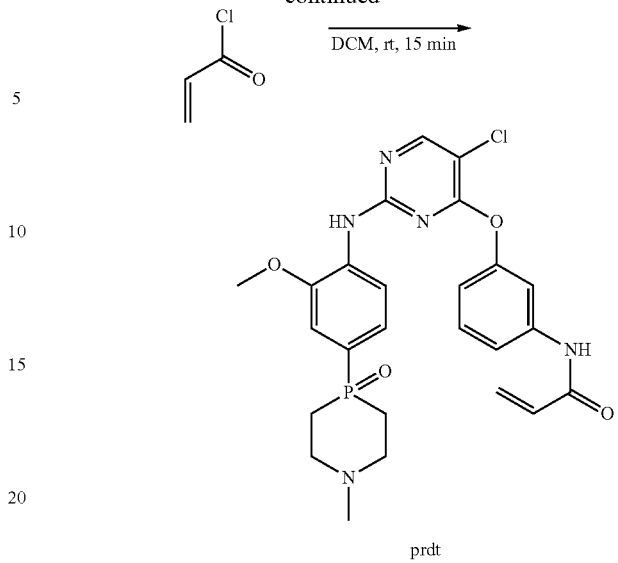

prdt

IM5 (26 mg) was converted into corresponding acrylamide under standard acroylation procedure described previously. Conventional workup followed by preparative TLC (eluent: 10% MeOH in DCM) afforded the desired product as a light yellow solid (20 mg, 77%).

COMPOUNDS OF THE INVENTION

The compounds depicted below were synthesized using methods described herein or by methods analogous thereto and can be useful for treating EGFR-driven cancers.

Examples 1-21 were made in accordance with the methods shown in Scheme 24 by substituting appropriate alcohols for 1-(2-hydroxyethyl)-4-methylpiperazine.

EXAMPLE 1

N-(5-((5-chloro-4-((2-(dimethylphosphoryl)phenyl)amino)pyrimidin-2-yl)amino)-4-methoxy-2-(2-(pyrrolidin-1-yl)ethoxy)phenyl)acrylamide

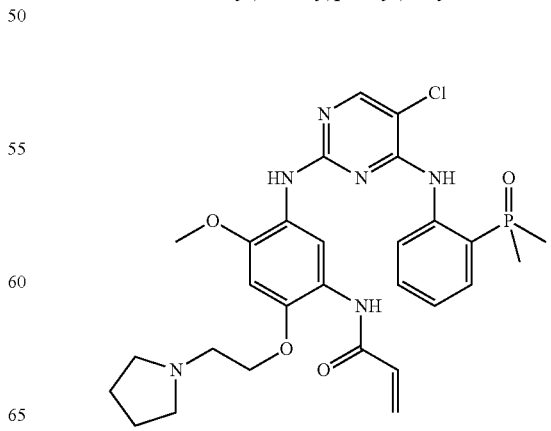

EXAMPLE 2

N-(5-((5-chloro-4-((2-(dimethylphosphoryl)phenyl)amino)pyrimidin-2-yl)amino)-4-methoxy-2-(2-(4-methylpiperazin-1-yl)ethoxy)phenyl)acrylamide

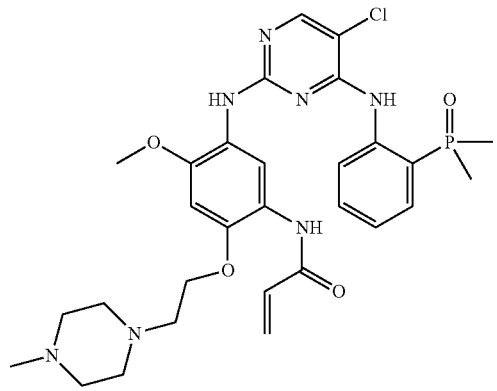

EXAMPLE 3

N-(5-((5-chloro-4-((2-(dimethylphosphoryl)phenyl)amino)pyrimidin-2-yl)amino)-4-methoxy-2-((1-methylpiperidin-4-yl)methoxy)phenyl)acrylamide

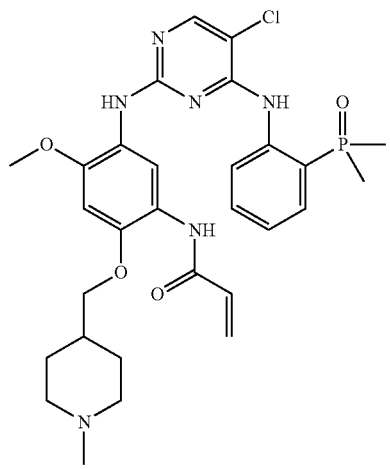

EXAMPLE 4

N-(5-((5-chloro-4-((2-(dimethylphosphoryl)phenyl)amino)pyrimidin-2-yl)amino)-4-methoxy-2-(2-morpholinoethoxy)phenyl)acrylamide

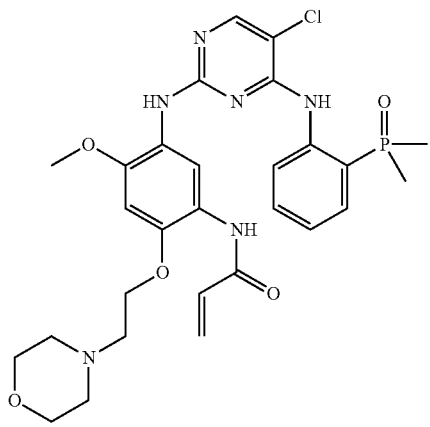 [SMILES: C=CC(=O)Nc1cc(Nc2ncc(Cl)c(Nc3ccccc3P(C)(C)=O)n2)c(OC)cc1OCCN1CCOCC1]

EXAMPLE 5

N-(5-((5-chloro-4-((2-(dimethylphosphoryl)phenyl)amino)pyrimidin-2-yl)amino)-4-methoxy-2-(3-morpholinopropoxy)phenyl)acrylamide

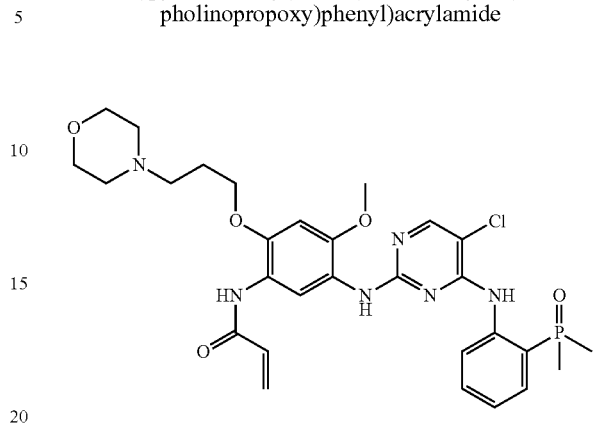

EXAMPLE 6

N-(5-((5-chloro-4-((2-(dimethylphosphoryl)phenyl)amino)pyrimidin-2-yl)amino)-4-methoxy-2-((tetrahydro-2H-pyran-4-yl)methoxy)phenyl)acrylamide

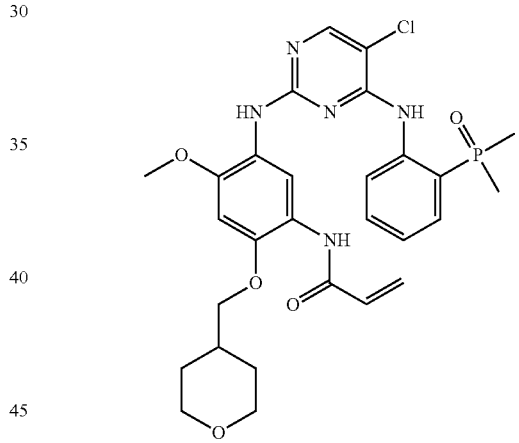

EXAMPLE 7

N-(5-((5-chloro-4-((2-(dimethylphosphoryl)phenyl)amino)pyrimidin-2-yl)amino)-4-methoxy-2-((1-methylpiperidin-2-yl)methoxy)phenyl)acrylamide

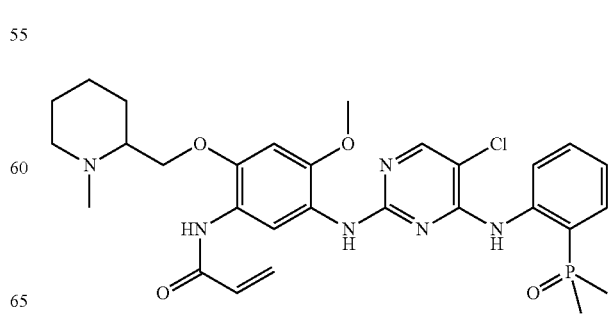

EXAMPLE 8

N-(5-((5-chloro-4-((2-(dimethylphosphoryl)phenyl)amino)pyrimidin-2-yl)amino)-4-methoxy-2-(2-(piperidin-1-yl)ethoxy)phenyl)acrylamide

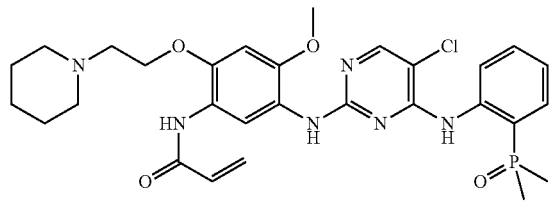 [SMILES: C=CC(=O)Nc1cc(Nc2ncc(Cl)c(Nc3ccccc3P(C)(C)=O)n2)c(OC)cc1OCCN1CCCCC1]

EXAMPLE 9

N-(5-((5-chloro-4-((2-(dimethylphosphoryl)phenyl)amino)pyrimidin-2-yl)amino)-4-methoxy-2-(oxetan-3-yloxy)phenyl)acrylamide

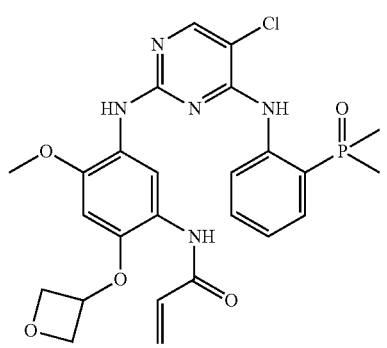

EXAMPLE 10

N-(5-((5-chloro-4-((2-(dimethylphosphoryl)phenyl)amino)pyrimidin-2-yl)amino)-4-methoxy-2-(pyridin-3-ylmethoxy)phenyl)acrylamide

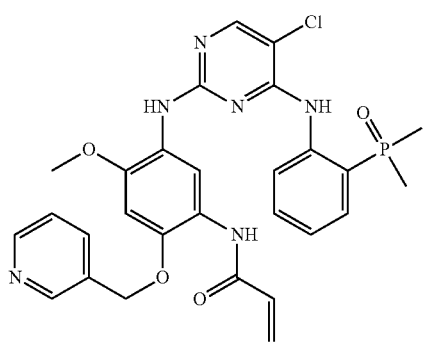 [SMILES: C=CC(=O)Nc1cc(Nc2ncc(Cl)c(Nc3ccccc3P(C)(C)=O)n2)c(OC)cc1OCc1cccnc1]

EXAMPLE 11

N-(5-((5-chloro-4-((2-(dimethylphosphoryl)phenyl)amino)pyrimidin-2-yl)amino)-4-methoxy-2-(pyridin-4-ylmethoxy)phenyl)acrylamide

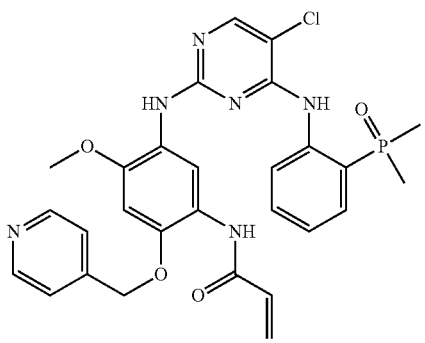 [SMILES: C=CC(=O)Nc1cc(Nc2ncc(Cl)c(Nc3ccccc3P(C)(C)=O)n2)c(OC)cc1OCc1ccncc1]

EXAMPLE 12

N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide

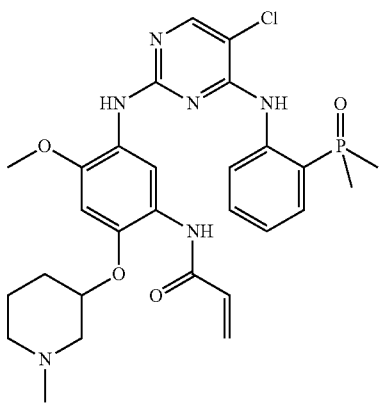

EXAMPLE 13

N-(5-((5-chloro-4-((2-(dimethylphosphoryl)phenyl)amino)pyrimidin-2-yl)amino)-4-methoxy-2-((1-methylpyrrolidin-3-yl)oxy)phenyl)acrylamide

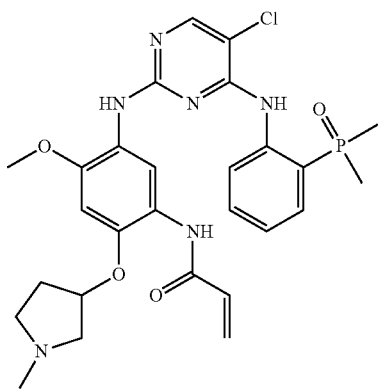

EXAMPLE 14 rel-(R)-N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide

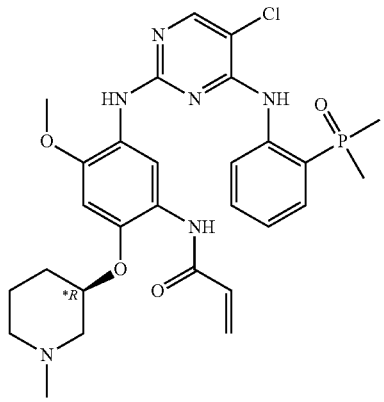 [SMILES: C=CC(=O)Nc1cc(Nc2ncc(Cl)c(Nc3ccccc3P(C)(C)=O)n2)c(OC)cc1O[C@@H]1CCCN(C)C1]

EXAMPLE 15

N-(2-((1-(azetidin-1-yl)-3-methoxypropan-2-yl)oxy)-5-((5-chloro-4-((2-(dimethylphosphoryl)phenyl)amino)pyrimidin-2-yl)amino)-4-methoxyphenyl)acrylamide

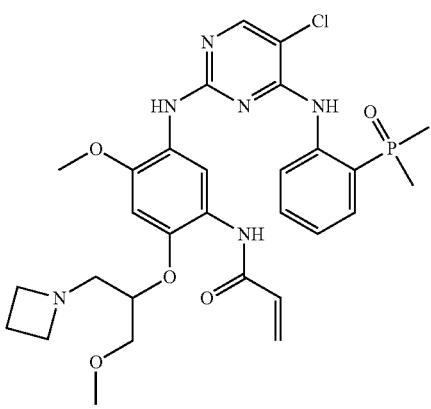 [SMILES: C=CC(=O)Nc1cc(Nc2ncc(Cl)c(Nc3ccccc3P(C)(C)=O)n2)c(OC)cc1OC(COC)CN1CCC1]

EXAMPLE 16 rel-(R)-N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide

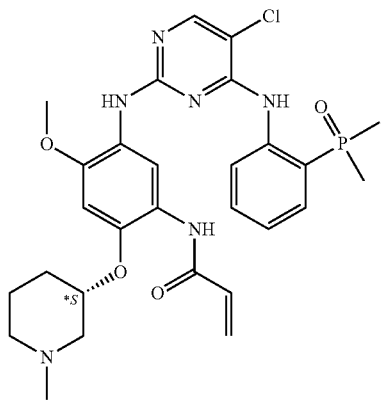 [SMILES: C=CC(=O)Nc1cc(Nc2ncc(Cl)c(Nc3ccccc3P(C)(C)=O)n2)c(OC)cc1O[C@H]1CCCN(C)C1]

EXAMPLE 17

N-(5-((5-chloro-4-((2-(dimethylphosphoryl)phenyl)amino)pyrimidin-2-yl)amino)-4-methoxy-2-((1-methylazetidin-3-yl)oxy)phenyl)acrylamide

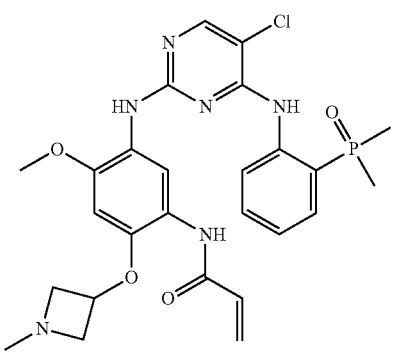

EXAMPLE 18

N-(5-((5-chloro-4-((2-(dimethylphosphoryl)phenyl)amino)pyrimidin-2-yl)amino)-4-methoxy-2-((1-methylpyrrolidin-2-yl)methoxy)phenyl)acrylamide

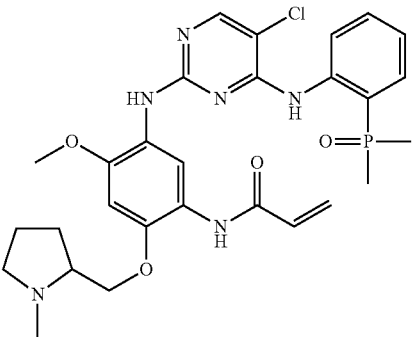 [SMILES: C=CC(=O)Nc1cc(Nc2ncc(Cl)c(Nc3ccccc3P(C)(C)=O)n2)c(OC)cc1OCC1CCCN1C]

EXAMPLE 19

N-(5-((5-chloro-4-((2-(dimethylphosphoryl)phenyl)amino)pyrimidin-2-yl)amino)-4-methoxy-2-((4-methyl-1,4-oxazepan-6-yl)oxy)phenyl)acrylamide

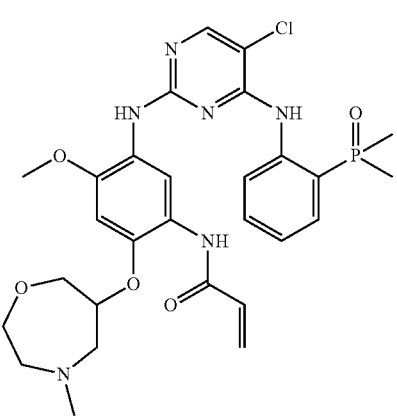 [SMILES: C=CC(=O)Nc1cc(Nc2ncc(Cl)c(Nc3ccccc3P(C)(C)=O)n2)c(OC)cc1OC1COCCN(C)C1]

EXAMPLE 20

N-(5-((5-chloro-4-((2-(dimethylphosphoryl)phenyl)amino)pyrimidin-2-yl)amino)-4-methoxy-2-((1-methylpyrrolidin-3-yl)methoxy)phenyl)acrylamide

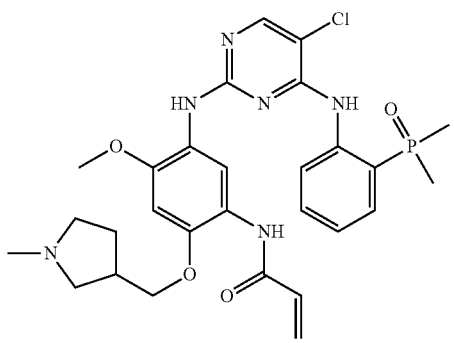

EXAMPLE 21

N-(5-((5-chloro-4-((2-(dimethylphosphoryl)phenyl)amino)pyrimidin-2-yl)amino)-2-((2-(dimethylamino)cyclohexyl)oxy)-4-methoxyphenyl)acrylamide

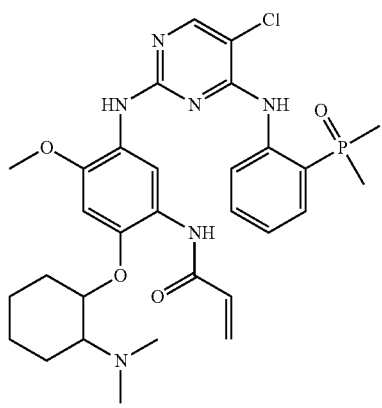

Examples 22-32 were made in accordance with the methods shown in Scheme 25.

EXAMPLE 22

N-(5-((5-chloro-4-((2-(dimethylphosphoryl)phenyl)amino)pyrimidin-2-yl)amino)-4-methoxy-2-(4-(4-methylpiperazin-1-yl)piperidin-1-yl)phenyl)acrylamide

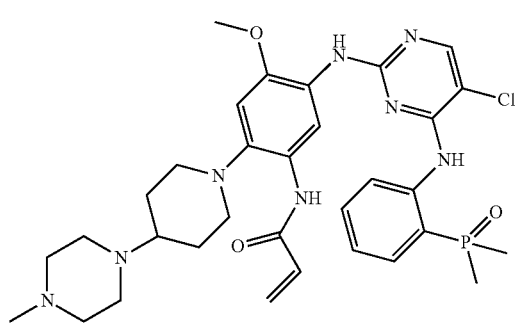

EXAMPLE 23

N-(5-((5-chloro-4-((2-(dimethylphosphoryl)phenyl)amino)pyrimidin-2-yl)amino)-2-(4-(dimethylamino)piperidin-1-yl)-4-methoxyphenyl)acrylamide

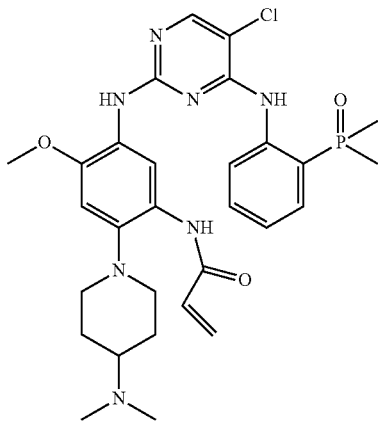

EXAMPLE 24

N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)acrylamide

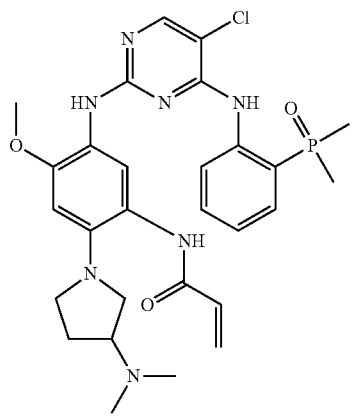 [SMILES: C=CC(=O)Nc1cc(Nc2ncc(Cl)c(Nc3ccccc3P(C)(C)=O)n2)c(OC)cc1N1CCC(N(C)C)C1]

EXAMPLE 25

N-(5-((5-chloro-4-((2-(dimethylphosphoryl)phenyl)amino)pyrimidin-2-yl)amino)-4-methoxy-2-(4-methyl-1,4-diazepan-1-yl)phenyl)acrylamide

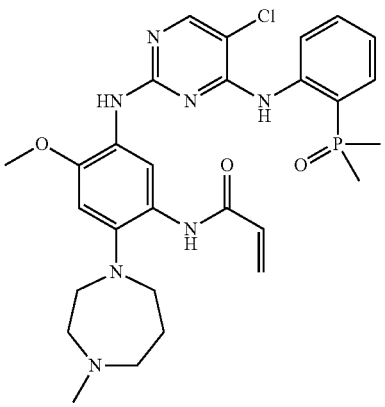

EXAMPLE 26 rac-(R)-N-(5-(((5-chloro-4-((2-(dimethylphosphoryl)
phenyl)amino)pyrimidin-2-yl)amino)-2-(3-(dimeth-
ylamino)pyrrolidin-1-yl)-4-methoxyphenyl)acrylam-
ide

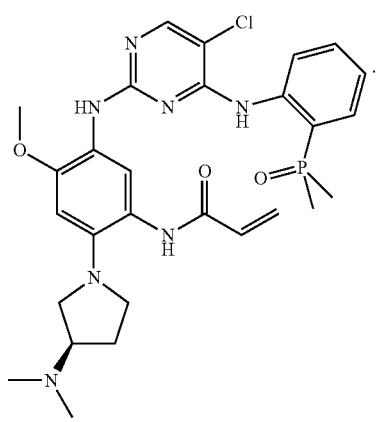 [SMILES: C=CC(=O)Nc1cc(Nc2ncc(Cl)c(Nc3ccccc3P(C)(C)=O)n2)c(OC)cc1N1CC[C@@H](N(C)C)C1]

EXAMPLE 27

N-(5-((5-chloro-4-((2-(dimethylphosphoryl)phenyl)
amino)pyrimidin-2-yl)amino)-4-methoxy-2-(4-(1-
methylpiperidin-4-yl)piperazin-1-yl)phenyl)acrylam-
ide

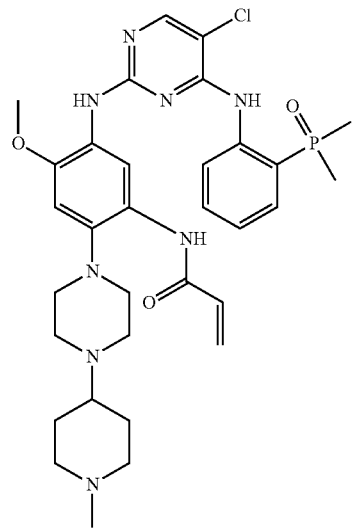 [SMILES: C=CC(=O)Nc1cc(Nc2ncc(Cl)c(Nc3ccccc3P(C)(C)=O)n2)c(OC)cc1N1CCN(C2CCN(C)CC2)CC1]

EXAMPLE 28

N-(5-((5-chloro-4-((2-(dimethylphosphoryl)phenyl)
amino)pyrimidin-2-yl)amino)-4-methoxy-2-(3-mor-
pholinopyrrolidin-1-yl)phenyl)acrylamide

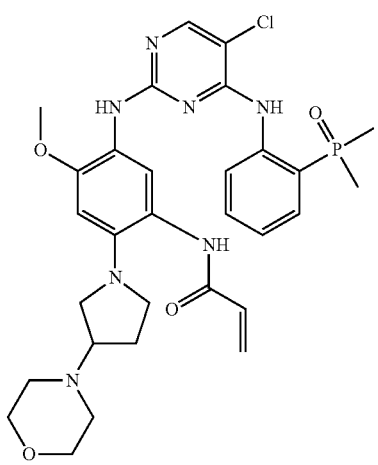 [SMILES: C=CC(=O)Nc1cc(Nc2ncc(Cl)c(Nc3ccccc3P(C)(C)=O)n2)c(OC)cc1N1CCC(N2CCOCC2)C1]

EXAMPLE 29 rac-(R)-N-(5-(((5-chloro-4-((2-(dimethylphosphoryl)
phenyl)amino)pyrimidin-2-yl)amino)-2-(3-(dimeth-
ylamino)pyrrolidin-1-yl)-4-methoxyphenyl)acrylam-
ide

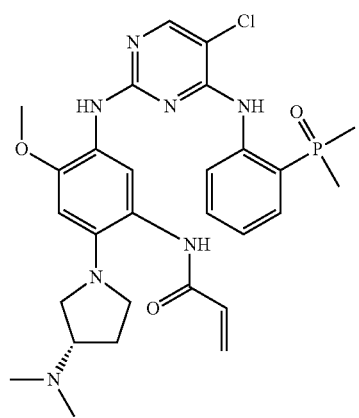

EXAMPLE 30

N-(5-(((5-chloro-4-((2-(dimethylphosphoryl)phenyl)amino)pyrimidin-2-yl)amino)-2-(3-(dimethylamino)piperidin-1-yl)-4-methoxyphenyl)acrylamide

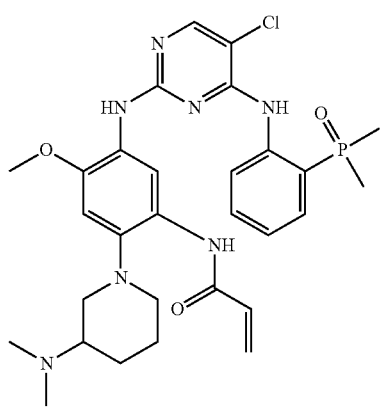

EXAMPLE 31

N-(5-(((5-chloro-4-((2-(dimethylphosphoryl)phenyl)amino)pyrimidin-2-yl)amino)-4-methoxy-2-(3-(pyrrolidin-1-yl)azetidin-1-yl)phenyl)acrylamide

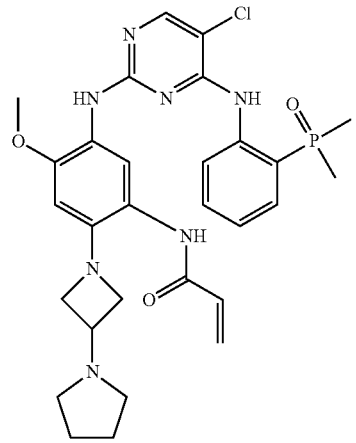 [SMILES: C=CC(=O)Nc1cc(Nc2ncc(Cl)c(Nc3ccccc3P(C)(C)=O)n2)c(OC)cc1N1CC(N2CCCC2)C1]

EXAMPLE 32

N-(5-(((5-chloro-4-((2-(dimethylphosphoryl)phenyl)amino)pyrimidin-2-yl)amino)-2-(3-hydroxypyrrolidin-1-yl)-4-methoxyphenyl)acrylamide

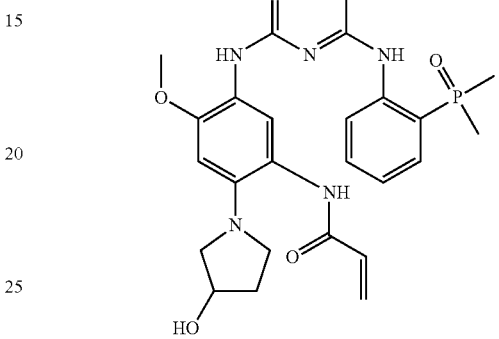

Examples 33-41 were made in accordance with the methods shown in Scheme 26 by substituting secondary amines for (3-dimethylamino)pyrrolidine.

EXAMPLE 33

N-(5-(((5-chloro-4-((2-(dimethylphosphoryl)phenyl)amino)pyrimidin-2-yl)amino)-4-methoxy-2-(3-(piperidin-1-yl)pyrrolidin-1-yl)phenyl)acrylamide

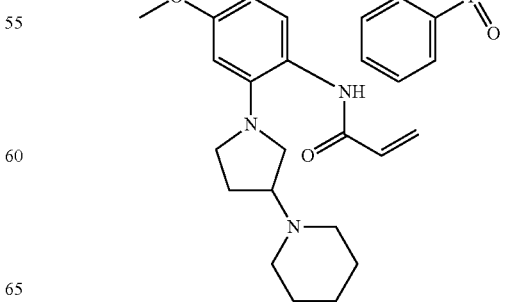

EXAMPLE 34

N-(5-((5-chloro-4-((2-(dimethylphosphoryl)phenyl)amino)pyrimidin-2-yl)amino)-2-(3-(diethylamino)pyrrolidin-1-yl)-4-methoxyphenyl)acrylamide

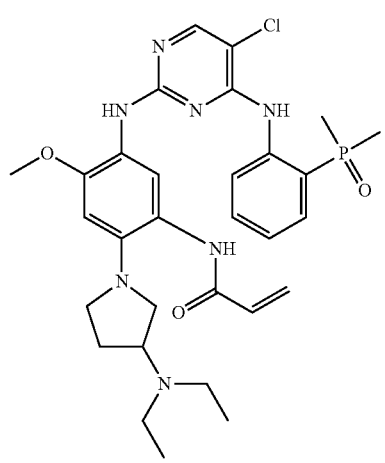

EXAMPLE 35

N-(5-((5-chloro-4-((2-(dimethylphosphoryl)phenyl)amino)pyrimidin-2-yl)amino)-2-(3-hydroxy-[1,3'-bipyrrolidin]-1'-yl)-4-methoxyphenyl)acrylamide

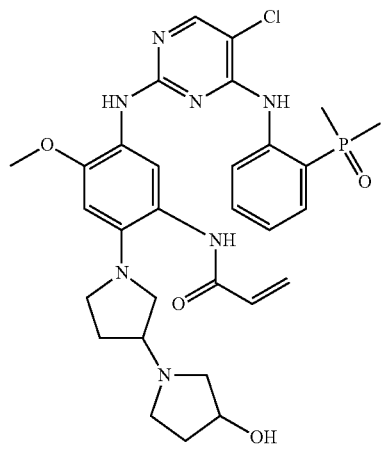

EXAMPLE 36

N-(2-([1,3'-bipyrrolidin]-1'-yl)-5-((5-chloro-4-((2-(dimethylphosphoryl)phenyl)amino)pyrimidin-2-yl)amino)-4-methoxyphenyl)acrylamide

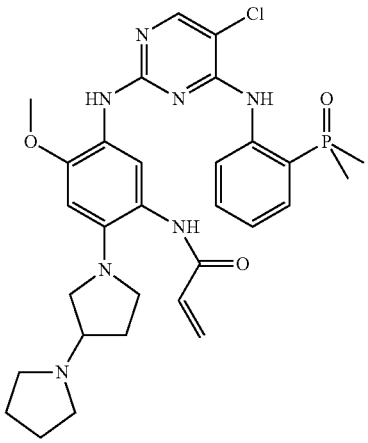 [SMILES: C=CC(=O)Nc1cc(Nc2ncc(Cl)c(Nc3ccccc3P(C)(C)=O)n2)c(OC)cc1N1CCC(N2CCCC2)C1]

EXAMPLE 37

N-(5-((5-chloro-4-((2-(dimethylphosphoryl)phenyl)amino)pyrimidin-2-yl)amino)-4-methoxy-2-(3-(4-methylpiperazin-1-yl)pyrrolidin-1-yl)phenyl)acrylamide

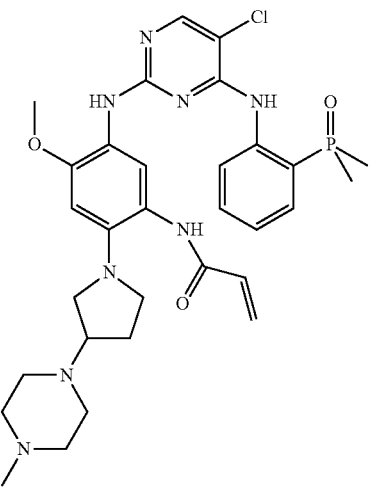 [SMILES: C=CC(=O)Nc1cc(Nc2ncc(Cl)c(Nc3ccccc3P(C)(C)=O)n2)c(OC)cc1N1CCC(N2CCN(C)CC2)C1]

EXAMPLE 38

N-(5-((5-chloro-4-((2-(dimethylphosphoryl)phenyl)amino)pyrimidin-2-yl)amino)-2-(3-((2-(diethylamino)ethyl)(methyl)amino)pyrrolidin-1-yl)-4-methoxyphenyl)acrylamide

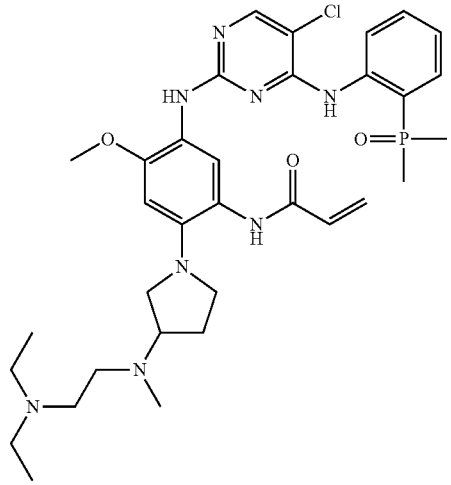 [SMILES: C=CC(=O)Nc1cc(Nc2ncc(Cl)c(Nc3ccccc3P(C)(C)=O)n2)c(OC)cc1N1CCC(N(C)CCN(CC)CC)C1]

EXAMPLE 39

N-(5-((5-chloro-4-((2-(dimethylphosphoryl)phenyl)amino)pyrimidin-2-yl)amino)-2-(3-(4-hydroxypiperidin-1-yl)pyrrolidin-1-yl)-4-methoxyphenyl)acrylamide

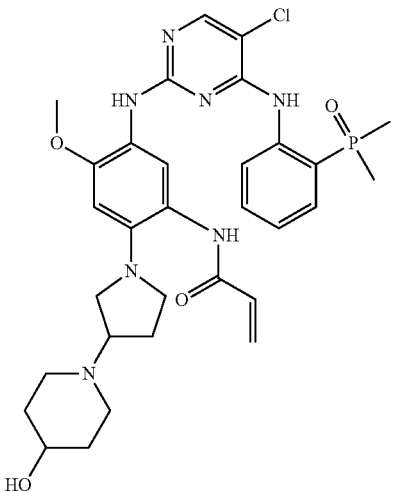 [SMILES: C=CC(=O)Nc1cc(Nc2ncc(Cl)c(Nc3ccccc3P(C)(C)=O)n2)c(OC)cc1N1CCC(N2CCC(O)CC2)C1]

EXAMPLE 40

N-(5-((5-chloro-4-((2-(dimethylphosphoryl)phenyl)amino)pyrimidin-2-yl)amino)-2-(3-(4-(2-hydroxyethyl)piperazin-1-yl)pyrrolidin-1-yl)-4-methoxyphenyl)acrylamide

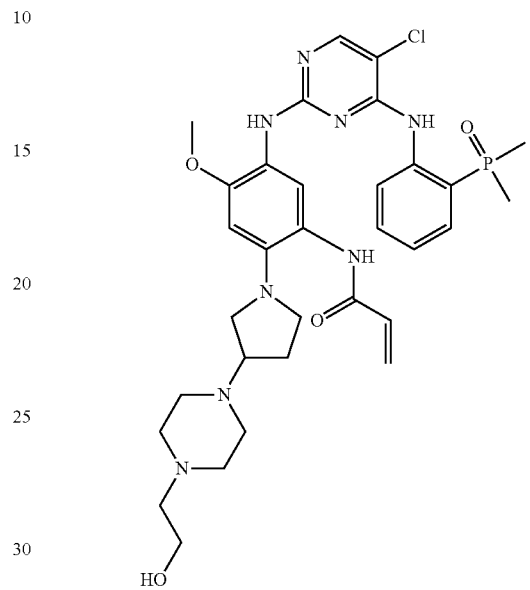

EXAMPLE 41

N-(5-((5-chloro-4-((2-(dimethylphosphoryl)phenyl)amino)pyrimidin-2-yl)amino)-4-methoxy-2-(3-((2-methoxyethyl)(methyl)amino)pyrrolidin-1-yl)phenyl)acrylamide

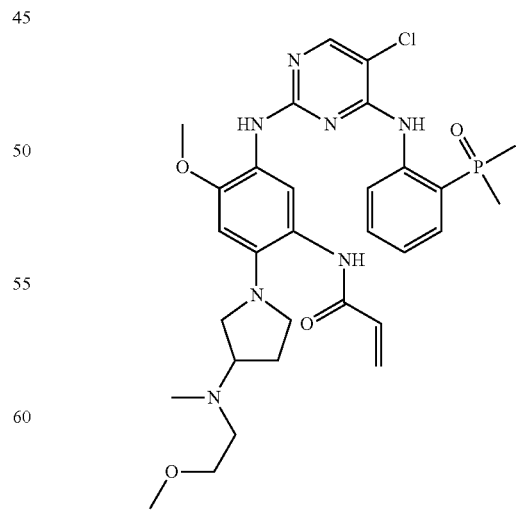

Examples 42-53 were made in accordance with the methods shown in Scheme 27.

EXAMPLE 42

N-(3-((5-chloro-4-((2-(dimethylphosphoryl)phenyl)amino)pyrimidin-2-yl)amino)-4-methoxyphenyl)-2-(pyrrolidin-1-ylmethyl)acrylamide

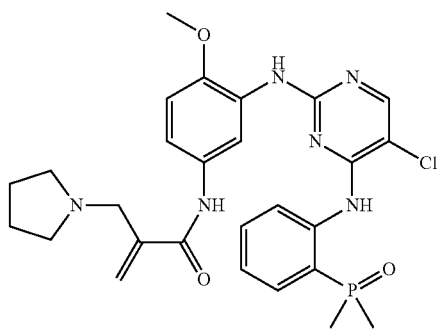 [SMILES: C=C(CN1CCCC1)C(=O)Nc1ccc(OC)c(Nc2ncc(Cl)c(Nc3ccccc3P(C)(C)=O)n2)c1]

EXAMPLE 43

N-(3-((5-chloro-4-((2-(dimethylphosphoryl)phenyl)amino)pyrimidin-2-yl)amino)-4-methoxyphenyl)-2-(piperidin-1-ylmethyl)acrylamide

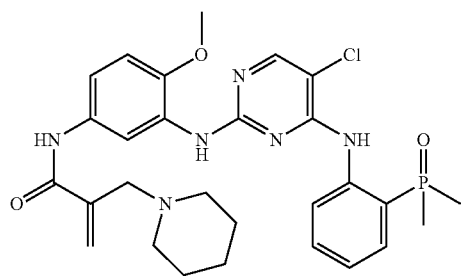 [SMILES: C=C(CN1CCCCC1)C(=O)Nc1ccc(OC)c(Nc2ncc(Cl)c(Nc3ccccc3P(C)(C)=O)n2)c1]

EXAMPLE 44

N-(3-((5-chloro-4-((2-(dimethylphosphoryl)phenyl)amino)pyrimidin-2-yl)amino)-4-methoxyphenyl)-2-((4-(methylsulfonyl)piperazin-1-yl)methyl)acrylamide

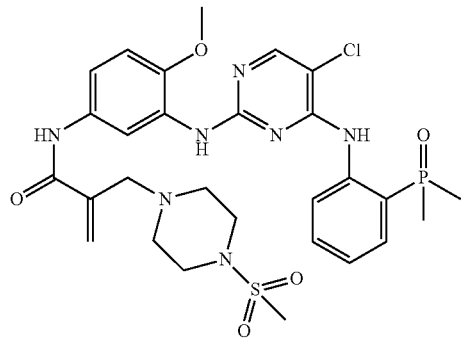 [SMILES: C=C(CN1CCN(S(C)(=O)=O)CC1)C(=O)Nc1ccc(OC)c(Nc2ncc(Cl)c(Nc3ccccc3P(C)(C)=O)n2)c1]

EXAMPLE 45

N-(3-((5-chloro-4-((2-(dimethylphosphoryl)phenyl)amino)pyrimidin-2-yl)amino)-4-methoxyphenyl)-2-((4-(4-methylpiperazin-1-yl)piperidin-1-yl)methyl)acrylamide

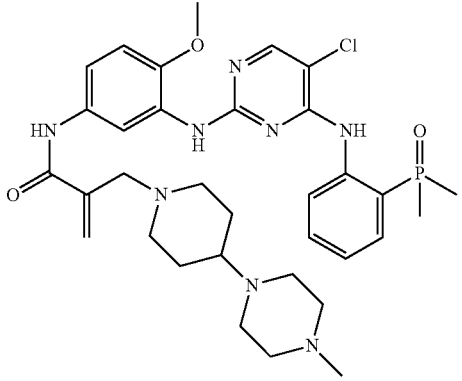 [SMILES: C=C(CN1CCC(N2CCN(C)CC2)CC1)C(=O)Nc1ccc(OC)c(Nc2ncc(Cl)c(Nc3ccccc3P(C)(C)=O)n2)c1]

EXAMPLE 46

N-(3-((5-chloro-4-((2-(dimethylphosphoryl)phenyl)amino)pyrimidin-2-yl)amino)-4-methoxyphenyl)-2-((1,1-dioxidothiomorpholino)methyl)acrylamide

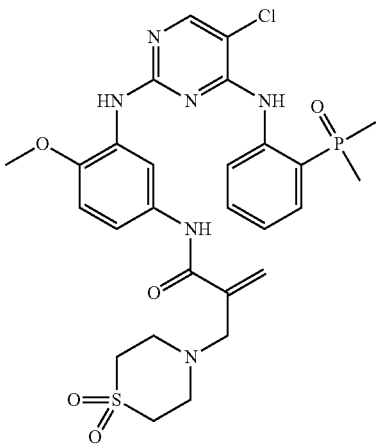

EXAMPLE 47

N-(3-((5-chloro-4-((2-(dimethylphosphoryl)phenyl)amino)pyrimidin-2-yl)amino)-4-methoxyphenyl)-2-((3-oxopiperazin-1-yl)methyl)acrylamide

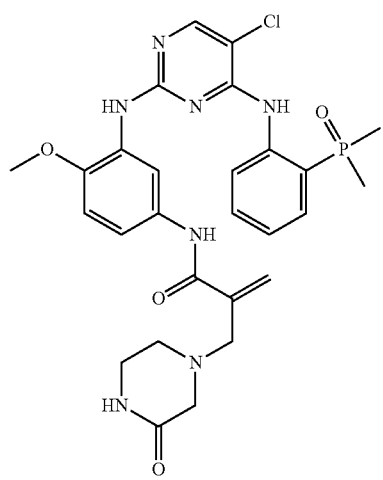

EXAMPLE 48

N-(3-((5-chloro-4-((2-(dimethylphosphoryl)phenyl)amino)pyrimidin-2-yl)amino)-4-methoxyphenyl)-2-(morpholinomethyl)acrylamide

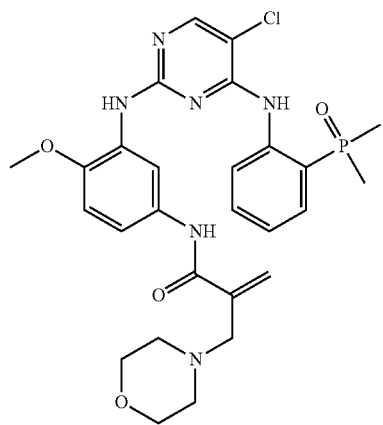

EXAMPLE 49

N-(3-((5-chloro-4-((2-(dimethylphosphoryl)phenyl)amino)pyrimidin-2-yl)amino)-4-methoxyphenyl)-2-((4-methylpiperazin-1-yl)methyl)acrylamide

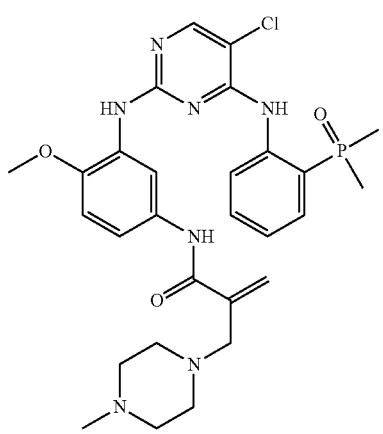

EXAMPLE 50

N-(3-((5-chloro-4-((2-(dimethylphosphoryl)phenyl)amino)pyrimidin-2-yl)amino)-4-methoxyphenyl)-2-((4-isopropylpiperazin-1-yl)methyl)acrylamide

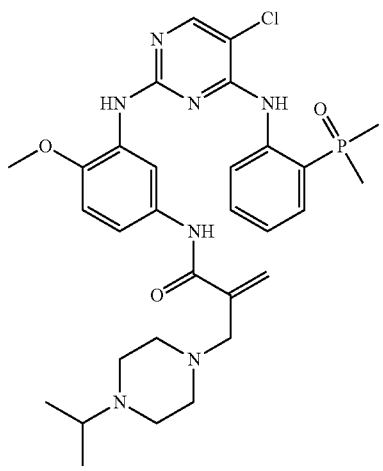

EXAMPLE 51

N-(3-((5-chloro-4-((2-(dimethylphosphoryl)phenyl)amino)pyrimidin-2-yl)amino)-4-methoxyphenyl)-2-((4-morpholinopiperidin-1-yl)methyl)acrylamide

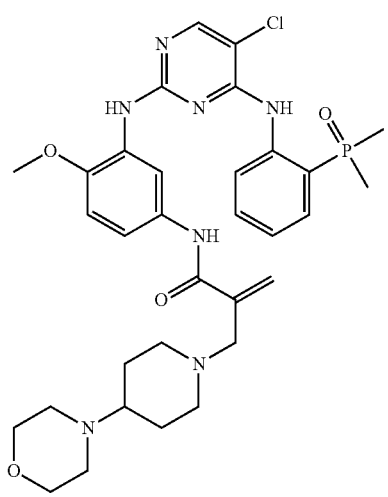

EXAMPLE 52

N-(3-((5-chloro-4-((2-(dimethylphosphoryl)phenyl)amino)pyrimidin-2-yl)amino)-4-methoxyphenyl)-2-((4-(2-hydroxyethyl)piperazin-1-yl)methyl)acrylamide

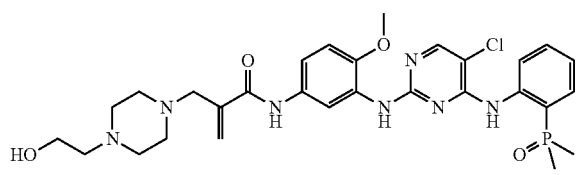 [SMILES: C=C(CN1CCN(CCO)CC1)C(=O)Nc1ccc(OC)c(Nc2ncc(Cl)c(Nc3ccccc3P(C)(C)=O)n2)c1]

EXAMPLE 53

N-(3-((5-chloro-4-((2-(dimethylphosphoryl)phenyl)amino)pyrimidin-2-yl)amino)-4-methoxyphenyl)-2-((3-hydroxypyrrolidin-1-yl)methyl)acrylamide

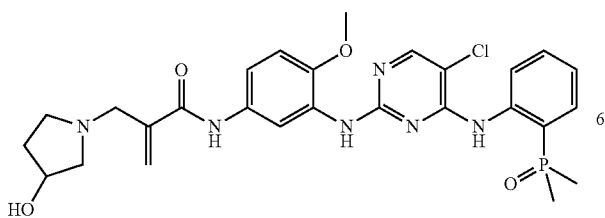

Example 54 was made in accordance with the methods shown in Scheme 28.

EXAMPLE 54

N-(3-((5-chloro-4-((2-(dimethylphosphoryl)phenyl)amino)pyrimidin-2-yl)amino)-4-fluorophenyl)acrylamide

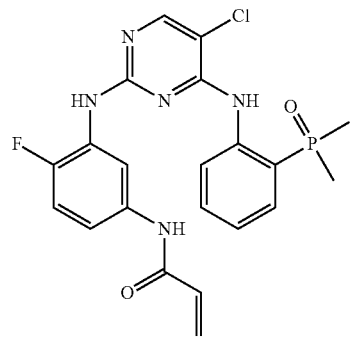 [SMILES: C=CC(=O)Nc1ccc(F)c(Nc2ncc(Cl)c(Nc3ccccc3P(C)(C)=O)n2)c1]

Examples 55-57 were made in accordance with the methods shown in Scheme 29.

EXAMPLE 55

N-(5-((5-chloro-4-((2-(dimethylphosphoryl)phenyl)amino)pyrimidin-2-yl)amino)-4-methoxy-2-((4-methylpiperazin-1-yl)methyl)phenyl)acrylamide

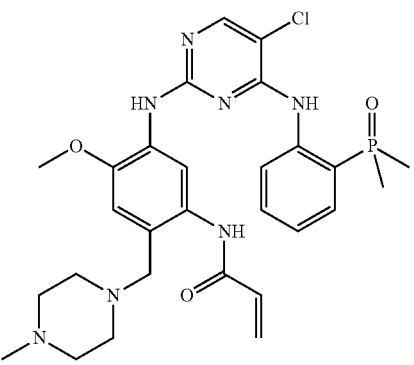

EXAMPLE 56

N-(5-((5-chloro-4-((2-(dimethylphosphoryl)phenyl)amino)pyrimidin-2-yl)amino)-4-methoxy-2-(4-methylpiperazine-1-carbonyl)phenyl)acrylamide

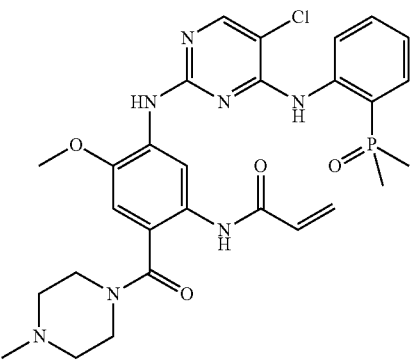

Example 57 was made in accordance with the methods shown in Scheme 30.

EXAMPLE 57

N-(2-(3-aminopyrrolidin-1-yl)-5-((5-chloro-4-((2-(dimethylphosphoryl)phenyl)amino)pyrimidin-2-yl)amino)-4-methoxyphenyl)acrylamide

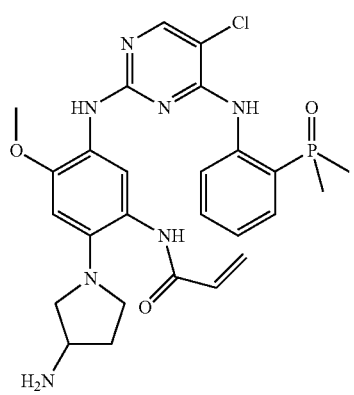 [SMILES: C=CC(=O)Nc1cc(Nc2ncc(Cl)c(Nc3ccccc3P(C)(C)=O)n2)c(OC)cc1N1CCC(N)C1]

Examples 58-64 were made in accordance with the methods shown in Scheme 31.

EXAMPLE 58

N1-(3-((5-chloro-4-((2-(dimethylphosphoryl)phenyl)amino)pyrimidin-2-yl)amino)-4-methoxyphenyl)-N4-(2-(dimethylamino)ethyl)fumaramide

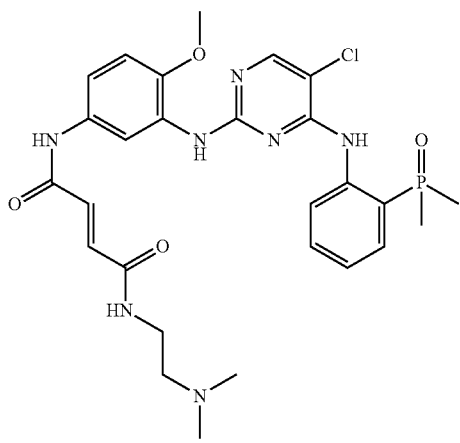 [SMILES: COc1ccc(NC(=O)/C=C/C(=O)NCCN(C)C)cc1Nc1ncc(Cl)c(Nc2ccccc2P(C)(C)=O)n1]

EXAMPLE 59

(E)—N-(3-((5-chloro-4-((2-(dimethylphosphoryl)phenyl)amino)pyrimidin-2-yl)amino)-4-methoxyphenyl)-4-(4-methylpiperazin-1-yl)-4-oxobut-2-enamide

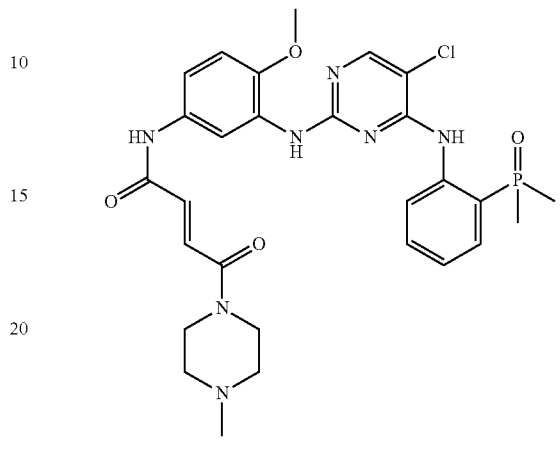

EXAMPLE 60

N1-(3-((5-chloro-4-((2-(dimethylphosphoryl)phenyl)amino)pyrimidin-2-yl)amino)-4-methoxyphenyl)-$N_4,N_4$-dimethylfumaramide

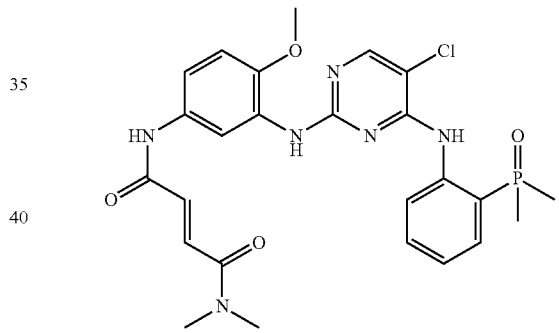

EXAMPLE 61

(Z)-4-((3-((5-chloro-4-((2-(dimethylphosphoryl)phenyl)amino)pyrimidin-2-yl)amino)-4-methoxyphenyl)amino)-4-oxobut-2-enoic acid

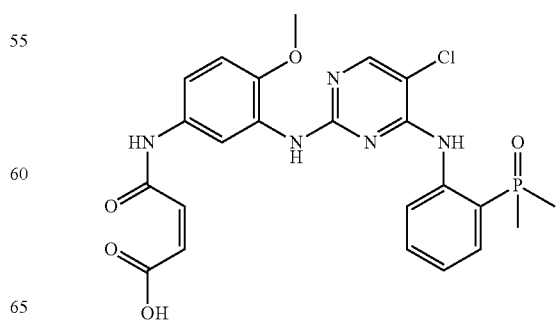

EXAMPLE 62

N1-(3-((5-chloro-4-((2-(dimethylphosphoryl)phenyl)amino)pyrimidin-2-yl)amino)-4-methoxyphenyl)-N4,N4-dimethylmaleamide

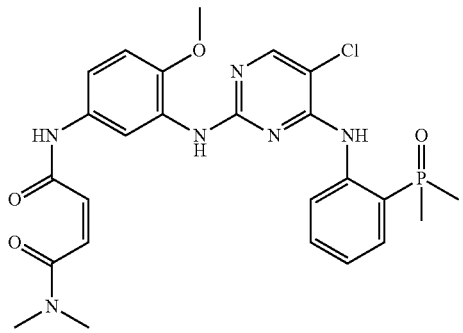 [SMILES: COc1ccc(NC(=O)/C=C\C(=O)N(C)C)cc1Nc1ncc(Cl)c(Nc2ccccc2P(C)(C)=O)n1]

EXAMPLE 63

(Z)-N-(3-((5-chloro-4-((2-(dimethylphosphoryl)phenyl)amino)pyrimidin-2-yl)amino)-4-methoxyphenyl)-4-(4-methylpiperazin-1-yl)-4-oxobut-2-enamide

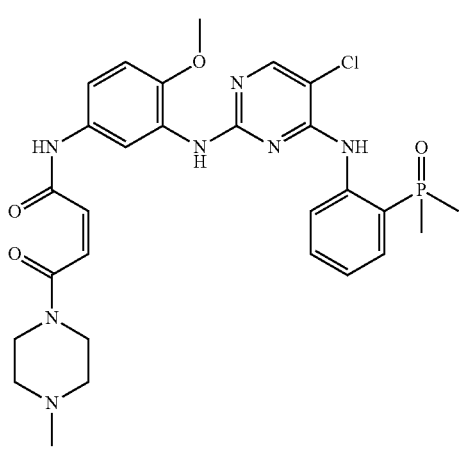 [SMILES: COc1ccc(NC(=O)/C=C\C(=O)N2CCN(C)CC2)cc1Nc1ncc(Cl)c(Nc2ccccc2P(C)(C)=O)n1]

EXAMPLE 64

N1-(3-((5-chloro-4-((2-(dimethylphosphoryl)phenyl)amino)pyrimidin-2-yl)amino)-4-methoxyphenyl)-N4-(2-(dimethylamino)ethyl)maleamide

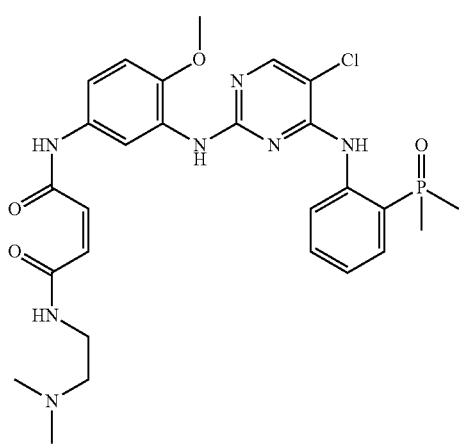 [SMILES: COc1ccc(NC(=O)/C=C\C(=O)NCCN(C)C)cc1Nc1ncc(Cl)c(Nc2ccccc2P(C)(C)=O)n1]

Example 65 was made in accordance with the methods shown in Scheme 32.

EXAMPLE 65

N-(2-(3-amino-3-methylbut-1-yn-1-yl)-5-((5-chloro-4-((2-(dimethylphosphoryl)phenyl)amino)pyrimidin-2-yl)amino)-4-methoxyphenyl)acrylamide

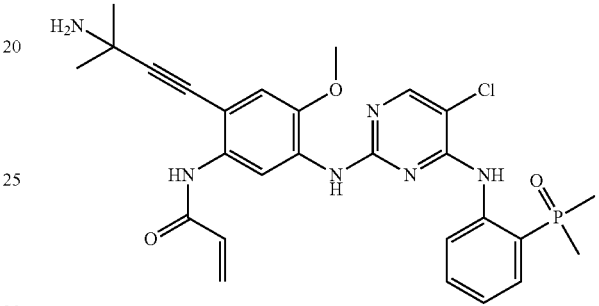

Example 66 was made in accordance with the methods shown in Scheme 33.

EXAMPLE 66

N-(5-((5-chloro-4-((2-(dimethylphosphoryl)phenyl)amino)pyrimidin-2-yl)amino)-2-(2-(dimethylamino)-3-hydroxypropoxy)-4-methoxyphenyl)acrylamide

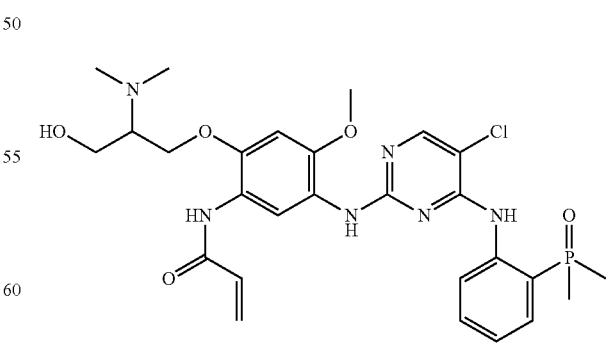

Example 67 was made in accordance with the methods shown in Scheme 35.

EXAMPLE 67

N-(5-((5-chloro-4-((2-(dimethylphosphoryl)phenyl)amino)pyrimidin-2-yl)amino)-2-((2-((2-fluoroethyl)(methyl)amino)ethyl)(methyl)amino)-4-methoxyphenyl)acrylamide

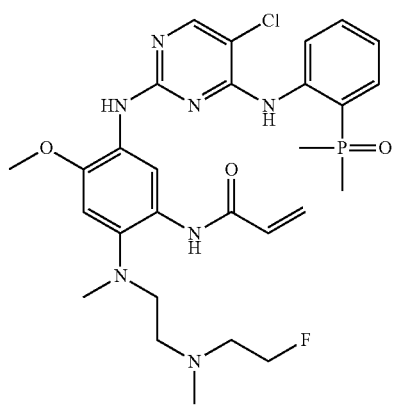 [SMILES: C=CC(=O)Nc1cc(Nc2ncc(Cl)c(Nc3ccccc3P(C)(C)=O)n2)c(OC)cc1N(C)CCN(C)CCF]

Examples 68-73 were made in accordance with the methods shown in Scheme 37.

EXAMPLE 68

N-(2-(3-(azetidin-1-yl)pyrrolidin-1-yl)-5-((5-chloro-4-((2-(dimethylphosphoryl)phenyl)amino)pyrimidin-2-yl)amino)-4-methoxyphenyl)acrylamide

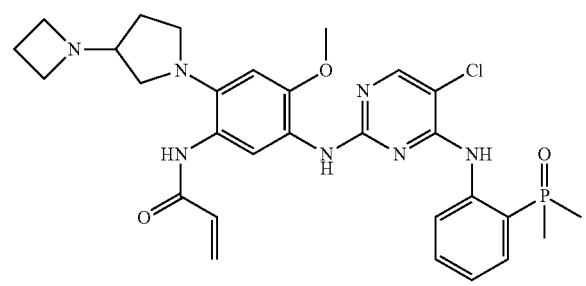 [SMILES: C=CC(=O)Nc1cc(Nc2ncc(Cl)c(Nc3ccccc3P(C)(C)=O)n2)c(OC)cc1N1CCC(N2CCC2)C1]

EXAMPLE 69

N-(2-([1,4'-bipiperidin]-1-yl)-5-((5-chloro-4-((2-(dimethylphosphoryl)phenyl)amino)pyrimidin-2-yl)amino)-4-methoxyphenyl)acrylamide

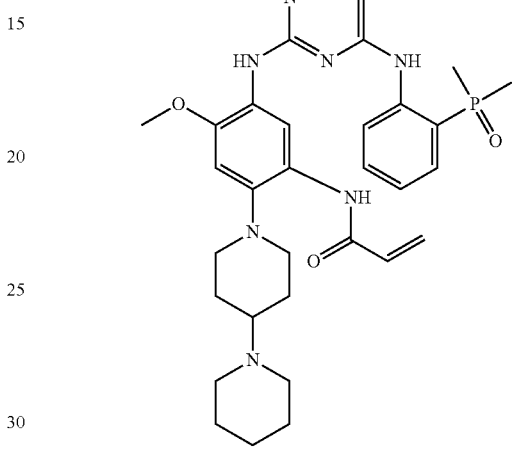

EXAMPLE 70

N-(5-((5-chloro-4-((2-(dimethylphosphoryl)phenyl)amino)pyrimidin-2-yl)amino)-4-methoxy-2-(4-morpholinopiperidin-1-yl)phenyl)acrylamide

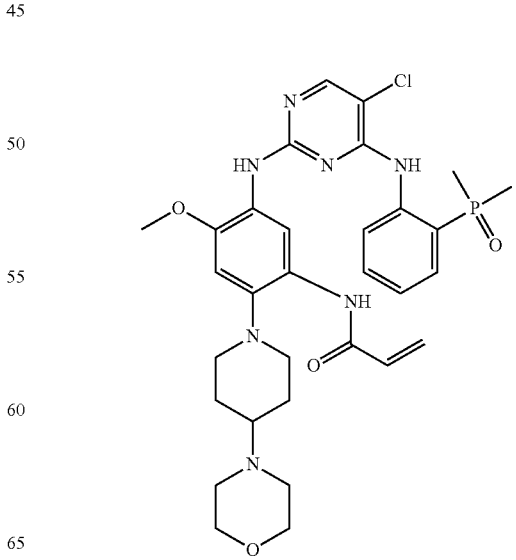

EXAMPLE 71

N-(5-((5-chloro-4-((2-(dimethylphosphoryl)phenyl)amino)pyrimidin-2-yl)amino)-4-methoxy-2-(4-(4-methyl-1,4-diazepan-1-yl)piperidin-1-yl)phenyl)acrylamide

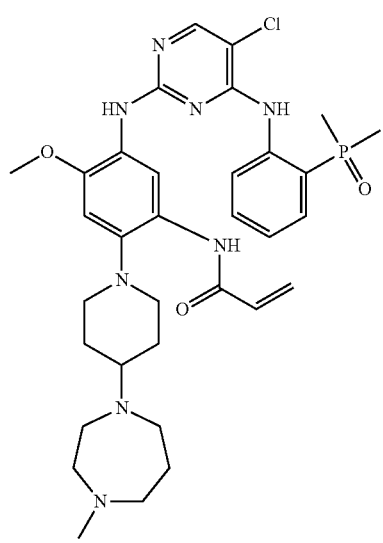

EXAMPLE 72

N-(5-((5-chloro-4-((2-(dimethylphosphoryl)phenyl)amino)pyrimidin-2-yl)amino)-4-methoxy-2-(4-(pyrrolidin-1-yl)piperidin-1-yl)phenyl)acrylamide

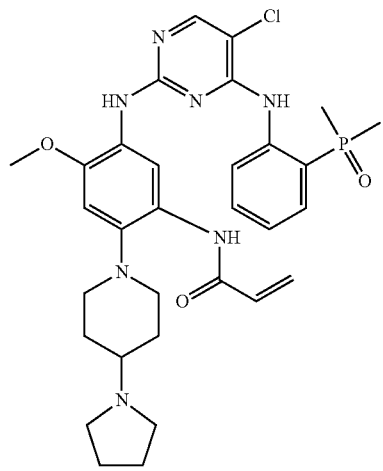

Example 73 was made in accordance with the methods shown in Scheme 38.

EXAMPLE 73

N-(5-((5-chloro-4-((2-(dimethylphosphoryl)phenyl)amino)pyrimidin-2-yl)amino)-2-((1-(dimethylamino)cyclopropyl)ethynyl)-4-methoxyphenyl)acrylamide

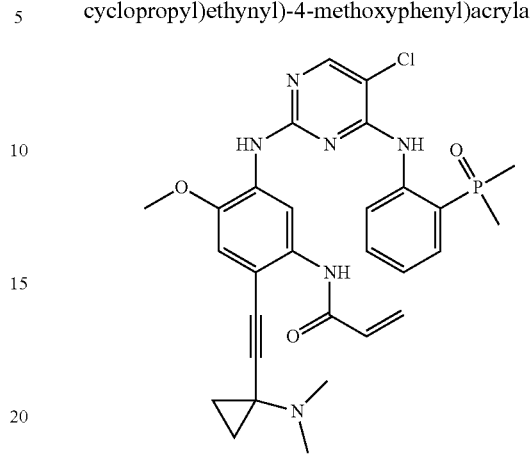

Example 74 was made in accordance with the methods shown in Scheme 40.

EXAMPLE 74

N-(5-((5-chloro-4-((2-(dimethylphosphoryl)phenyl)amino)pyrimidin-2-yl)amino)-4-methoxy-2-(2-(4-methylpiperazin-1-yl)ethyl)phenyl)acrylamide

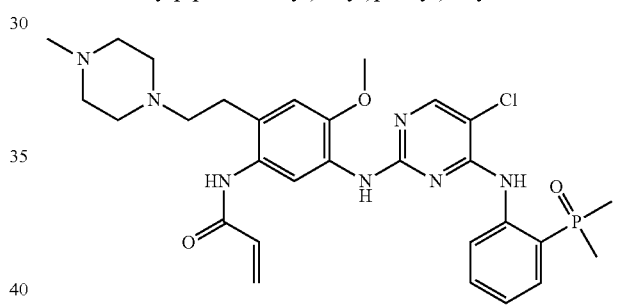

Example 75 was made in accordance with the methods shown in Scheme 41.

EXAMPLE 75

(E)-ethyl 4-((3-((5-chloro-4-((2-(dimethylphosphoryl)phenyl)amino)pyrimidin-2-yl)amino)-4-methoxyphenyl)amino)-4-oxobut-2-enoate

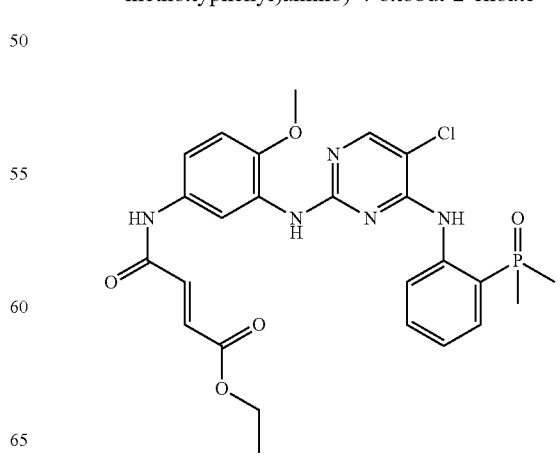

Example 76 was made in accordance with the methods shown in Scheme 42.

EXAMPLE 76

(E)-tert-butyl (1-(3-((3-((5-chloro-4-((2-(dimethyl-phosphoryl)phenyl)amino)pyrimidin-2-yl)amino)-4-methoxyphenyl)amino)-3-oxoprop-1-en-1-yl)cyclopropyl)carbamate

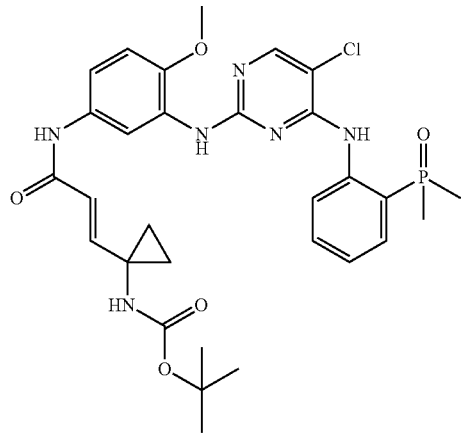 [SMILES: COc1ccc(NC(=O)/C=C/C2(NC(=O)OC(C)(C)C)CC2)cc1Nc1ncc(Cl)c(Nc2ccccc2P(C)(C)=O)n1]

EXAMPLE 77

N-(3-((5-chloro-4-((2-(dimethylphosphoryl)phenyl)amino)pyrimidin-2-yl)amino)-4-methoxyphenyl)-2-fluoroacrylamide

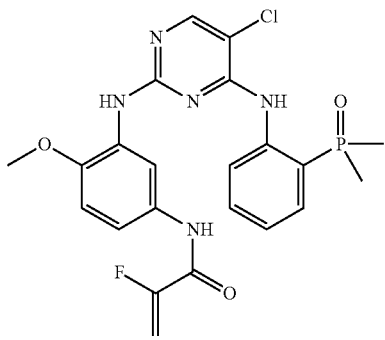

EXAMPLE 78

(E)-3-chloro-N-(3-((5-chloro-4-((2-(dimethylphosphoryl)phenyl)amino)pyrimidin-2-yl)amino)-4-methoxyphenyl)acrylamide

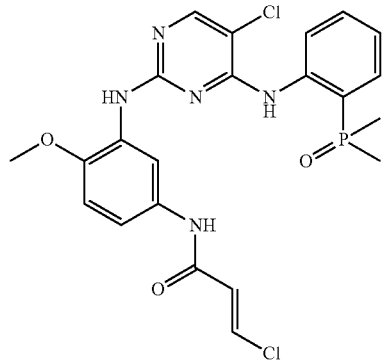

EXAMPLE 79

N-(3-((5-chloro-4-((2-(dimethylphosphoryl)phenyl)amino)pyrimidin-2-yl)amino)-4-methoxyphenyl)cyclohex-1-enecarboxamide

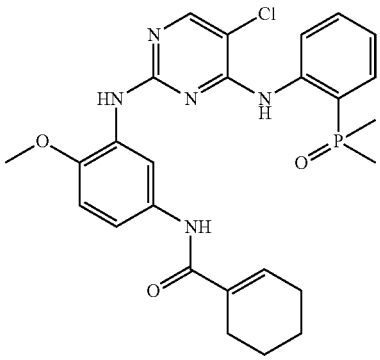

EXAMPLE 80

N-(5-((5-chloro-4-((2-(dimethylphosphoryl)phenyl)amino)pyrimidin-2-yl)amino)-4-methoxy-2-(2-(pyrrolidin-1-yl)ethoxy)phenyl)but-2-ynamide

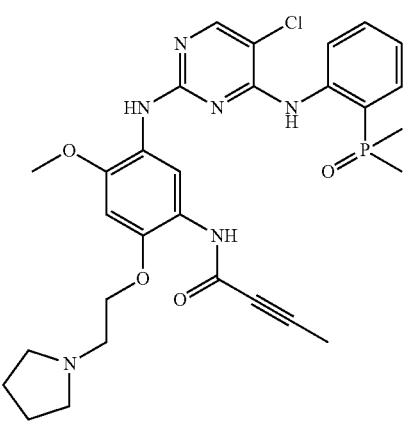 [SMILES: CC#CC(=O)Nc1cc(Nc2ncc(Cl)c(Nc3ccccc3P(C)(C)=O)n2)c(OC)cc1OCCN1CCCC1]

EXAMPLE 81

N-(3-((5-chloro-4-((2-(dimethylphosphoryl)phenyl)amino)pyrimidin-2-yl)amino)-4-methoxyphenyl)-4-(dimethylamino)but-2-ynamide

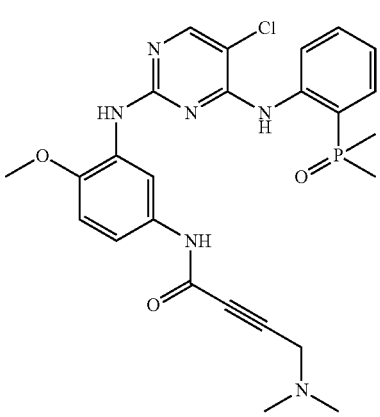

EXAMPLE 82

N-(3-((5-chloro-4-((2-(dimethylphosphoryl)phenyl)amino)pyrimidin-2-yl)amino)-4-methoxyphenyl)-2-(trifluoromethyl)acrylamide

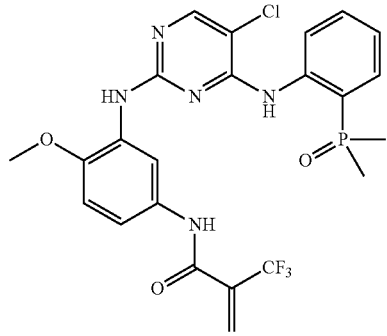

EXAMPLE 83

N-(3-((5-chloro-2-((4-(dimethylphosphoryl)-2-methoxyphenyl)amino)pyrimidin-4-yl)oxy)phenyl)-4-(dimethylamino)but-2-ynamide

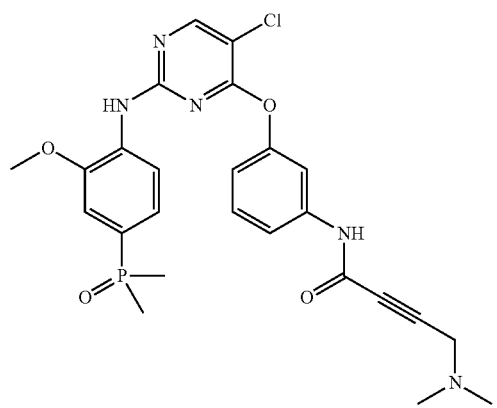

EXAMPLE 84

N-(3-((5-chloro-4-((2-(dimethylphosphoryl)phenyl)amino)pyrimidin-2-yl)amino)-4-methoxyphenyl)-1-methyl-1,2,5,6-tetrahydropyridine-3-carboxamide

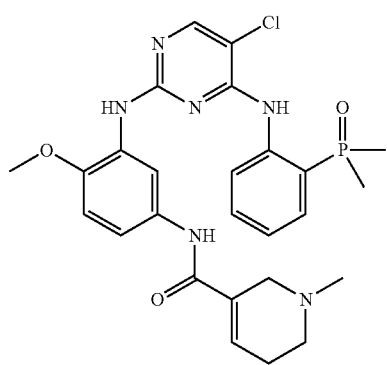

EXAMPLE 85

(E)-3-chloro-N-(5-((5-chloro-4-((2-(dimethylphosphoryl)phenyl)amino)pyrimidin-2-yl)amino)-2-fluoro-4-methoxyphenyl)acrylamide

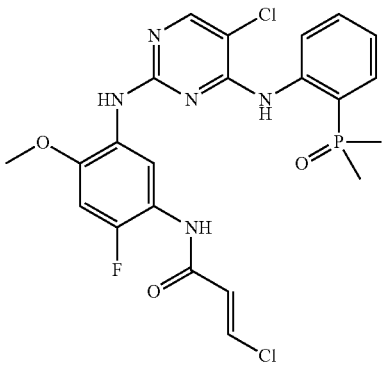

EXAMPLE 86

N-(3-((5-chloro-4-((2-(dimethylphosphoryl)-4-(2-methoxyethoxy)phenyl)amino)pyrimidin-2-yl)amino)-4-methoxyphenyl)acrylamide

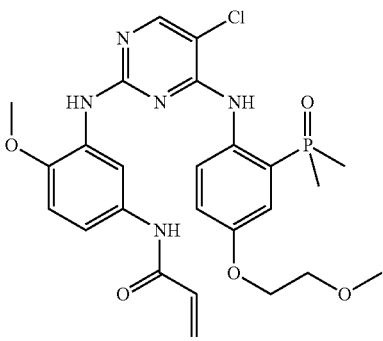 [SMILES: C=CC(=O)Nc1ccc(OC)c(Nc2ncc(Cl)c(Nc3ccc(OCCOC)cc3P(C)(C)=O)n2)c1]

EXAMPLE 87

N-(5-((5-chloro-4-((2-(dimethylphosphoryl)phenyl)amino)pyrimidin-2-yl)amino)-2-fluoro-4-methoxyphenyl)-4-(dimethylamino)but-2-ynamide

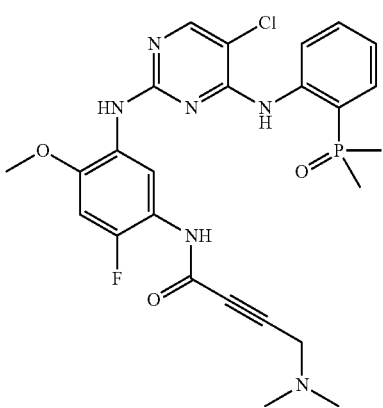

EXAMPLE 88

N-(5-((5-chloro-4-((2-(dimethylphosphoryl)phenyl)amino)pyrimidin-2-yl)amino)-2-fluoro-4-methoxyphenyl)-5-(piperidin-1-yl)pent-2-ynamide

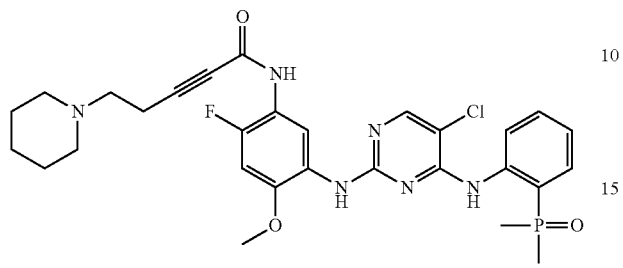

EXAMPLE 89

N-(5-((5-chloro-4-((2-(dimethylphosphoryl)phenyl)amino)pyrimidin-2-yl)amino)-2-fluoro-4-methoxyphenyl)-4-(pyrrolidin-1-yl)but-2-ynamide

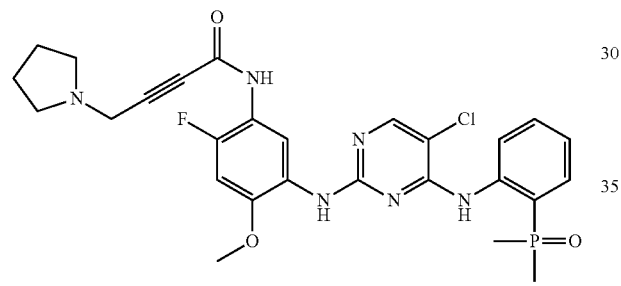

EXAMPLE 90

N-(5-((5-chloro-4-((2-(dimethylphosphoryl)phenyl)amino)pyrimidin-2-yl)amino)-2-fluoro-4-methoxyphenyl)-4-methyl-4-(pyrrolidin-1-yl)pent-2-ynamide

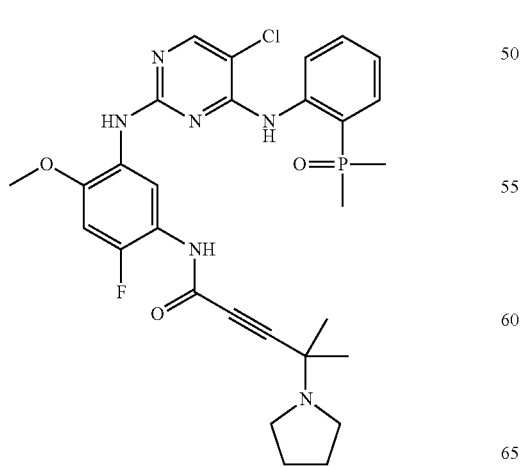

EXAMPLE 91

N-(3-((5-chloro-4-((2-(dimethylphosphoryl)phenyl)amino)pyrimidin-2-yl)amino)-4-methoxyphenyl)-4-methyl-4-(pyrrolidin-1-yl)pent-2-ynamide

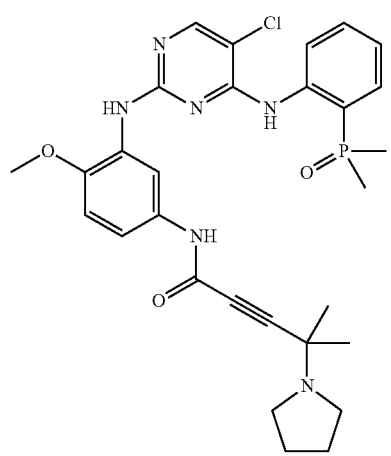

EXAMPLE 92

(E)—N-(3-((5-chloro-4-((2-(dimethylphosphoryl)phenyl)amino)pyrimidin-2-yl)amino)-4-methoxyphenyl)-4-(piperidin-1-yl)but-2-enamide

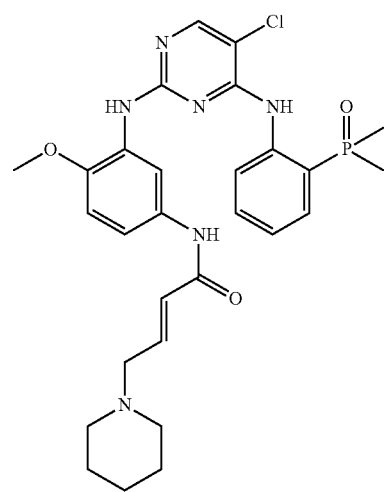

EXAMPLE 93

N-(3-((5-chloro-4-((2-(dimethylphosphoryl)phenyl)amino)pyrimidin-2-yl)amino)-4-methoxyphenyl)-3-phenylpropiolamide

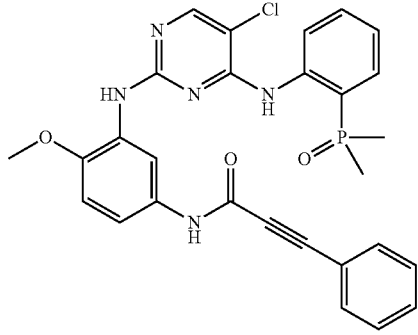 [SMILES: COc1ccc(NC(=O)C#Cc2ccccc2)cc1Nc1ncc(Cl)c(Nc2ccccc2P(C)(C)=O)n1]

EXAMPLE 94

(E)-3-(1-aminocyclopropyl)-N-(3-((5-chloro-4-((2-(dimethylphosphoryl)phenyl)amino)pyrimidin-2-yl)amino)-4-methoxyphenyl)acrylamide

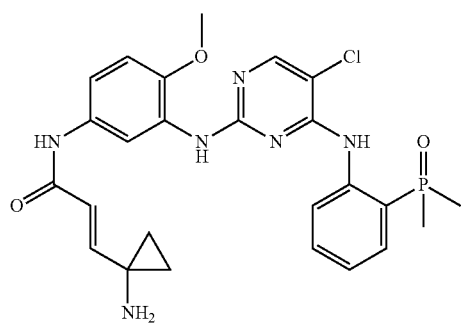 [SMILES: COc1ccc(NC(=O)/C=C/C2(N)CC2)cc1Nc1ncc(Cl)c(Nc2ccccc2P(C)(C)=O)n1]

EXAMPLE 95

(E)—N-(3-((5-chloro-4-((2-(dimethylphosphoryl)phenyl)amino)pyrimidin-2-yl)amino)-4-methoxyphenyl)-4-(pyrrolidin-1-yl)but-2-enamide

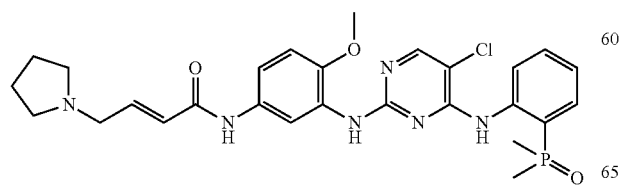

EXAMPLE 96

N-(5-((5-chloro-4-((2-(dimethylphosphoryl)phenyl)amino)pyrimidin-2-yl)amino)-2-(3-(diethylamino)prop-1-yn-1-yl)-4-methoxyphenyl)acrylamide

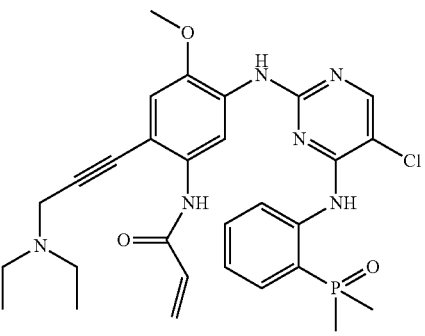 [SMILES: C=CC(=O)Nc1cc(Nc2ncc(Cl)c(Nc3ccccc3P(C)(C)=O)n2)c(OC)cc1C#CCN(CC)CC]

EXAMPLE 97

N-(3-((5-chloro-4-((2-(dimethylphosphoryl)phenyl)amino)pyrimidin-2-yl)amino)-4-methoxyphenyl)-4-methoxybut-2-ynamide

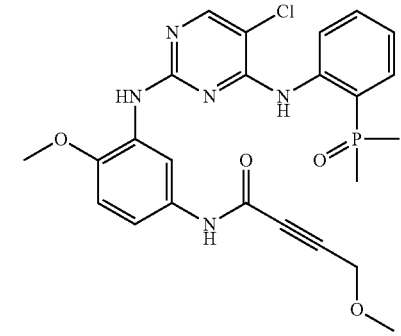

EXAMPLE 98

N-(5-((5-chloro-4-((2-(dimethylphosphoryl)-4-(2-(pyrrolidin-1-yl)ethoxy)phenyl)amino)pyrimidin-2-yl)amino)-2-fluoro-4-methoxyphenyl)acrylamide

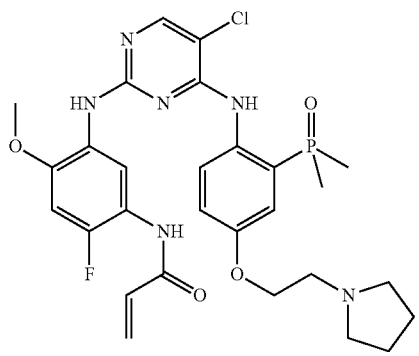 [SMILES: C=CC(=O)Nc1cc(Nc2ncc(Cl)c(Nc3ccc(OCCN4CCCC4)cc3P(C)(C)=O)n2)c(OC)cc1F]

EXAMPLE 99

N-(3-((5-chloro-4-((2-(dimethylphosphoryl)-4-((tetrahydrofuran-3-yl)oxy)phenyl)amino)pyrimidin-2-yl)amino)-4-methoxyphenyl)acrylamide

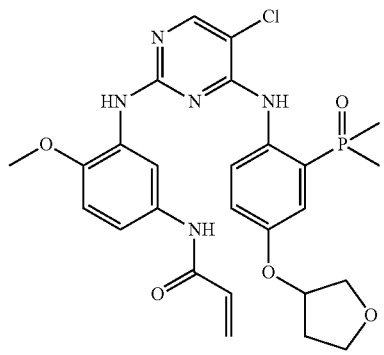

EXAMPLE 100

N-(3-((5-chloro-4-((2-(dimethylphosphoryl)-4-((tetrahydro-2H-pyran-4-yl)methoxy)phenyl)amino)pyrimidin-2-yl)amino)-4-methoxyphenyl)acrylamide

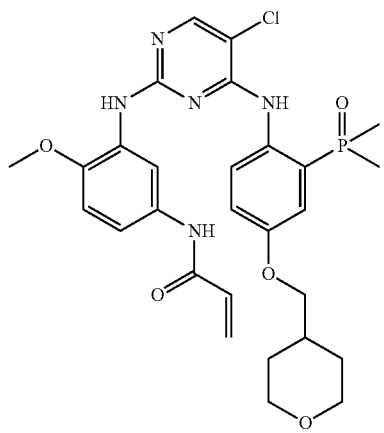

EXAMPLE 101

N-(5-((5-chloro-4-((2-(dimethylphosphoryl)phenyl)amino)pyrimidin-2-yl)amino)-4-methoxy-2-morpholinophenyl)-5-(piperidin-1-yl)pent-2-ynamide

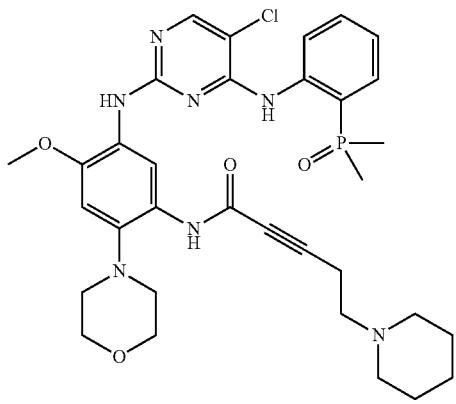 [SMILES: COc1cc(N2CCOCC2)c(NC(=O)C#CCCN2CCCCC2)cc1Nc1ncc(Cl)c(Nc2ccccc2P(C)(C)=O)n1]

EXAMPLE 102

N-(5-((5-chloro-4-((2-(dimethylphosphoryl)phenyl)amino)pyrimidin-2-yl)amino)-4-methoxy-2-((tetrahydro-2H-pyran-4-yl)methoxy)phenyl)but-2-ynamide

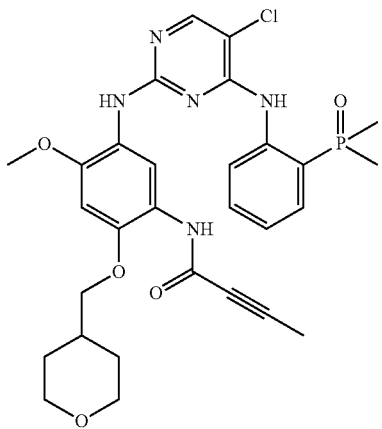

EXAMPLE 103

N-(5-((5-chloro-4-((2-(dimethylphosphoryl)phenyl)amino)pyrimidin-2-yl)amino)-4-methoxy-2-(oxetan-3-yloxy)phenyl)but-2-ynamide

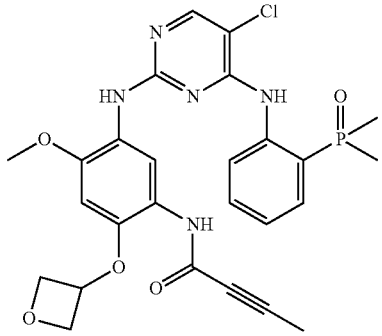

EXAMPLE 104

N-(5-((5-chloro-4-((2-(dimethylphosphoryl)phenyl)amino)pyrimidin-2-yl)amino)-4-methoxy-2-morpholinophenyl)-4-(dimethylamino)but-2-ynamide

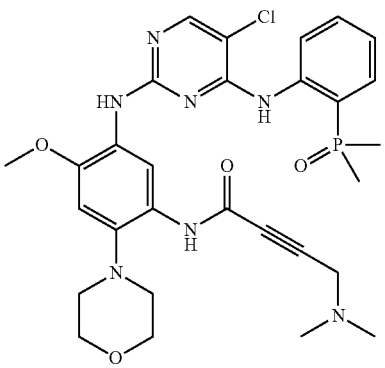

EXAMPLE 105

N-(5-((5-chloro-4-((2-(dimethylphosphoryl)phenyl)amino)pyrimidin-2-yl)amino)-4-methoxy-2-morpholinophenyl)-4-methoxybut-2-ynamide

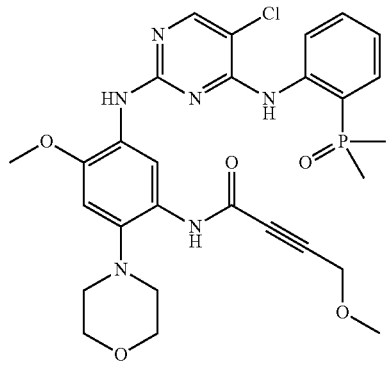

EXAMPLE 106

N-(5-((5-chloro-4-((2-(dimethylphosphoryl)phenyl)amino)pyrimidin-2-yl)amino)-4-methoxy-2-(4-(4-methylpiperazin-1-yl)piperidin-1-yl)phenyl)but-2-ynamide

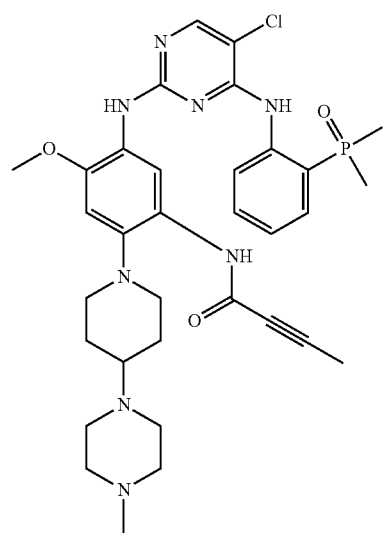

EXAMPLE 107

N-(4-((5-chloro-4-((2-(dimethylphosphoryl)-3-(2-(piperidin-1-yl)ethoxy)phenyl)amino)pyrimidin-2-yl)amino)-3-methoxyphenyl)acrylamide

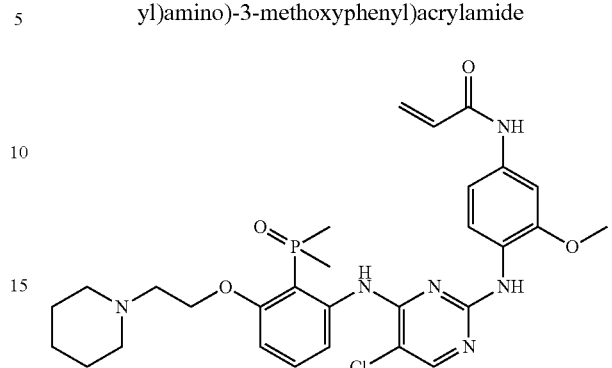

EXAMPLE 108

N-(3-((5-chloro-4-((2-(dimethylphosphoryl)-4-(2-(piperidin-1-yl)ethoxy)phenyl)amino)pyrimidin-2-yl)amino)-4-methoxyphenyl)acrylamide

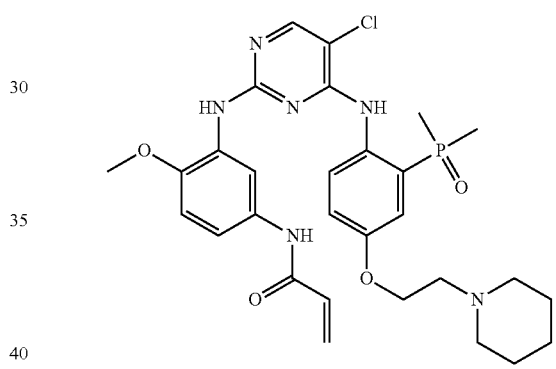

EXAMPLE 109

N1-(3-((5-chloro-4-((2-(dimethylphosphoryl)phenyl)amino)pyrimidin-2-yl)amino)-4-methoxyphenyl)-N4-methylfumaramide

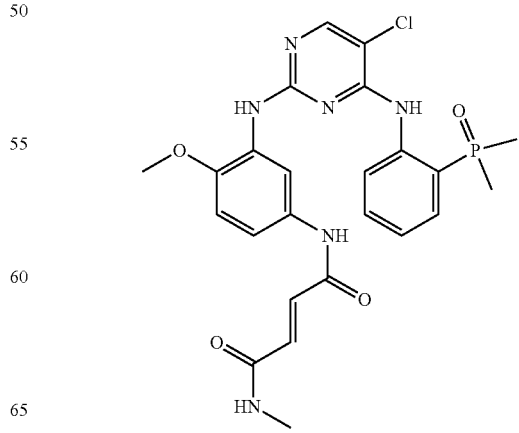

EXAMPLE 110

N1-(3-((5-chloro-4-((2-(dimethylphosphoryl)phenyl)amino)pyrimidin-2-yl)amino)-4-methoxyphenyl)-N4-methylmaleamide

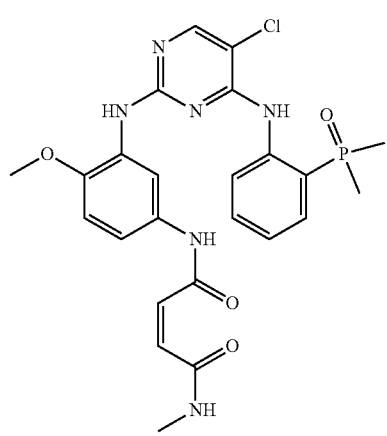

EXAMPLE 111

N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)-4-methoxybut-2-ynamide

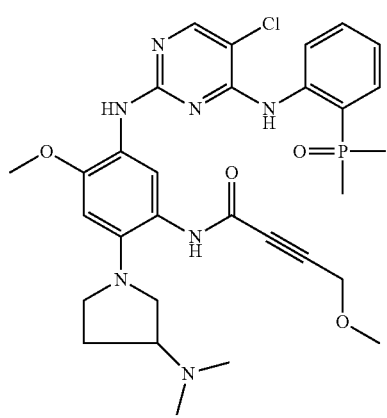

EXAMPLE 112

N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)but-2-ynamide

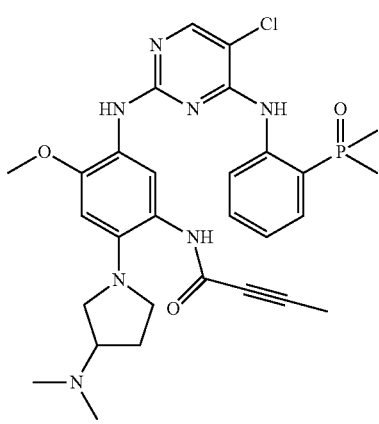

EXAMPLE 113 rac-(R)-N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)methacrylamide

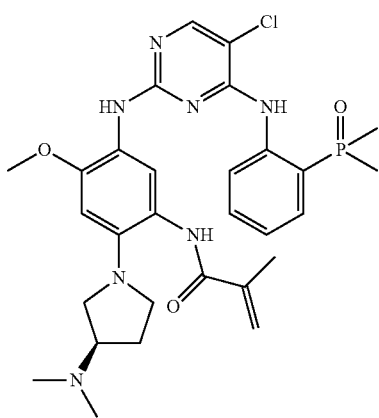

EXAMPLE 114

N-(5-((5-chloro-4-((2-(dimethylphosphoryl)phenyl)amino)pyrimidin-2-yl)amino)-4-methoxy-2-morpholinophenyl)-5-(dimethylamino)pent-2-ynamide

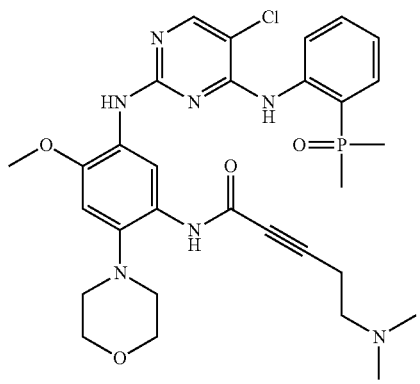

EXAMPLE 115

N-(5-((5-chloro-4-((2-(dimethylphosphoryl)phenyl)amino)pyrimidin-2-yl)amino)-4-methoxy-2-morpholinophenyl)-5-methoxypent-2-ynamide

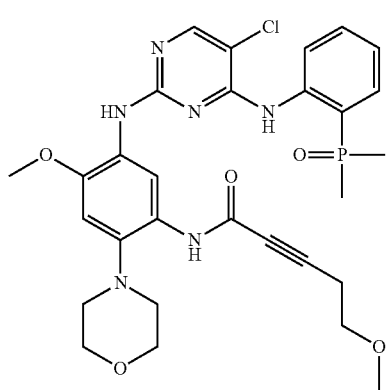

EXAMPLE 116

N-(5-((5-chloro-4-((2-(dimethylphosphoryl)phenyl)amino)pyrimidin-2-yl)amino)-4-methoxy-2-(3-methyl-3-(pyrrolidin-1-yl)but-1-yn-1-yl)phenyl)acrylamide

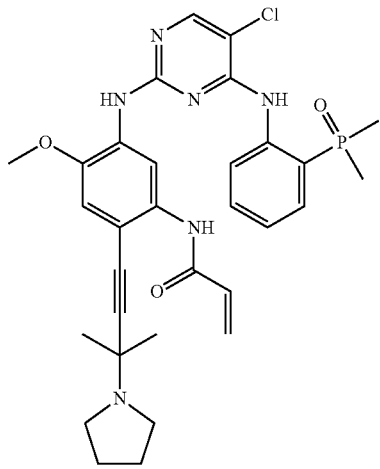

EXAMPLE 117

N-(3-((5-chloro-4-((2-(dimethylphosphoryl)phenyl)amino)pyrimidin-2-yl)amino)-4-(2-(dimethylamino)ethoxy)phenyl)acrylamide

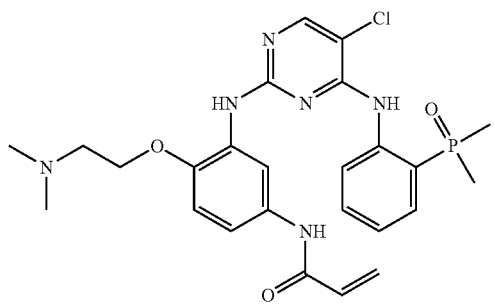

EXAMPLE 118

N-(5-((5-chloro-4-((2-(dimethylphosphoryl)phenyl)amino)pyrimidin-2-yl)amino)-4-methoxy-2-morpholinophenyl)-5-(4-methylpiperazin-1-yl)pent-2-ynamide

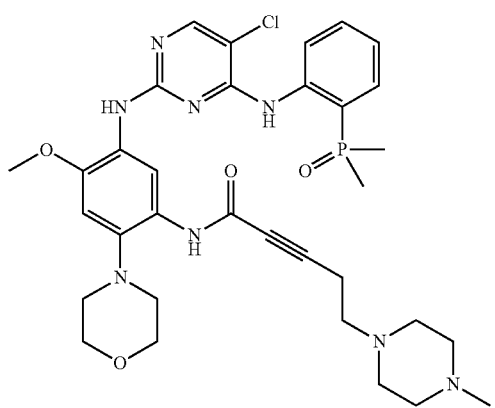

EXAMPLE 119

N-(5-((5-chloro-4-((2-(dimethylphosphoryl)phenyl)amino)pyrimidin-2-yl)amino)-4-methoxy-2-(pyrrolidin-1-yl)phenyl)-5-(4-methylpiperazin-1-yl)pent-2-ynamide

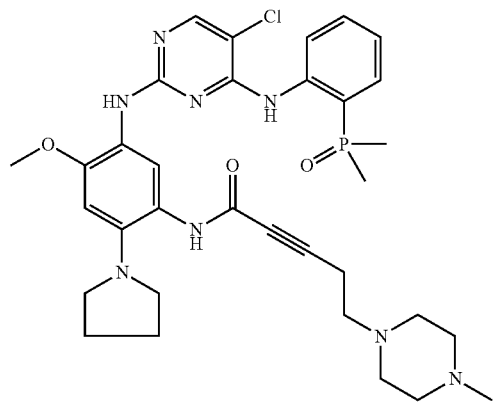

EXAMPLE 120

N-(5-((5-cyclopropyl-4-((2-(dimethylphosphoryl)phenyl)amino)pyrimidin-2-yl)amino)-2-((2-(diethylamino)ethyl)(methyl)amino)-4-methoxyphenyl)acrylamide

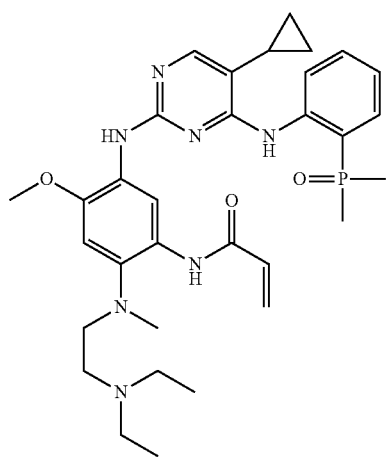

EXAMPLE 121

N-(5-((5-chloro-4-((2-(dimethylphosphoryl)phenyl)amino)pyrimidin-2-yl)amino)-2-((1-(diethylamino)-3-fluoropropan-2-yl)oxy)-4-methoxyphenyl)acrylamide

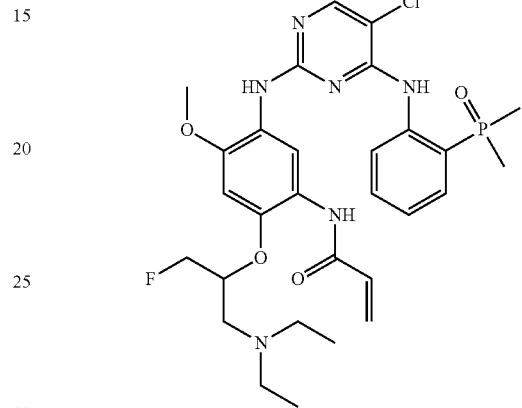

EXAMPLE 122

N-(5-((5-chloro-4-((2-(dimethylphosphoryl)phenyl)amino)pyrimidin-2-yl)amino)-4-methoxy-2-morpholinophenyl)-5-(2-(methoxymethyl)pyrrolidin-1-yl)pent-2-ynamide

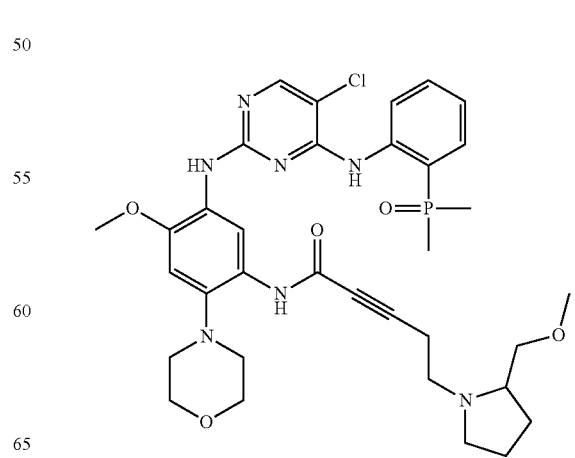

EXAMPLE 123

N-(5-((5-chloro-4-((2-(dimethylphosphoryl)phenyl)amino)pyrimidin-2-yl)amino)-4-methoxy-2-((1-(2-methoxyethyl)piperidin-3-yl)oxy)phenyl)acrylamide

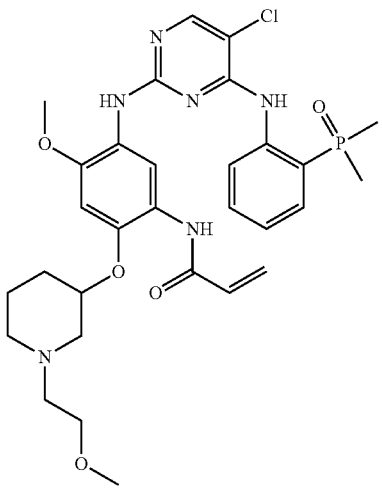 [SMILES: C=CC(=O)Nc1cc(Nc2ncc(Cl)c(Nc3ccccc3P(C)(C)=O)n2)c(OC)cc1OC1CCCN(CCOC)C1]

EXAMPLE 124

N-(5-((5-chloro-4-((2-(dimethylphosphoryl)phenyl)amino)pyrimidin-2-yl)amino)-2-(3-(dimethylamino)prop-1-yn-1-yl)-4-methoxyphenyl)acrylamide

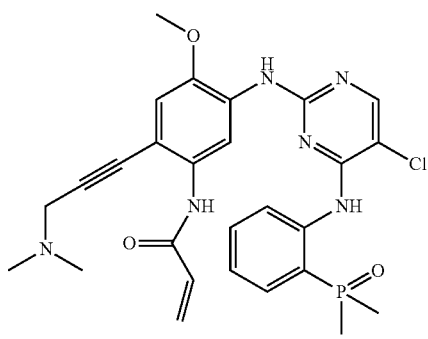 [SMILES: C=CC(=O)Nc1cc(Nc2ncc(Cl)c(Nc3ccccc3P(C)(C)=O)n2)c(OC)cc1C#CCN(C)C]

EXAMPLE 125

N-(3-((5-chloro-4-((4-(2-(dimethylamino)ethoxy)-2-(dimethylphosphoryl)phenyl)amino)pyrimidin-2-yl)amino)-4-methoxyphenyl)acrylamide

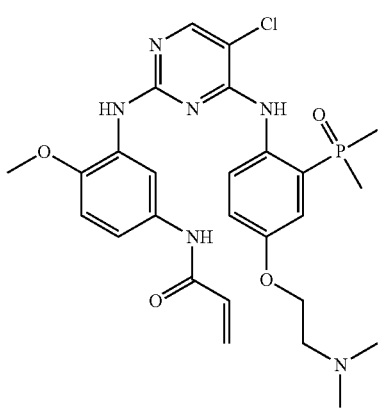

EXAMPLE 126

N-(3-((5-chloro-4-((4-(3-(dimethylamino)propoxy)-2-(dimethylphosphoryl)phenyl)amino)pyrimidin-2-yl)amino)-4-methoxyphenyl)acrylamide

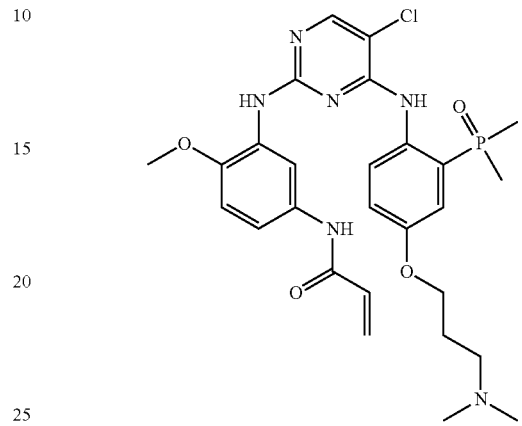

EXAMPLE 127

1-(6-((5-chloro-4-((2-(dimethylphosphoryl)phenyl)amino)pyrimidin-2-yl)amino)-5-methoxyindolin-1-yl)prop-2-en-1-one

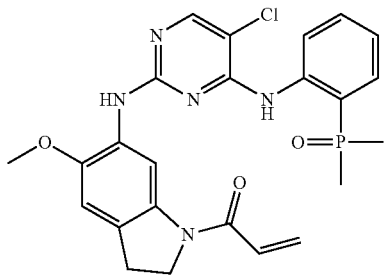

EXAMPLE 128

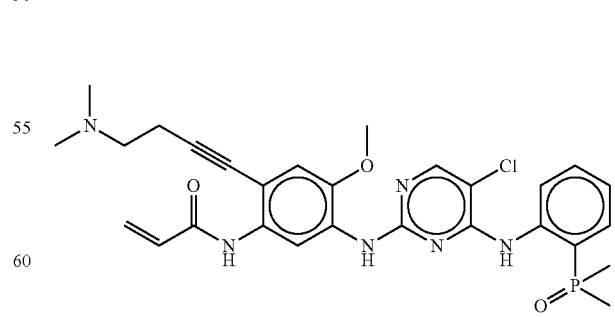

N-(5-((5-chloro-4-((2-(dimethylphosphoryl)phenyl)amino)pyrimidin-2-yl)amino)-2-(4-(dimethylamino)but-1-yn-1-yl)-4-methoxyphenyl)acrylamide

EXAMPLE 129

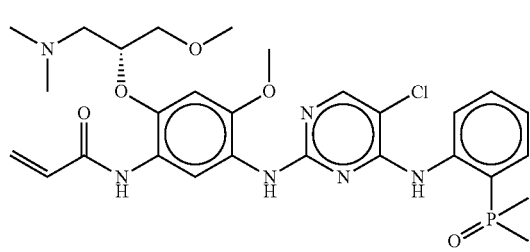

(R)-N-(5-((5-chloro-4-((2-(dimethylphosphoryl)phenyl)amino)pyrimidin-2-yl)amino)-2-((1-(dimethylamino)-3-methoxypropan-2-yl)oxy)-4-methoxyphenyl)acrylamide

EXAMPLE 130

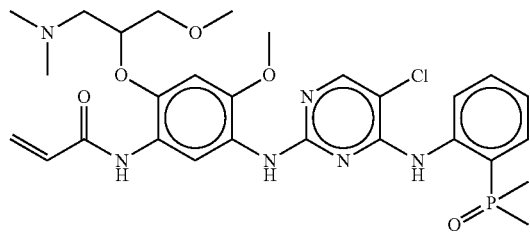

N-(5-((5-chloro-4-((2-(dimethylphosphoryl)phenyl)amino)pyrimidin-2-yl)amino)-2-((1-(dimethylamino)-3-methoxypropan-2-yl)oxy)-4-methoxyphenyl)acrylamide

EXAMPLE 131

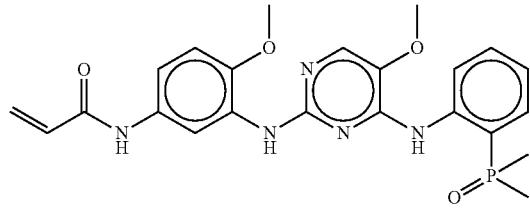

N-(3-((4-((2-(dimethylphosphoryl)phenyl)amino)-5-methoxypyrimidin-2-yl)amino)-4-methoxyphenyl)acrylamide

EXAMPLE 132

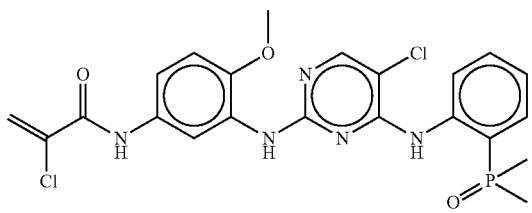

2-chloro-N-(3-((5-chloro-4-((2-(dimethylphosphoryl)phenyl)amino)pyrimidin-2-yl)amino)-4-methoxyphenyl)acrylamide

EXAMPLE 133

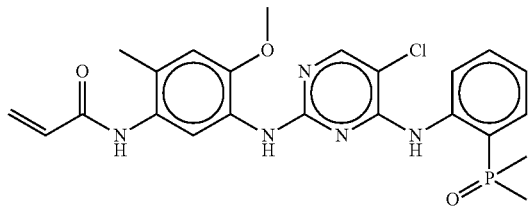

N-(5-((5-chloro-4-((2-(dimethylphosphoryl)phenyl)amino)pyrimidin-2-yl)amino)-4-methoxy-2-methylphenyl)acrylamide

EXAMPLE 134

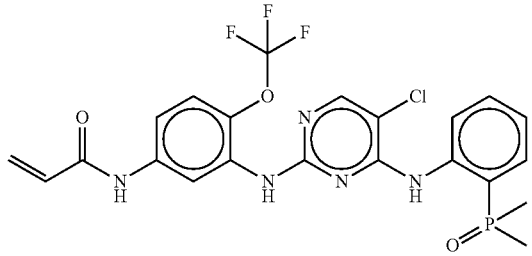

N-(3-((5-chloro-4-((2-(dimethylphosphoryl)phenyl)amino)pyrimidin-2-yl)amino)-4-(trifluoromethoxy)phenyl)acrylamide

EXAMPLE 135

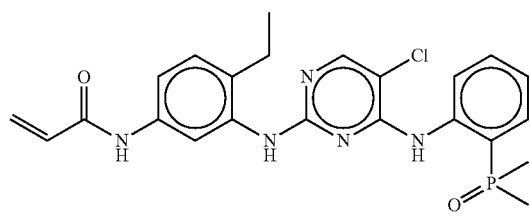

N-(3-((5-chloro-4-((2-(dimethylphosphoryl)phenyl)amino)pyrimidin-2-yl)amino)-4-ethylphenyl)acrylamide

EXAMPLE 136

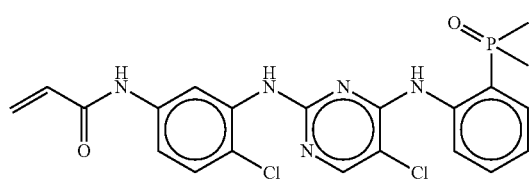

N-(4-chloro-3-((5-chloro-4-((2-(dimethylphosphoryl)phenyl)amino)pyrimidin-2-yl)amino)phenyl)acrylamide

EXAMPLE 137

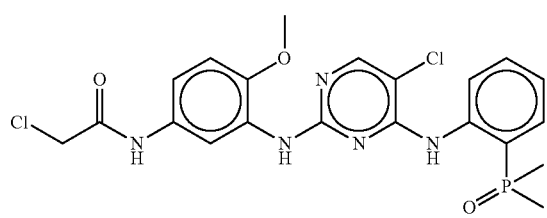

2-chloro-N-(3-((5-chloro-4-((2-(dimethylphosphoryl)phenyl)amino)pyrimidin-2-yl)amino)-4-methoxyphenyl)acetamide

EXAMPLE 138

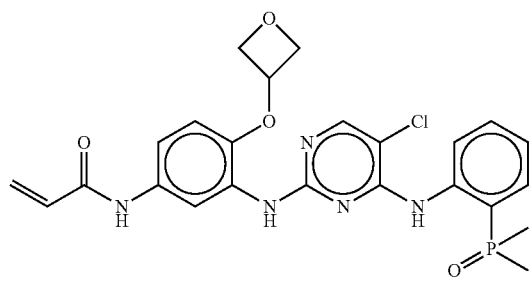

N-(3-((5-chloro-4-((2-(dimethylphosphoryl)phenyl)amino)pyrimidin-2-yl)amino)-4-(oxetan-3-yloxy)phenyl)acrylamide

EXAMPLE 139

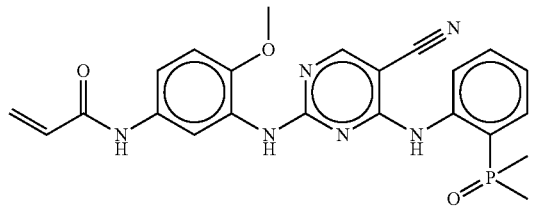

N-(3-((5-cyano-4-((2-(dimethylphosphoryl)phenyl)amino)pyrimidin-2-yl)amino)-4-methoxyphenyl)acrylamide

EXAMPLE 140

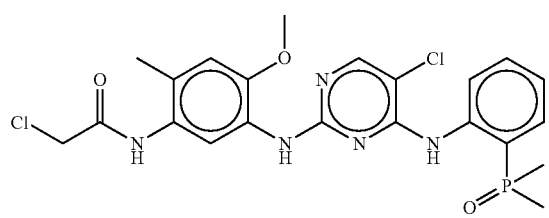

2-chloro-N-(5-((5-chloro-4-((2-(dimethylphosphoryl)phenyl)amino)pyrimidin-2-yl)amino)-4-methoxy-2-methylphenyl)acetamide

EXAMPLE 141

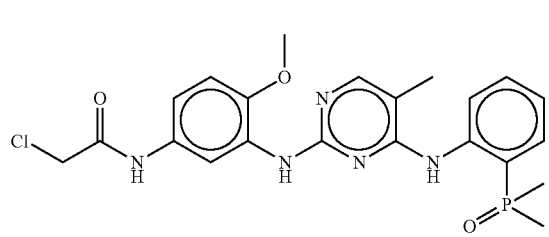

2-chloro-N-(3-((4-((2-(dimethylphosphoryl)phenyl)amino)-5-methylpyrimidin-2-yl)amino)-4-methoxyphenyl)acetamide

EXAMPLE 142

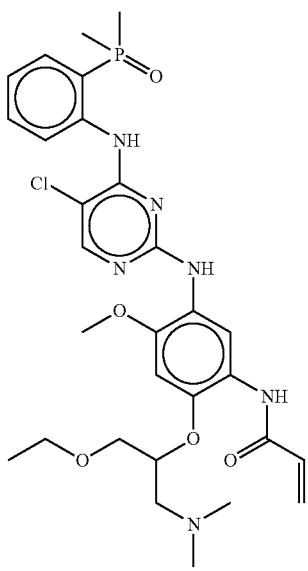

N-(5-((5-chloro-4-((2-(dimethylphosphoryl)phenyl)amino)pyrimidin-2-yl)amino)-2-((1-(dimethylamino)-3-ethoxypropan-2-yl)oxy)-4-methoxyphenyl)acrylamide

EXAMPLE 143

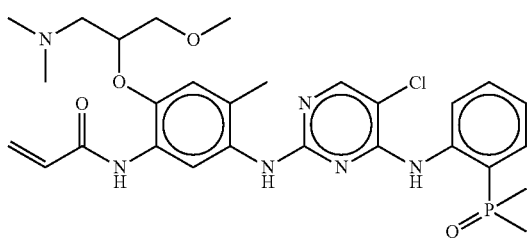

N-(5-((5-chloro-4-((2-(dimethylphosphoryl)phenyl)amino)pyrimidin-2-yl)amino)-2-((1-(dimethylamino)-3-methoxypropan-2-yl)oxy)-4-methyl)phenyl)acrylamide

EXAMPLE 144

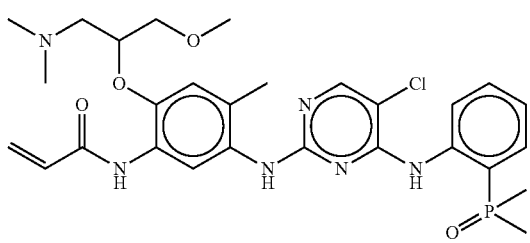

N-(5-((5-chloro-4-((2-(dimethylphosphoryl)phenyl)amino)pyrimidin-2-yl)amino)-2-((1-(dimethylamino)-3-methoxypropan-2-yl)oxy)-4-methylphenyl)acrylamide

EXAMPLE 145

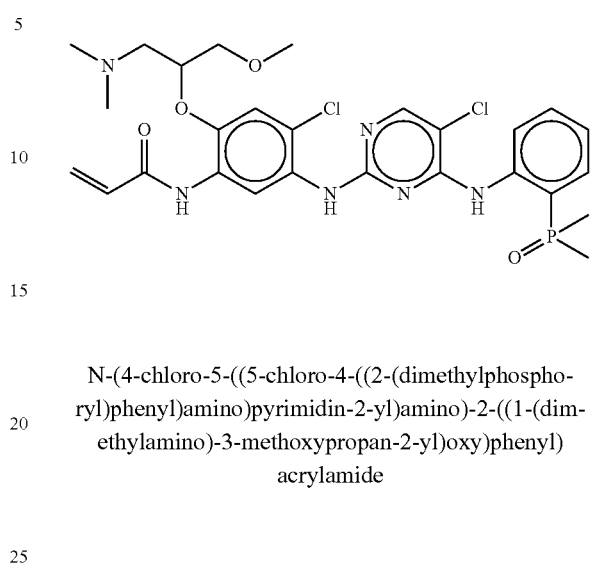

N-(4-chloro-5-((5-chloro-4-((2-(dimethylphosphoryl)phenyl)amino)pyrimidin-2-yl)amino)-2-((1-(dimethylamino)-3-methoxypropan-2-yl)oxy)phenyl)acrylamide

EXAMPLE 146

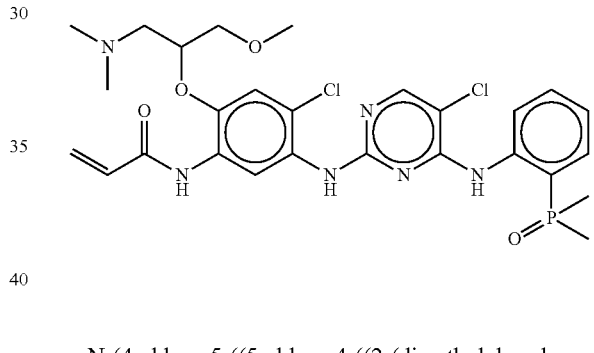

N-(4-chloro-5-((5-chloro-4-((2-(dimethylphosphoryl)phenyl)amino)pyrimidin-2-yl)amino)-2-((1-(dimethylamino)-3-methoxypropan-2-yl)oxy)phenyl)acrylamide

EXAMPLE 147

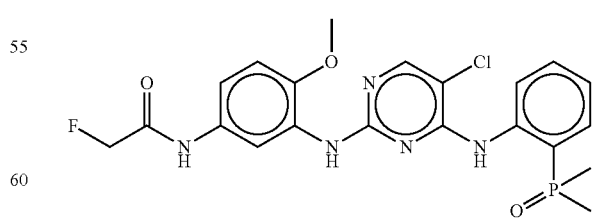

N-(3-((5-chloro-4-((2-(dimethylphosphoryl)phenyl)amino)pyrimidin-2-yl)amino)-4-methoxyphenyl)-2-fluoroacetamide

EXAMPLE 148

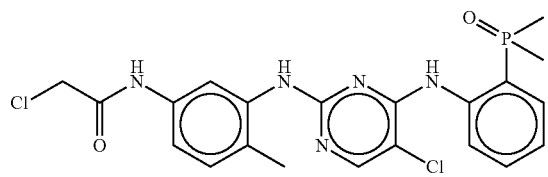

2-chloro-N-(3-((5-chloro-4-((2-(dimethylphosphoryl)phenyl)amino)pyrimidin-2-yl)amino)-4-methylphenyl)acetamide

EXAMPLE 149

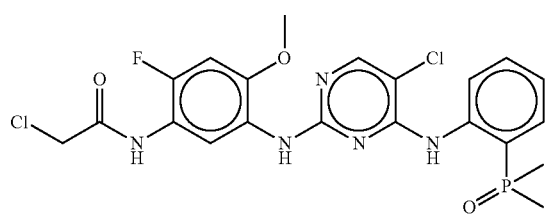

2-chloro-N-(5-((5-chloro-4-((2-(dimethylphosphoryl)phenyl)amino)pyrimidin-2-yl)amino)-2-fluoro-4-methoxyphenyl)acetamide

EXAMPLE 150

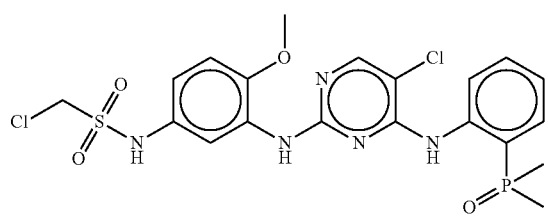

1-chloro-N-(3-((5-chloro-4-((2-(dimethylphosphoryl)phenyl)amino)pyrimidin-2-yl)amino)-4-methoxyphenyl)methanesulfonamide

EXAMPLE 151

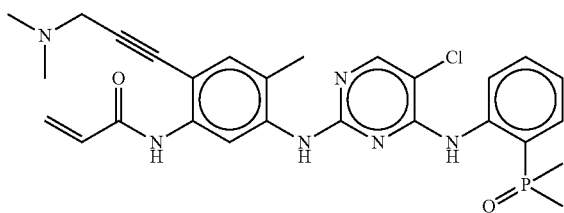

N-(5-((5-chloro-4-((2-(dimethylphosphoryl)phenyl)amino)pyrimidin-2-yl)amino)-2-(3-(dimethylamino)prop-1-yn-1-yl)-4-methylphenyl)acrylamide

EXAMPLE 152

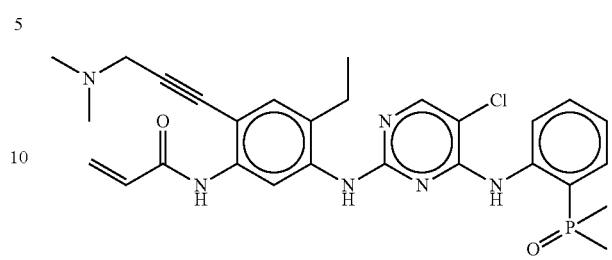

N-(5-((5-chloro-4-((2-(dimethylphosphoryl)phenyl)amino)pyrimidin-2-yl)amino)-2-(3-(dimethylamino)prop-1-yn-1-yl)-4-ethylphenyl)acrylamide

EXAMPLE 153

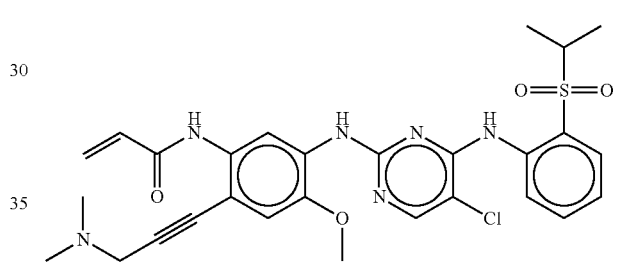

N-(5-((5-chloro-4-((2-(isopropylsulfonyl)phenyl)amino)pyrimidin-2-yl)amino)-2-(3-(dimethylamino)prop-1-yn-1-yl)-4-methoxyphenyl)acrylamide

EXAMPLE 154

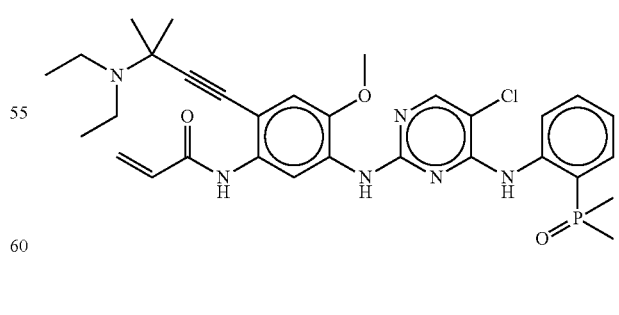

N-(5-((5-chloro-4-((2-(dimethylphosphoryl)phenyl)amino)pyrimidin-2-yl)amino)-2-(3-(diethylamino)-3-methylbut-1-yn-1-yl)-4-methoxyphenyl)acrylamide

EXAMPLE 155

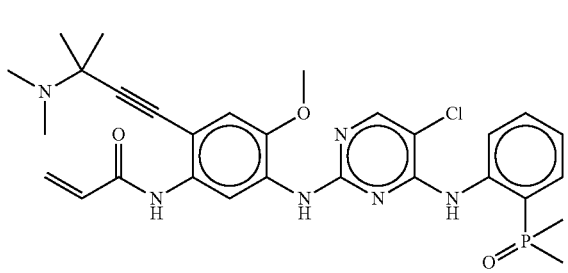

N-(5-((5-chloro-4-((2-(dimethylphosphoryl)phenyl)amino)pyrimidin-2-yl)amino)-2-(3-(dimethylamino)-3-methylbut-1-yn-1-yl)-4-methoxyphenyl)acrylamide

EXAMPLE 156

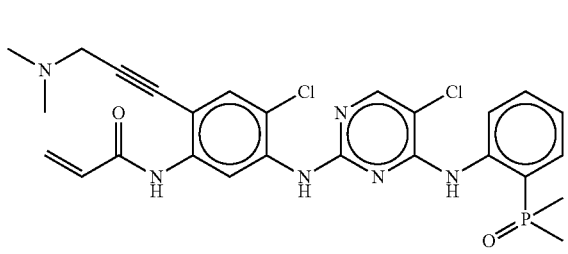

N-(4-chloro-5-((5-chloro-4-((2-(dimethylphosphoryl)phenyl)amino)pyrimidin-2-yl)amino)-2-(3-(dimethylamino)prop-1-yn-1-yl)phenyl)acrylamide

EXAMPLE 157

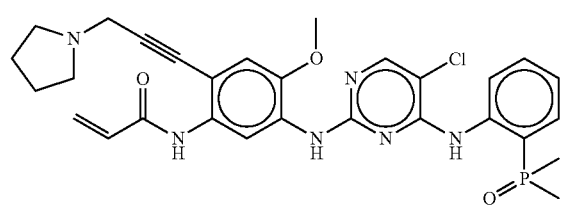

N-(5-((5-chloro-4-((2-(dimethylphosphoryl)phenyl)amino)pyrimidin-2-yl)amino)-4-methoxy-2-(3-(pyrrolidin-1-yl)prop-1-yn-1-yl)phenyl)acrylamide

EXAMPLE 158

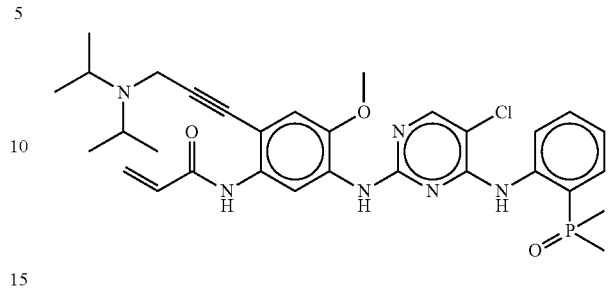

N-(5-((5-chloro-4-((2-(dimethylphosphoryl)phenyl)amino)pyrimidin-2-yl)amino)-2-(3-(diisopropylamino)prop-1-yn-1-yl)-4-methoxyphenyl)acrylamide

EXAMPLE 159

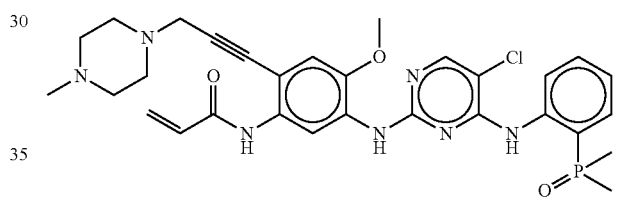

N-(5-((5-chloro-4-((2-(dimethylphosphoryl)phenyl)amino)pyrimidin-2-yl)amino)-4-methoxy-2-(3-(4-methylpiperazin-1-yl)prop-1-yn-1-yl)phenyl)acrylamide

EXAMPLE 160

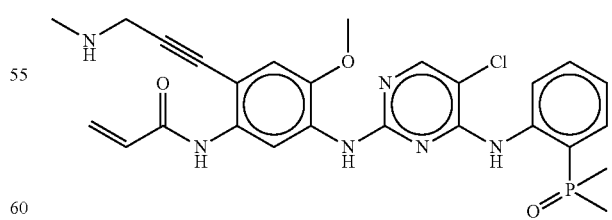

N-(5-((5-chloro-4-((2-(dimethylphosphoryl)phenyl)amino)pyrimidin-2-yl)amino)-4-methoxy-2-(3-(methylamino)prop-1-yn-1-yl)phenyl)acrylamide

EXAMPLE 161

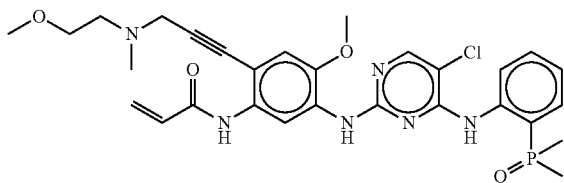

N-(5-((5-chloro-4-((2-(dimethylphosphoryl)phenyl)amino)pyrimidin-2-yl)amino)-4-methoxy-2-(3-((2-methoxyethyl)(methyl)amino)prop-1-yn-1-yl)phenyl)acrylamide

EXAMPLE 162

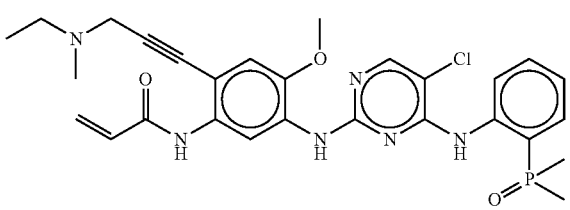

N-(5-((5-chloro-4-((2-(dimethylphosphoryl)phenyl)amino)pyrimidin-2-yl)amino)-2-(3-(ethyl(methyl)amino)prop-1-yn-1-yl)-4-methoxyphenyl)acrylamide

EXAMPLE 163

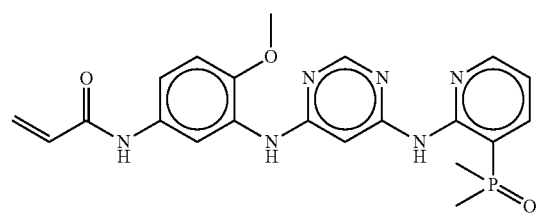

N-(3-((6-((3-(dimethylphosphoryl)pyridin-2-yl)amino)pyrimidin-4-yl)amino)-4-methoxyphenyl)acrylamide

EXAMPLE 164

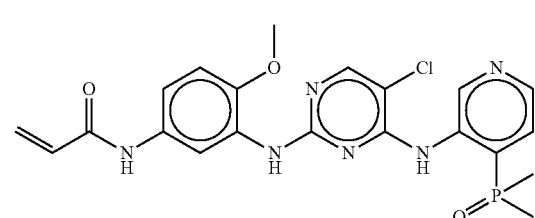

N-(3-((5-chloro-4-((4-(dimethylphosphoryl)pyridin-3-yl)amino)pyrimidin-2-yl)amino)-4-methoxyphenyl)acrylamide

EXAMPLE 165

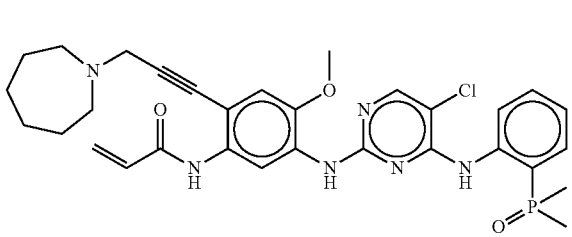

N-(2-(3-(azepan-1-yl)prop-1-yn-1-yl)-5-((5-chloro-4-((2-(dimethylphosphoryl)phenyl)amino)pyrimidin-2-yl)amino)-4-methoxyphenyl)acrylamide

EXAMPLE 166

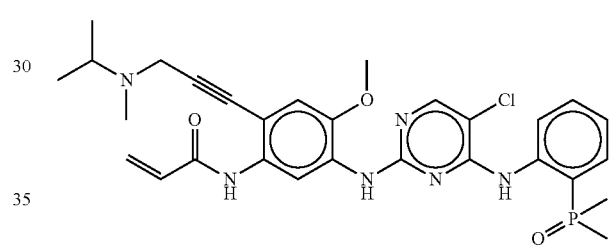

N-(5-((5-chloro-4-((2-(dimethylphosphoryl)phenyl)amino)pyrimidin-2-yl)amino)-2-(3-(isopropyl(methyl)amino)prop-1-yn-1-yl)-4-methoxyphenyl)acrylamide

EXAMPLE 167

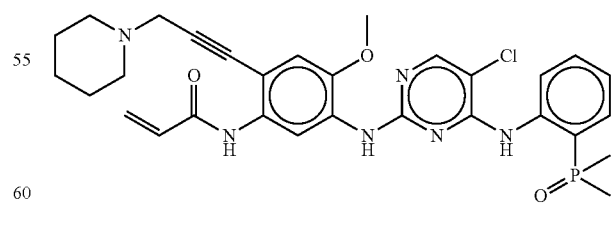

N-(5-((5-chloro-4-((2-(dimethylphosphoryl)phenyl)amino)pyrimidin-2-yl)amino)-4-methoxy-2-(3-(piperidin-1-yl)prop-1-yn-1-yl)phenyl)acrylamide

EXAMPLE 168

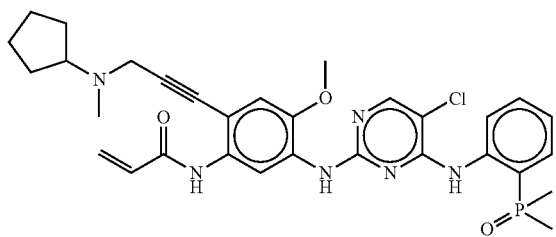

N-(5-((5-chloro-4-((2-(dimethylphosphoryl)phenyl)amino)pyrimidin-2-yl)amino)-2-(3-(cyclopentyl(methyl)amino)prop-1-yn-1-yl)-4-methoxyphenyl)acrylamide

EXAMPLE 169

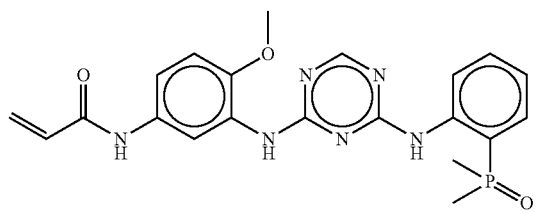

N-(3-((4-((2-(dimethylphosphoryl)phenyl)amino)-1,3,5-triazin-2-yl)amino)-4-methoxyphenyl)acrylamide

EXAMPLE 170

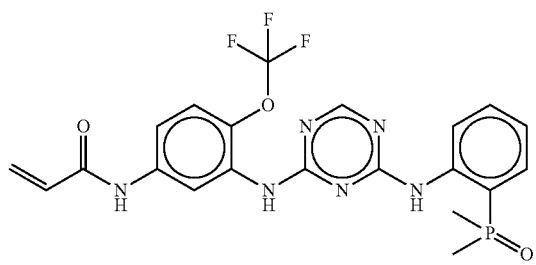

N-(3-((4-((2-(dimethylphosphoryl)phenyl)amino)-1,3,5-triazin-2-yl)amino)-4-(trifluoromethoxy)phenyl)acrylamide

EXAMPLE 171

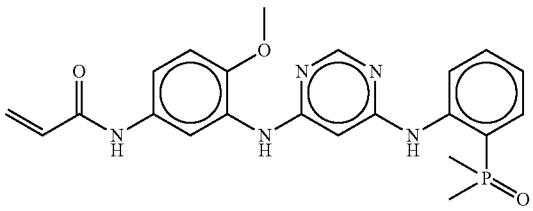

N-(3-((6-((2-(dimethylphosphoryl)phenyl)amino)pyrimidin-4-yl)amino)-4-methoxyphenyl)acrylamide

EXAMPLE 172

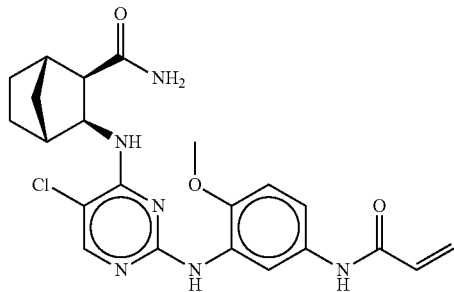

(1S,2R,3S,4R)-3-((2-((5-acrylamido-2-methoxyphenyl)amino)-5-chloropyrimidin-4-yl)amino)bicyclo[2.2.1]heptane-2-carboxamide

EXAMPLE 173

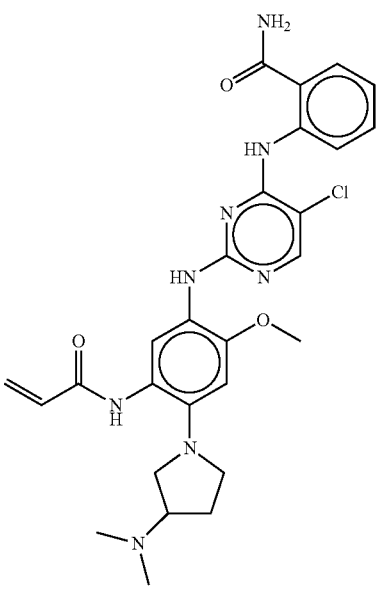

2-((2-(5-acrylamido-4-(3-(dimethylamino)pyrrolidin-1-yl)-2-methoxyphenyl)amino)-5-chloropyrimidin-4-yl)amino)benzamide

EXAMPLE 174

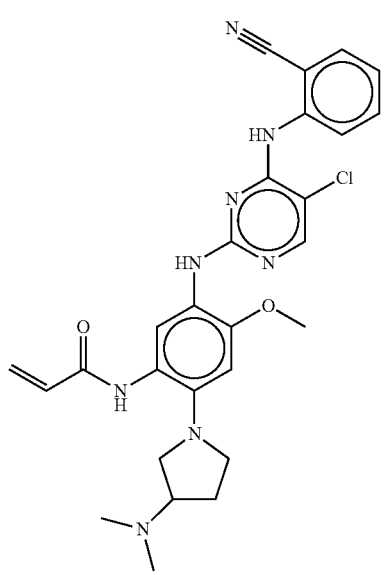

N-(5-((5-chloro-4-((2-cyanophenyl)amino)pyrimidin-2-yl)amino)-2-(3-(dimethylamino)pyrrolidin-1-yl)-4-methoxyphenyl)acrylamide

EXAMPLE 175

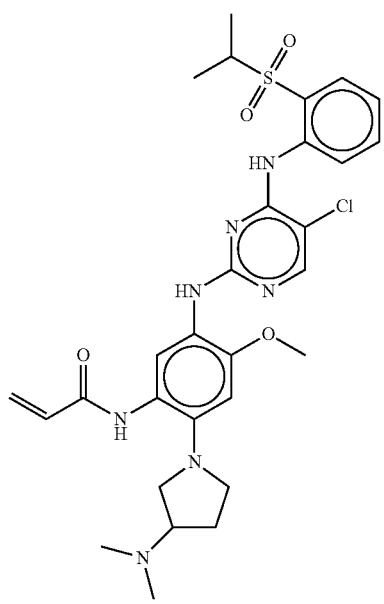

N-(5-((5-chloro-4-(isopropylsulfonyl)phenyl)amino)pyrimidin-2-yl)amino)-2-(3-(dimethylamino)pyrrolidin-1-yl)-4-methoxyphenyl)acrylamide

EXAMPLE 176

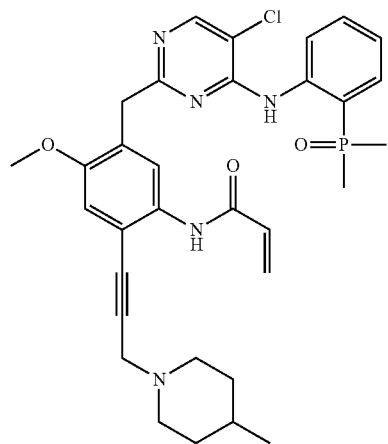

N-(5-((5-chloro-4-((2-(dimethylphosphoryl)phenyl)amino)pyrimidin-2-yl)methyl)-4-methoxy-2-(3-(4-methylpiperidin-1-yl)prop-1-yn-1-yl)phenyl)acrylamide

EXAMPLE 177

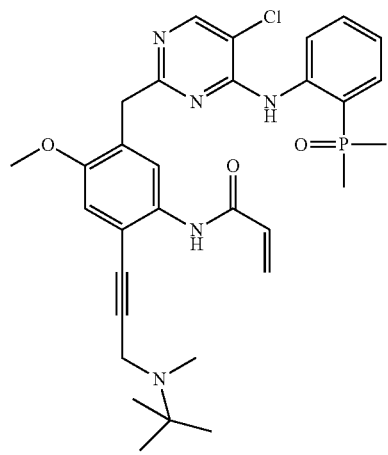

N-(2-(3-(tert-butyl(methyl)amino)prop-1-yn-1-yl)-5-((5-chloro-4-((2-(dimethylphosphoryl)phenyl)amino)pyrimidin-2-yl)methyl)-4-methoxyphenyl)acrylamide

EXAMPLE 178

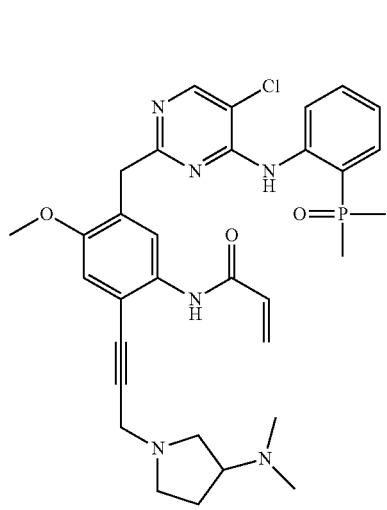

N-(5-((5-chloro-4-((2-(dimethylphosphoryl)phenyl)
amino)pyrimidin-2-yl)methyl)-2-(3-(2-(dimethyl-
amino)pyrrolidin-1-yl)prop-1-yn-1-yl)-4-methoxy-
phenyl)acrylamide

EXAMPLE 179

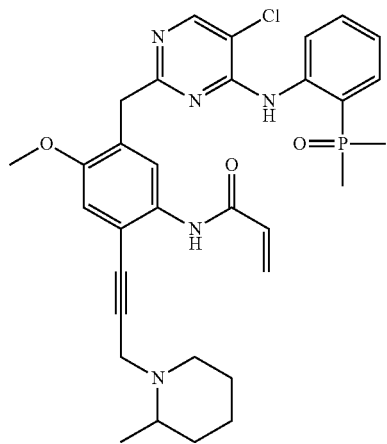

N-(5-((5-chloro-4-((2-(dimethylphosphoryl)phenyl)
amino)pyrimidin-2-yl)methyl)-4-methoxy-2-(3-(2-
methylpiperidin-1-yl)prop-1-yn-1-yl)phenyl)acryl-
amide

EXAMPLE 180

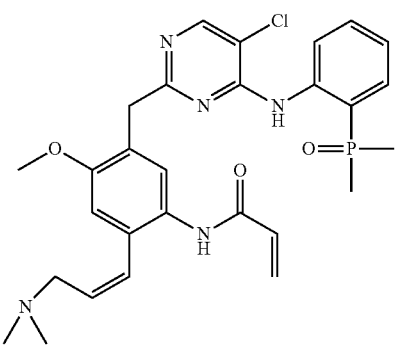

(Z)-N-(5-((5-chloro-4-((2-yl)methyl)-2-(3-(dimethyl-
amino)prop-1-en-1-yl)-(dimethylphosphoryl)phenyl)amino)
pyrimidin-2-4-methoxyphenyl)acrylamide

EXAMPLE 181

(E)—N-(5-((5-chloro-4-((2-(dimethylphosphoryl)
phenyl)amino)pyrimidin-2-yl)methyl)-2-(3-(dimeth-
ylamino)prop-1-en-1-yl)-4-methoxyphenyl)acrylam-
ide

EXAMPLE 182

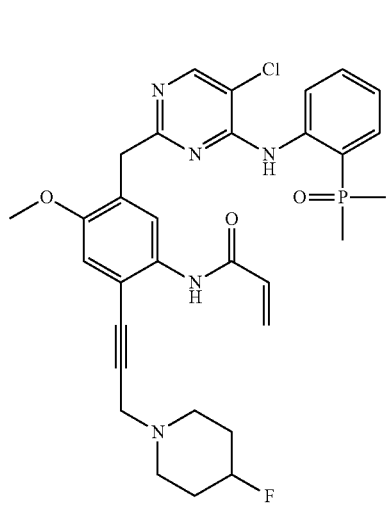

N-(5-((5-chloro-4-((2-(dimethylphosphoryl)phenyl)amino)pyrimidin-2-yl)methyl)-2-(3-(4-fluoropiperidin-1-yl)prop-1-yn-1-yl)-4-methoxyphenyl)acrylamide

EXAMPLE 183

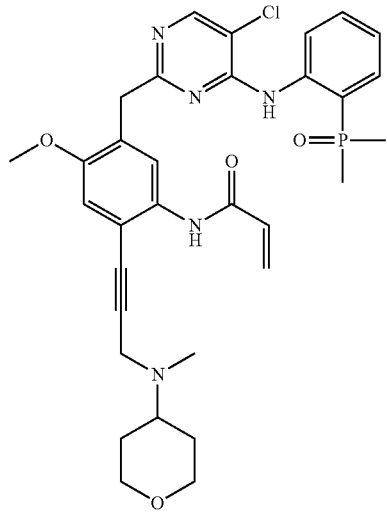

N-(5-((5-chloro-4-((2-(dimethylphosphoryl)phenyl)amino)pyrimidin-2-yl)methyl)-4-methoxy-2-(3-(methyl(tetrahydro-2H-pyran-4-yl)amino)prop-1-yn-1-yl)phenyl)acrylamide

EXAMPLE 184

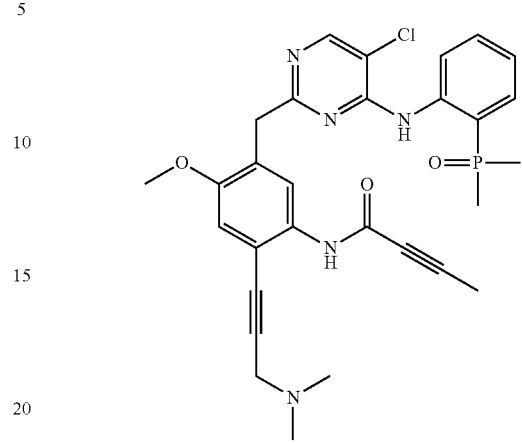

N-(5-((5-chloro-4-((2-(dimethylphosphoryl)phenyl)amino)pyrimidin-2-yl)methyl)-2-(3-(dimethylamino)prop-1-yn-1-yl)-4-methoxyphenyl)but-2-ynamide

EXAMPLE 185

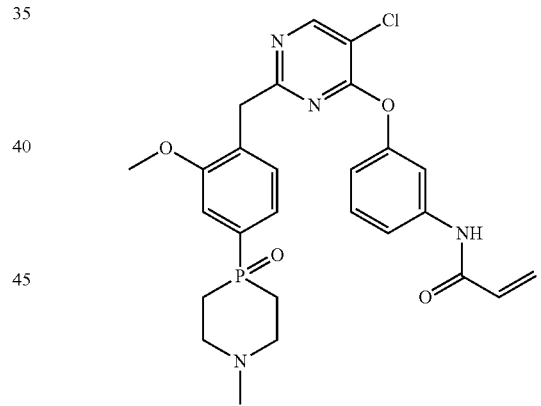

N-(3-((5-chloro-2-(2-methoxy-4-(1-methyl-4-oxido-1,4-azaphosphinan-4-yl)benzyl)pyrimidin-4-yl)oxy)phenyl)acrylamide

EXAMPLE 186

Additional Compounds of the Invention

The compounds depicted below can be synthesized using methods analogous to those described herein and can be useful for treating EGFR-driven cancers.

201
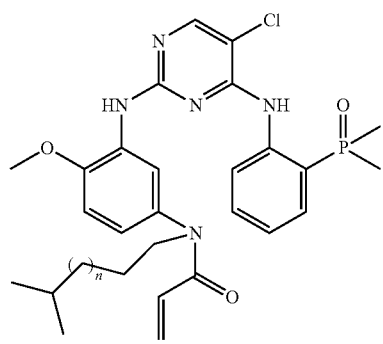
n = 1, 2
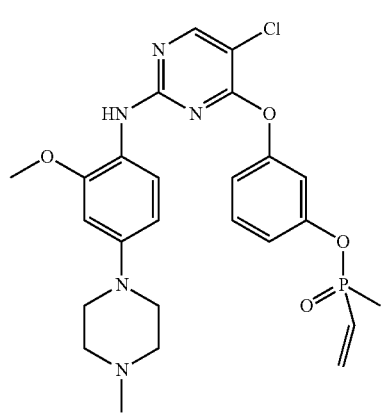
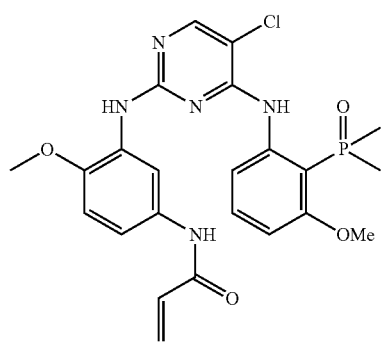
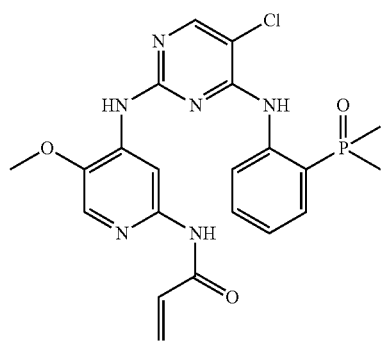
202
-continued
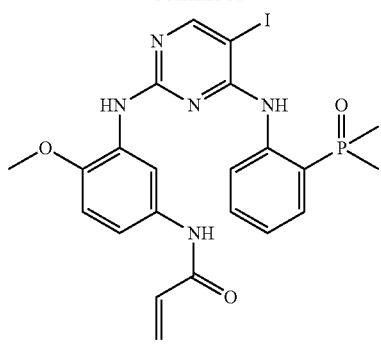
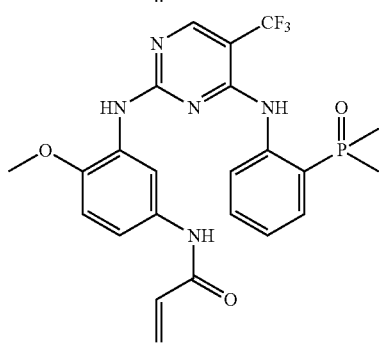
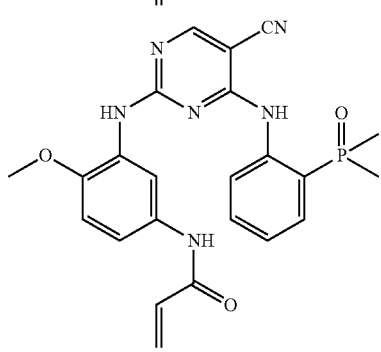
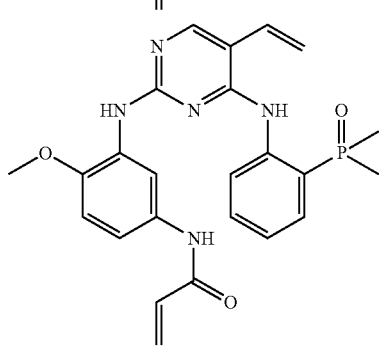
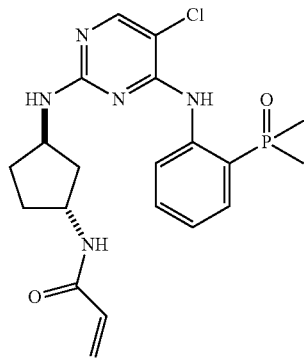

203
-continued
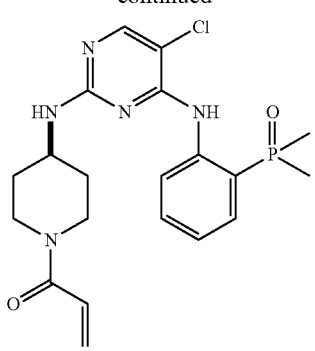
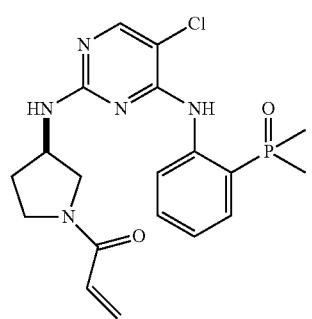
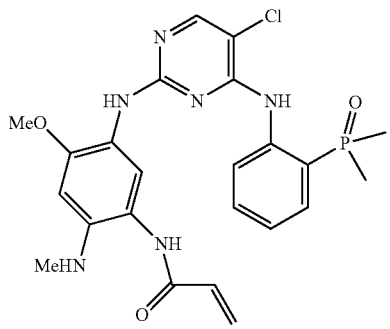
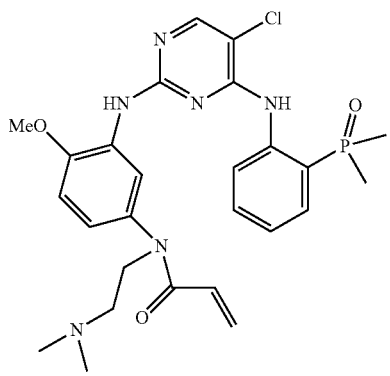
204
-continued
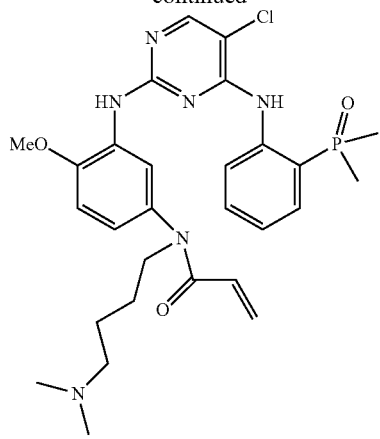
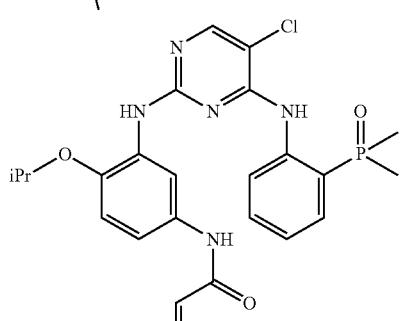
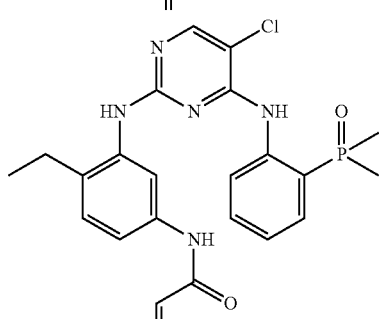
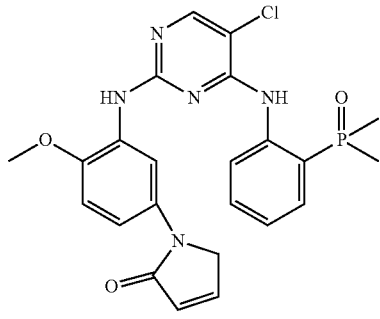
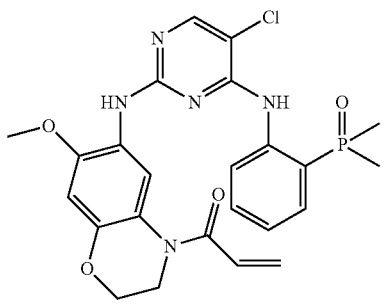

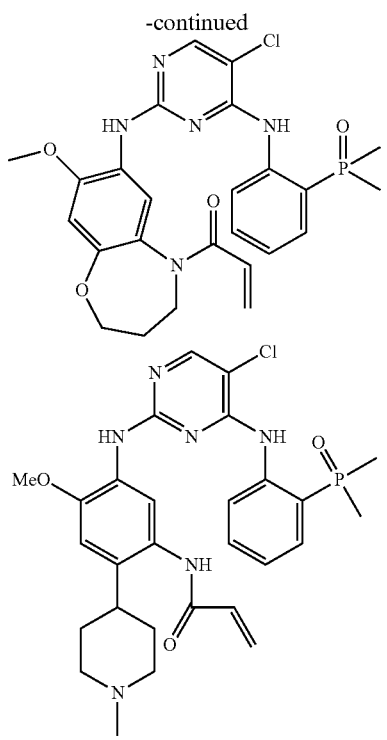

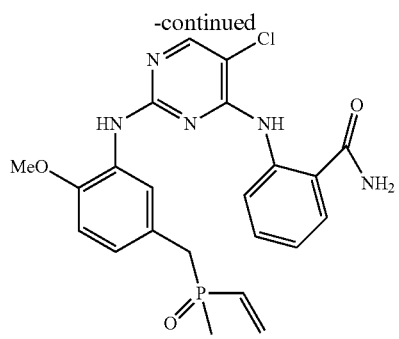

Biological Assays.

Kinase inhibitory activity of the compounds was measured against human EGFR (native sequence) and against EGFR bearing the L858R mution and the L858R/T790M double mutation (EGFR, L858R, and L858R/T790M, respectively in Table 1). Additional assays can be conducted with EGFR deletion mutants such as delE746-A750 with or without the additional T790M mutation. Assay conditions included 10 pt curves with 3 μM top concentration (singlicates) and 10 μM ATP.

We also assessed the antiproliferative activity of compounds of Formula (I) against BaF3 cells expressing the target EGFR mutations or control (i.e., cell lines expressing wildtype EGFR). Assays were conducted using MTT.

TABLE 1

| Example # | Chemical Name (ChemDraw Ultra 12.0) | LC-MS (M + H) | IC50 for kinase inhibition (nM)[1] | | | | | |
|---|---|---|---|---|---|---|---|---|
| | | | EGFR | EGFR L858R | EGFR L858R T790M | BAF3 PARENTAL | BAF3 EGFR DEL T790M PURO POOL | BAF3 EGFR L858R-T790M PURO POOL |
| 1 | N-(5-((5-chloro-4-((2-(dimethylphosphoryl)phenyl)amino)pyrimidin-2-yl)amino)-4-methoxy-2-(2-(pyrrolidin-1-yl)ethoxy)phenyl)acrylamide | 585.2 | A | A | A | D | A | A |
| 2 | N-(5-((5-chloro-4-((2-(dimethylphosphoryl)phenyl)amino)pyrimidin-2-yl)amino)-4-methoxy-2-(2-(4-methylpiperazin-1-yl)ethoxy)phenyl)acrylamide | 614.2 | C | A | A | D | D | N/A |
| 3 | N-(5-((5-chloro-4-((2-(dimethylphosphoryl)phenyl)amino)pyrimidin-2-yl)amino)-4-methoxy-2-((1-methylpiperidin-4-yl)methoxy)phenyl)acrylamide | 599.2 | B | A | A | D | C | D |
| 4 | N-(5-((5-chloro-4-((2-(dimethylphosphoryl)phenyl)amino)pyrimidin-2-yl)amino)-4-methoxy-2-(2-morpholinoethoxy)phenyl)acrylamide | 601.2 | A | A | A | D | B | C |
| 5 | N-(5-((5-chloro-4-((2-(dimethylphosphoryl)phenyl)amino)pyrimidin-2-yl)amino)-4-methoxy-2-(3-morpholinopropoxy)phenyl)acrylamide | 615.2 | C | A | A | D | C | C |
| 6 | N-(5-((5-chloro-4-((2-(dimethylphosphoryl)phenyl)amino)pyrimidin-2-yl)amino)-4-methoxy-2-((tetrahydro-2H-pyran-4-yl)methoxy)phenyl)acrylamide | 586.2 | D | A | B | D | B | C |
| 7 | N-(5-((5-chloro-4-((2-(dimethylphosphoryl)phenyl)amino)pyrimidin-2-yl)amino)-4-methoxy-2-((1-methylpiperidin-2-yl)methoxy)phenyl)acrylamide | 599.2 | A | A | A | D | A | A |
| 8 | N-(5-((5-chloro-4-((2-(dimethylphosphoryl)phenyl)amino)pyrimidin-2-yl)amino)-4-methoxy-2-(2-(piperidin-1-yl)ethoxy)phenyl)acrylamide | 599.2 | A | A | A | D | A | A |

TABLE 1-continued

| | | | IC50 for kinase inhibition (nM)[1] | | | | | |
|---|---|---|---|---|---|---|---|---|
| Example # | Chemical Name (ChemDraw Ultra 12.0) | LC-MS (M + H) | EGFR | EGFR L858R | EGFR L858R T790M | BAF3 PARENTAL | BAF3 EGFR DEL T790M PURO POOL | BAF3 EGFR L858R-T790M PURO POOL |
| 9 | N-(5-((5-chloro-4-((2-(dimethylphosphoryl)phenyl)amino)pyrimidin-2-yl)amino)-4-methoxy-2-(oxetan-3-yloxy)phenyl)acrylamide | 544.1 | D | A | A | D | A | B |
| 10 | N-(5-((5-chloro-4-((2-(dimethylphosphoryl)phenyl)amino)pyrimidin-2-yl)amino)-4-methoxy-2-(pyridin-3-ylmethoxy)phenyl)acrylamide | 579.2 | B | A | A | D | B | C |
| 11 | N-(5-((5-chloro-4-((2-(dimethylphosphoryl)phenyl)amino)pyrimidin-2-yl)amino)-4-methoxy-2-(pyridin-4-ylmethoxy)phenyl)acrylamide | 579.1 | A | A | A | D | A | C |
| 12 | N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide | 585.2 | A | A | A | D | A | A |
| 13 | N-(5-((5-chloro-4-((2-(dimethylphosphoryl)phenyl)amino)pyrimidin-2-yl)amino)-4-methoxy-2-((1-methylpyrrolidin-3-yl)oxy)phenyl)acrylamide | 571.2 | A | A | A | D | A | A |
| 14 | rel-(R)-N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide | 585.2 | A | A | A | D | A | A |
| 15 | N-(2-((1-(azetidin-1-yl)-3-methoxypropan-2-yl)oxy)-5-((5-chloro-4-((2-(dimethylphosphoryl)phenyl)amino)pyrimidin-2-yl)amino)-4-methoxyphenyl)acrylamide | 615.2 | A | A | A | D | A | A |
| 16 | rel-(R)-N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide | 585.2 | A | A | A | D | A | A |
| 17 | N-(5-((5-chloro-4-((2-(dimethylphosphoryl)phenyl)amino)pyrimidin-2-yl)amino)-4-methoxy-2-((1-methylazetidin-3-yl)oxy)phenyl)acrylamide | 557.2 | N/A | N/A | N/A | D | B | C |
| 18 | N-(5-((5-chloro-4-((2-(dimethylphosphoryl)phenyl)amino)pyrimidin-2-yl)amino)-4-methoxy-2-((1-methylpyrrolidin-2-yl)methoxy)phenyl)acrylamide | 585.2 | N/A | N/A | N/A | D | A | A |
| 19 | N-(5-((5-chloro-4-((2-(dimethylphosphoryl)phenyl)amino)pyrimidin-2-yl)amino)-4-methoxy-2-((4-methyl-1,4-oxazepan-6-yl)oxy)phenyl)acrylamide | 601.2 | N/A | N/A | N/A | N/A | N/A | N/A |
| 20 | N-(5-((5-chloro-4-((2-(dimethylphosphoryl)phenyl)amino)pyrimidin-2-yl)amino)-4-methoxy-2-((1-methylpyrrolidin-3-yl)methoxy)phenyl)acrylamide | 585.2 | N/A | N/A | N/A | N/A | N/A | N/A |
| 21 | N-(5-((5-chloro-4-((2-(dimethylphosphoryl)phenyl)amino)pyrimidin-2-yl)amino)-2-((2-(dimethylamino)cyclohexyl)oxy)-4-methoxyphenyl)acrylamide | 613.2 | N/A | N/A | N/A | N/A | N/A | N/A |
| 22 | N-(5-((5-chloro-4-((2-(dimethylphosphoryl)phenyl)amino)pyrimidin-2-yl)amino)-4-methoxy-2-(4-(4-methylpiperazin-1-yl)piperidin-1-yl)phenyl)acrylamide | 653.2 | A | A | A | D | B | B |
| 23 | N-(5-((5-chloro-4-((2-(dimethylphosphoryl)phenyl)amino)pyrimidin-2-yl)amino)-2-(4-(dimethylamino)piperidin-1-yl)-4-methoxyphenyl)acrylamide | 598.2 | A | A | A | D | A | C |
| 24 | N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)acrylamide | 584.2 | A | A | A | D | A | A |
| 25 | N-(5-((5-chloro-4-((2-(dimethylphosphoryl)phenyl)amino)pyrimidin-2-yl)amino)-4-methoxy-2-(4-methyl-1,4-diazepan-1-yl)phenyl)acrylamide | 584.2 | A | A | A | D | A | A |

TABLE 1-continued

| | | | IC50 for kinase inhibition (nM)[1] | | | | | |
|---|---|---|---|---|---|---|---|---|
| Example # | Chemical Name (ChemDraw Ultra 12.0) | LC-MS (M + H) | EGFR | EGFR L858R | EGFR L858R T790M | BAF3 PARENTAL | BAF3 EGFR DEL T790M PURO POOL | BAF3 EGFR L858R-T790M PURO POOL |
| 26 | rac-(R)-N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)acrylamide | 584.2 | A | A | A | D | A | A |
| 27 | N-(5-((5-chloro-4-((2-(dimethylphosphoryl)phenyl)amino)pyrimidin-2-yl)amino)-4-methoxy-2-(4-(1-methylpiperidin-4-yl)piperazin-1-yl)phenyl)acrylamide | 653.3 | A | A | A | D | B | C |
| 28 | N-(5-((5-chloro-4-((2-(dimethylphosphoryl)phenyl)amino)pyrimidin-2-yl)amino)-4-methoxy-2-(3-morpholinopyrrolidin-1-yl)phenyl)acrylamide | 626.2 | A | A | A | D | A | A |
| 29 | rac-(R)-N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)acrylamide | 584.2 | A | A | A | D | A | A |
| 30 | N-(5-((5-chloro-4-((2-(dimethylphosphoryl)phenyl)amino)pyrimidin-2-yl)amino)-2-(3-(dimethylamino)piperidin-1-yl)-4-methoxyphenyl)acrylamide | 598.2 | A | A | A | D | A | A |
| 31 | N-(5-((5-chloro-4-((2-(dimethylphosphoryl)phenyl)amino)pyrimidin-2-yl)amino)-4-methoxy-2-(3-(pyrrolidin-1-yl)azetidin-1-yl)phenyl)acrylamide | 596.2 | A | A | A | D | A | A |
| 32 | N-(5-((5-chloro-4-((2-(dimethylphosphoryl)phenyl)amino)pyrimidin-2-yl)amino)-2-(3-hydroxypyrrolidin-1-yl)-4-methoxyphenyl)acrylamide | 557.2 | A | A | A | D | B | C |
| 33 | N-(5-((5-chloro-4-((2-(dimethylphosphoryl)phenyl)amino)pyrimidin-2-yl)amino)-4-methoxy-2-(3-(piperidin-1-yl)pyrrolidin-1-yl)phenyl)acrylamide | 624.3 | A | A | A | D | A | A |
| 34 | N-(5-((5-chloro-4-((2-(dimethylphosphoryl)phenyl)amino)pyrimidin-2-yl)amino)-2-(3-(diethylamino)pyrrolidin-1-yl)-4-methoxyphenyl)acrylamide | 612.2 | A | A | A | D | A | A |
| 35 | N-(5-((5-chloro-4-((2-(dimethylphosphoryl)phenyl)amino)pyrimidin-2-yl)amino)-2-(3-hydroxy-[1,3'-bipyrrolidin]-1'-yl)-4-methoxyphenyl)acrylamide | 626.2 | A | A | A | D | C | D |
| 36 | N-(2-([1,3'-bipyrrolidin]-1'-yl)-5-((5-chloro-4-((2-(dimethylphosphoryl)phenyl)amino)pyrimidin-2-yl)amino)-4-methoxyphenyl)acrylamide | 610.2 | A | A | A | D | A | A |
| 37 | N-(5-((5-chloro-4-((2-(dimethylphosphoryl)phenyl)amino)pyrimidin-2-yl)amino)-4-methoxy-2-(3-(4-methylpiperazin-1-yl)pyrrolidin-1-yl)phenyl)acrylamide | 639.3 | A | A | A | D | B | C |
| 38 | N-(5-((5-chloro-4-((2-(dimethylphosphoryl)phenyl)amino)pyrimidin-2-yl)amino)-2-(3-((2-(diethylamino)ethyl)(methyl)amino)pyrrolidin-1-yl)-4-methoxyphenyl)acrylamide | 669.3 | A | A | A | D | A | C |
| 39 | N-(5-((5-chloro-4-((2-(dimethylphosphoryl)phenyl)amino)pyrimidin-2-yl)amino)-2-(3-(4-hydroxypiperidin-1-yl)pyrrolidin-1-yl)-4-methoxyphenyl)acrylamide | 640.3 | A | A | A | D | C | D |
| 40 | N-(5-((5-chloro-4-((2-(dimethylphosphoryl)phenyl)amino)pyrimidin-2-yl)amino)-2-(3-(4-(2-hydroxyethyl)piperazin-1-yl)pyrrolidin-1-yl)-4-methoxyphenyl)acrylamide | 669.2 | A | A | A | D | D | D |
| 41 | N-(5-((5-chloro-4-((2-(dimethylphosphoryl)phenyl)amino)pyrimidin-2-yl)amino)-4-methoxy-2-(3-((2-methoxyethyl)(methyl)amino)pyrrolidin-1-yl)phenyl)acrylamide | 628.2 | A | A | A | D | A | A |
| 42 | N-(3-((5-chloro-4-((2-(dimethylphosphoryl)phenyl)amino)pyrimidin-2-yl)amino)-4-methoxyphenyl)-2-(pyrrolidin-1-ylmethyl)acrylamide | 555.2 | A | A | A | D | A | A |

TABLE 1-continued

| | | | IC50 for kinase inhibition (nM)[1] | | | | | |
|---|---|---|---|---|---|---|---|---|
| Example # | Chemical Name (ChemDraw Ultra 12.0) | LC-MS (M + H) | EGFR | EGFR L858R | EGFR L858R T790M | BAF3 PARENTAL | BAF3 EGFR DEL T790M PURO POOL | BAF3 EGFR L858R-T790M PURO POOL |
| 43 | N-(3-((5-chloro-4-((2-(dimethylphosphoryl)phenyl)amino)pyrimidin-2-yl)amino)-4-methoxyphenyl)-2-(piperidin-1-ylmethyl)acrylamide | 569.2 | A | A | A | D | A | A |
| 44 | N-(3-((5-chloro-4-((2-(dimethylphosphoryl)phenyl)amino)pyrimidin-2-yl)amino)-4-methoxyphenyl)-2-((4-(methylsulfonyl)piperazin-1-yl)methyl)acrylamide | 648.1 | A | A | A | D | A | A |
| 45 | N-(3-((5-chloro-4-((2-(dimethylphosphoryl)phenyl)amino)pyrimidin-2-yl)amino)-4-methoxyphenyl)-2-((4-(4-methylpiperazin-1-yl)piperidin-1-yl)methyl)acrylamide | 667.3 | A | A | A | D | A | A |
| 46 | N-(3-((5-chloro-4-((2-(dimethylphosphoryl)phenyl)amino)pyrimidin-2-yl)amino)-4-methoxyphenyl)-2-((1,1-dioxidothiomorpholino)methyl)acrylamide | 619.1 | D | B | A | D | D | D |
| 47 | N-(3-((5-chloro-4-((2-(dimethylphosphoryl)phenyl)amino)pyrimidin-2-yl)amino)-4-methoxyphenyl)-2-((3-oxopiperazin-1-yl)methyl)acrylamide | 584.2 | A | A | A | D | C | D |
| 48 | N-(3-((5-chloro-4-((2-(dimethylphosphoryl)phenyl)amino)pyrimidin-2-yl)amino)-4-methoxyphenyl)-2-(morpholinomethyl)acrylamide | 571.2 | A | A | A | D | A | A |
| 49 | N-(3-((5-chloro-4-((2-(dimethylphosphoryl)phenyl)amino)pyrimidin-2-yl)amino)-4-methoxyphenyl)-2-((4-methylpiperazin-1-yl)methyl)acrylamide | 584.2 | A | A | A | D | A | A |
| 50 | N-(3-((5-chloro-4-((2-(dimethylphosphoryl)phenyl)amino)pyrimidin-2-yl)amino)-4-methoxyphenyl)-2-((4-isopropylpiperazin-1-yl)methyl)acrylamide | 612.2 | B | A | A | D | A | A |
| 51 | N-(3-((5-chloro-4-((2-(dimethylphosphoryl)phenyl)amino)pyrimidin-2-yl)amino)-4-methoxyphenyl)-2-((4-morpholinopiperidin-1-yl)methyl)acrylamide | 654.3 | A | A | A | D | A | A |
| 52 | N-(3-((5-chloro-4-((2-(dimethylphosphoryl)phenyl)amino)pyrimidin-2-yl)amino)-4-methoxyphenyl)-2-((4-(2-hydroxyethyl)piperazin-1-yl)methyl)acrylamide | 614.2 | A | A | A | D | A | A |
| 53 | N-(3-((5-chloro-4-((2-(dimethylphosphoryl)phenyl)amino)pyrimidin-2-yl)amino)-4-methoxyphenyl)-2-((3-hydroxypyrrolidin-1-yl)methyl)acrylamide | 571.2 | A | A | A | D | A | A |
| 54 | N-(3-((5-chloro-4-((2-(dimethylphosphoryl)phenyl)amino)pyrimidin-2-yl)amino)-4-fluorophenyl)acrylamide | 460.1 | N/A | N/A | N/A | D | A | A |
| 55 | N-(5-((5-chloro-4-((2-(dimethylphosphoryl)phenyl)amino)pyrimidin-2-yl)amino)-4-methoxy-2-((4-methylpiperazin-1-yl)methyl)phenyl)acrylamide | 584.2 | A | A | A | D | A | B |
| 56 | N-(5-((5-chloro-4-((2-(dimethylphosphoryl)phenyl)amino)pyrimidin-2-yl)amino)-4-methoxy-2-(4-methylpiperazine-1-carbonyl)phenyl)acrylamide | 598.2 | C | A | A | D | D | D |
| 57 | N-(2-(3-aminopyrrolidin-1-yl)-5-((5-chloro-4-((2-(dimethylphosphoryl)phenyl)amino)pyrimidin-2-yl)amino)-4-methoxyphenyl)acrylamide | 556.2 | A | A | A | D | D | D |
| 58 | N1-(3-((5-chloro-4-((2-(dimethylphosphoryl)phenyl)amino)pyrimidin-2-yl)amino)-4-methoxyphenyl)-N4-(2-(dimethylamino)ethyl)fumaramide | 586.2 | A | A | A | D | D | D |
| 59 | (E)-N-(3-((5-chloro-4-((2-(dimethylphosphoryl)phenyl)amino)pyrimidin-2-yl)amino)-4-methoxyphenyl)-4-(4-methylpiperazin-1-yl)-4-oxobut-2-enamide | 598.2 | A | A | A | D | C | D |
| 60 | N1-(3-((5-chloro-4-((2-(dimethylphosphoryl)phenyl)amino)pyrimidin-2-yl)amino)-4-methoxyphenyl)-N4,N4-dimethylfumaramide | 543.2 | D | B | C | D | D | D |

TABLE 1-continued

| Example # | Chemical Name (ChemDraw Ultra 12.0) | LC-MS (M + H) | EGFR | EGFR L858R | EGFR L858R T790M | BAF3 PARENTAL | BAF3 EGFR DEL T790M PURO POOL | BAF3 EGFR L858R-T790M PURO POOL |
|---|---|---|---|---|---|---|---|---|
| 61 | (Z)-4-((3-((5-chloro-4-((2-dimethylphosphoryl)phenyl)amino)pyrimidin-2-yl)amino)-4-methoxyphenyl)amino)-4-oxobut-2-enoic acid | 516.1 | D | D | C | D | D | D |
| 62 | N1-(3-((5-chloro-4-((2-dimethylphosphoryl)phenyl)amino)pyrimidin-2-yl)amino)-4-methoxyphenyl)-N4,N4-dimethylmaleamide | 543.2 | D | D | D | D | D | D |
| 63 | (Z)-N-(3-((5-chloro-4-((2-dimethylphosphoryl)phenyl)amino)pyrimidin-2-yl)amino)-4-methoxyphenyl)-4-(4-methylpiperazin-1-yl)-4-oxobut-2-enamide | 598.2 | D | C | D | D | D | D |
| 64 | N1-(3-((5-chloro-4-((2-dimethylphosphoryl)phenyl)amino)pyrimidin-2-yl)amino)-4-methoxyphenyl)-N4-(2-(dimethylamino)ethyl)maleamide | 586.2 | D | A | A | D | D | D |
| 65 | N-(2-(3-amino-3-methylbut-1-yn-1-yl)-5-((5-chloro-4-((2-dimethylphosphoryl)phenyl)amino)pyrimidin-2-yl)amino)-4-methoxyphenyl)acrylamide | 553.2 | A | A | A | D | A | A |
| 66 | N-(5-((5-chloro-4-((2-dimethylphosphoryl)phenyl)amino)pyrimidin-2-yl)amino)-2-(2-(dimethylamino)-3-hydroxypropoxy)-4-methoxyphenyl)acrylamide | 589.2 | N/A | N/A | N/A | D | C | D |
| 67 | N-(5-((5-chloro-4-((2-dimethylphosphoryl)phenyl)amino)pyrimidin-2-yl)amino)-2-((2-((2-fluoroethyl)(methyl)amino)ethyl)(methyl)amino)-4-methoxyphenyl)acrylamide | 604.2 | A | A | A | D | A | A |
| 68 | N-(2-(3-(azetidin-1-yl)pyrrolidin-1-yl)-5-((5-chloro-4-((2-dimethylphosphoryl)phenyl)amino)pyrimidin-2-yl)amino)-4-methoxyphenyl)acrylamide | 596.2 | A | A | A | D | A | A |
| 69 | N-(2-([1,4'-bipiperidin]-1'-yl)-5-((5-chloro-4-((2-dimethylphosphoryl)phenyl)amino)pyrimidin-2-yl)amino)-4-methoxyphenyl)acrylamide | 638.3 | A | A | A | D | A | A |
| 70 | N-(5-((5-chloro-4-((2-dimethylphosphoryl)phenyl)amino)pyrimidin-2-yl)amino)-4-methoxy-2-(4-morpholinopiperidin-1-yl)phenyl)acrylamide | 640.3 | A | A | A | D | A | A |
| 71 | N-(5-((5-chloro-4-((2-dimethylphosphoryl)phenyl)amino)pyrimidin-2-yl)amino)-4-methoxy-2-(4-(4-methyl-1,4-diazepan-1-yl)piperidin-1-yl)phenyl)acrylamide | 667.3 | A | A | A | D | B | C |
| 72 | N-(5-((5-chloro-4-((2-dimethylphosphoryl)phenyl)amino)pyrimidin-2-yl)amino)-4-methoxy-2-(4-(pyrrolidin-1-yl)piperidin-1-yl)phenyl)acrylamide | 624.2 | B | A | A | D | A | C |
| 73 | N-(5-((5-chloro-4-((2-dimethylphosphoryl)phenyl)amino)pyrimidin-2-yl)amino)-2-((1-(dimethylamino)cyclopropyl)ethynyl)-4-methoxyphenyl)acrylamide | 579.2 | D | A | A | D | C | C |
| 74 | N-(5-((5-chloro-4-((2-dimethylphosphoryl)phenyl)amino)pyrimidin-2-yl)amino)-4-methoxy-2-(2-(4-methylpiperazin-1-yl)ethyl)phenyl)acrylamide | 598.3 | A | A | A | D | C | D |
| 75 | (E)-ethyl 4-((3-((5-chloro-4-((2-dimethylphosphoryl)phenyl)amino)pyrimidin-2-yl)amino)-4-methoxyphenyl)amino)-4-oxobut-2-enoate | 544.1 | A | A | A | D | A | A |
| 76 | (E)-tert-butyl(1-(3-((3-((5-chloro-4-((2-dimethylphosphoryl)phenyl)amino)pyrimidin-2-yl)amino)-4-methoxyphenyl)amino)-3-oxoprop-1-en-1-yl)cyclopropyl)carbamate | 627.2 | D | D | D | D | D | D |
| 77 | N-(3-((5-chloro-4-((2-dimethylphosphoryl)phenyl)amino)pyrimidin-2-yl)amino)-4-methoxyphenyl)-2-fluoroacrylamide | 490.1 | D | A | B | D | A | B |
| 78 | (E)-3-chloro-N-(3-((5-chloro-4-((2-dimethylphosphoryl)phenyl)amino)pyrimidin-2-yl)amino)-4-methoxyphenyl)acrylamide | 506 | A | A | A | D | A | A |
| 79 | N-(3-((5-chloro-4-((2-dimethylphosphoryl)phenyl)amino)pyrimidin-2-yl)amino)-4-methoxyphenyl)cyclohex-1-enecarboxamide | 526.2 | D | D | D | D | D | D |
| 80 | N-(5-((5-chloro-4-((2-dimethylphosphoryl)phenyl)amino)pyrimidin-2- | 597.2 | D | A | A | D | A | C |

TABLE 1-continued

| | | | IC50 for kinase inhibition (nM)[1] | | | | | |
|---|---|---|---|---|---|---|---|---|
| Example # | Chemical Name (ChemDraw Ultra 12.0) | LC-MS (M + H) | EGFR | EGFR L858R | EGFR L858R T790M | BAF3 PARENTAL | BAF3 EGFR DEL T790M PURO POOL | BAF3 EGFR L858R-T790M PURO POOL |
| | yl)amino)-4-methoxy-2-(2-(pyrrolidin-1-yl)ethoxy)phenyl)but-2-ynamide | | | | | | | |
| 81 | N-(3-((5-chloro-4-((2-(dimethylphosphoryl)phenyl)amino)pyrimidin-2-yl)amino)-4-methoxyphenyl)-4-(dimethylamino)but-2-ynamide | 527.2 | A | A | A | D | A | A |
| 82 | N-(3-((5-chloro-4-((2-(dimethylphosphoryl)phenyl)amino)pyrimidin-2-yl)amino)-4-methoxyphenyl)-2-(trifluoromethyl)acrylamide | 540.1 | A | A | A | D | D | D |
| 83 | N-(3-((5-chloro-2-((4-(dimethylphosphoryl)-2-methoxyphenyl)amino)pyrimidin-4-yl)oxy)phenyl)-4-(dimethylamino)but-2-ynamide | 528.2 | A | A | A | D | C | D |
| 84 | N-(3-((5-chloro-4-((2-(dimethylphosphoryl)phenyl)amino)pyrimidin-2-yl)amino)-4-methoxyphenyl)-1-methyl-1,2,5,6-tetrahydropyridine-3-carboxamide | 541.2 | D | A | A | D | D | D |
| 85 | (E)-3-chloro-N-(5-((5-chloro-4-((2-(dimethylphosphoryl)phenyl)amino)pyrimidin-2-yl)amino)-2-fluoro-4-methoxyphenyl)acrylamide | 524 | A | A | A | D | A | A |
| 86 | N-(3-((5-chloro-4-((2-(dimethylphosphoryl)-4-(2-methoxyethoxy)phenyl)amino)pyrimidin-2-yl)amino)-4-methoxyphenyl)acrylamide | 546.1 | B | A | A | D | A | B |
| 87 | N-(5-((5-chloro-4-((2-(dimethylphosphoryl)phenyl)amino)pyrimidin-2-yl)amino)-2-fluoro-4-methoxyphenyl)-4-(dimethylamino)but-2-ynamide | 545.1 | A | A | A | C | A | A |
| 88 | N-(5-((5-chloro-4-((2-(dimethylphosphoryl)phenyl)amino)pyrimidin-2-yl)amino)-2-fluoro-4-methoxyphenyl)-5-(piperidin-1-yl)pent-2-ynamide | 599.2 | A | A | A | D | A | A |
| 89 | N-(5-((5-chloro-4-((2-(dimethylphosphoryl)phenyl)amino)pyrimidin-2-yl)amino)-2-fluoro-4-methoxyphenyl)-4-(pyrrolidin-1-yl)but-2-ynamide | 571.2 | A | A | A | D | A | A |
| 90 | N-(5-((5-chloro-4-((2-(dimethylphosphoryl)phenyl)amino)pyrimidin-2-yl)amino)-2-fluoro-4-methoxyphenyl)-4-methyl-4-(pyrrolidin-1-yl)pent-2-ynamide | 599.2 | A | A | A | D | A | A |
| 91 | N-(3-((5-chloro-4-((2-(dimethylphosphoryl)phenyl)amino)pyrimidin-2-yl)amino)-4-methoxyphenyl)-4-methyl-4-(pyrrolidin-1-yl)pent-2-ynamide | 581.2 | A | A | A | D | A | A |
| 92 | (E)-N-(3-((5-chloro-4-((2-(dimethylphosphoryl)phenyl)amino)pyrimidin-2-yl)amino)-4-methoxyphenyl)-4-(piperidin-1-yl)but-2-enamide | 569.2 | A | A | A | D | A | A |
| 93 | N-(3-((5-chloro-4-((2-(dimethylphosphoryl)phenyl)amino)pyrimidin-2-yl)amino)-4-methoxyphenyl)-3-phenylpropiolamide | 546.1 | D | A | A | D | A | A |
| 94 | (E)-3-(1-aminocyclopropyl)-N-(3-((5-chloro-4-((2-(dimethylphosphoryl)phenyl)amino)pyrimidin-2-yl)amino)-4-methoxyphenyl)acrylamide | 527.1 | C | A | A | D | D | D |
| 95 | (E)-N-(3-((5-chloro-4-((2-(dimethylphosphoryl)phenyl)amino)pyrimidin-2-yl)amino)-4-methoxyphenyl)-4-(pyrrolidin-1-yl)but-2-enamide | 555.2 | D | A | A | D | B | D |
| 96 | N-(5-((5-chloro-4-((2-(dimethylphosphoryl)phenyl)amino)pyrimidin-2-yl)amino)-2-(3-(diethylamino)prop-1-yn-1-yl)-4-methoxyphenyl)acrylamide | 581.2 | D | A | A | D | A | A |
| 97 | N-(3-((5-chloro-4-((2-(dimethylphosphoryl)phenyl)amino)pyrimidin-2-yl)amino)-4-methoxyphenyl)-4-methoxybut-2-ynamide | 514.1 | A | A | A | D | A | A |
| 98 | N-(5-((5-chloro-4-((2-(dimethylphosphoryl)-4-(2-(pyrrolidin-1-yl)ethoxy)phenyl)amino)pyrimidin-2-yl)amino)-2-fluoro-4-methoxyphenyl)acrylamide | 603.2 | A | A | A | D | A | A |
| 99 | N-(3-((5-chloro-4-((2-(dimethylphosphoryl)-4-((tetrahydrofuran-3-yl)oxy)phenyl)amino)pyrimidin-2-yl)amino)-4-methoxyphenyl)acrylamide | 558.2 | A | A | A | D | A | B |

TABLE 1-continued

| | | | IC50 for kinase inhibition (nM)[1] | | | | | |
|---|---|---|---|---|---|---|---|---|
| Example # | Chemical Name (ChemDraw Ultra 12.0) | LC-MS (M + H) | EGFR | EGFR L858R | EGFR L858R T790M | BAF3 PARENTAL | BAF3 EGFR DEL T790M PURO POOL | BAF3 EGFR L858R-T790M PURO POOL |
| 100 | N-(3-((5-chloro-4-((2-(dimethylphosphoryl)-4-((tetrahydro-2H-pyran-4-yl)methoxy)phenyl)amino)pyrimidin-2-yl)amino)-4-methoxyphenyl)acrylamide | 584.2 | B | A | A | D | A | A |
| 101 | N-(5-((5-chloro-4-((2-(dimethylphosphoryl)phenyl)amino)pyrimidin-2-yl)amino)-4-methoxy-2-morpholinophenyl)-5-(piperidin-1-yl)pent-2-ynamide | 666.2 | A | A | A | D | A | A |
| 102 | N-(5-((5-chloro-4-((2-(dimethylphosphoryl)phenyl)amino)pyrimidin-2-yl)amino)-4-methoxy-2-((tetrahydro-2H-pyran-4-yl)methoxy)phenyl)but-2-ynamide | 598.2 | D | C | D | D | A | B |
| 103 | N-(5-((5-chloro-4-((2-(dimethylphosphoryl)phenyl)amino)pyrimidin-2-yl)amino)-4-methoxy-2-(oxetan-3-yloxy)phenyl)but-2-ynamide | 556.1 | D | A | B | D | A | B |
| 104 | N-(5-((5-chloro-4-((2-(dimethylphosphoryl)phenyl)amino)pyrimidin-2-yl)amino)-4-methoxy-2-morpholinophenyl)-4-(dimethylamino)but-2-ynamide | 612.2 | A | A | A | D | A | A |
| 105 | N-(5-((5-chloro-4-((2-(dimethylphosphoryl)phenyl)amino)pyrimidin-2-yl)amino)-4-methoxy-2-morpholinophenyl)-4-methoxybut-2-ynamide | 599.2 | A | A | A | D | A | A |
| 106 | N-(5-((5-chloro-4-((2-(dimethylphosphoryl)phenyl)amino)pyrimidin-2-yl)amino)-4-methoxy-2-(4-(4-methylpiperazin-1-yl)piperidin-1-yl)phenyl)but-2-ynamide | 665.2 | B | A | A | D | A | A |
| 107 | N-(4-((5-chloro-4-((2-(dimethylphosphoryl)-3-(2-(piperidin-1-yl)ethoxy)phenyl)amino)pyrimidin-2-yl)amino)-3-methoxyphenyl)acrylamide | 599.2 | C | A | A | D | A | C |
| 108 | N-(3-((5-chloro-4-((2-(dimethylphosphoryl)-4-(2-(piperidin-1-yl)ethoxy)phenyl)amino)pyrimidin-2-yl)amino)-4-methoxyphenyl)acrylamide | 599.2 | A | A | A | D | A | A |
| 109 | N1-(3-((5-chloro-4-((2-(dimethylphosphoryl)phenyl)amino)pyrimidin-2-yl)amino)-4-methoxyphenyl)-N4-methylfumaramide | 529.1 | D | A | A | D | B | C |
| 110 | N1-(3-((5-chloro-4-((2-(dimethylphosphoryl)phenyl)amino)pyrimidin-2-yl)amino)-4-methoxyphenyl)-N4-methylmaleamide | 529.1 | D | A | A | D | A | C |
| 111 | N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)-4-methoxybut-2-ynamide | 626.2 | A | A | A | D | A | A |
| 112 | N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)but-2-ynamide | 596.2 | A | A | A | D | A | B |
| 113 | rac-(R)-N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)methacrylamide | 598.2 | C | A | A | D | A | A |
| 114 | N-(5-((5-chloro-4-((2-(dimethylphosphoryl)phenyl)amino)pyrimidin-2-yl)amino)-4-methoxy-2-morpholinophenyl)-5-(dimethylamino)pent-2-ynamide | 626.2 | A | A | A | D | A | A |
| 115 | N-(5-((5-chloro-4-((2-(dimethylphosphoryl)phenyl)amino)pyrimidin-2-yl)amino)-4-methoxy-2-morpholinophenyl)-5-methoxypent-2-ynamide | 613.2 | A | A | A | D | A | A |
| 116 | N-(5-((5-chloro-4-((2-(dimethylphosphoryl)phenyl)amino)pyrimidin-2-yl)amino)-4-methoxy-2-(3-methyl-3-(pyrrolidin-1-yl)but-1-yn-1-yl)phenyl)acrylamide | 607.2 | B | A | A | D | A | A |
| 117 | N-(3-((5-chloro-4-((2-(dimethylphosphoryl)phenyl)amino)pyrimidin-2-yl)amino)-4-(2-(dimethylamino)ethoxy)phenyl)acrylamide | 529.2 | D | D | D | D | D | D |

TABLE 1-continued

| | | | IC50 for kinase inhibition (nM)[1] | | | | | |
|---|---|---|---|---|---|---|---|---|
| Example # | Chemical Name (ChemDraw Ultra 12.0) | LC-MS (M + H) | EGFR | EGFR L858R | EGFR L858R T790M | BAF3 PARENTAL | BAF3 EGFR DEL T790M PURO POOL | BAF3 EGFR L858R-T790M PURO POOL |
| 118 | N-(5-((5-chloro-4-((2-(dimethylphosphoryl)phenyl)amino)pyrimidin-2-yl)amino)-4-methoxy-2-morpholinophenyl)-5-(4-methylpiperazin-1-yl)pent-2-ynamide | 681.2 | A | A | A | D | A | A |
| 119 | N-(5-((5-chloro-4-((2-(dimethylphosphoryl)phenyl)amino)pyrimidin-2-yl)amino)-4-methoxy-2-(pyrrolidin-1-yl)phenyl)-5-(4-methylpiperazin-1-yl)pent-2-ynamide | 665.2 | A | A | A | D | C | C |
| 120 | N-(5-((5-cyclopropyl-4-((2-(dimethylphosphoryl)phenyl)amino)pyrimidin-2-yl)amino)-2-((2-(diethylamino)ethyl)(methyl)amino)-4-methoxyphenyl)acrylamide | 606.3 | A | A | A | D | A | A |
| 121 | N-(5-((5-chloro-4-((2-(dimethylphosphoryl)phenyl)amino)pyrimidin-2-yl)amino)-2-((1-(diethylamino)-3-fluoropropan-2-yl)oxy)-4-methoxyphenyl)acrylamide | 619.2 | A | A | A | D | A | A |
| 122 | N-(5-((5-chloro-4-((2-(dimethylphosphoryl)phenyl)amino)pyrimidin-2-yl)amino)-4-methoxy-2-morpholinophenyl)-5-(2-(methoxymethyl)pyrrolidin-1-yl)pent-2-ynamide | 696.3 | A | A | A | D | A | A |
| 123 | N-(5-((5-chloro-4-((2-(dimethylphosphoryl)phenyl)amino)pyrimidin-2-yl)amino)-4-methoxy-2-((1-(2-methoxyethyl)piperidin-3-yl)oxy)phenyl)acrylamide | 629.2 | A | A | A | D | A | A |
| 124 | N-(5-((5-chloro-4-((2-(dimethylphosphoryl)phenyl)amino)pyrimidin-2-yl)amino)-2-(3-(dimethylamino)prop-1-yn-1-yl)-4-methoxyphenyl)acrylamide | 553.2 | A | A | A | D | A | A |
| 125 | N-(3-((5-chloro-4-((4-(2-(dimethylamino)ethoxy)-2-(dimethylphosphoryl)phenyl)amino)pyrimidin-2-yl)amino)-4-methoxyphenyl)acrylamide | 559.2 | A | A | A | D | A | A |
| 126 | N-(3-((5-chloro-4-((4-(3-(dimethylamino)propoxy)-2-(dimethylphosphoryl)phenyl)amino)pyrimidin-2-yl)amino)-4-methoxyphenyl)acrylamide | 573.2 | A | A | A | D | A | A |
| 127 | 1-(6-((5-chloro-4-((2-(dimethylphosphoryl)phenyl)amino)pyrimidin-2-yl)amino)-5-methoxyindolin-1-yl)prop-2-en-1-one | 498.1 | N/A | N/A | N/A | D | C | D |
| 128 | N-(5-((5-chloro-4-((2-(dimethylphosphoryl)phenyl)amino)pyrimidin-2-yl)amino)-2-(4-(dimethylamino)but-1-yn-1-yl)-4-methoxyphenyl)acrylamide | 567.2 | A | A | A | D | A | A |
| 129 | (R)-N-(5-((5-chloro-4-((2-(dimethylphosphoryl)phenyl)amino)pyrimidin-2-yl)amino)-2-((1-(dimethylamino)-3-methoxypropan-2-yl)oxy)-4-methoxyphenyl)acrylamide | 603.2 | A | A | A | D | A | A |
| 130 | N-(5-((5-chloro-4-((2-(dimethylphosphoryl)phenyl)amino)pyrimidin-2-yl)amino)-2-((1-(dimethylamino)-3-methoxypropan-2-yl)oxy)-4-methoxyphenyl)acrylamide | 603.2 | A | A | A | D | A | A |
| 131 | N-(3-((4-((2-(dimethylphosphoryl)phenyl)amino)-5-methoxypyrimidin-2-yl)amino)-4-methoxyphenyl)acrylamide | 468.1 | B | A | A | D | A | B |
| 132 | 2-chloro-N-(3-((5-chloro-4-((2-(dimethylphosphoryl)phenyl)amino)pyrimidin-2-yl)amino)-4-methoxyphenyl)acrylamide | 506.1 | A | A | A | D | A | C |
| 133 | N-(5-((5-chloro-4-((2-(dimethylphosphoryl)phenyl)amino)pyrimidin-2-yl)amino)-4-methoxy-2-methylphenyl)acrylamide | 486.1 | A | A | A | D | A | A |
| 134 | N-(3-((5-chloro-4-((2-(dimethylphosphoryl)phenyl)amino)pyrimidin-2-yl)amino)-4-(trifluoromethoxy)phenyl)acrylamide | 526.1 | A | A | A | D | A | A |
| 135 | N-(3-((5-chloro-4-((2-(dimethylphosphoryl)phenyl)amino)pyrimidin-2-yl)amino)-4-ethylphenyl)acrylamide | 470.1 | A | A | A | D | A | A |
| 136 | N-(4-chloro-3-((5-chloro-4-((2-(dimethylphosphoryl)phenyl)amino)pyrimidin-2-yl)amino)phenyl)acrylamide | 476 | A | A | A | D | A | A |
| 137 | 2-chloro-N-(3-((5-chloro-4-((2-(dimethylphosphoryl)phenyl)amino)pyrimidin-2-yl)amino)-4-methoxyphenyl)acetamide | 514.1 | A | A | A | D | A | A |

TABLE 1-continued

| Example # | Chemical Name (ChemDraw Ultra 12.0) | LC-MS (M + H) | EGFR | EGFR L858R | EGFR L858R T790M | BAF3 PARENTAL | BAF3 EGFR DEL T790M PURO POOL | BAF3 EGFR L858R-T790M PURO POOL |
|---|---|---|---|---|---|---|---|---|
| 138 | N-(3-((5-chloro-4-((2-(dimethylphosphoryl)phenyl)amino)pyrimidin-2-yl)amino)-4-(oxetan-3-yloxy)phenyl)acrylamide | 463.1 | D | D | D | D | D | D |
| 139 | N-(3-((5-cyano-4-((2-(dimethylphosphoryl)phenyl)amino)pyrimidin-2-yl)amino)-4-methoxyphenyl)acrylamide | 508.1 | A | A | A | D | C | D |
| 140 | 2-chloro-N-(5-((5-chloro-4-((2-(dimethylphosphoryl)phenyl)amino)pyrimidin-2-yl)amino)-4-methoxy-2-methylphenyl)acetamide | 474.1 | A | A | A | D | A | A |
| 141 | 2-chloro-N-(3-((4-((2-(dimethylphosphoryl)phenyl)amino)-5-methylpyrimidin-2-yl)amino)-4-methoxyphenyl)acetamide | 617.2 | A | A | A | D | A | A |
| 142 | N-(5-((5-chloro-4-((2-(dimethylphosphoryl)phenyl)amino)pyrimidin-2-yl)amino)-2-((1-(dimethylamino)-3-ethoxypropan-2-yl)oxy)-4-methoxyphenyl)acrylamide | 587.2 | A | A | A | D | A | A |
| 143 | N-(5-((5-chloro-4-((2-(dimethylphosphoryl)phenyl)amino)pyrimidin-2-yl)amino)-2-((1-(dimethylamino)-3-methoxypropan-2-yl)oxy)-4-methylphenyl)acrylamide | 587.2 | A | A | A | D | A | A |
| 144 | N-(5-((5-chloro-4-((2-(dimethylphosphoryl)phenyl)amino)pyrimidin-2-yl)amino)-2-((1-(dimethylamino)-3-methoxypropan-2-yl)oxy)-4-methylphenyl)acrylamide | 607.1 | A | A | A | D | A | A |
| 145 | N-(4-chloro-5-((5-chloro-4-((2-(dimethylphosphoryl)phenyl)amino)pyrimidin-2-yl)amino)-2-((1-(dimethylamino)-3-methoxypropan-2-yl)oxy)phenyl)acrylamide | 606.7 | A | A | A | D | A | A |
| 146 | N-(4-chloro-5-((5-chloro-4-((2-(dimethylphosphoryl)phenyl)amino)pyrimidin-2-yl)amino)-2-((1-(dimethylamino)-3-methoxypropan-2-yl)oxy)phenyl)acrylamide | 514.1 | A | A | A | D | A | A |
| 147 | N-(3-((5-chloro-4-((2-(dimethylphosphoryl)phenyl)amino)pyrimidin-2-yl)amino)-4-methoxyphenyl)-2-fluoroacetamide | 478.1 | D | B | C | D | D | D |
| 148 | 2-chloro-N-(3-((5-chloro-4-((2-(dimethylphosphoryl)phenyl)amino)pyrimidin-2-yl)amino)-4-methylphenyl)acetamide | 478.1 | A | A | A | D | A | A |
| 149 | 2-chloro-N-(5-((5-chloro-4-((2-(dimethylphosphoryl)phenyl)amino)pyrimidin-2-yl)amino)-2-fluoro-4-methoxyphenyl)acetamide | 512.1 | A | A | A | D | A | A |
| 150 | 1-chloro-N-(3-((5-chloro-4-((2-(dimethylphosphoryl)phenyl)amino)pyrimidin-2-yl)amino)-4-methoxyphenyl)methanesulfonamide | 530.0 | D | D | D | D | D | D |
| 151 | N-(5-((5-chloro-4-((2-(dimethylphosphoryl)phenyl)amino)pyrimidin-2-yl)amino)-2-(3-(dimethylamino)prop-1-yn-1-yl)-4-methylphenyl)acrylamide | 537.2 | A | A | A | D | A | A |
| 152 | N-(5-((5-chloro-4-((2-(dimethylphosphoryl)phenyl)amino)pyrimidin-2-yl)amino)-2-(3-(dimethylamino)prop-1-yn-1-yl)-4-ethylphenyl)acrylamide | 551.2 | A | A | A | D | A | A |
| 153 | N-(5-((5-chloro-4-((2-(isopropylsulfonyl)phenyl)amino)pyrimidin-2-yl)amino)-2-(3-(dimethylamino)prop-1-yn-1-yl)-4-methoxyphenyl)acrylamide | 583.2 | A | A | A | D | A | A |
| 154 | N-(5-((5-chloro-4-((2-(dimethylphosphoryl)phenyl)amino)pyrimidin-2-yl)amino)-2-(3-(diethylamino)-3-methylbut-1-yn-1-yl)-4-methoxyphenyl)acrylamide | 536.1 | A | A | A | D | A | A |
| 155 | N-(5-((5-chloro-4-((2-(dimethylphosphoryl)phenyl)amino)pyrimidin-2-yl)amino)-2-(3-(dimethylamino)-3-methylbut-1-yn-1-yl)-4-methoxyphenyl)acrylamide | 581.2 | A | A | A | D | A | A |
| 156 | N-(4-chloro-5-((5-chloro-4-((2-(dimethylphosphoryl)phenyl)amino)pyrimidin-2-yl)amino)-2-(3-(dimethylamino)prop-1-yn-1-yl)phenyl)acrylamide | 557.1 | A | A | A | D | A | A |

TABLE 1-continued

| | | | IC50 for kinase inhibition (nM)[1] | | | | | |
|---|---|---|---|---|---|---|---|---|
| Example # | Chemical Name (ChemDraw Ultra 12.0) | LC-MS (M + H) | EGFR | EGFR L858R | EGFR L858R T790M | BAF3 PARENTAL | BAF3 EGFR DEL T790M PURO POOL | BAF3 EGFR L858R-T790M PURO POOL |
| 157 | N-(5-((5-chloro-4-((2-(dimethylphosphoryl)phenyl)amino)pyrimidin-2-yl)amino)-4-methoxy-2-(3-(pyrrolidin-1-yl)prop-1-yn-1-yl)phenyl)acrylamide | 579.2 | A | A | A | D | A | A |
| 158 | N-(5-((5-chloro-4-((2-(dimethylphosphoryl)phenyl)amino)pyrimidin-2-yl)amino)-2-(3-(diisopropylamino)prop-1-yn-1-yl)-4-methoxyphenyl)acrylamide | 609.2 | A | A | A | D | A | A |
| 159 | N-(5-((5-chloro-4-((2-(dimethylphosphoryl)phenyl)amino)pyrimidin-2-yl)amino)-4-methoxy-2-(3-(4-methylpiperazin-1-yl)prop-1-yn-1-yl)phenyl)acrylamide | 608.2 | A | A | A | D | A | C |
| 160 | N-(5-((5-chloro-4-((2-(dimethylphosphoryl)phenyl)amino)pyrimidin-2-yl)amino)-4-methoxy-2-(3-(methylamino)prop-1-yn-1-yl)phenyl)acrylamide | 539.1 | A | A | A | D | A | A |
| 161 | N-(5-((5-chloro-4-((2-(dimethylphosphoryl)phenyl)amino)pyrimidin-2-yl)amino)-4-methoxy-2-(3-((2-methoxyethyl)(methyl)amino)prop-1-yn-1-yl)phenyl)acrylamide | 597.2 | A | A | A | D | A | A |
| 162 | N-(5-((5-chloro-4-((2-(dimethylphosphoryl)phenyl)amino)pyrimidin-2-yl)amino)-2-(3-(ethyl(methyl)amino)prop-1-yn-1-yl)-4-methoxyphenyl)acrylamide | 567.2 | A | A | A | D | A | A |
| 163 | N-(3-((6-((3-(dimethylphosphoryl)pyridin-2-yl)amino)pyrimidin-4-yl)amino)-4-methoxyphenyl)acrylamide | 439.1 | B | A | C | D | D | D |
| 164 | N-(3-((5-chloro-4-((4-(dimethylphosphoryl)pyridin-3-yl)amino)pyrimidin-2-yl)amino)-4-methoxyphenyl)acrylamide | 473.1 | D | A | A | D | C | D |
| 165 | N-(2-(3-(azepan-1-yl)prop-1-yn-1-yl)-5-((5-chloro-4-((2-(dimethylphosphoryl)phenyl)amino)pyrimidin-2-yl)amino)-4-methoxyphenyl)acrylamide | 607.2 | A | A | A | D | A | A |
| 166 | N-(5-((5-chloro-4-((2-(dimethylphosphoryl)phenyl)amino)pyrimidin-2-yl)amino)-2-(3-(isopropyl(methyl)amino)prop-1-yn-1-yl)-4-methoxyphenyl)acrylamide | 581.2 | A | A | A | D | A | A |
| 167 | N-(5-((5-chloro-4-((2-(dimethylphosphoryl)phenyl)amino)pyrimidin-2-yl)amino)-4-methoxy-2-(3-(piperidin-1-yl)prop-1-yn-1-yl)phenyl)acrylamide | 593.2 | A | A | A | A | A | A |
| 168 | N-(5-((5-chloro-4-((2-(dimethylphosphoryl)phenyl)amino)pyrimidin-2-yl)amino)-2-(3-(cyclopentyl(methyl)amino)prop-1-yn-1-yl)-4-methoxyphenyl)acrylamide | 607.2 | A | A | A | A | A | A |
| 176 | N-(5-((5-chloro-4-((2-(dimethylphosphoryl)phenyl)amino)pyrimidin-2-yl)methyl)-4-methoxy-2-(3-(4-methylpiperidin-1-yl)prop-1-yn-1-yl)phenyl)acrylamide | 607.2 | A | A | A | D | | |
| 177 | N-(2-(3-(tert-butyl(methyl)amino)prop-1-yn-1-yl)-5-((5-chloro-4-((2-(dimethylphosphoryl)phenyl)amino)pyrimidin-2-yl)methyl)-4-methoxyphenyl)acrylamide | 595.2 | A | A | A | D | | |
| 178 | N-(5-((5-chloro-4-((2-(dimethylphosphoryl)phenyl)amino)pyrimidin-2-yl)methyl)-2-(3-(2-(dimethylamino)pyrrolidin-1-yl)prop-1-yn-1-yl)-4-methoxyphenyl)acrylamide | 622.2 | B | A | A | D | | |
| 179 | N-(5-((5-chloro-4-((2-(dimethylphosphoryl)phenyl)amino)pyrimidin-2-yl)methyl)-4-methoxy-2-(3-(2-methylpiperidin-1-yl)prop-1-yn-1-yl)phenyl)acrylamide | 607.2 | | | | | | |
| 180 | (Z)-N-(5-((5-chloro-4-((2-(dimethylphosphoryl)phenyl)amino)pyrimidin-2-yl)methyl)-2-(3-(dimethylamino)prop-1-en-1-yl)-4-methoxyphenyl)acrylamide | 555.2 | | | | | | |
| 181 | (E)-N-(5-((5-chloro-4-((2-(dimethylphosphoryl)phenyl)amino)pyrimidin-2-yl)methyl)-2-(3-(dimethylamino)prop-1-en-1-yl)-4-methoxyphenyl)acrylamide | 555.2 | | | | | | |

TABLE 1-continued

| | | | IC50 for kinase inhibition (nM)[1] | | | | | |
|---|---|---|---|---|---|---|---|---|
| Example # | Chemical Name (ChemDraw Ultra 12.0) | LC-MS (M + H) | EGFR | EGFR L858R | EGFR L858R T790M | BAF3 PARENTAL | BAF3 EGFR DEL T790M PURO POOL | BAF3 EGFR L858R- T790M PURO POOL |
| 182 | N-(5-((5-chloro-4-((2-(dimethylphosphoryl)phenyl)amino)pyrimidin-2-yl)methyl)-2-(3-(4-fluoropiperidin-1-yl)prop-1-yn-1-yl)-4-methoxyphenyl)acrylamide | 611.2 | | | | | | |
| 183 | N-(5-((5-chloro-4-((2-(dimethylphosphoryl)phenyl)amino)pyrimidin-2-yl)methyl)-4-methoxy-2-(3-(methyl(tetrahydro-2H-pyran-4-yl)amino)prop-1-yn-1-yl)phenyl)acrylamide | 623.2 | | | | | | |
| 184 | N-(5-((5-chloro-4-((2-(dimethylphosphoryl)phenyl)amino)pyrimidin-2-yl)methyl)-2-(3-(dimethylamino)prop-1-yn-1-yl)-4-methoxyphenyl)but-2-ynamide | 565.2 | | | | | | |
| 185 | N-(3-((5-chloro-2-(2-methoxy-4-(1-methyl-4-oxido-1,4-azaphosphinan-4-yl)benzyl)pyrimidin-4-yl)oxy)phenyl)acrylamide | 528.1 | | | | | | |

[1]A = <50 nM; B = 50 → 100 nM; C = 101 nM → <250 nM; D = ≥250 nM

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A compound of the Formula:

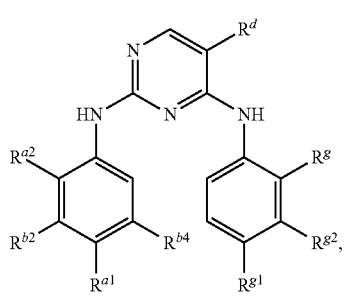

(IIIa)

or a pharmaceutically acceptable salt thereof, wherein $R^d$ is H, Cl, F, Br, I, CN, $CH_3$ $CF_3$ —$CH_2CH$=$CH_2$, or cyclopropyl;

$R^g$ is —$P(O)(R^{3A})(R^{3B})$ or —$S(O)_2R^{3E}$;

each $R^{3A}$, $R^{3B}$, and $R^{3E}$ is, independently, selected from H, alkyl, alkenyl, alkynyl, cycloalkyl, cycloalkenyl, cycloalkynyl, and heteroalkyl;

$R^{g2}$ is H, F, $C_{1-6}$ alkyl, or $C_{1-6}$ alkoxy;

$R^{g1}$ is H, —$P(O)(R^{3A})(R^{3B})$ or —$OR^2$;

$R^{b2}$ is H;

$R^{b4}$ is $W^1$ ;

$R^{a1}$ is of the Formula:

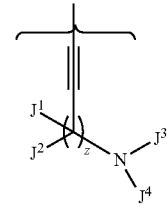

wherein:

$J^1$ and $J^2$ are independently H, halo or $R^J$; or $J^1$ and $J^2$ together with the atom to which each is attached form an optionally substituted ring which is $C_{3-8}$ cycloalkyl, 3- to 7-membered heterocyclic, or heteroaryl;

$J^3$ and $J^4$ are independently H or $R^J$; or $J^3$ and $J^4$ together with the atom to which each is attached form an optionally substituted ring which is 3- to 7-membered heterocyclic or heteroaryl ring;

$R^J$ $C_{1-6}$ alkyl, $C_{3-8}$ cycloalkyl, $C_{1-8}$ heteroalkyl, or 3- to 7-membered heterocyclyl, wherein each $R^J$ is independently selected from halo, haloalkyl, hydroxyl, hydroxyalkyl, amino, alkylamino, dialkylamino, cycloalkyl, alkoxy, cycloalkoxy and heterocyclic groups, wherein the alkyl, cycloalkyl, and heterocyclic groups on $R^J$ are optionally substituted with one or more halo, alkyl, haloalkyl, hydroxyalkyl, alkoxyalkyl, amino, alkylamino, dialkylamino or cycloalkyl groups; and, z is 1- 3
$R^{a2}$ is H, halo, —$CH_3$, —$CF_3$, —$CH_2CH_3$, —$OCH_3$, —$OCF_3$, —$OCH_2CH_3$, —$OCH_2CH_2N(CH_3)_2$, or —O-heterocyclyl;
$W^1$ is —NHC(O)CH=$CH_2$ or is
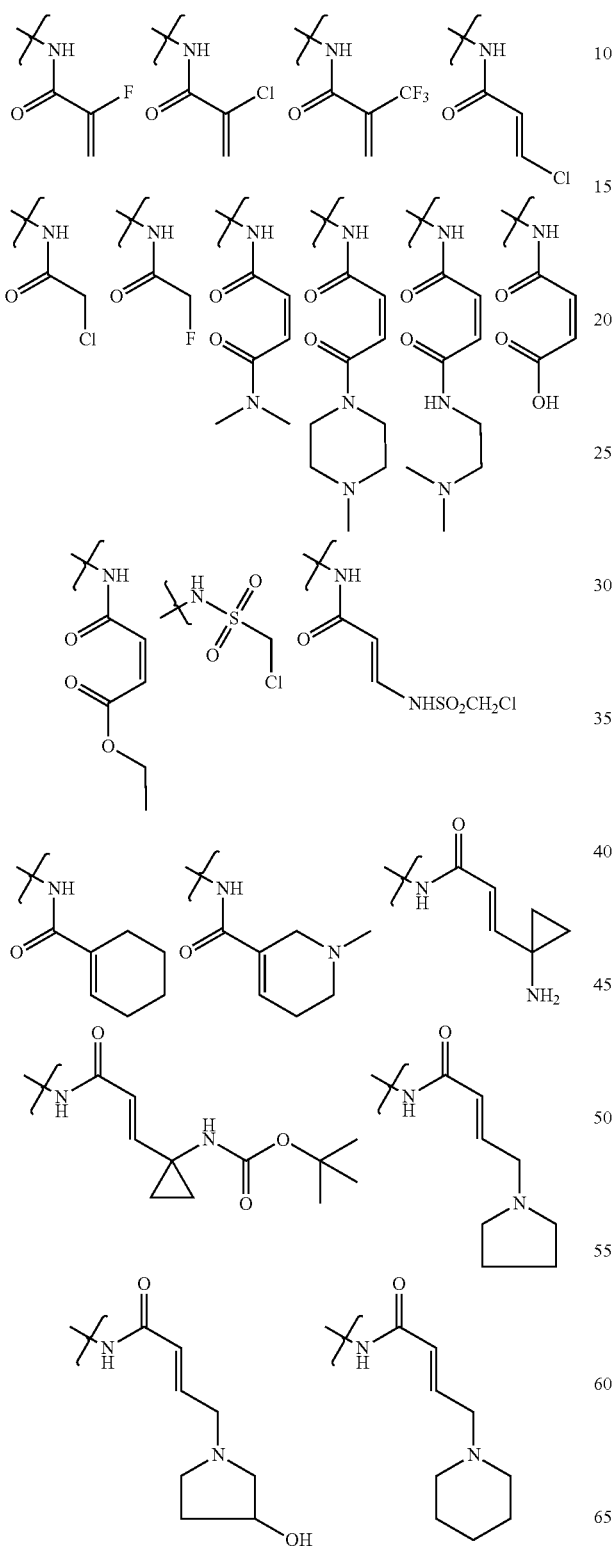
-continued
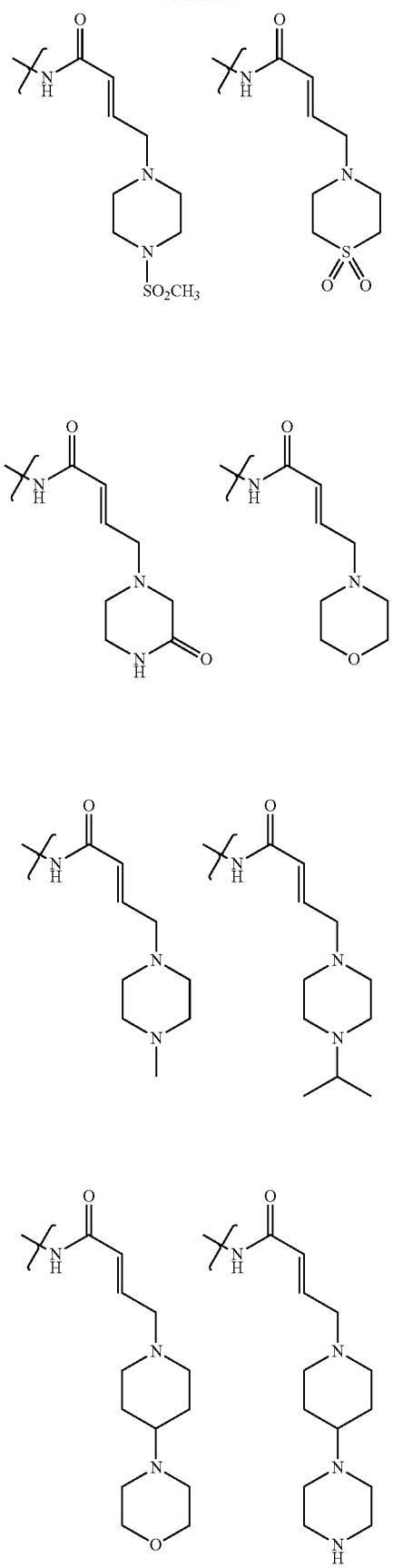

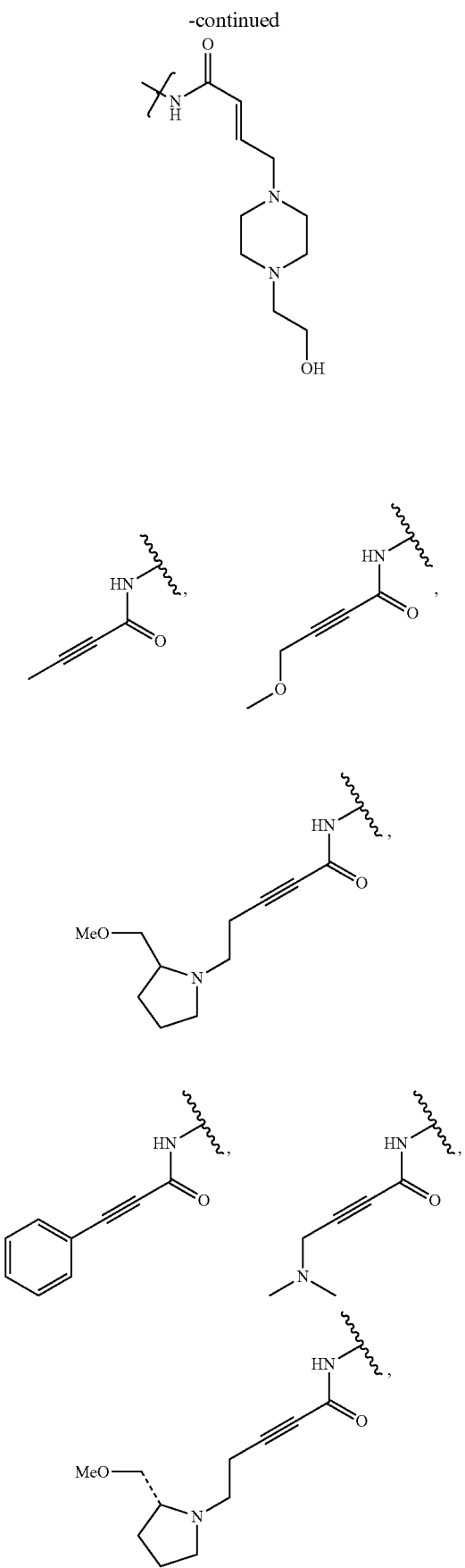
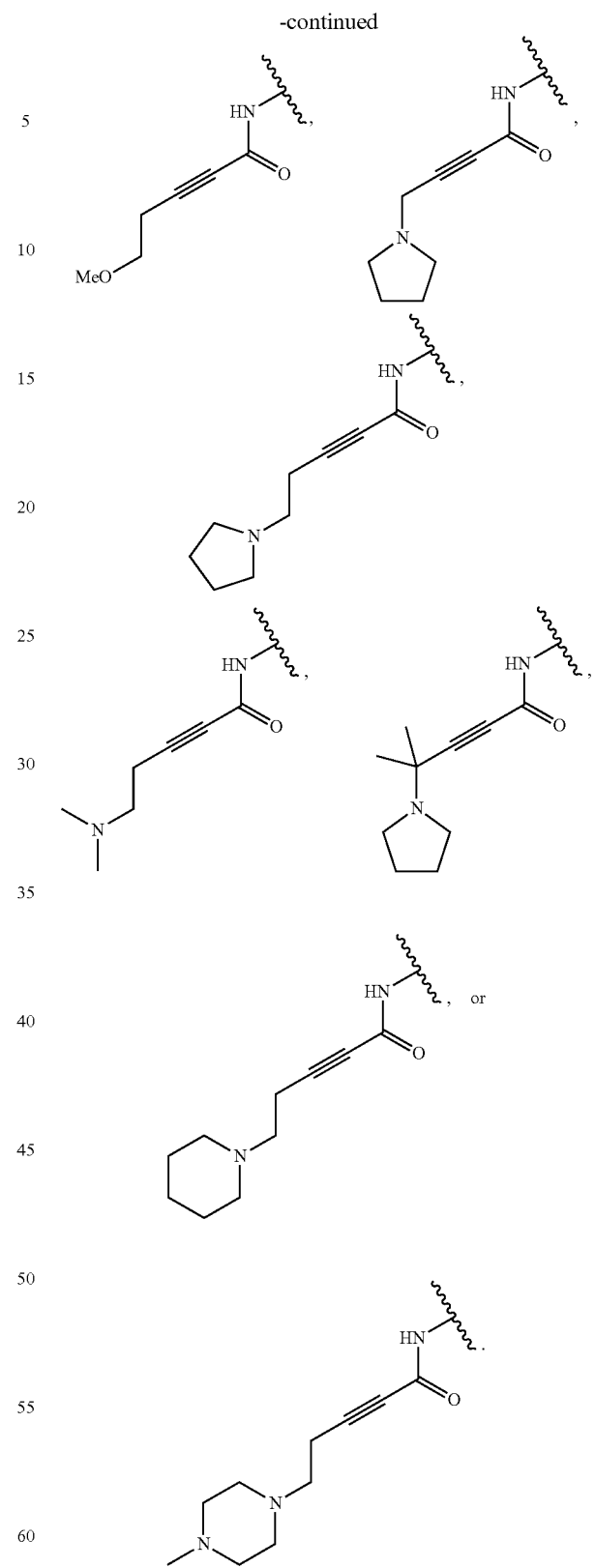
2. The compound of claim 1, or a pharmaceutically acceptable salt thereof, wherein $R^{a1}$ is selected from the following:

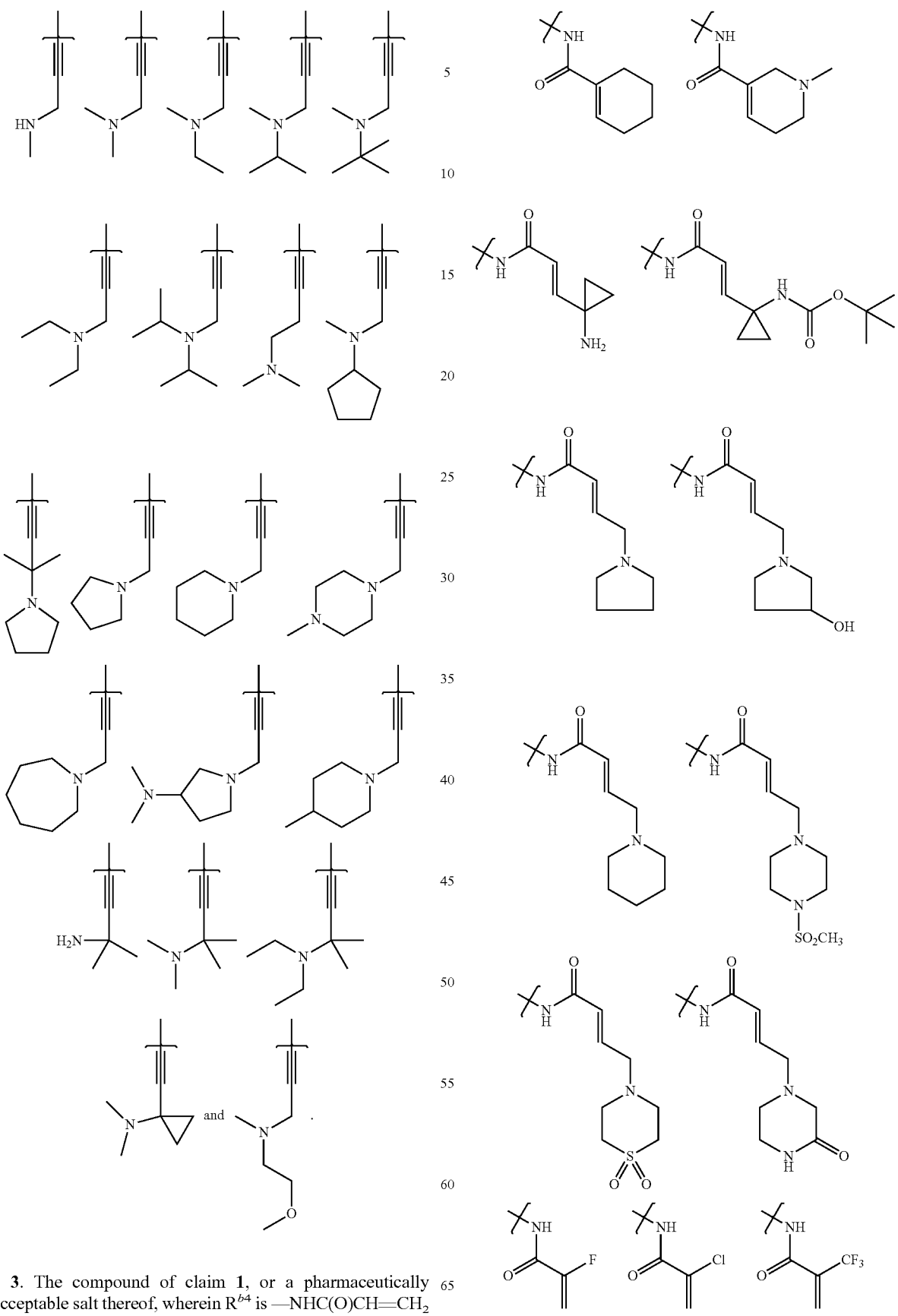
3. The compound of claim 1, or a pharmaceutically acceptable salt thereof, wherein $R^{b4}$ is —NHC(O)CH=CH$_2$ or is selected from the following:

233
-continued

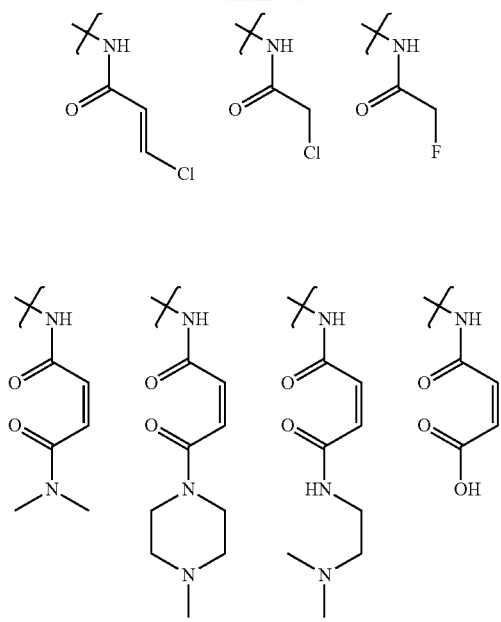

234
-continued

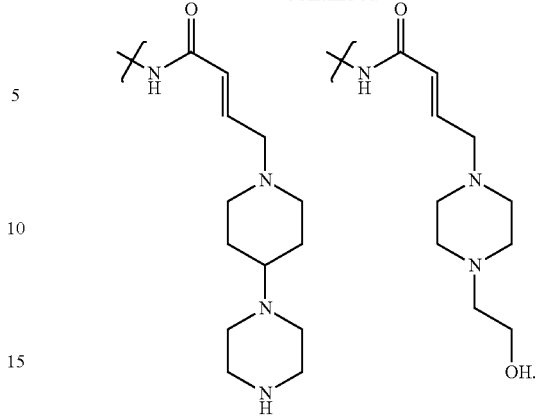

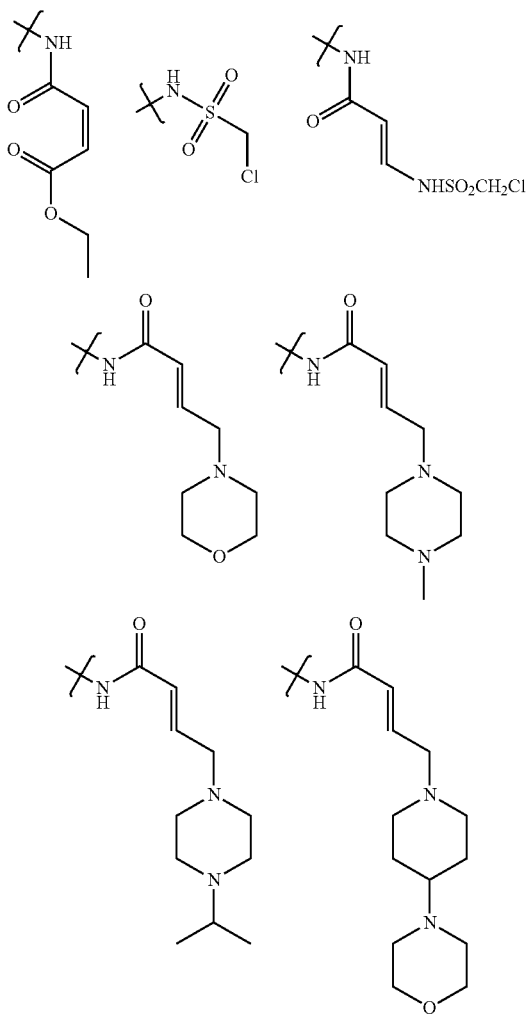

4. A method for treating an EGFR-driven cancer in a subject, said method comprising administering to said subject a therapeutically effective amount of a compound of claim 1, or a pharmaceutically acceptable salt thereof, wherein said EGFR-driven cancer is a non-small cell lung cancer (NSCLS); pancreatic cancer; head and neck cancer; or colorectal cancer.

5. A pharmaceutical composition comprising a compound of claim 1, or a pharmaceutically acceptable salt thereof.

6. A compound selected from the group consisting of:
N-(5-((5-chloro-4-((2-(dimethylphosphoryl)phenyl)amino)pyrimidin-2-yl)amino)-4-methoxy-2-(2-(pyrrolidin-1-yl)ethoxy)phenyl)acrylamide (Example 1);
N-(5-((5-chloro-4-((2-(dimethylphosphoryl)phenyl)amino)pyrimidin-2-yl)amino)-4-methoxy-2-(2-(4-methylpiperazin-1-yl)ethoxy)phenyl)acrylamide (Example 2);
N-(5-((5-chloro-4-((2-(dimethylphosphoryl)phenyl)amino)pyrimidin-2-yl)amino)-4-methoxy-2-((1-methylpiperidin-4-yl)methoxy)phenyl)acrylamide (Example 3);
N-(5-((5-chloro-4-((2-(dimethylphosphoryl)phenyl)amino)pyrimidin-2-yl)amino)-4-methoxy-2-(2-morpholinoethoxy)phenyl)acrylamide (Example 4);
N-(5-((5-chloro-4-((2-(dimethylphosphoryl)phenyl)amino)pyrimidin-2-yl)amino)-4-methoxy-2-(3-morpholinopropoxy)phenyl)acrylamide (Example 5);
N-(5-((5-chloro-4-((2-(dimethylphosphoryl)phenyl)amino)pyrimidin-2-yl)amino)-4-methoxy-2-((tetrahydro-2H-pyran-4-yl)methoxy)phenyl)acrylamide (Example 6);
N-(5-((5-chloro-4-((2-(dimethylphosphoryl)phenyl)amino)pyrimidin-2-yl)amino)-4-methoxy-2-((1-methylpiperidin-2-yl)methoxy)phenyl)acrylamide (Example 7);
N-(5-((5-chloro-4-((2-(dimethylphosphoryl)phenyl)amino)pyrimidin-2-yl)amino)-4-methoxy-2-(2-(piperidin-1-yl)ethoxy)phenyl)acrylamide (Example 8);
N-(5-((5-chloro-4-((2-(dimethylphosphoryl)phenyl)amino)pyrimidin-2-yl)amino)-4-methoxy-2-(oxetan-3-yloxy)phenyl)acrylamide (Example 9);
N-(5-((5-chloro-4-((2-(dimethylphosphoryl)phenyl)amino)pyrimidin-2-yl)amino)-4-methoxy-2-(pyridin-3-ylmethoxy)phenyl)acrylamide (Example 10);
N-(5-((5-chloro-4-((2-(dimethylphosphoryl)phenyl)amino)pyrimidin-2-yl)amino)-4-methoxy-2-(pyridin-4-ylmethoxy)phenyl)acrylamide (Example 11);

N-(5-((5-chloro-4-((2-(dimethylphosphoryl)phenyl) amino)pyrimidin-2-yl)amino)-4-methoxy-2-((1-methylpiperidin-3-yl)oxy)phenyl)acrylamide (Example 12);

N-(5-((5-chloro-4-((2-(dimethylphosphoryl)phenyl) amino)pyrimidin-2-yl)amino)-4-methoxy-2-((1-methylpyrrolidin-3-yl)oxy)phenyl)acrylamide (Example 13);

rel-(R)-N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide (Example 14);

N-(2-((1-(azetidin-1-yl)-3-methoxypropan-2-yl)oxy)-5-((5-chloro-4-((2-(dimethylphosphoryl)phenyl)amino) pyrimidin-2-yl)amino)-4-methoxyphenyl)acrylamide (Example 15);

rel-(R)-N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide (Example 16);

N-(5-((5-chloro-4-((2-(dimethylphosphoryl)phenyl) amino)pyrimidin-2-yl)amino)-4-methoxy-2-((1-methylazetidin-3-yl)oxy)phenyl)acrylamide (Example 17);

N-(5-((5-chloro-4-((2-(dimethylphosphoryl)phenyl) amino)pyrimidin-2-yl)amino)-4-methoxy-2-((1-methylpyrrolidin-2-yl)methoxy)phenyl)acrylamide (Example 18);

N-(5-((5-chloro-4-((2-(dimethylphosphoryl)phenyl) amino)pyrimidin-2-yl)amino)-4-methoxy-2-((4-methyl-1,4-oxazepan-6-yl)oxy)phenyl)acrylamide (Example 19);

N-(5-((5-chloro-4-((2-(dimethylphosphoryl)phenyl) amino)pyrimidin-2-yl)amino)-4-methoxy-2-((1-methylpyrrolidin-3-yl)methoxy)phenyl)acrylamide (Example 20);

N-(5-((5-chloro-4-((2-(dimethylphosphoryl)phenyl) amino)pyrimidin-2-yl)amino)-2-((2-(dimethylamino) cyclohexyl)oxy)-4-methoxyphenyl)acrylamide (Example 21);

N-(5-((5-chloro-4-((2-(dimethylphosphoryl)phenyl) amino)pyrimidin-2-yl)amino)-4-methoxy-2-(4-(4-methylpiperazin-1-yl)piperidin-1-yl)phenyl)acrylamide (Example 22);

N-(5-((5-chloro-4-((2-(dimethylphosphoryl)phenyl) amino)pyrimidin-2-yl)amino)-2-(4-(dimethylamino) piperidin-1-yl)-4-methoxyphenyl)acrylamide (Example 23);

N-(5-((5-chloro-4-((2-(dimethylphosphoryl)phenyl) amino)pyrimidin-2-yl)amino)-2-(3-(dimethylamino) pyrrolidin-1-yl)-4-methoxyphenyl)acrylamide (Example 24);

N-(5-((5-chloro-4-((2-(dimethylphosphoryl)phenyl) amino)pyrimidin-2-yl)amino)-4-methoxy-2-(4-methyl-1,4-diazepan-1-yl)phenyl)acrylamide (Example 25);

rac-(R)-N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)acrylamide (Example 26);

N-(5-((5-chloro-4-((2-(dimethylphosphoryl)phenyl) amino)pyrimidin-2-yl)amino)-4-methoxy-2-(4-(1-methylpiperidin-4-yl)piperazin-1-yl)phenyl)acrylamide (Example 27);

N-(5-((5-chloro-4-((2-(dimethylphosphoryl)phenyl) amino)pyrimidin-2-yl)amino)-4-methoxy-2-(3-morpholinopyrrolidin-1-yl)phenyl)acrylamide (Example 28);

rac-(R)-N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)acrylamide (Example 29);

N-(5-((5-chloro-4-((2-(dimethylphosphoryl)phenyl) amino)pyrimidin-2-yl)amino)-2-(3-(dimethylamino) piperidin-1-yl)-4-methoxyphenyl)acrylamide (Example 30);

N-(5-((5-chloro-4-((2-(dimethylphosphoryl)phenyl) amino)pyrimidin-2-yl)amino)-4-methoxy-2-(3-(pyrrolidin-1-yl)azetidin-1-yl)phenyl)acrylamide (Example 31);

N-(5-((5-chloro-4-((2-(dimethylphosphoryl)phenyl) amino)pyrimidin-2-yl)amino)-2-(3-hydroxypyrrolidin-1-yl)-4-methoxyphenyl)acrylamide (Example 32);

N-(5-((5-chloro-4-((2-(dimethylphosphoryl)phenyl) amino)pyrimidin-2-yl)amino)-4-methoxy-2-(3-(piperidin-1-yl)pyrrolidin-1-yl)phenyl)acrylamide (Example 33);

N-(5-((5-chloro-4-((2-(dimethylphosphoryl)phenyl) amino)pyrimidin-2-yl)amino)-2-(3-(diethylamino)pyrrolidin-1-yl)-4-methoxyphenyl)acrylamide (Example 34);

N-(5-((5-chloro-4-((2-(dimethylphosphoryl)phenyl) amino)pyrimidin-2-yl)amino)-2-(3-hydroxy-[1,3'-bipyrrolidin]-1'-yl)-4-methoxyphenyl)acrylamide (Example 35);

N-(2-([1,3'-bipyrrolidin]-1'-yl)-5-((5-chloro-4-((2-(dimethylphosphoryl)phenyl)amino)pyrimidin-2-yl) amino)-4-methoxyphenyl)acrylamide (Example 36);

N-(5-((5-chloro-4-((2-(dimethylphosphoryl)phenyl) amino)pyrimidin-2-yl)amino)-4-methoxy-2-(3-(4-methylpiperazin-1-yl)pyrrolidin-1-yl)phenyl)acrylamide (Example 37);

N-(5-((5-chloro-4-((2-(dimethylphosphoryl)phenyl) amino)pyrimidin-2-yl)amino)-2-(3-((2-(diethylamino)ethyl)(methypamino)pyrrolidin-1-yl)-4-methoxyphenyl)acrylamide (Example 38);

N-(5-((5-chloro-4-((2-(dimethylphosphoryl)phenyl) amino)pyrimidin-2-yl)amino)-2-(3-(4-hydroxypiperidin-1-yl)pyrrolidin-1-yl)-4-methoxyphenyl)acrylamide (Example 39);

N-(5-((5-chloro-4-((2-(dimethylphosphoryl)phenyl) amino)pyrimidin-2-yl)amino)-2-(3-(4-(2-hydroxyethyl)piperazin-1-yl)pyrrolidin-1-yl)-4-methoxyphenyl)acrylamide (Example 40);

N-(5-((5-chloro-4-((2-(dimethylphosphoryl)phenyl) amino)pyrimidin-2-yl)amino)-4-methoxy-2-(3-((2-methoxyethyl)(methyl)amino)pyrrolidin-1-yl)phenyl) acrylamide (Example 41);

N-(3-((5-chloro-4-((2-(dimethylphosphoryl)phenyl) amino)pyrimidin-2-yl)amino)-4-methoxyphenyl)-2-(pyrrolidin-1-ylmethyl)acrylamide (Example 42);

N-(3-((5-chloro-4-((2-(dimethylphosphoryl)phenyl) amino)pyrimidin-2-yl)amino)-4-methoxyphenyl)-2-(piperidin-1-ylmethyl)acrylamide (Example 43);

N-(3-((5-chloro-4-((2-(dimethylphosphoryl)phenyl) amino)pyrimidin-2-yl)amino)-4-methoxyphenyl)-2-((4-(methylsulfonyl)piperazin-1-yl)methyl)acrylamide (Example 44);

N-(3-((5-chloro-4-((2-(dimethylphosphoryl)phenyl) amino)pyrimidin-2-yl)amino)-4-methoxyphenyl)-2-((4-(4-methylpiperazin-1-yl)piperidin-1-yl)methyl) acrylamide (Example 45);

N-(3-((5-chloro-4-((2-(dimethylphosphoryl)phenyl)amino)pyrimidin-2-yl)amino)-4-methoxyphenyl)-2-((1,1-dioxidothiomorpholino)methyl)acrylamide (Example 46);

N-(3-((5-chloro-4-((2-(dimethylphosphoryl)phenyl)amino)pyrimidin-2-yl)amino)-4-methoxyphenyl)-2-((3-oxopiperazin-1-yl)methyl)acrylamide (Example 47);

N-(3-((5-chloro-4-((2-(dimethylphosphoryl)phenyl)amino)pyrimidin-2-yl)amino)-4-methoxyphenyl)-2-(morpholinomethyl)acrylamide (Example 48);

N-(3-((5-chloro-4-((2-(dimethylphosphoryl)phenyl)amino)pyrimidin-2-yl)amino)-4-methoxyphenyl)-2-((4-methylpiperazin-1-yl)methyl)acrylamide (Example 49);

N-(3-((5-chloro-4-((2-(dimethylphosphoryl)phenyl)amino)pyrimidin-2-yl)amino)-4-methoxyphenyl)-2-((4-isopropylpiperazin-1-yl)methyl)acrylamide (Example 50);

N-(3-((5-chloro-4-((2-(dimethylphosphoryl)phenyl)amino)pyrimidin-2-yl)amino)-4-methoxyphenyl)-2-((4-morpholinopiperidin-1-yl)methyl)acrylamide (Example 51);

N-(3-((5-chloro-4-((2-(dimethylphosphoryl)phenyl)amino)pyrimidin-2-yl)amino)-4-methoxyphenyl)-2-((4-(2-hydroxyethyl)piperazin-1-yl)methyl)acrylamide (Example 52);

N-(3-((5-chloro-4-((2-(dimethylphosphoryl)phenyl)amino)pyrimidin-2-yl)amino)-4-methoxyphenyl)-2-((3-hydroxypyrrolidin-1-yl)methyl)acrylamide (Example 53);

N-(3-((5-chloro-4-((2-(dimethylphosphoryl)phenyl)amino)pyrimidin-2-yl)amino)-4-fluorophenyl)acrylamide (Example 54);

N-(5-((5-chloro-4-((2-(dimethylphosphoryl)phenyl)amino)pyrimidin-2-yl)amino)-4-methoxy-2-((4-methylpiperazin-1-yl)methyl)phenyl)acrylamide (Example 55);

N-(5-((5-chloro-4-((2-(dimethylphosphoryl)phenyl)amino)pyrimidin-2-yl)amino)-4-methoxy-2-(4-methylpiperazine-1-carbonyl)phenyl)acrylamide (Example 56);

N-(2-(3-aminopyrrolidin-1-yl)-5-((5-chloro-4-((2-(dimethylphosphoryl)phenyl)amino)pyrimidin-2-yl)amino)-4-methoxyphenyl)acrylamide (Example 57);

N1-(3-((5-chloro-4-((2-(dimethylphosphoryl)phenyl)amino)pyrimidin-2-yl)amino)-4-methoxyphenyl)-N4-(2-(dimethylamino)ethyl)fumaramide (Example 58);

(E)-N-(3-((5-chloro-4-((2-(dimethylphosphoryl)phenyl)amino)pyrimidin-2-yl)amino)-4-methoxyphenyl)-4-(4-methylpiperazin-1-yl)-4-oxobut-2-enamide (Example 59);

N1-(3-((5-chloro-4-((2-(dimethylphosphoryl)phenyl)amino)pyrimidin-2-yl)amino)-4-methoxyphenyl)-N4,N4-dimethylfumaramide (Example 60);

(Z)-4-((3-((5-chloro-4-((2-(dimethylphosphoryl)phenyl)amino)pyrimidin-2-yl)amino)-4-methoxyphenyl)amino)-4-oxobut-2-enoic acid (Example 61);

N1-(3-((5-chloro-4-((2-(dimethylphosphoryl)phenyl)amino)pyrimidin-2-yl)amino)-4-methoxyphenyl)-N4,N4-dimethylmaleamide (Example 62);

(Z)-N-(3-((5-chloro-4-((2-(dimethylphosphoryl)phenyl)amino)pyrimidin-2-yl)amino)-4-methoxyphenyl)-4-(4-methylpiperazin-1-yl)-4-oxobut-2-enamide (Example 63);

N1-(3-((5-chloro-4-((2-(dimethylphosphoryl)phenyl)amino)pyrimidin-2-yl)amino)-4-methoxyphenyl)-N4-(2-(dimethylamino)ethyl)maleamide (Example 64);

N-(2-(3-amino-3-methylbut-1-yn-1-yl)-5-((5-chloro-4-((2-(dimethylphosphoryl)phenyl)amino)pyrimidin-2-yl)amino)-4-methoxyphenyl)acrylamide (Example 65);

N-(5-((5-chloro-4-((2-(dimethylphosphoryl)phenyl)amino)pyrimidin-2-yl)amino)-2-(2-(dimethylamino)-3-hydroxypropoxy)-4-methoxyphenyl)acrylamide (Example 66);

N-(5-((5-chloro-4-((2-(dimethylphosphoryl)phenyl)amino)pyrimidin-2-yl)amino)-2-((2-((2-fluoroethyl)(methyl)amino)ethyl)(methyl)amino)-4-methoxyphenyl)acrylamide (Example 67);

N-(2-(3-(azetidin-1-yl)pyrrolidin-1-yl)-5-((5-chloro-4-((2-(dimethylphosphoryl)phenyl)amino)pyrimidin-2-yl)amino)-4-methoxyphenyl)acrylamide (Example 68);

N-(2-([1,4'-bipiperidin]-1'-yl)-5-((5-chloro-4-((2-(dimethylphosphoryl)phenyl)amino)pyrimidin-2-yl)amino)-4-methoxyphenyl)acrylamide (Example 69);

N-(5-((5-chloro-4-((2-(dimethylphosphoryl)phenyl)amino)pyrimidin-2-yl)amino)-4-methoxy-2-(4-morpholinopiperidin-1-yl)phenyl)acrylamide (Example 70);

N-(5-((5-chloro-4-((2-(dimethylphosphoryl)phenyl)amino)pyrimidin-2-yl)amino)-4-methoxy-2-(4-(4-methyl-1,4-diazepan-1-yl)piperidin-1-yl)phenyl)acrylamide (Example 71);

N-(5-((5-chloro-4-((2-(dimethylphosphoryl)phenyl)amino)pyrimidin-2-yl)amino)-4-methoxy-2-(4-(pyrrolidin-1-yl)piperidin-1-yl)phenyl)acrylamide (Example 72);

N-(5-((5-chloro-4-((2-(dimethylphosphoryl)phenyl)amino)pyrimidin-2-yl)amino)-2-((1-(dimethylamino)cyclopropyl)ethynyl)-4-methoxyphenyl)acrylamide (Example 73);

N-(5-((5-chloro-4-((2-(dimethylphosphoryl)phenyl)amino)pyrimidin-2-yl)amino)-4-methoxy-2-(2-(4-methylpiperazin-1-yl)ethyl)phenyl)acrylamide (Example 74);

(E)-ethyl 4-((3-((5-chloro-4-((2-(dimethylphosphoryl)phenyl)amino)pyrimidin-2-yl)amino)-4-methoxyphenyl)amino)-4-oxobut-2-enoate (Example 75);

(E)-tert-butyl (1-(3-((3-((5-chloro-4-((2-(dimethylphosphoryl)phenyl)amino)pyrimidin-2-yl)amino)-4-methoxyphenyl)amino)-3-oxoprop-1-en-1-yl)cyclopropyl)carbamate (Example 76);

N-(3-((5-chloro-4-((2-(dimethylphosphoryl)phenyl)amino)pyrimidin-2-yl)amino)-4-methoxyphenyl)-2-fluoroacrylamide (Example 77);

(E)-3-chloro-N-(3-((5-chloro-4-((2-(dimethylphosphoryl)phenyl)amino)pyrimidin-2-yl)amino)-4-methoxyphenyl)acrylamide (Example 78);

N-(3-((5-chloro-4-((2-(dimethylphosphoryl)phenyl)amino)pyrimidin-2-yl)amino)-4-methoxyphenyl)cyclohex-1-enecarboxamide (Example 79);

N-(5-((5-chloro-4-((2-(dimethylphosphoryl)phenyl)amino)pyrimidin-2-yl)amino)-4-methoxy-2-(2-(pyrrolidin-1-yl)ethoxy)phenyl)but-2-ynamide (Example 80);

N-(3-((5-chloro-4-((2-(dimethylphosphoryl)phenyl)amino)pyrimidin-2-yl)amino)-4-methoxyphenyl)-4-(dimethylamino)but-2-ynamide (Example 81);

N-(3-((5-chloro-4-((2-(dimethylphosphoryl)phenyl)amino)pyrimidin-2-yl)amino)-4-methoxyphenyl)-2-(trifluoromethyl)acrylamide (Example 82);

N-(3-((5-chloro-2-((4-(dimethylphosphoryl)-2-methoxyphenyl)amino)pyrimidin-4-yl)oxy)phenyl)-4-(dimethylamino)but-2-ynamide (Example 83);

N-(3-((5-chloro-4-((2-(dimethylphosphoryl)phenyl)amino)pyrimidin-2-yl)amino)-4-methoxyphenyl)-1-methyl-1,2,5,6-tetrahydropyridine-3-carboxamide (Example 84);

(E)-3-chloro-N-(5-((5-chloro-4-((2-(dimethylphosphoryl)phenyl)amino)pyrimidin-2-yl)amino)-2-fluoro-4-methoxyphenyl)acrylamide (Example 85);

N-(3-((5-chloro-4-((2-(dimethylphosphoryl)-4-(2-methoxyethoxy)phenyl)amino)pyrimidin-2-yl)amino)-4-methoxyphenyl)acrylamide (Example 86);

N-(5-((5-chloro-4-((2-(dimethylphosphoryl)phenyl)amino)pyrimidin-2-yl)amino)-2-fluoro-4-methoxyphenyl)-4-(dimethylamino)but-2-ynamide (Example 87);

N-(5-((5-chloro-4-((2-(dimethylphosphoryl)phenyl)amino)pyrimidin-2-yl)amino)-2-fluoro-4-methoxyphenyl)-5-(piperidin-1-yl)pent-2-ynamide (Example 88);

N-(5-((5-chloro-4-((2-(dimethylphosphoryl)phenyl)amino)pyrimidin-2-yl)amino)-2-fluoro-4-methoxyphenyl)-4-(pyrrolidin-1-yl)but-2-ynamide (Example 89);

N-(5-((5-chloro-4-((2-(dimethylphosphoryl)phenyl)amino)pyrimidin-2-yl)amino)-2-fluoro-4-methoxyphenyl)-4-methyl-4-(pyrrolidin-1-yl)pent-2-ynamide (Example 90);

N-(3-((5-chloro-4-((2-(dimethylphosphoryl)phenyl)amino)pyrimidin-2-yl)amino)-4-methoxyphenyl)-4-methyl-4-(pyrrolidin-1-yl)pent-2-ynamide (Example 91);

(E)-N-(3-((5-chloro-4-((2-(dimethylphosphoryl)phenyl)amino)pyrimidin-2-yl)amino)-4-methoxyphenyl)-4-(piperidin-1-yl)but-2-enamide (Example 92);

N-(3-((5-chloro-4-((2-(dimethylphosphoryl)phenyl)amino)pyrimidin-2-yl)amino)-4-methoxyphenyl)-3-phenylpropiolamide (Example 93);

(E)-3-(1-aminocyclopropyl)-N-(3-((5-chloro-4-((2-(dimethylphosphoryl)phenyl)amino)pyrimidin-2-yl)amino)-4-methoxyphenyl)acrylamide (Example 94);

(E)-N-(3-((5-chloro-4-((2-(dimethylphosphoryl)phenyl)amino)pyrimidin-2-yl)amino)-4-methoxyphenyl)-4-(pyrrolidin-1-yl)but-2-enamide (Example 95);

N-(5-((5-chloro-4-((2-(dimethylphosphoryl)phenyl)amino)pyrimidin-2-yl)amino)-2-(3-(diethylamino)prop-1-yn-1-yl)-4-methoxyphenyl)acrylamide (Example 96);

N-(3-((5-chloro-4-((2-(dimethylphosphoryl)phenyl)amino)pyrimidin-2-yl)amino)-4-methoxyphenyl)-4-methoxybut-2-ynamide (Example 97);

N-(5-((5-chloro-4-((2-(dimethylphosphoryl)-4-(2-(pyrrolidin-1-yl)ethoxy)phenyl)amino)pyrimidin-2-yl)amino)-2-fluoro-4-methoxyphenyl)acrylamide (Example 98);

N-(3-((5-chloro-4-((2-(dimethylphosphoryl)-4-((tetrahydrofuran-3-yl)oxy)phenyl)amino)pyrimidin-2-yl)amino)-4-methoxyphenyl)acrylamide (Example 99);

N-(3-((5-chloro-4-((2-(dimethylphosphoryl)-4-((tetrahydro-2H-pyran-4-yl)methoxy)phenyl)amino)pyrimidin-2-yl)amino)-4-methoxyphenyl)acrylamide (Example 100);

N-(5-((5-chloro-4-((2-(dimethylphosphoryl)phenyl)amino)pyrimidin-2-yl)amino)-4-methoxy-2-morpholinophenyl)-5-(piperidin-1-yl)pent-2-ynamide (Example 101);

N-(5-((5-chloro-4-((2-(dimethylphosphoryl)phenyl)amino)pyrimidin-2-yl)amino-4-methoxy-2-((tetrahydro-2H-pyran-4-yl)methoxy)phenyl)but-2-ynamide (Example 102);

N-(5-((5-chloro-4-((2-(dimethylphosphoryl)phenyl)amino)pyrimidin-2-yl)amino)-4-methoxy-2-(oxetan-3-yloxy)phenyl)but-2-ynamide (Example 103);

N-(5-((5-chloro-4-((2-(dimethylphosphoryl)phenyl)amino)pyrimidin-2-yl)amino)-4-methoxy-2-morpholinophenyl)-4-(dimethylamino)but-2-ynamide (Example 104);

N-(5-((5-chloro-4-((2-(dimethylphosphoryl)phenyl)amino)pyrimidin-2-yl)amino)-4-methoxy-2-morpholinophenyl)-4-methoxybut-2-ynamide (Example 105);

N-(5-((5-chloro-4-((2-(dimethylphosphoryl)phenyl)amino)pyrimidin-2-yl)amino)-4-methoxy-2-(4-(4-methylpiperazin-1-yl)piperidin-1-yl)phenyl)but-2-ynamide (Example 106);

N-(4-((5-chloro-4-((2-(dimethylphosphoryl)-3-(2-(piperidin-1-yl)ethoxy)phenyl)amino)pyrimidin-2-yl)amino)-3-methoxyphenyl)acrylamide (Example 107);

N-(3-((5-chloro-4-((2-(dimethylphosphoryl)-4-(2-(piperidin-1yl)ethoxy)phenyl)amino)pyrimidin-2-yl)amino)-4-methoxyphenyl)acrylamide (Example 108);

N1-(3-((5-chloro-4-((2-(dimethylphosphoryl)phenyl)amino)pyrimidin-2-yl)amino)-4-methoxyphenyl)-N4-methylfumaramide (Example 109);

N1-(3-((5-chloro-4-((2-(dimethylphosphoryl)phenyl)amino)pyrimidin-2-yl)amino)-4-methoxyphenyl)-N4-methylmaleamide (Example 110);

N-(5-((5-chloro-4-((2-(dimethylphosphoryl)phenyl)amino)pyrimidin-2-yl)amino)-2-(3(dimethylamino)pyrrolidin-1-yl)-4-methoxyphenyl)-4-methoxybut-2-ynamide (Example 111);

N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)but-2-ynamide (Example 112);

rac-(R)-N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)methacrylamide (Example 113);

N-(5-((5-chloro-4-((2-(dimethylphosphoryl)phenyl)amino)pyrimidin-2-yl)amino)-4-methoxy-2-morpholinophenyl)-5-(dimethylamino)pent-2-ynamide (Example 114);

N-(5-((5-chloro-4-((2-(dimethylphosphoryl)phenyl)amino)pyrimidin-2-yl)amino)-4-methoxy-2-morpholinophenyl)-5-methoxypent-2-ynamide (Example 115);

N-(5-((5-chloro-4-((2-(dimethylphosphoryl)phenyl)amino)pyrimidin-2-yl)amino)-4-methoxy-2-(3-methyl-3-(pyrrolidin-1-yl)but-1-yn-1-yl)phenyl)acrylamide (Example 116);

N-(3-((5-chloro-4-((2-(dimethylphosphoryl)phenyl)amino)pyrimidin-2-yl)amino)-4-(2-(dimethylamino)ethoxy)phenyl)acrylamide (Example 117);

N-(5-((5-chloro-4-((2-(dimethylphosphoryl)phenyl)amino)pyrimidin-2-yl)amino)-4-methoxy-2-morpholinophenyl)-5-(4-methylpiperazin-1-yl)pent-2-ynamide (Example 118);

N-(5-((5-chloro-4-((2-(dimethylphosphoryl)phenyl)amino)pyrimidin-2-yl)amino)-4-methoxy-2-(pyrrolidin-1-yl)phenyl)-5-(4-methylpiperazin-1-yl)pent-2-ynamide (Example 119);

N-(5-((5-cyclopropyl-4-((2-(dimethylphosphoryl)phenyl)amino)pyrimidin-2-yl)amino)-2-((2-(diethylamino)ethyl)(methyl)amino)-4-methoxyphenyl)acrylamide (Example 120);

N-(5-((5-chloro-4-((2-(dimethylphosphoryl)phenyl)amino)pyrimidin-2-yl)amino)-2-((1-(diethylamino)-3-fluoropropan-2-yl)oxy)-4-methoxyphenyl)acrylamide (Example 121);

N-(5-((5-chloro-4-((2-(dimethylphosphoryl)phenyl)amino)pyrimidin-2-yl)amino)-4-methoxy-2-morpholinophenyl)-5-(2-(methoxymethyl)pyrrolidin-1-yl)pent-2-ynamide (Example 122);

N-(5-((5-chloro-4-((2-(dimethylphosphoryl)phenyl)amino)pyrimidin-2-yl)amino)-4-methoxy-2-((1-(2-methoxyethyl)piperidin-3-yl)oxy)phenyl)acrylamide (Example 123);

N-(5-((5-chloro-4-((2-(dimethylphosphoryl)phenyl)amino)pyrimidin-2-yl)amino)-2-(3-(dimethylamino)prop-1-yn-1-yl)-4-methoxyphenyl)acrylamide (Example 124);

N-(3-((5-chloro-4-((4-(2-(dimethylamino)ethoxy)-2(dimethylphosphoryl)phenyl)amino)pyrimidin-2-yl)amino)-4-methoxyphenyl)acrylamide (Example 125);

N-(3-((5-chloro-4-((4-(3-(dimethylamino)propoxy)-2-(dimethylphosphoryl)phenyl)amino)pyrimidin-2-yl)amino)-4-methoxyphenyl)acrylamide (Example 126);

1-(6-((5-chloro-4-((2-(dimethylphosphoryl)phenyl)amino)pyrimidin-2-yl)amino)-5-methoxylndolin-1-yl)prop-2-en-1-one (Example 127);

N-(5-((5-chloro-4-((2-(dimethylphosphoryl)phenyl)amino)pyrimidin-2-yl)amino)-2-(4-(dimethylamino)but-1-yn-1-yl)-4-methoxyphenyl)acrylamide (Example 128);

(R)-N-(5-((5-chloro-4-((2-(dimethylphosphoryl)phenyl)amino)pyrimidin-2-yl)amino)-2-((1-(dimethylamino)-3-methoxypropan-2-yl)oxy)-4-methoxyphenyl)acrylamide (Example 129);

N-(5-((5-chloro-4-((2-(dimethylphosphoryl)phenyl)amino)pyrimidin-2-yl)amino)-2-((1-(dimethylamino)-3-methoxypropan-2-yl)oxy)-4-methoxyphenyl)acrylamide (Example 130);

N-(3-((4-((2-(dimethylphosphoryl)phenyl)amino)-5-methoxypyrimidin-2-yl)amino)-4-methoxyphenyl)acrylamide (Example 131);

2-chloro-N-(3-((5-chloro-4-((2-(dimethylphosphoryl)phenyl)amino)pyrimidin-2-yl)amino)-4methoxyphenyl)acrylamide (Example 132);

N-(5-((5-chloro-4-((2-(dimethylphosphoryl)phenyl)amino)pyrimidin-2-yl)amino)-4-methoxy-2-methylphenyl)acrylamide (Example 133);

N-(3-((5-chloro-4-((2-(dimethylphosphoryl)phenyl)amino)pyrimidin-2-yl)amino)-4-(trifluoromethoxy)phenyl)acrylamide (Example 134);

N-(3-((5-chloro-4-((2-(dimethylphosphoryl)phenyl)amino)pyrimidin-2-yl)amino)-4-ethylphenyl)acrylamide (Example 135);

N-(4-chloro-3-((5-chloro-4-((2-(dimethylphosphoryl)phenyl)amino)pyrimidin-2yl)amino)phenyl)acrylamide (Example 136);

2-chloro-N-(3-((5-chloro-4-((2-(dimethylphosphoryl)phenyl)amino)pyrimidin-2-yl)amino)-4-methoxyphenyl)acetamide (Example 137);

N-(3-((5-chloro-4-((2-(dimethylphosphoryl)phenyl)amino)pyrimidin-2-yl)amino)-4-(oxetan-3-yloxy)phenyl)acrylamide (Example 138);

N-(3-((5-cyano-4-((2-(dimethylphosphoryl)phenyl)amino)pyrimidin-2-yl)amino)-4-methoxyphenyl)acrylamide (Example 139);

2-chloro-N-(5-((5-chloro-4-((2-(dimethylphosphoryl)phenyl)amino)pyrimidin-2-yl)amino)-4-methoxy-2-methylphenyl)acetamide (Example 140);

2-chloro-N-(3-((4-((2-(dimethylphosphoryl)phenyl)amino)-5-methylpyrimidin-2-yl)amino)-4-methoxyphenyl)acetamide (Example 141);

N-(5-((5-chloro-4-((2-(dimethylphosphoryl)phenyl)amino)pyrimidin-2-yl)amino)-2-((1-(dimethylamino)-3-ethoxypropan-2-yl)oxy)-4-methoxyphenyl)acrylamide (Example 142);

N-(5-((5-chloro-4-((2-(dimethylphosphoryl)phenyl)amino)pyrimidin-2-yl)amino)-2-((1-(dimethylamino)-3-methoxypropan-2-yl)oxy)-4-methylphenyl)acrylamide (Example 143);

N-(5-((5-chloro-4-((2-(dimethylphosphoryl)phenyl)amino)pyrimidin-2-yl)amino)-2-((1-(dimethylamino)-3-methoxypropan-2-yl)oxy)-4-methylphenyl)acrylamide (Example 144);

N-(4-chloro-5-((5-chloro-4-((2-(dimethylphosphoryl)phenyl)amino)pyrimidin-2-yl)amino)-2-((1-(dimethylamino)-3-methoxypropan-2-yl)oxy)phenyl)acrylamide (Example 145);

N-(4-chloro-5-((5-chloro-4-((2-(dimethylphosphoryl)phenyl)amino)pyrimidin-2-yl)amino)-2-((1-(dimethylamino)-3-methoxypropan-2-yl)oxy)phenyl)acrylamide (Example 146);

N-(3-((5-chloro-4-((2-(dimethylphosphoryl)phenyl)amino)pyrimidin-2-yl)amino)-4-methoxyphenyl)-2-fluoroacetamide (Example 147);

2-chloro-N-(3-((5-chloro-4-((2-(dimethylphosphoryl)phenyl)amino)pyrimidin-2-yl)amino)-4-methylphenyl)acetamide (Example 148);

2-chloro-N-(5-((5-chloro-4-((2-(dimethylphosphoryl)phenyl)amino)pyrimidin-2-yl)amino)-2-fluoro-4-methoxyphenyl)acetamide (Example 149);

1-chloro-N-(3-((5-chloro-4-((2-(dimethylphosphoryl)phenyl)amino)pyrimidin-2-yl)amino)-4-methoxyphenyl)methanesulfonamide (Example 150);

N-(5-((5-chloro-4-((2-(dimethylphosphoryl)phenyl)amino)pyrimidin-2-yl)amino)-2-(3-(dimethylamino)prop-1-yn-1-yl)-4-methylphenyl)acrylamide (Example 151);

N-(5-((5-chloro-4-((2-(dimethylphosphoryl)phenyl)amino)pyrimidin-2-yl)amino)-2-(3-(dimethylamino)prop-1-yn-1-yl)-4-ethylphenyl)acrylamide (Example 152);

N-(5-((5-chloro-4-((2-(isopropylsulfonyl)phenyl)amino)pyrimidin-2-yl)amino)-2-(3-(dimethylamino)prop-1-yn-1-yl)-4-methoxyphenyl)acrylamide (Example 153);

N-(5-((5-chloro-4-((2-(dimethylphosphoryl)phenyl)amino)pyrimidin-2-yl)amino)-2-(3-(diethylamino)-3-methylbut-1-yn-1-yl)-4-methoxyphenyl)acrylamide (Example 154);

N-(5-((5-chloro-4-((2-(dimethylphosphoryl)phenyl)amino)pyrimidin-2-yl)amino)-2-(3-(dimethylamino)-3-methylbut-1-yn-1-yl)-4-methoxyphenyl)acrylamide (Example 155);

N-(4-chloro-5-((5-chloro-4-((2-(dimethylphosphoryl)phenyl)amino)pyrimidin-2-yl)amino)-2-(3-(dimethylamino)prop-1-yn-1-yl)phenyl)acrylamide (Example 156);

N-(5-((5-chloro-4-((2-(dimethylphosphoryl)phenyl)amino)pyrimidin-2-yl)amino)-4-methoxy-2-(3-(pyrrolidin-1-yl)prop-1-yn-1-yl)phenyl)acrylamide (Example 157);

N-(5-((5-chloro-4-((2-(dimethylphosphoryl)phenyl)amino)pyrimidin-2-yl)amino)-2-(3-(diisopropylamino)prop-1-yn-1-yl)-4-methoxyphenyl)acrylamide (Example 158);

N-(5-((5-chloro-4-((2-(dimethylphosphoryl)phenyl)amino)pyrimidin-2-yl)amino)-4-methoxy-2-(3-(4-methylpiperazin-1-yl)prop-1-yn-1-yl)phenyl)acrylamide (Example 159);

N-(5-((5-chloro-4-((2-(dimethylphosphoryl)phenyl)amino)pyrimidin-2-yl)amino)-4-methoxy-2-(3-(methylamino)prop-1-yn-1-yl)phenyl)acrylamide (Example 160);

N-(5-((5-chloro-4-((2-(dimethylphosphoryl)phenyl)amino)pyrimidin-2-yl)amino)-4-methoxy-2-(3-((2-methoxyethyl)(methyl)amino)prop-1-yn-1-yl)phenyl)acrylamide (Example 161);

N-(5-((5-chloro-4-((2-(dimethylphosphoryl)phenyl)amino)pyrimidin-2-yl)amino)-2-(3-(ethyl(methyl)amino)prop-1-yn-1-yl)-4-methoxyphenyl)acrylamide (Example 162);

N-(3-((6-((3-(dimethylphosphoryl)pyridin-2-yl)amino)pyrimidin-4-yl)amino)-4-methoxyphenyl)acrylamide (Example 163);

N-(3-((5-chloro-4-((4-(dimethylphosphoryl)pyridin-3-yl)amino)pyrimidin-2-yl)amino)-4-methoxyphenyl)acrylamide (Example 164);

N-(2-(3-(azepan-1-yl)prop-1-yn-1-yl)-5-((5-chloro-4-((2-(dimethylphosphoryl)phenyl)amino)pyrimidin-2-yl)amino)-4-methoxyphenyl)acrylamide (Example 165);

N-(5-((5-chloro-4-((2-(dimethylphosphoryl)phenyl)amino)pyrimidin-2-yl)amino)-2-(3-(isopropyl(methyl)amino)prop-1-yn-1-yl)-4-methoxyphenyl)acrylamide (Example 166);

N-(5-((5-chloro-4-((2-(dimethylphosphoryl)phenyl)amino)pyrimidin-2-yl)amino)-4-methoxy-2-(3-(piperidin-1-yl)prop-1-yn-1-yl)phenyl)acrylamide (Example 167);

N-(5-((5-chloro-4-((2-(dimethylphosphoryl)phenyl)amino)pyrimidin-2-yl)amino)-2-(3-(cyclopentyl(methyl)amino)prop-1-yn-1-yl)-4-methoxyphenyl)acrylamide (Example 168);

N-(3-((4-((2-(dimethylphosphoryl)phenyl)amino)-1,3,5-triazin-2-yl)amino)-4-methoxyphenyl)acrylamide (Example 169);

N-(3-((4-((2-(dimethylphosphoryl)phenyl)amino)-1,3,5-triazin-2-yl)amino)-4-(trifluoromethoxy)phenyl)acrylamide (Example 170);

N-(3-((6-((2-(dimethylphosphoryl)phenyl)amino)pyrimidin-4-yl)amino)-4-methoxyphenyl)acrylamide (Example 171);

(1S,2R,3S,4R)-3-((2-((5-acrylamido-2-methoxyphenyl)amino)-5-chloropyrimidin-4-yl)amino)bicyclo[2.2.1]heptane-2-carboxamide (Example 172);

2-((2-((5-acrylamido-4-(3-(dimethylamino)pyrrolidin-1-yl)-2-methoxyphenyl)amino)-5-chloropyrimidin-4-yl)amino)benzamide (Example 173);

N-(5-((5-chloro-4-((2-cyanophenyl)amino)pyrimidin-2-yl)amino)-2-(3-(dimethylamino)pyrrolidin-1-yl)-4-methoxyphenyl)acrylamide (Example 174);

N-(5-((5-chloro-4-((2-(isopropylsulfonyl)phenyl)amino)pyrimidin-2-yl)amino)-2-(3-(dimethylamino)pyrrolidin-1-yl)-4-methoxyphenyl)acrylamide (Example 175);

N-(5-((5-chloro-4-((2-(dimethylphosphoryl)phenyl)amino)pyrimidin-2-yl)methyl)-4-methoxy-2-(3-(4-methylpiperidin-1-yl)prop-1-yn-1-yl)phenyl)acrylamide (Example 176);

N-(2-(3-(tert-butyl(methyl)amino)prop-1-yn-1-yl)-5-((5-chloro-4-((2-(dimethylphosphoryl)phenyl)amino)pyrimidin-2-yl)methyl)-4-methoxyphenyl)acrylamide (Example 177);

N-(5-((5-chloro-4-((2-(dimethylphosphoryl)phenyl)amino)pyrimidin-2-yl)methyl)-2-(3-(2-(dimethylamino)pyrrolidin-1-yl)prop-1-yn-1-yl)-4-methoxyphenyl)acrylamide (Example 178);

N-(5-((5-chloro-4-((2-(dimethylphosphoryl)phenyl)amino)pyrimidin-2-yl)methyl)-4-methoxy-2-(3-(2-methylpiperidin-1-yl)prop-1-yn-1-yl)phenyl)acrylamide (Example 179);

(Z)-N-(5-((5-chloro-4-((2-(dimethylphosphoryl)phenyl)amino)pyrimidin-2-yl)methyl)-2-(3-(dimethylamino)prop-1-en-1-yl)-4-methoxyphenyl)acrylamide (Example 180);

(E)-N-(5-((5-chloro-4-((2-(dimethylphosphoryl)phenyl)amino)pyrimidin-2-yl)methyl)-2-(3-(dimethylamino)prop-1-en-1-yl)-4-methoxyphenyl)acrylamide (Example 181);

N-(5-((5-chloro-4-((2-(dimethylphosphoryl)phenyl)amino)pyrimidin-2-yl)methyl)-2-(3-(4-fluoropiperidin-1-yl)prop-1-yn-1-yl)-4-methoxyphenyl)acrylamide (Example 182);

N-(5-((5-chloro-4-((2-(dimethylphosphoryl)phenyl)amino)pyrimidin-2-yl)methyl)-4-methoxy-2-(3-(methyl(tetrahydro-2H-pyran-4-yl)amino)prop-1-yn-1-yl)phenyl)acrylamide (Example 183);

N-(5-((5-chloro-4-((2-(dimethylphosphoryl)phenyl)amino)pyrimidin-2-yl)methyl)-2-(3-(dimethylamino)prop-1-yn-1-yl)-4-methoxyphenyl)but-2-ynamide (Example 184); and N-(3-((5-chloro-2-(2-methoxy-4-(1-methyl-4-oxido-1,4-azaphosphinan-4-yl)benzyl)pyrimidin-4-yl)oxy)phenyl)acrylamide (Example 185);

or a pharmaceutically acceptable salt thereof.

7. The compound of claim 6, selected from the group consisting of:

N-(5-((5-chloro-4-((2-(dimethylphosphoryl)phenyl)amino)pyrimidin-2-yl)amino)-4-methoxy-2-(2-(pyrrolidin-1-yl)ethoxy)phenyl)acrylamide (Example 1);

N-(5-((5-chloro-4-((2-(dimethylphosphoryl)phenyl)amino)pyrimidin-2-yl)amino)-4-methoxy-2-((1-methylpiperidin-2-yl)methoxy)phenyl)acrylamide (Example 7);

N-(5-((5-chloro-4-((2-(dimethylphosphoryl)phenyl)amino)pyrimidin-2-yl)amino)-4-methoxy-2-(2-(piperidin-1-yl)ethoxy)phenyl)acrylamide (Example 8);

N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide (Example 12);

N-(5-((5-chloro-4-((2-(dimethylphosphoryl)phenyl)amino)pyrimidin-2-yl)amino)-4-methoxy-2-((1-methylpyrrolidin-3-yl)oxy)phenyl)acrylamide (Example 13);

rel-(R)-N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide (Example 14);

N-(2-((1-(azetidin-1-yl)-3-methoxypropan-2-yl)oxy)-5-((5-chloro-4-((2-(dimethylphosphoryl)phenyl)amino)pyrimidin-2-yl)amino)-4-methoxyphenyl)acrylamide (Example 15);

rel-(R)-N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide (Example 16);

N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)acrylamide (Example 24);

N-(5-((5-chloro-4-((2-(dimethylphosphoryl)phenyl)amino)pyrimidin-2-yl)amino)-4-methoxy-2-(4-methyl-1,4-diazepan-1-yl)phenyl)acrylamide (Example 25);

rac-(R)-N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)acrylamide (Example 26);

N-(5-((5-chloro-4-((2-(dimethylphosphoryl)phenyl)amino)pyrimidin-2-yl)amino)-4-methoxy-2-(3-morpholinopyrrolidin-1-yl)phenyl)acrylamide (Example 28);

rac-(R)-N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)acrylamide (Example 29);

N-(5-((5-chloro-4-((2-(dimethylphosphoryl)phenyl)amino)pyrimidin-2-yl)amino)-2-(3-(dimethylamino)piperidin-1-yl)-4-methoxyphenyl)acrylamide (Example 30);

N-(5-((5-chloro-4-((2-(dimethylphosphoryl)phenyl)amino)pyrimidin-2-yl)amino)-4-methoxy-2-(3-(pyrrolidin-1-yl)azetidin-1-yl)phenyl)acrylamide (Example 31);

N-(5-((5-chloro-4-((2-(dimethylphosphoryl)phenyl)amino)pyrimidin-2-yl)amino)-4-methoxy-2-(3-(piperidin-1-yl)pyrrolidin-1-yl)phenyl)acrylamide (Example 33);

N-(5-((5-chloro-4-((2-(dimethylphosphoryl)phenyl)amino)pyrimidin-2-yl)amino)-2-(3-(diethylamino)pyrrolidin-1-yl)-4-methoxyphenyl)acrylamide (Example 34);

N-(2-([1,3'-bipyrrolidin]-1'-yl)-5-((5-chloro-4-((2-(dimethylphosphoryl)phenyl)amino)pyrimidin-2-yl)amino)-4-methoxyphenyl)acrylamide (Example 36);

N-(5-((5-chloro-4-((2-(dimethylphosphoryl)phenyl)amino)pyrimidin-2-yl)amino)-4-methoxy-2-(3-((2-methoxyethyl)(methyl)amino)pyrrolidin-1-yl)phenyl)acrylamide (Example 41);

N-(3-((5-chloro-4-((2-(dimethylphosphoryl)phenyl)amino)pyrimidin-2-yl)amino)-4-methoxyphenyl)-2-(pyrrolidin-1-ylmethyl)acrylamide (Example 42);

N-(3-((5-chloro-4-((2-(dimethylphosphoryl)phenyl)amino)pyrimidin-2-yl)amino)-4-methoxyphenyl)-2-(piperidin-1-ylmethyl)acrylamide (Example 43);

N-(3-((5-chloro-4-((2-(dimethylphosphoryl)phenyl)amino)pyrimidin-2-yl)amino)-4-methoxyphenyl)-2-((4-(methylsulfonyl)piperazin-1-yl)methyl)acrylamide (Example 44);

N-(3-((5-chloro-4-((2-(dimethylphosphoryl)phenyl)amino)pyrimidin-2-yl)amino)-4-methoxyphenyl)-2-((4-(4-methylpiperazin-1-yl)piperidin-1-yl)methyl)acrylamide (Example 45);

N-(3-((5-chloro-4-((2-(dimethylphosphoryl)phenyl)amino)pyrimidin-2-yl)amino)-4-methoxyphenyl)-2-(morpholinomethyl)acrylamide (Example 48);

N-(3-((5-chloro-4-((2-(dimethylphosphoryl)phenyl)amino)pyrimidin-2-yl)amino)-4-methoxyphenyl)-2-((4-methylpiperazin-1-yl)methyl)acrylamide (Example 49);

N-(3-((5-chloro-4-((2-(dimethylphosphoryl)phenyl)amino)pyrimidin-2-yl)amino)-4-methoxyphenyl)-2-((4-morpholinopiperidin-1-yl)methyl)acrylamide (Example 51);

N-(3-((5-chloro-4-((2-(dimethylphosphoryl)phenyl)amino)pyrimidin-2-yl)amino)-4-methoxyphenyl)-2-((4-(2-hydroxyethyl)piperazin-1-yl)methyl)acrylamide (Example 52);

N-(3-((5-chloro-4-((2-(dimethylphosphoryl)phenyl)amino)pyrimidin-2-yl)amino)-4-methoxyphenyl)-2-((3-hydroxypyrrolidin-1-yl)methyl)acrylamide (Example 53);

N-(2-(3-amino-3-methylbut-1-yn-1-yl)-5-((5-chloro-4-((2-(dimethylphosphoryl)phenyl)amino)pyrimidin-2-yl)amino)-4-methoxyphenyl)acrylamide (Example 65);

N-(5-((5-chloro-4-((2-(dimethylphosphoryl)phenyl)amino)pyrimidin-2-yl)amino)-2-((2-((2-fluoroethyl)(methyl)amino)ethyl)(methyl)amino)-4-methoxyphenyl)acrylamide (Example 67);

N-(2-(3-(azetidin-1-yl)pyrrolidin-1-yl)-5-((5-chloro-4-((2-(dimethylphosphoryl)phenyl)amino)pyrimidin-2-yl)amino)-4-methoxyphenyl)acrylamide (Example 68);

N-(2-([1,4'-bipiperidin]-1'-yl)-5-((5-chloro-4-((2-(dimethylphosphoryl)phenyl)amino)pyrimidin-2-yl)amino)-4-methoxyphenyl)acrylamide (Example 69);

N-(5-((5-chloro-4-((2-(dimethylphosphoryl)phenyl)amino)pyrimidin-2-yl)amino)-4-methoxy-2-(4-morpholinopiperidin-1-yl)phenyl)acrylamide (Example 70);

(E)-ethyl 4-((3-((5-chloro-4-((2-(dimethylphosphoryl)phenyl)amino)pyrimidin-2-yl)amino)-4-methoxyphenyl)amino)-4-oxobut-2-enoate (Example 75);

(E)-3-chloro-N-(3-((5-chloro-4-((2-(dimethylphosphoryl)phenyl)amino)pyrimidin-2-yl)amino)-4-methoxyphenyl)acrylamide (Example 78);

N-(3-((5-chloro-4-((2-(dimethylphosphoryl)phenyl)amino)pyrimidin-2-yl)amino)-4-methoxyphenyl)-4-(dimethylamino)but-2-ynamide (Example 81);

(E)-3-chloro-N-(5-((5-chloro-4-((2-(dimethylphosphoryl)phenyl)amino)pyrimidin-2-yl)amino)-2-fluoro-4-methoxyphenyl)acrylamide (Example 85);

N-(5-((5-chloro-4-((2-(dimethylphosphoryl)phenyl)amino)pyrimidin-2-yl)amino)-2-fluoro-4-methoxyphenyl)-4-(dimethylamino)but-2-ynamide (Example 87);

N-(5-((5-chloro-4-((2-(dimethylphosphoryl)phenyl)amino)pyrimidin-2-yl)amino)-2-fluoro-4-methoxyphenyl)-5-(piperidin-1-yl)pent-2-ynamide (Example 88);

N-(5-((5-chloro-4-((2-(dimethylphosphoryl)phenyl)amino)pyrimidin-2-yl)amino)-2-fluoro-4-methoxyphenyl)-4-(pyrrolidin-1-yl)but-2-ynamide (Example 89);

N-(5-((5-chloro-4-((2-(dimethylphosphoryl)phenyl)amino)pyrimidin-2-yl)amino)-2-fluoro-4-methoxyphenyl)-4-methyl-4-(pyrrolidin-1-yl)pent-2-ynamide (Example 90);

N-(3-((5-chloro-4-((2-(dimethylphosphoryl)phenyl)amino)pyrimidin-2-yl)amino)-4-methoxyphenyl)-4-methyl-4-(pyrrolidin-1-yl)pent-2-ynamide (Example 91);

(E)-N-(3-((5-chloro-4-((2-(dimethylphosphoryl)phenyl)amino)pyrimidin-2-yl)amino)-4-methoxyphenyl)-4-(piperidin-1-yl)but-2-enamide (Example 92);

N-(3-((5-chloro-4-((2-(dimethylphosphoryl)phenyl)amino)pyrimidin-2-yl)amino)-4-methoxyphenyl)-4-methoxybut-2-ynamide (Example 97);

N-(5-((5-chloro-4-((2-(dimethylphosphoryl)-4-(2-(pyrrolidin-1-yl)ethoxy)phenyl)amino)pyrimidin-2-yl)amino)-2-fluoro-4-methoxyphenyl)acrylamide (Example 98);

N-(5-((5-chloro-4-((2-(dimethylphosphoryl)phenyl)amino)pyrimidin-2-yl)amino)-4-methoxy-2-morpholinophenyl)-5-(piperidin-1-yl)pent-2-ynamide (Example 101);

N-(5-((5-chloro-4-((2-(dimethylphosphoryl)phenyl)amino)pyrimidin-2-yl)amino)-4-methoxy-2-morpholinophenyl)-4-(dimethylamino)but-2-ynamide (Example 104);

N-(5-((5-chloro-4-((2-(dimethylphosphoryl)phenyl)amino)pyrimidin-2-yl)amino)-4-methoxy-2-morpholinophenyl)-4-methoxybut-2-ynamide (Example 105);

N-(3-((5-chloro-4-((2-(dimethylphosphoryl)-4-(2-(piperidin-1-yl)ethoxy)phenyl)amino)pyrimidin-2-yl)amino)-4-methoxyphenyl)acrylamide (Example 108);

N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)-4-methoxybut-2-ynamide (Example 111);

N-(5-((5-chloro-4-((2-(dimethylphosphoryl)phenyl)amino)pyrimidin-2-yl)amino)-4-methoxy-2-morpholinophenyl)-5-(dimethylamino)pent-2-ynamide (Example 114);

N-(5-((5-chloro-4-((2-(dimethylphosphoryl)phenyl)amino)pyrimidin-2-yl)amino)-4-methoxy-2-morpholinophenyl)-5-methoxypent-2-ynamide (Example 115);

N-(5-((5-chloro-4-((2-(dimethylphosphoryl)phenyl)amino)pyrimidin-2-yl)amino)-4-methoxy-2-morpholinophenyl)-5-(4-methylpiperazin-1-yl)pent-2-ynamide (Example 118);

N-(5-((5-cyclopropyl-4-((2-(dimethylphosphoryl)phenyl)amino)pyrimidin-2-yl)amino)-2-((2-(diethylamino)ethyl)(methyl)amino)-4-methoxyphenyl)acrylamide (Example 120);

N-(5-((5-chloro-4-((2-(dimethylphosphoryl)phenyl)amino)pyrimidin-2-yl)amino)-2-((1-(diethylamino)-3-fluoropropan-2-yl)oxy)-4-methoxyphenyl)acrylamide (Example 121);

N-(5-((5-chloro-4-((2-(dimethylphosphoryl)phenyl)amino)pyrimidin-2-yl)amino)-4-methoxy-2-morpholinophenyl)-5-(2-(methoxymethyl)pyrrolidin-1-yl)pent-2-ynamide (Example 122);

N-(5-((5-chloro-4-((2-(dimethylphosphoryl)phenyl)amino)pyrimidin-2-yl)amino)-4-methoxy-2-((1-(2-methoxyethyl)piperidin-3-yl)oxy)phenyl)acrylamide (Example 123);

N-(5-((5-chloro-4-((2-(dimethylphosphoryl)phenyl)amino)pyrimidin-2-yl)amino)-2-(3-(dimethylamino)prop-1-yn-1-yl)-4-methoxyphenyl)acrylamide (Example 124);

N-(3-((5-chloro-4-((4-(2-(dimethylamino)ethoxy)-2-(dimethylphosphoryl)phenyl)amino)pyrimidin-2-yl)amino)-4-methoxyphenyl)acrylamide (Example 125);

N-(3-((5-chloro-4-((4-(3-(dimethylamino)propoxy)-2-(dimethylphosphoryl)phenyl)amino)pyrimidin-2-yl)amino)-4-methoxyphenyl)acrylamide (Example 126);

N-(5-((5-chloro-4-((2-(dimethylphosphoryl)phenyl)amino)pyrimidin-2-yl)amino)-2-(4-(dimethylamino)but-1-yn-1-yl)-4-methoxyphenyl)acrylamide (Example 128);

(R)-N-(5-((5-chloro-4-((2-(dimethylphosphoryl)phenyl)amino)pyrimidin-2-yl)amino)-2-((1-(dimethylamino)-3-methoxypropan-2-yl)oxy)-4-methoxyphenyl)acrylamide (Example 129);

N-(5-((5-chloro-4-((2-(dimethylphosphoryl)phenyl)amino)pyrimidin-2-yl)amino)-4-methoxy-2-methylphenyl)acrylamide (Example 133);

N-(3-((5-chloro-4-((2-(dimethylphosphoryl)phenyl)amino)pyrimidin-2-yl)amino)-4-(trifluoromethoxy)phenyl)acrylamide (Example 134);

N-(3-((5-chloro-4-((2-(dimethylphosphoryl)phenyl)amino)pyrimidin-2-yl)amino)-4-ethylphenyl)acrylamide (Example 135);

N-(4-chloro-3-((5-chloro-4-((2-(dimethylphosphoryl)phenyl)amino)pyrimidin-2yl)amino)phenyl)acrylamide (Example 136);

2-chloro-N-(3-((5-chloro-4-((2-(dimethylphosphoryl)phenyl)amino)pyrimidin-2-yl)amino)-4-methoxyphenyl)acetamide (Example 137);

2-chloro-N-(5-((5-chloro-4-((2-(dimethylphosphoryl)phenyl)amino)pyrimidin-2-yl)amino)-4-methoxy-2-methylphenyl)acetamide (Example 140);

2-chloro-N-(3-((4-((2-(dimethylphosphoryl)phenyl)amino)-5-methylpyrimidin-2-yl)amino)-4-methoxyphenyl)acetamide (Example 141);

N-(5-((5-chloro-4-((2-(dimethylphosphoryl)phenyl)amino)pyrimidin-2-yl)amino)-2-((1-(dimethylamino)-3-ethoxypropan-2-yl)oxy)-4-methoxyphenyl)acrylamide (Example 142);

N-(5-((5-chloro-4-((2-(dimethylphosphoryl)phenyl)amino)pyrimidin-2-yl)amino)-2-((1-(dimethylamino)-3-methoxypropan-2-yl)oxy)-4-methylphenyl)acrylamide (Example 143);

N-(5-((5-chloro-4-((2-(dimethylphosphoryl)phenyl)amino)pyrimidin-2-yl)amino)-2-((1-(dimethylamino)-3-methoxypropan-2-yl)oxy)-4-methylphenyl)acrylamide (Example 144);

N-(4-chloro-5-((5-chloro-4-((2-(dimethylphosphoryl)phenyl)amino)pyrimidin-2-yl)amino)-2-((1-(dimethylamino)-3-methoxypropan-2-yl)oxy)phenyl)acrylamide (Example 145);

N-(4-chloro-5-((5-chloro-4-((2-(dimethylphosphoryl)phenyl)amino)pyrimidin-2-yl)amino)-2-((1-(dimethylamino)-3-methoxypropan-2-yl)oxy)phenyl)acrylamide (Example 146);

2-chloro-N-(3-((5-chloro-4-((2-(dimethylphosphoryl)phenyl)amino)pyrimidin-2-yl)amino)-4-methylphenyl)acetamide (Example 148);

2-chloro-N-(5-((5-chloro-4-((2-(dimethylphosphoryl)phenyl)amino)pyrimidin-2-yl)amino)-2-fluoro-4-methoxyphenyl)acetamide (Example 149);

N-(5-((5-chloro-4-((2-(dimethylphosphoryl)phenyl)amino)pyrimidin-2-yl)amino)-2-(3-(dimethylamino)prop-1-yn-1-yl)-4-methylphenyl)acrylamide (Example 151);

N-(5-((5-chloro-4-((2-(dimethylphosphoryl)phenyl)amino)pyrimidin-2-yl)amino)-2-(3-(dimethylamino)prop-1-yn-1-yl)-4-ethylphenyl)acrylamide (Example 152);

N-(5-((5-chloro-4-((2-(isopropylsulfonyl)phenyl)amino)pyrimidin-2-yl)amino)-2-(3-(dimethylamino)prop-1-yn-1-yl)-4-methoxyphenyl)acrylamide (Example 153);

N-(5-((5-chloro-4-((2-(dimethylphosphoryl)phenyl)amino)pyrimidin-2-yl)amino)-2-(3-(diethylamino)-3-methylbut-1-yn-1-yl)-4-methoxyphenyl)acrylamide (Example 154);

N-(5-((5-chloro-4-((2-(dimethylphosphoryl)phenyl)amino)pyrimidin-2-yl)amino)-2-(3-(dimethylamino)-3-methylbut-1-yn-1-yl)-4-methoxyphenyl)acrylamide (Example 155);

N-(4-chloro-5-((5-chloro-4-((2-(dimethylphosphoryl)phenyl)amino)pyrimidin-2-yl)amino)-2-(3-(dimethylamino)prop-1-yn-1-yl)phenyl)acrylamide (Example 156);

N-(5-((5-chloro-4-((2-(dimethylphosphoryl)phenyl)amino)pyrimidin-2-yl)amino)-4-methoxy-2-(3-(pyrrolidin-1-yl)prop-1-yn-1-yl)phenyl)acrylamide (Example 157);

N-(5-((5-chloro-4-((2-(dimethylphosphoryl)phenyl)amino)pyrimidin-2-yl)amino)-2-(3-(diisopropylamino)prop-1-yn-1-yl)-4-methoxyphenyl)acrylamide (Example 158);

N-(5-((5-chloro-4-((2-(dimethylphosphoryl)phenyl)amino)pyrimidin-2-yl)amino)-4-methoxy-2-(3-(methylamino)prop-1-yn-1-yl)phenyl)acrylamide (Example 160);

N-(5-((5-chloro-4-((2-(dimethylphosphoryl)phenyl)amino)pyrimidin-2-yl)amino)-4-methoxy-2-(3-((2-methoxyethyl)(methyl)amino)prop-1-yn-1-yl)phenyl)acrylamide (Example 161);

N-(5-((5-chloro-4-((2-(dimethylphosphoryl)phenyl)amino)pyrimidin-2-yl)amino)-2-(3-(ethyl(methyl)amino)prop-1-yn-1-yl)-4-methoxyphenyl)acrylamide (Example 162);

N-(2-(3-(azepan-1-yl)prop-1-yn-1-yl)-5-((5-chloro-4-((2-(dimethylphosphoryl)phenyl)amino)pyrimidin-2-yl)amino)-4-methoxyphenyl)acrylamide (Example 165);

N-(5-((5-chloro-4-((2-(dimethylphosphoryl)phenyl)amino)pyrimidin-2-yl)amino)-2-(3-(isopropyl(methyl)amino)prop-1-yn-1-yl)-4-methoxyphenyl)acrylamide (Example 166);

N-(5-((5-chloro-4-((2-(dimethylphosphoryl)phenyl)amino)pyrimidin-2-yl)amino)-4-methoxy-2-(3-(piperidin-1-yl)prop-1-yn-1-yl)phenyl)acrylamide (Example 167); and N-(5-((5-chloro-4-((2-(dimethylphosphoryl)phenyl)amino)pyrimidin-2-yl)amino)-2-(3-(cyclopentyl(methyl)amino)prop-1-yn-1-yl)-4-methoxyphenyl)acrylamide (Example 168);

or a pharmaceutically acceptable salt thereof.

8. The compound of claim 6, selected from the group consisting of:

N-(2-(3-amino-3-methylbut-1-yn-1-yl)-5-((5-chloro-4-((2-(dimethylphosphoryl)phenyl)amino) pyrimidin-2-yl)amino)-4-methoxyphenyl)acrylamide (Example 65);

N-(5-((5-chloro-4-((2-(dimethylphosphoryl)phenyl)amino)pyrimidin-2-yl)amino)-2-((1-(dimethylamino)cyclopropyl)ethynyl)-4-methoxyphenyl)acrylamide (Example 73);

N-(5-((5-chloro-4-((2-(dimethylphosphoryl)phenyl)amino)pyrimidin-2-yl)amino)-4-methoxy-2-(3-methyl-3-(pyrrolidin-1-yl)but-1-yn-1-yl)phenyl)acrylamide (Example 116);

N-(5-((5-chloro-4-((2-(dimethylphosphoryl)phenyl)amino)pyrimidin-2-yl)amino)-2-(3-(dimethylamino)prop-1-yn-1-yl)-4-methoxyphenyl)acrylamide (Example 124);

N-(5-((5-chloro-4-((2-(dimethylphosphoryl)phenyl)amino)pyrimidin-2-yl)amino)-2-(4-(dimethylamino)but-1-yn-1-yl)-4-methoxyphenyl)acrylamide (Example 128);

N-(5-((5-chloro-4-((2-(dimethylphosphoryl)phenyl)amino)pyrimidin-2-yl)amino)-2-(3-(dimethylamino)prop-1-yn-1-yl)-4-methylphenyl)acrylamide (Example 151);

N-(5-((5-chloro-4-((2-(dimethylphosphoryl)phenyl)amino)pyrimidin-2-yl)amino)-2-(3-(dimethylamino)prop-1-yn-1-yl)-4-ethylphenyl)acrylamide (Example 152);

N-(5-((5-chloro-4-((2-(isopropylsulfonyl)phenyl)amino)pyrimidin-2-yl)amino)-2-(3-(dimethylamino)prop-1-yn-1-yl)-4-methoxyphenyl)acrylamide (Example 153);

N-(5-((5-chloro-4-((2-(dimethylphosphoryl)phenyl)amino)pyrimidin-2-yl)amino)-2-(3-(diethylamino)-3-methylbut-1-yn-1-yl)-4-methoxyphenyl)acrylamide (Example 154);

N-(5-((5-chloro-4-((2-(dimethylphosphoryl)phenyl)amino)pyrimidin-2-yl)amino)-2-(3-(dimethylamino)-3-methylbut-1-yn-1-yl)-4-methoxyphenyl)acrylamide (Example 155);

N-(4-chloro-5-((5-chloro-4-((2-(dimethylphosphoryl)phenyl)amino)pyrimidin-2-yl)amino)-2-(3-(dimethylamino)prop-1-yn-1-yl)phenyl)acrylamide (Example 156);

N-(5-((5-chloro-4-((2-(dimethylphosphoryl)phenyl)amino)pyrimidin-2-yl)amino)-4-methoxy-2-(3-(pyrrolidin-1-yl)prop-1-yn-1-yl)phenyl)acrylamide (Example 157);

N-(5-((5-chloro-4-((2-(dimethylphosphoryl)phenyl)amino)pyrimidin-2-yl)amino)-2-(3-(diisopropylamino)prop-1-yn-1-yl)-4-methoxyphenyl)acrylamide (Example 158);

N-(5-((5-chloro-4-((2-(dimethylphosphoryl)phenyl)amino)pyrimidin-2-yl)amino)-4-methoxy-2-(3-(4-methylpiperazin-1-yl)prop-1-yn-1-yl)phenyl)acrylamide (Example 159);

N-(5-((5-chloro-4-((2-(dimethylphosphoryl)phenyl)amino)pyrimidin-2-yl)amino)-4-methoxy-2-(3-(methylamino)prop-1-yn-1-yl)phenyl)acrylamide (Example 160);

N-(5-((5-chloro-4-((2-(dimethylphosphoryl)phenyl)amino)pyrimidin-2-yl)amino)-4-methoxy-2-(3-((2-methoxyethyl)(methyl)amino)prop-1-yn-1-yl)phenyl)acrylamide (Example 161);

N-(5-((5-chloro-4-((2-(dimethylphosphoryl)phenyl)amino)pyrimidin-2-yl)amino)-2-(3-(ethyl(methyl)amino)prop-1-yn-1-yl)-4-methoxyphenyl)acrylamide (Example 162);

N-(2-(3-(azepan-1-yl)prop-1-yn-1-yl)-5-((5-chloro-4-((2-(dimethylphosphoryl)phenyl)amino)pyrimidin-2-yl)amino)-4-methoxyphenyl)acrylamide (Example 165);

N-(5-((5-chloro-4-((2-(dimethylphosphoryl)phenyl)amino)pyrimidin-2-yl)amino)-2-(3-(isopropyl(methyl)amino)prop-1-yn-1-yl)-4-methoxyphenyl)acrylamide (Example 166);

N-(5-((5-chloro-4-((2-(dimethylphosphoryl)phenyl)amino)pyrimidin-2-yl)amino)-4-methoxy-2-(3-(piperidin-1-yl)prop-1-yn-1-yl)phenyl)acrylamide (Example 167);

N-(5-((5-chloro-4-((2-(dimethylphosphoryl)phenyl)amino)pyrimidin-2-yl)amino)-2-(3-(cyclopentyl(methyl)amino)prop-1-yn-1-yl)-4-methoxyphenyl)acrylamide (Example 168);

N-(5-((5-chloro-4-((2-(dimethylphosphoryl)phenyl)amino)pyrimidin-2-yl)methyl)-4-methoxy-2-(3-(4-methylpiperidin-1-yl)prop-1-yn-1-yl)phenyl)acrylamide (Example 176);

N-(2-(3-(tert-butyl(methyl)amino)prop-1-yn-1-yl)-5-((5-chloro-4-((2-(dimethylphosphoryl)phenypamino)pyrimidin-2-yl)methyl)-4-methoxyphenyl)acrylamide (Example 177);

N-(5-((5-chloro-4-((2-(dimethylphosphoryl)phenyl)amino)pyrimidin-2-yl)methyl)-2-(3-(2-(dimethylamino)pyrrolidin-1-yl)prop-1-yn-1-yl)-4-methoxyphenyl)acrylamide (Example 178);

N-(5-((5-chloro-4-((2-(dimethylphosphoryl)phenyl)amino)pyrimidin-2-yl)methyl)-4-methoxy-2-(3-(2-methylpiperidin-1-yl)prop-1-yn-1-yl)phenyl)acrylamide (Example 179);

N-(5-((5-chloro-4-((2-(dimethylphosphoryl)phenyl)amino)pyrimidin-2-yl)methyl)-2-(3-(4-fluoropiperidin-1-yl)prop-1-yn-1-yl)-4-methoxyphenyl)acrylamide (Example 182);

N-(5-((5-chloro-4-((2-(dimethylphosphoryl)phenyl)amino)pyrimidin-2-yl)methyl)-4-methoxy-2-(3-(methyl(tetrahydro-2H-pyran-4-yl)amino)prop-1-yn-1-yl)phenyl)acrylamide (Example 183); and N-(5-((5-chloro-4-((2-(dimethylphosphoryl)phenyl)amino)pyrimidin-2-yl)methyl)-2-(3-(dimethylamino)prop-1-yn-1-yl)-4-methoxyphenyl)but-2-ynamide (Example 184);

or a pharmaceutically acceptable salt thereof.

9. The compound of claim 6, wherein the compound is selected from:

N-(5-((5-chloro-4-((2-(dimethylphosphoryl)phenyl)amino)pyrimidin-2-yl)amino)-4-methoxy-2-(2-(pyrrolidin-1-yl)ethoxy)phenyl)acrylamide (Example 1);

N-(5-((5-chloro-4-((2-(dimethylphosphoryl)phenyl)amino)pyrimidin-2-yl)amino)-4-methoxy-2-(2-(4-methylpiperazin-1-yl)ethoxy)phenyl)acrylamide (Example 2);

N-(5-((5-chloro-4-((2-(dimethylphosphoryl)phenyl)amino)pyrimidin-2-yl)amino)-4-methoxy-2-((1-methylpiperidin-4-yl)methoxy)phenyl)acrylamide (Example 3);

N-(5-((5-chloro-4-((2-(dimethylphosphoryl)phenyl)amino)pyrimidin-2-yl)amino)-4-methoxy-2-(2-morpholinoethoxy)phenyl)acrylamide (Example 4);

N-(5-((5-chloro-4-((2-(dimethylphosphoryl)phenyl)amino)pyrimidin-2-yl)amino)-4-methoxy-2-(3-morpholinopropoxy)phenyl)acrylamide (Example 5);

N-(5-((5-chloro-4-((2-(dimethylphosphoryl)phenyl)amino)pyrimidin-2-yl)amino)-4-methoxy-2-((tetrahydro-2H-pyran-4-yl)methoxy)phenyl)acrylamide (Example 6);

N-(5-((5-chloro-4-((2-(dimethylphosphoryl)phenyl)amino)pyrimidin-2-yl)amino)-4-methoxy-2-((1-methylpiperidin-2-yl)methoxy)phenyl)acrylamide (Example 7);

N-(5-((5-chloro-4-((2-(dimethylphosphoryl)phenyl)amino)pyrimidin-2-yl)amino)-4-methoxy-2-(2-(piperidin-1-yl)ethoxy)phenyl)acrylamide (Example 8);

N-(5-((5-chloro-4-((2-(dimethylphosphoryl)phenyl)amino)pyrimidin-2-yl)amino)-4-methoxy-2-(pyridin-3-ylmethoxy)phenyl)acrylamide (Example 10);

N-(5-((5-chloro-4-((2-(dimethylphosphoryl)phenyl)amino)pyrimidin-2-yl)amino)-4-methoxy-2-(pyridin-4-ylmethoxy)phenyl)acrylamide (Example 11);

N-(5-((5-chloro-4-((2-(dimethylphosphoryl)phenyl)amino)pyrimidin-2-yl)amino)-4-methoxy-2-((1-methylpyrrolidin-2-yl)methoxy)phenyl)acrylamide (Example 18);

N-(5-((5-chloro-4-((2-(dimethylphosphoryl)phenyl)amino)pyrimidin-2-yl)amino)-4-methoxy-2-((1-methylpyrrolidin-3-yl)methoxy)phenyl)acrylamide (Example 20);

N-(5-((5-chloro-4-((2-(dimethylphosphoryl)phenyl)amino)pyrimidin-2-yl)amino)-4-methoxy-2-(2-(pyrrolidin-1-yl)ethoxy)phenyl)but-2-ynamide (Example 80);

N-(5-((5-chloro-4-((2-(dimethylphosphoryl)phenyl)amino)pyrimidin-2-yl)amino)-4-methoxy-2-morpholinophenyl)-5-(piperidin-1-yl)pent-2-ynamide (Example 101);

N-(5-((5-chloro-4-((2-(dimethylphosphoryl)phenyl)amino)pyrimidin-2-yl)amino)-4-methoxy-2-((tetrahydro-2H-pyran-4-yl)methoxy)phenyl)but-2-ynamide (Example 102);

or a pharmaceutically acceptable salt thereof.

10. The compound of claim 6, wherein the compound is selected from:

N-(5-((5-chloro-4-((2-(dimethylphosphoryl)phenyl)amino)pyrimidin-2-yl)amino)-4-methoxy-2-(oxetan-3-yloxy)phenyl)acrylamide (Example 9);

N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide (Example 12);

N-(5-((5-chloro-4-((2-(dimethylphosphoryl)phenyl)amino)pyrimidin-2-yl)amino)-4-methoxy-2-((1-methylpyrrolidin-3-yl)oxy)phenyl)acrylamide (Example 13);

rel-(R)-N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide (Example 14);

rel-(R)-N-(5-((5-chloro-4-((2-(dimethylphosphoryl)phenyl)amino)pyrimidin-2-yl)amino)-4-methoxy-2-((1-methylpiperidin-3-yl)oxy)phenyl)acrylamide (Example 16);

N-(5-((5-chloro-4-((2-(dimethylphosphoryl)phenyl)amino)pyrimidin-2-yl)amino)-4-methoxy-2-((1-methylazetidin-3-yl)oxy)phenyl)acrylamide (Example 17);

N-(5-((5-chloro-4-((2-(dimethylphosphoryl)phenyl)amino)pyrimidin-2-yl)amino)-4-methoxy-2-((4-methyl-1,4-oxazepan-6-yl)oxy)phenyl)acrylamide (Example 19);

N-(5-((5-chloro-4-((2-(dimethylphosphoryl)phenyl)amino)pyrimidin-2-yl)amino)-2-((2-(dimethylamino)cyclohexyl)oxy)-4-methoxyphenyl)acrylamide (Example 21);

N-(5-((5-chloro-4-((2-(dimethylphosphoryl)phenyl)amino)pyrimidin-2-yl)amino)-4-methoxy-2-(oxetan-3-yloxy)phenyl)but-2-ynamide (Example 103); and N-(5-((5-chloro-4-((2-(dimethylphosphoryl)phenyl)amino)pyrimidin-2-yl)amino)-4-methoxy-2-((1-(2-methoxyethyl)piperidin-3-yl)oxy)phenyl)acrylamide (Example 123);

or a pharmaceutically acceptable salt thereof.

11. The compound of claim 6, wherein the compound is selected from:

N-(5-((5-chloro-4-((2-(dimethylphosphoryl)phenyl)amino)pyrimidin-2-yl)amino)-4-methoxy-2-(4-(4-methylpiperazin-1-yl)piperidin-1-yl)phenyl)acrylamide (Example 22);

N-(5-((5-chloro-4-((2-(dimethylphosphoryl)phenyl)amino)pyrimidin-2-yl)amino)-2-(4-(dimethylamino)piperidin-1-yl)-4-methoxyphenyl)acrylamide (Example 23);

N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)acrylamide (Example 24);

N-(5-((5-chloro-4-((2-(dimethylphosphoryl)phenyl)amino)pyrimidin-2-yl)amino)-4-methoxy-2-(4-methyl-1,4-diazepan-1-yl)phenyl)acrylamide (Example 25);

rac-(R)-N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)acrylamide (Example 26);

N-(5-((5-chloro-4-((2-(dimethylphosphoryl)phenyl)amino)pyrimidin-2-yl)amino)-4-methoxy-2-(4-(1-methylpiperidin-4-yl)piperazin-1-yl)phenyl)acrylamide (Example 27);

N-(5-((5-chloro-4-((2-(dimethylphosphoryl)phenyl)amino)pyrimidin-2-yl)amino)-4-methoxy-2-(3-morpholinopyrrolidin-1-yl)phenyl)acrylamide (Example 28);

rac-(R)-N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)acrylamide (Example 29);

N-(5-((5-chloro-4-((2-(dimethylphosphoryl)phenyl)amino)pyrimidin-2-yl)amino)-2-(3-(dimethylamino)piperidin-1-yl)-4-methoxyphenyl)acrylamide (Example 30);

N-(5-((5-chloro-4-((2-(dimethylphosphoryl)phenyl)amino)pyrimidin-2-yl)amino)-4-methoxy-2-(3-(pyrrolidin-1-yl)azetidin-1-yl)phenyl)acrylamide (Example 31);

N-(5-((5-chloro-4-((2-(dimethylphosphoryl)phenyl)amino)pyrimidin-2-yl)amino)-2-(3-hydroxypyrrolidin-1-yl)-4-methoxyphenyl)acrylamide (Example 32);

N-(5-((5-chloro-4-((2-(dimethylphosphoryl)phenyl)amino)pyrimidin-2-yl)amino)-4-methoxy-2-(3-(piperidin-1-yl)pyrrolidin-1-yl)phenyl)acrylamide (Example 33);

N-(5-((5-chloro-4-((2-(dimethylphosphoryl)phenyl)amino)pyrimidin-2-yl)amino)-2-(3-(diethylamino)pyrrolidin-1-yl)-4-methoxyphenyl)acrylamide (Example 34);

N-(5-((5-chloro-4-((2-(dimethylphosphoryl)phenyl)amino)pyrimidin-2-yl)amino)-2-(3-hydroxy-[1,3'-bipyrrolidin]-1'-yl)-4-methoxyphenyl)acrylamide (Example 35);

N-(2-([1,3'-bipyrrolidin]-1'-yl)-5-((5-chloro-4-((2-(dimethylphosphoryl)phenyl)amino)pyrimidin-2-yl)amino)-4-methoxyphenyl)acrylamide (Example 36);

N-(5-((5-chloro-4-((2-(dimethylphosphoryl)phenyl)amino)pyrimidin-2-yl)amino)-4-methoxy-2-(3-(4-methylpiperazin-1-yl)pyrrolidin-1-yl)phenyl)acrylamide (Example 37);

N-(5-((5-chloro-4-((2-(dimethylphosphoryl)phenyl)amino)pyrimidin-2-yl)amino)-2-(3-((2-(diethylamino)ethyl)(methyl)amino)pyrrolidin-1-yl)-4-methoxyphenyl)acrylamide (Example 38);

N-(5-((5-chloro-4-((2-(dimethylphosphoryl)phenyl)amino)pyrimidin-2-yl)amino)-2-(3-(4-hydroxypiperidin-1-yl)pyrrolidin-1-yl)-4-methoxyphenyl)acrylamide (Example 39);

N-(5-((5-chloro-4-((2-(dimethylphosphoryl)phenyl)amino)pyrimidin-2-yl)amino)-2-(3-(4-(2-hydroxyethyl)piperazin-1-yl)pyrrolidin-1-yl)-4-methoxyphenyl)acrylamide (Example 40);

N-(5-((5-chloro-4-((2-(dimethylphosphoryl)phenyl)amino)pyrimidin-2-yl)amino)-4-methoxy-2-(3-((2-methoxyethyl)(methyl)amino)pyrrolidin-1-yl)phenyl)acrylamide (Example 41);

N-(5-((5-chloro-4-((2-(dimethylphosphoryl)phenyl)amino)pyrimidin-2-yl)amino)-4-methoxy-2-morpholinophenyl)-5-(piperidin-1-yl)pent-2-ynamide (Example 101);

N-(5-((5-chloro-4-((2-(dimethylphosphoryl)phenyl)amino)pyrimidin-2-yl)amino)-4-methoxy-2-morpholinophenyl)-4-(dimethylamino)but-2-ynamide (Example 104);

N-(5-((5-chloro-4-((2-(dimethylphosphoryl)phenyl)amino)pyrimidin-2-yl)amino)-4-methoxy-2-morpholinophenyl)-4-methoxybut-2-ynamide (Example 105);

N-(5-((5-chloro-4-((2-(dimethylphosphoryl)phenyl)amino)pyrimidin-2-yl)amino)-4-methoxy-2-(4-(4-methylpiperazin-1-yl)piperidin-1-yl)phenyl)but-2-ynamide (Example 106);

N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)-4-methoxybut-2-ynamide (Example 111);

N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)but-2-ynamide (Example 112);

rac-(R)-N-(5-((5-chloro-4-((2-(dimethylphosphoryl)phenyl)amino)pyrimidin-2-yl)amino)-2-(3-(dimethylamino)pyrrolidin-1-yl)-4-methoxyphenyl)methacrylamide (Example 113);

N-(5-((5-chloro-4-((2-(dimethylphosphoryl)phenyl)amino)pyrimidin-2-yl)amino)-4-methoxy-2-morpholinophenyl)-5-(dimethylamino)pent-2-ynamide (Example 114);

N-(5-((5-chloro-4-((2-(dimethylphosphoryl)phenyl)amino)pyrimidin-2-yl)amino)-4-methoxy-2-morpholinophenyl)-5-methoxypent-2-ynamide (Example 115);

N-(5-((5-chloro-4-((2-(dimethylphosphoryl)phenyl)amino)pyrimidin-2-yl)amino)-4-methoxy-2-morpholinophenyl)-5-(4-methylpiperazin-1-yl)pent-2-ynamide (Example 118);

N-(5-((5-chloro-4-((2-(dimethylphosphoryl)phenyl)amino)pyrimidin-2-yl)amino)-4-methoxy-2-(pyrrolidin-1-yl)phenyl)-5-(4-methylpiperazin-1-yl)pent-2-ynamide (Example 119);

N-(5-((5-chloro-4-((2-(dimethylphosphoryl)phenyl)amino)pyrimidin-2-yl)amino)-4-methoxy-2-morpholinophenyl)-5-(2-(methoxymethyl)pyrrolidin-1-yl)pent-2-ynamide (Example 122);

2-((2-((5-acrylamido-4-(3-(dimethylamino)pyrrolidin-1-yl)-2-methoxyphenyl)amino)-5-chloropyrimidin-4-yl)amino)benzamide (Example 173);

N-(5-((5-chloro-4-((2-cyanophenyl)amino)pyrimidin-2-yl)amino)-2-(3(dimethylamino)pyrrolidin-1-yl)-4-methoxyphenyl)acrylamide (Example 174); and N-(5-((5-chloro-4-((2-(isopropylsulfonyl)phenyl)amino)pyrimidin-2-yl)amino)-2-(3-(dimethylamino)pyrrolidin-1-yl)-4-methoxyphenyl)acrylamide (Example 175);

or a pharmaceutically acceptable salt thereof.

12. The compound of claim 6, wherein the compound is selected from the group consisting of:

N-(3-((5-chloro-4-((2-(dimethylphosphoryl)phenyl)amino)pyrimidin-2-yl)amino)-4-methoxyphenyl)-2-(pyrrolidin-1-ylmethyl)acrylamide (Example 42);

N-(3-((5-chloro-4-((2-(dimethylphosphoryl)phenyl)amino)pyrimidin-2-yl)amino)-4-methoxyphenyl)-2-(piperidin-1-ylmethyl)acrylamide (Example 43);

N-(3-((5-chloro-4-((2-(dimethylphosphoryl)phenyl)amino)pyrimidin-2-yl)amino)-4-methoxyphenyl)-2-((4-(methylsulfonyl)piperazin-1-yl)methyl)acrylamide (Example 44);

N-(3-((5-chloro-4-((2-(dimethylphosphoryl)phenyl)amino)pyrimidin-2-yl)amino)-4-methoxyphenyl)-2-((4-(4-methylpiperazin-1-yl)piperidin-1-yl)methyl)acrylamide (Example 45);

N-(3-((5-chloro-4-((2-(dimethylphosphoryl)phenyl)amino)pyrimidin-2-yl)amino)-4-methoxyphenyl)-2-((1,1-dioxidothiomorpholino)methyl)acrylamide (Example 46);

N-(3-((5-chloro-4-((2-(dimethylphosphoryl)phenyl)amino)pyrimidin-2-yl)amino)-4-methoxyphenyl)-2-((3-oxopiperazin-1-yl)methyl)acrylamide (Example 47);

N-(3-((5-chloro-4-((2-(dimethylphosphoryl)phenyl)amino)pyrimidin-2-yl)amino)-4-methoxyphenyl)-2-(morpholinomethyl)acrylamide (Example 48);

N-(3-((5-chloro-4-((2-(dimethylphosphoryl)phenyl)amino)pyrimidin-2-yl)amino)-4-methoxyphenyl)-2-((4-methylpiperazin-1-yl)methyl)acrylamide (Example 49);

N-(3-((5-chloro-4-((2-(dimethylphosphoryl)phenyl)amino)pyrimidin-2-yl)amino)-4-methoxyphenyl)-2-((4-isopropylpiperazin-1-yl)methyl)acrylamide (Example 50);

N-(3-((5-chloro-4-((2-(dimethylphosphoryl)phenyl)amino)pyrimidin-2-yl)amino)-4-methoxyphenyl)-2-((4-morpholinopiperidin-1-yl)methyl)acrylamide (Example 51);

N-(3-((5-chloro-4-((2-(dimethylphosphoryl)phenyl)amino)pyrimidin-2-yl)amino)-4-methoxyphenyl)-2-((4-(2-hydroxyethyl)piperazin-1-yl)methyl)acrylamide (Example 52); and N-(3-((5-chloro-4-((2-(dimethylphosphoryl)phenyl)amino)pyrimidin-2-yl)amino)-4-methoxyphenyl)-2-((3-hydroxypyrrolidin-1-yl)methyl)acrylamide (Example 53);

or a pharmaceutically acceptable salt thereof.

13. The compound of claim 6, wherein the compound is selected from the group consisting of:

N-(3-((5-chloro-4-((2-(dimethylphosphoryl)phenyl)amino)pyrimidin-2-yl)amino)-4-methoxyphenyl)-4-(dimethylamino)but-2-ynamide (Example 81);

N-(3-((5-chloro-4-((2-(dimethylphosphoryl)phenyl)amino)pyrimidin-2-yl)amino)-4-methoxyphenyl)-2-(trifluoromethyl)acrylamide (Example 82);

N-(3-((5-chloro-2-((4-(dimethylphosphoryl)-2-methoxyphenyl)amino)pyrimidin-4-yl)oxy)phenyl)-4-(dimethylamino)but-2-ynamide (Example 83);

N-(5-((5-chloro-4-((2-(dimethylphosphoryl)phenyl)amino)pyrimidin-2-yl)amino)-2-fluoro-4-methoxyphenyl)-4-(dimethylamino)but-2-ynamide (Example 87);

N-(5-((5-chloro-4-((2-(dimethylphosphoryl)phenyl)amino)pyrimidin-2-yl)amino)-2-fluoro-4-methoxyphenyl)-5-(piperidin-1-yl)pent-2-ynamide (Example 88);

N-(5-((5-chloro-4-((2-(dimethylphosphoryl)phenyl)amino)pyrimidin-2-yl)amino)-2-fluoro-4-methoxyphenyl)-4-(pyrrolidin-1-yl)but-2-ynamide (Example 89);

N-(5-((5-chloro-4-((2-(dimethylphosphoryl)phenyl)amino)pyrimidin-2-yl)amino)-2-fluoro-4-methoxyphenyl)-4-methyl-4-(pyrrolidin-1-yl)pent-2-ynamide (Example 90);

N-(3-((5-chloro-4-((2-(dimethylphosphoryl)phenyl)amino)pyrimidin-2-yl)amino)-4-methoxyphenyl)-4-methyl-4-(pyrrolidin-1-yl)pent-2-ynamide (Example 91);

N-(3-((5-chloro-4-((2-(dimethylphosphoryl)phenyl)amino)pyrimidin-2-yl)amino)-4-methoxyphenyl)-3-phenylpropiolamide (Example 93); and N-(3-((5-chloro-4-((2-(dimethylphosphoryl)phenyl)amino)pyrimidin-2-yl)amino)-4-methoxyphenyl)-4-methoxybut-2-ynamide (Example 97);

or a pharmaceutically acceptable salt thereof.

14. The compound of claim 6, wherein the compound is selected from the group consisting of:

N-(5-((5-chloro-4-((2-(dimethylphosphoryl)phenyl)amino)pyrimidin-2-yl)amino)-2-(2-(dimethylamino)-3-hydroxypropoxy)-4-methoxyphenyl)acrylamide (Example 66);

N-(5-((5-chloro-4-((2-(dimethylphosphoryl)phenyl)amino)pyrimidin-2-yl)amino)-2-((2-((2-fluoroethyl)(methyl)amino)ethyl)(methyl)amino)-4-methoxyphenyl)acrylamide (Example 67);

N-(5-((5-cyclopropyl-4-((2-(dimethylphosphoryl)phenyl)amino)pyrimidin-2-yl)amino)-2-((2-(diethylamino)ethyl)(methyl)amino)-4-methoxyphenyl)acrylamide (Example 120);

N-(5-((5-chloro-4-((2-(dimethylphosphoryl)phenyl)amino)pyrimidin-2-yl)amino)-2-((1-(diethylamino)-3-fluoropropan-2-yl)oxy)-4-methoxyphenyl)acrylamide (Example 121);

(R)-N-(5-((5-chloro-4-((2-(dimethylphosphoryl)phenyl)amino)pyrimidin-2-yl)amino)-2-((1-(dimethylamino)-3-methoxypropan-2-yl)oxy)-4-methoxyphenyl)acrylamide (Example 129);

N-(5-((5-chloro-4-((2-(dimethylphosphoryl)phenyl)amino)pyrimidin-2-yl)amino)-2-((1-(dimethylamino)-3-methoxypropan-2-yl)oxy)-4-methoxyphenyl)acrylamide (Example 130);

N-(5-((5-chloro-4-((2-(dimethylphosphoryl)phenyl)amino)pyrimidin-2-yl)amino)-2-((1-(dimethylamino)-3-ethoxypropan-2-yl)oxy)-4-methoxyphenyl)acrylamide (Example 142);

N-(5-((5-chloro-4-((2-(dimethylphosphoryl)phenyl)amino)pyrimidin-2-yl)amino)-2-((1-(dimethylamino)-3-methoxypropan-2-yl)oxy)-4-methylphenyl)acrylamide (Example 143);

N-(5-((5-chloro-4-((2-(dimethylphosphoryl)phenyl)amino)pyrimidin-2-yl)amino)-2-((1-(dimethylamino)-3-methoxypropan-2-yl)oxy)-4-methylphenyl)acrylamide (Example 144);

N-(4-chloro-5-((5-chloro-4-((2-(dimethylphosphoryl)phenyl)amino)pyrimidin-2-yl)amino)-2-((1-(dimethylamino)-3-methoxypropan-2-yl)oxy)phenyl)acrylamide (Example 145);

N-(4-chloro-5-((5-chloro-4-((2-(dimethylphosphoryl)phenyl)amino)pyrimidin-2-yl)amino)-2-((1-(dimethylamino)-3-methoxypropan-2-yl)oxy)phenyl)acrylamide (Example 146);

or a pharmaceutically acceptable salt thereof.

15. A pharmaceutical composition comprising a compound of claim 6 or a pharmaceutically acceptable salt thereof.

16. A method for treating an EGFR-driven cancer in a subject, said method comprising administering to said subject a therapeutically effective amount of a compound of claim 6, or a pharmaceutically acceptable salt thereof, wherein said EGFR-driven cancer is a non-small cell lung cancer (NSCLS); pancreatic cancer; head and neck cancer; or colorectal cancer.

* * * * *

UNITED STATES PATENT AND TRADEMARK OFFICE
CERTIFICATE OF CORRECTION

PATENT NO. : 9,834,571 B2
APPLICATION NO. : 15/044382
DATED : December 5, 2017
INVENTOR(S) : Zhu et al.

Page 1 of 1

It is certified that error appears in the above-identified patent and that said Letters Patent is hereby corrected as shown below:

In the Claims

Claim 1, Column 225:
Delete the structure at Lines 50 through 62:

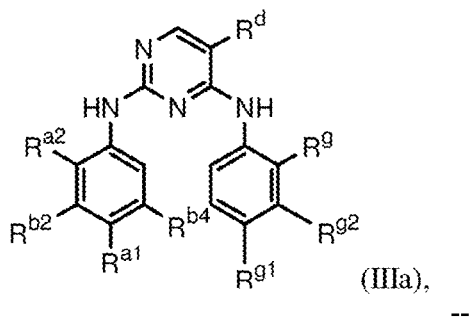

Replace it with -- --

Claim 6, Column 236, Line 39:
Delete "(methypamino)"
Replace it with --(methyl)amino)--

Claim 11, Column 253, Line 58:
Delete "(methypamino)"
Replace it with --(methyl)amino)--

Signed and Sealed this
Tenth Day of April, 2018

Andrei Iancu
*Director of the United States Patent and Trademark Office*